US009763952B2

(12) United States Patent
Caravatti et al.

(10) Patent No.: US 9,763,952 B2
(45) Date of Patent: Sep. 19, 2017

(54) DIHYDRO-BENZO-OXAZINE AND DIHYDRO-PYRIDO-OXAZINE DERIVATIVES

(71) Applicants: Giorgio Caravatti, Bottmingen (CH); Sylvie Chamoin, Saint Louis (FR); Pascal Furet, Thann (FR); Klemens Hogenauer, Oberwil (CH); Konstanze Hurth, Lorrach (DE); Karen Kammertoens, Village-Neuf (FR); Ian Lewis, Riehen (CH); Henrik Moebitz, Freiburg (DE); Alexander Baxter Smith, Niffer (FR); Nicolas Soldermann, Village-Neuf (FR); Romain Wolf, Schlierbach (CH); Frederic Zecri, Brookline (MA)

(72) Inventors: Giorgio Caravatti, Bottmingen (CH); Sylvie Chamoin, Saint Louis (FR); Pascal Furet, Thann (FR); Klemens Hogenauer, Oberwil (CH); Konstanze Hurth, Lorrach (DE); Karen Kammertoens, Village-Neuf (FR); Ian Lewis, Riehen (CH); Henrik Moebitz, Freiburg (DE); Alexander Baxter Smith, Niffer (FR); Nicolas Soldermann, Village-Neuf (FR); Romain Wolf, Schlierbach (CH); Frederic Zecri, Brookline (MA)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/976,998

(22) Filed: Dec. 21, 2015

(65) Prior Publication Data
US 2016/0106753 A1 Apr. 21, 2016

Related U.S. Application Data

(62) Division of application No. 13/721,805, filed on Dec. 20, 2012.

(60) Provisional application No. 61/579,231, filed on Dec. 22, 2011.

(51) Int. Cl.
A61K 31/538 (2006.01)
A61K 31/5383 (2006.01)
C07D 498/04 (2006.01)
C07D 413/14 (2006.01)
C12Q 1/25 (2006.01)
C12N 9/12 (2006.01)

(52) U.S. Cl.
CPC ........ A61K 31/5383 (2013.01); A61K 31/538 (2013.01)

(58) Field of Classification Search
CPC .............. A61K 31/538; A61K 31/5383; C07D 471/04; C07D 498/04
USPC ....................... 544/105; 514/230.5
See application file for complete search history.

(56) References Cited

U.S. PATENT DOCUMENTS

| 2004/0121996 A1 | 6/2004 | Barvian et al. |
| 2006/0161001 A1 | 7/2006 | Hong et al. |
| 2008/0221091 A1 | 9/2008 | Gege et al. |
| 2008/0306093 A1 | 12/2008 | Servant et al. |
| 2009/0042773 A1 | 2/2009 | Wetzker et al. |
| 2010/0137302 A1 | 6/2010 | Alexander et al. |
| 2010/0152160 A1 | 6/2010 | Khamrai et al. |
| 2011/0172217 A1 | 7/2011 | Fujioka et al. |

FOREIGN PATENT DOCUMENTS

| EP | 432893 A2 | 6/1991 |
| EP | 1777225 A | 4/2007 |
| EP | 2298731 A1 | 3/2011 |
| EP | 2341052 A1 | 7/2011 |
| KR | 20120018236 | 3/2012 |
| WO | 9426739 A1 | 11/1994 |
| WO | 0039103 A1 | 7/2000 |
| WO | 200123389 A2 | 4/2001 |

(Continued)

OTHER PUBLICATIONS

Matsumoto Y. et al., Novel Potassium Channel Activators: Synthesis and Structure-Activity Relationship Studies of 3,4-dihydro-2H-1,4-benzoxazine Derivatives. Chem Pharm Bulletin. Jan. 1996; 44(1)103-114.
Okkenhaug K. et al., PI3K in lymphocyte development, differentiation and activation; Nature Reviews Immunology. Apr. 2003; 3:317-330.
Marone R. et al., Targeting phosphoinositide 3-kinase—Moving towards therapy; Biochimica et Biophysica Acta (BBA)—Proteins and Proteomics. Jan. 2008; 1784(1): 159-185.
Okkenhaug K. et al., Impaired B and T Cell Antigen Receptor Signaling in p110δ PI 3-Kinase Mutant Mice. Science. Aug. 2002; 297: 1031-1034.

(Continued)

Primary Examiner — Susanna Moore
(74) Attorney, Agent, or Firm — Laura K. Madden

(57) ABSTRACT

The invention relates to dihydro-benzo-oxazine and dihydro-pyrido-oxazine compounds of the formula (I) and/or pharmaceutically acceptable salts and/or solvates thereof,

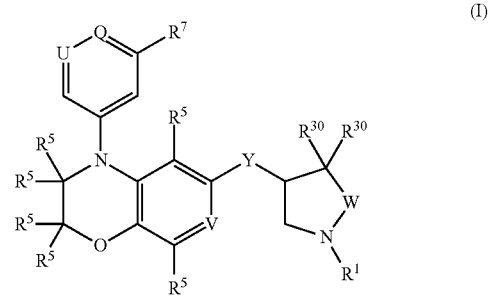

wherein Y, V, W, U, Q, $R^1$, $R^5$, $R^7$ and $R^{30}$ are as defined in the description. Such compounds are suitable for the treatment of a disorder or disease which is mediated by the activity of the PI3K enzymes.

10 Claims, 1 Drawing Sheet

(56) References Cited

FOREIGN PATENT DOCUMENTS

| WO | 0157003 | A1 | 8/2001 |
|---|---|---|---|
| WO | 02072049 | A1 | 9/2002 |
| WO | 2004056820 | A1 | 7/2004 |
| WO | 2004087646 | A2 | 10/2004 |
| WO | 2005040355 | A2 | 5/2005 |
| WO | 2006032342 | A2 | 3/2006 |
| WO | 2006034769 | A1 | 4/2006 |
| WO | 2006050054 | A2 | 5/2006 |
| WO | 2007089034 | A1 | 8/2007 |
| WO | 2008/001076 | A1 | 1/2008 |
| WO | 2008044022 | A | 4/2008 |
| WO | 2008051493 | A2 | 5/2008 |
| WO | 2008098058 | A1 | 8/2008 |
| WO | 2009026444 | A1 | 2/2009 |
| WO | 2009071895 | A1 | 6/2009 |
| WO | 2009/157196 | A1 | 12/2009 |
| WO | 2010/027002 | A1 | 3/2010 |
| WO | 2010111626 | A2 | 9/2010 |
| WO | 2010117425 | A1 | 10/2010 |
| WO | 2010151737 | A2 | 12/2010 |
| WO | 2011143495 | A1 | 11/2011 |
| WO | 2012004299 | A2 | 1/2012 |
| WO | 2012068096 | A2 | 5/2012 |
| WO | 2012068106 | A2 | 5/2012 |
| WO | 2012136080 | A1 | 10/2012 |
| WO | 2013093849 | A1 | 6/2013 |
| WO | 2014102630 | A1 | 7/2014 |

OTHER PUBLICATIONS

Martin F. et al, B Cell Immunobiology in Disease: Evolving Concepts from the Clinic. Annual Review of Immunology. Apr. 2006; 24:467-496.

Gerard C. et al.., Chemokines and disease. Nature Immunology. Feb. 2001; 2(2):108-115.

Liu L. et al. ,Leukocyte PI3Kγ and PI3Kδ have temporally distinct roles for leukocyte recruitment in vivo. Blood. Aug. 2007; 110(4): 1191-1198.

Maira S.-M. et al., Class IA phosphatidylinositol 3-kinase: from their biologic implication in human cancers to drug discovery. Expert Opinion in Therapeutic Targets. Feb. 2008; 12(2): 223-238.

Foukas L.C. et al.; Critical role for the p110α phosphoinositide-3-OH kinase in growth and metabolic regulation. Nature. May 2006; 441: 366-370.

Schofield L et al., Immunological processes in malaria pathogenesis. Nature Reviews Immunology. Sep. 2005; 5: 122-735.

Schofield L. et al., Intravascular infiltrates and organ-specific inflammation in malaria pathogenesis. Immunology and Cell Biology. Feb. 2007; 85(2):130-137.

Mishra B.B. et al., Toll-Like Receptors in CNS Parasitic Infections. Current Topics in Microbiology and Immunology. Feb. 2009; 336: 83-104.

Bottieau E. et al., Therapy of vector-borne protozoan infections in nonendemic settings. Expert Review of Anti-Infective Therapy. May 2011; 9(5); 583-608.

Hedayat M. et al., Targeting of Toll-like receptors: a decade of progress in combating infectious diseases. The Lancet Infectious Diseases. Sep. 2011; 11(9): 702-712.

Kawai T. et al., Toll-like Receptors and Their Crosstalk with Other Innate Receptors in Infection and Immunity. Immunity. May 2011; 34(5); 637-650.

Higgins S. J. et al., Immunopathogenesis of falciparum malaria: implications for adjunctive therapy in the management of severe and cerebral malaria. Expert review of anti-infective therapy. Sep. 2011; 9(9): 803-819.

Gowda N. M. et al., The Nucleosome Is the TLR9-Specific Immunostimulatory Component of Plasmodium falciparum That Activates DCs. PLoS ONE. Jun. 2011; 6(6): 1-14.

Peixoto-Rangel et al., Candidate gene analysis of ocular toxoplasmosis in Brazil: evidence for a role for toll-like receptor 9 (TLR9). Memórias do Instituto Oswaldo Cruz. Dec. 2009; 104(8): 1187-1190.

Pellegrini A. et al., The role of Toll-like receptors and adaptive immunity in the development of protective or pathological immune response triggered by the Trypanosoma cruzi protozoan. Future Microbiology. Dec. 2011; 6 (12):1521-1533.

Franklin B. S. et al., Therapeutical targeting of nucleic acid-sensing Toll-like receptors prevents experimental cerebral malaria. PNAS. Mar. 2011; 108(9): 3689-3694.

Arevalo J.F. et al., Ocular Toxoplasmosis in the Developing World. International Ophthalmology Clinics. 2010; 50 (2): 57-69.

Rommel, Christian, et al., "PI3Kδ and PI3Kγ: partners in crime in inflammation in rheumatoid arthritis and beyond?", Nature Reviews, Immunology, 7:191-201 (2007).

Lin (Counts)

2-Theta - Scale

DIHYDRO-BENZO-OXAZINE AND DIHYDRO-PYRIDO-OXAZINE DERIVATIVES

This application claims priority to U.S. Provisional Application No. 61/579,231 filed Dec. 22, 2011, the contents of which are incorporated herein by reference in their entirety.

FIELD OF THE INVENTION

The invention relates to the preparation and use of new dihydro-benzo-oxazine and dihydro-pyrido-oxazine derivatives as drug candidates in free form or in pharmaceutically acceptable salt form with valuable druglike properties, such as e.g. metabolic stability and suitable pharmacokinetics, form for the modulation, notably the inhibition of the activity or function of the phosphoinositide 3' OH kinase family (hereinafter PI3K).

BACKGROUND OF THE INVENTION

Members of the phosphoinositide-3 kinase (PI3K) family are involved in cell growth, differentiation, survival, cytoskeletal remodeling and the trafficking of intracellular organelles in many different types of cells (Okkenhaug and Wymann, Nature Rev. Immunol. 3:317 (2003).

To date, eight mammalian PI3Ks have been identified, divided into three main classes (I, II and III) on the basis of their genetic sequence, structure, adapter molecules, expression, mode of activation, and preferred substrate.

PI3Kδ is a lipid kinase belonging to the class I PI3K family (PI3K α, β, γ and δ) that generates second messenger signals downstream of tyrosine kinase-linked receptors. PI3Kδ is a heterodimer composed of an adaptor protein and a p110δ catalytic subunit which converts phosphatidylinositol-4,5-bis-phosphate (PtdlnsP2) to phosphatidylinositol-3,4,5-tri-phosphate (PtdlnsP3). Effector proteins interact with PtdlnsP3 and trigger specific signaling pathways involved in cell activation, differentiation, migration, and cell survival.

Expression of the p110δ and p110γ catalytic subunits is preferential to leukocytes. Expression is also observed in smooth muscle cells, myocytes and endothelial cells. In contrast, p110α and p110β are expressed by all cell types (Marone et al. Biochimica et Biophysica Acta 1784:159 (2008)).

PI3Kδ is associated with B cell development and function (Okkenhaug et al. Science 297:1031 (2002)).

B cells play also a critical role in the pathogenesis of a number of autoimmune and allergic diseases as well as in the process of transplant rejection (Martin and Chan, Annu. Rev. Immunol. 24:467 (2006)).

Chemotaxis is involved in many autoimmune or inflammatory diseases, in angiogenesis, invasion/metastasis, neurodegeneration or wound healing (Gerard et al. Nat. Immunol. 2:108 (2001)). Temporarily distinct events in leukocyte migration in response to chemokines are fully dependent on PI3Kδ and PI3Kγ (Liu et al. Blood 110:1191 (2007)).

PI3Kα and PI3Kβ play an essential role in maintaining homeostasis and pharmacological inhibition of these molecular targets has been associated with cancer therapy (Maira et al. Expert Opin. Ther. Targets 12:223 (2008)).

PI3Kα is involved in insulin signaling and cellular growth pathways (Foukas et al. Nature 441:366 (2006)). PI3Kδ isoform-selective inhibition is expected to avoid potential side effects such as hyperglycemia, and metabolic or growth disregulation.

Parasitic infections still represent one of the most important causes of morbidity and mortality worldwide. Among the parasites that cause human and animal pathology the phylum apicomplexa comprises a group of vector-borne parasites that is responsible for a wide variety of serious illnesses including but not limited to malaria, leishmaniasis and trypanosomiasis. Malaria alone infects 5-10% of humanity and causes around two million deaths per year. [Schofield et al, "Immunological processes in malaria pathogenesis", Nat Rev Imm 2005], [Schofield L, "Intravascular infiltrates and organ-specific inflammation in malaria pathogenesis], [Mishra et al, "TLRs in CNS Parasitic infections", Curr Top Micro Imm 2009], [Bottieau et al, "Therapy of vector-borne protozoan infections in nonendemic settings", Expert Rev. Anti infect. Ther., 2011].

Toll-like receptors (TLRs) are germ-line encoded, phylogenetically ancient molecules that recognize evolutionary conserved structural relevant molecules (known as pathogen—associated molecular patterns (PAMPs)) within microbial pathogens. Various different cell types including cells of the immune system express TLRs and are thereby able to detect the presence of PAMPs. So far 10 functional TLR family members (TLR1-10) have been described in humans, all of which recognize specific PAMP molecules. Following recognition of these specific PAMPs TLRs induce and orchestrate the immuneresponse of the host to infections with bacteria, viruses, fungi and parasites. [Hedayat et al, "Targeting of TLRs: a decade of progress in combating infectious disease", review, Lancet Infectious disease 2011], [Kwai et al, "TLRs and their crosstalk with other innate receptors in infection and immunity", review, Immunity May-2011].

The immune system of the infected host responds to infection with the TLR induced production of pro-inflammatory cytokines mainly of the T-helper 1 type (Th1). While adequate amounts of these cytokines are beneficial and required to clear the infection an overproduction of these mediators is harmful to the host and associated with immune mediated pathology including neuropathology and tissue damage with severe and often fatal consequences. One prominent and highly relevant example of such immune mediated pathology is acute and cerebral malaria (CM) which causes severe clinical symptoms and is often fatal. [Schofield et al, "Immunological processes in malaria pathogenesis", Nat Rev Imm 2005], [Schofield L, "Intravascular infiltrates and organ-specific inflammation in malaria pathogenesis], [Mishra et al, "TLRs in CNS Parasitic infections", Curr Top Micro Imm 2009], [Bottieau et al, "Therapy of vector-borne protozoan infections in nonendemic settings", Expert Rev. Anti infect. Ther., 2011][Hedayat et al, "Targeting of TLRs: a decade of progress in combating infectious disease", review, Lancet Infectious disease 2011]. Despite progress made in treatment and eradication of malaria, the mortality rate that is associated with severe malaria, including CM remains unacceptably high. Strategies directed solely at the eradication of the parasite in the host might therefore not be sufficient to prevent neurological complications and death in all cases of CM. Development of new innovative adjunct therapeutic strategies to efficiently reduce the CM-associated mortality and morbidity that is caused, in part, by host-mediated immunopathology remains therefore an urgent medical need. [Higgins et al, "Immunopathogenesis of falciparum malaria: implications for adjunctive therapy in the management of severe and cerebral malaria", Expert Rev. Anti Infect. Ther. 2011]

Recently further evidence has been provided that TLR9 plays a key role in the recognition and response to parasites including but not limited to Plasmodium, Leishmania, Trypanosoma and *Toxoplasma* [Gowda et al, "*The Nucleosome is the TLR9-specific Immunostimulatory component of plasmodium falciparum that activates DCs*", PLoS ONE, June 2011], [Peixoto-Rangel et al, "*Candidate gene analysis of ocular toxoplasmosis in Brazil: evidence for a role for TLR9*", Mem Inst Oswaldo Cruz 2009], [Pellegrini et al, "*The role of TLRs and adoptive immunity in the development of protective or pathological immune response triggered by the Trypanosoma cruzi protozoan*", Future Microbiol 2011] and that interference with the activation of TLRs including TLR9 represents a promising strategy to prevent the deleterious inflammatory responses in severe and cerebral malaria [Franklin et al, "*Therapeutical targeting of nucleic acid-sensing TLRs prevents experimental cerebral malaria*", PNAS 2011]

Malaria is an infectious disease caused by four protozoan parasites: *Plasmodium falciparum*; *Plasmodium vivax*; *Plasmodium ovale*; and *Plasmodium* malaria. These four parasites are typically transmitted by the bite of an infected female *Anopheles* mosquito. Malaria is a problem in many parts of the world and over the last few decades the malaria burden has steadily increased. An estimated 1-3 million people die every year from malaria—mostly children under the age of 5. This increase in malaria mortality is due in part to the fact that *Plasmodium falciparum*, the deadliest malaria parasite, has acquired resistance against nearly all available antimalarial drugs, with the exception of the artemisinin derivatives.

Leishmaniasis is caused by one or more than 20 varieties of parasitic protozoa that belong to the genus *Leishmania*, and is transmitted by the bite of female sand flies. Leishmaniasis is endemic in about 88 countries, including many tropical and sub-tropical areas. There are four main forms of Leishmaniasis. Visceral leishmaniasis, also called kala-azar, is the most serious form and is caused by the parasite *Leishmania donovani*. Patients who develop visceral leishmaniasis can die within months unless they receive treatment. The two main therapies for visceral leishmaniasis are the antimony derivatives sodium stibogluconate (Pentostam®) and meglumine antimoniate (Glucantim®). Sodium stibogluconate has been used for about 70 years and resistance to this drug is a growing problem. In addition, the treatment is relatively long and painful, and can cause undesirable side effects.

Human African Trypanosomiasis, also known as sleeping sickness, is a vector-borne parasitic disease. The parasites concerned are protozoa belonging to the *Trypanosoma* Genus. They are transmitted to humans by tsetse fly (*Glossina* Genus) bites which have acquired their infection from human beings or from animals harboring the human pathogenic parasites.

Chagas disease (also called American Trypanosomiasis) is another human parasitic disease that is endemic amongst poor populations on the American continent. The disease is caused by the protozoan parasite *Trypanosoma cruzi*, which is transmitted to humans by blood-sucking insects. The human disease occurs in two stages: the acute stage, which occurs shortly after infection and the chronic stage, which can develop over many years. Chronic infections result in various neurological disorders, including dementia, damage to the heart muscle and sometimes dilation of the digestive tract, as well as weight loss. Untreated, the chronic disease is often fatal. The drugs currently available for treating Chagas disease are Nifurtimox and benznidazole. However, problems with these current therapies include their diverse side effects, the length of treatment, and the requirement for medical supervision during treatment. Furthermore, treatment is really only effective when given during the acute stage of the disease. Resistance to the two frontline drugs has already occurred. The antifungal agent Amphotericin b has been proposed as a second-line drug, but this drug is costly and relatively toxic.

Toxoplasmosis is endemic through most of the world, which can infect a large proportion of the adult population.1,2 However, its prevalence differs in different countries.3 It is estimated to infect at least 10% of adults in northern temperate countries and more than half of adults in Mediterranean and tropical contries.4 *Toxoplasma gondii* is a ubiquitous, obligate intracellular protozoan and is considered to be the most common cause of infective retinitis in humans, which depends on a variety of factors, including climate, hygiene, and dietary habits.5-7 The course of disease in immunocompetent adults is usually asymptomatic and self-limiting. As soon as infection has occurred, the parasite forms latent cysts in the retina and in other organs of the body, which can reactivate years after the initial infection giving rise to acute retinochoroiditis and the formation of new retinochoroidal lesions. [Arevalo et al, "*Ocular Toxoplasmosis in the developing world*", Internat. Ophthal. Clin 2010]

Neurocysticercosis is the most common parasitic disease of the CNS (incidence ~2.5 million worldwide) caused by the larvae of *Taenia solium*. The disease has a long asymptomatic phase in humans characterized by the absence of a detectable inflammatory response surrounding the parasite. The overall immune response during the asymptomatic phase is of the Th2 phenotype. However, the destruction of larvae by therapeutic treatment or by normal parasite attrition causes a strong inflammatory response, often consisting of a chronic granulomatous reaction and manifestation of typical symptoms of the disease. The immune response in the CNS of symptomatic patients consists of an overt Th1 phenotype or a mixed Th1, Th2, and Th3 response, depending upon the absence or presence of granulomas. The hyperinflammatory response prevailing during the symptomatic phase in the CNS is responsible for the severe neuropathology and mortality associated with neurocysticercosis. [Mishra et al, "*TLRs in CNS Parasitic infections*", Curr Top Micro Imm 2009]

There is a need to provide new PI3K inhibitors that are good drug candidates. In particular, compounds of the invention should bind potently to PI3K whilst showing little affinity for other receptors and show functional activity as inhibitors. They should be well absorbed from the gastrointestinal tract, be metabolically stable and possess favourable pharmacokinetic properties. When targeted against receptors in the central nervous system they should cross the blood brain barrier freely and when targeted selectively against receptors in the peripheral nervous system they should not cross the blood brain barrier. They should be non-toxic and demonstrate few side-effects. Furthermore, the ideal drug candidate will exist in a physical form that is stable, non-hygroscopic and easily formulated.

The compounds of the invention show a certain level of selectivity against the different paralogs PI3Kα, β, γ and δ. In particular, show a certain level of selectivity for the isoform PI3Kδ.

The compounds of the present invention are therefore potentially useful in the treatment of a wide range of disorders, particularly disorders including but not limited to autoimmune disorders, inflammatory diseases, allergic diseases, disease or infection associated immunopathologies, airway diseases, such as asthma and COPD, transplant rejection, cancers eg of hematopoietic origin or solid tumors.

The invention also relates to the treatment, either alone or in combination, with one or more other pharmacologically active compounds, includes methods of treating conditions, diseases or disorders in which one or more of the functions of B cells such as antibody production, antigen presentation, cytokine production or lymphoid organogenesis are abnormal or are undesirable including rheumatoid arthritis, pemphigus vulgaris and related diseases, idiopathic thrombocytopenia purpura, systemic lupus erythematosus, multiple sclerosis, myasthenia gravis, Sjögren's syndrome, autoimmune hemolytic anemia, ANCA-associated vasculitides, cryoglobulinemia, thrombotic thrombocytopenic purpura, chronic autoimmune urticaria, allergy (atopic dermatitis, contact dermatitis, allergic rhinitis), goodpasture's syndrome, AMR (antibody-mediated transplant rejection), B cell-mediated hyperacute, acute and chronic transplant rejection and cancers of haematopoietic origin including but not limited to multiple myeloma; acute myelogenous leukemia; chronic myelogenous leukemia; lymphocytic leukemia; myeloid leukemia; non-Hodgkin lymphoma; lymphomas; polycythemia vera; essential thrombocythemia; myelofibrosis with myeloid metaplasia; and Walden stroem disease as well as in disease or infection associated immunopathology.

SUMMARY OF THE INVENTION

The invention relates to dihydro-benzo-oxazine and dihydro-pyrido-oxazine compounds of the formula (I) and/or pharmaceutically acceptable salts and/or solvates thereof,

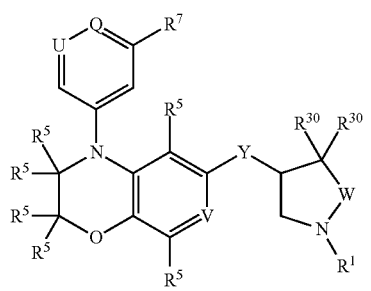

(I)

wherein
Y is selected from O or NH;
V is selected from $CR^5$ or N;
W is selected from $CH_2$, or O;
U is selected from N or CH;
Q is selected from N or $CR_6$;
wherein U and Q are not both N;
$R^1$ is selected from phenyl, pyridyl, pyrimininyl, pyrazinyl, pyridazinyl, 1,2,3-triazinyl, 1,2,4-triazinyl, 1,3,5-triazinyl,
or
—X—$R^4$
wherein X is selected from C(O), S(O)$_2$ or $CH_2$
and
$R^4$ is selected from $C_1$-$C_8$-alkyl, halo-$C_1$-$C_8$-alkyl, hydroxy-$C_1$-$C_8$-alkyl, $C_1$-$C_8$-alkoxy-$C_1$-$C_8$-alkyl, cyano-$C_1$-$C_8$-alkyl, N,N-di-$C_1$-$C_4$-alkyl-amino-$C_1$-$C_8$-alkyl, $C_1$-$C_4$-alkyl-sulfonyl-$C_1$-$C_8$-alkyl, phenyl, heterocyclyl, heterocyclyl-oxy, heterocyclyl-$C_1$-$C_8$-alkyl, $C_3$-$C_{12}$-cycloalkyl, $C_3$-$C_{12}$-cycloalkyl-oxy, $C_3$-$C_{12}$-cycloalkyl-$C_1$-$C_8$-alkyl, heteroaryl, heteroaryl-oxy, heteroaryl-$C_1$-$C_8$-alkyl, hydroxy, $C_1$-$C_8$-alkoxy, amino, N—$C_1$-$C_8$-alkyl-amino or N,N-di-$C_1$-$C_8$-alkyl-amino,
wherein $C_1$-$C_8$-alkyl in N—$C_1$-$C_8$-alkyl-amino and in N,N-di-$C_1$-$C_8$-alkyl-amino may be unsubstituted or substituted by halogen, hydroxy or $C_1$-$C_4$-alkoxy,
wherein $C_3$-$C_{12}$-cycloalkyl in $C_3$-$C_{12}$-cycloalkyl and in $C_3$-$C_{12}$-cycloalkyl-$C_1$-$C_8$-alkyl may be unsubstituted or substituted by 1-5 substituents selected from halogen, hydroxy or $C_1$-$C_4$-alkoxy;
wherein 'heterocyclyl' is a 3 to 7 membered saturated or partially unsaturated monocyclic ring system containing 1 to 3 heteroatoms selected from N, O or S, each of which is unsubstituted or substituted by 1-5 substituents selected from oxo, halogen, $C_1$-$C_8$-alkyl, halo-$C_1$-$C_8$-alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, halo-$C_1$-$C_8$-alkyl-carbonyl, hydroxy-$C_1$-$C_8$-alkyl-carbonyl or $C_1$-$C_8$-alkoxy-$C_1$-$C_8$-alkyl-carbonyl; wherein 'heterocyclyl' can be attached at a heteroatom or a carbon atom and where the N and/or S heteroatoms can also optionally be oxidized to various oxidation states,
wherein 'heteroaryl' is a 3 to 7 membered fully unsaturated monocyclic ring system containing 1 to 3 heteroatoms selected from N, O or S, or pyrazolo[1,5-a]pyrimidine or imidazo[2,1-b]thiazole, each of which is unsubstituted or substituted by 1-5 substituents selected from halogen, $C_1$-$C_8$-alkyl, halo-$C_1$-$C_8$-alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, halo-$C_1$-$C_8$-alkyl-carbonyl, hydroxy-$C_1$-$C_8$-alkyl-carbonyl or $C_1$-$C_8$-alkoxy-$C_1$-$C_8$-alkyl-carbonyl; wherein 'heteroaryl' can be attached at a heteroatom or a carbon atom and where the N and/or S heteroatoms can also optionally be oxidized to various oxidation states;
$R^6$ is selected from hydrogen, halogen, $C_1$-$C_4$-alkyl, halo-$C_1$-$C_4$-alkyl, $C_1$-$C_4$-alkoxy, $C_1$-$C_4$-alkyl-sulfonyl, $C_1$-$C_4$-alkyl-sulfinyl, $C_1$-$C_4$-alkyl-sulfanyl, halo-$C_1$-$C_4$-alkoxy, $C_1$-$C_4$-alkoxy-$C_1$-$C_4$-alkyl, amino, N—$C_1$-$C_8$-alkyl-amino, N,N-di-$C_1$-$C_8$-alkyl-amino;
$R^7$ is selected from hydrogen, halogen, cyano, nitro, $C_1$-$C_4$-alkyl, halo-$C_1$-$C_4$-alkyl, $C_1$-$C_4$-alkoxy, N($R^8$)$_2$-sulfonyl, $C_1$-$C_4$-alkyl-sulfonyl, $C_1$-$C_4$-alkyl-sulfonyl-amino, $C_1$-$C_8$-alkoxy-$C_1$-$C_8$-alkyl, amino, N—$C_1$-$C_8$-alkyl-amino, or N,N-di-$C_1$-$C_8$-alkyl-amino;
or $R^6$ and $R^7$, together are CH=CH—CH=CH,
wherein $R^8$ is independently selected from hydrogen, $C_1$-$C_4$-alkyl, $C_1$-$C_4$-alkoxy or two $R^8$ together with the nitrogen they are attached to form a 4 to 7 membered heterocyclic ring containing 1-2 heteroatoms selected from N, O, S, which is unsubstituted or substituted by 1-3 substituents selected from $C_1$-$C_4$-alkyl;
$R^5$ is independently selected from H, D, F or $C_1$-$C_2$-alkyl;
$R^{30}$ is independently selected from H, D or F.

DETAILED DESCRIPTION OF THE INVENTION

Figure 1:
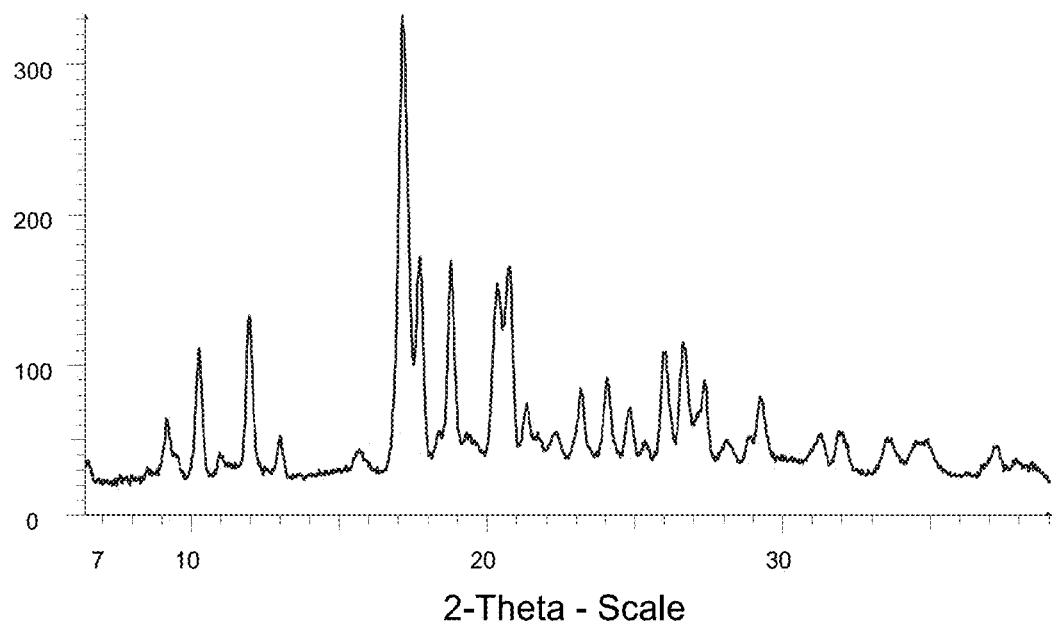
FIG. 1 is the X-ray Powder Diffraction Pattern of Example F1, crystalline anhydrous form
Figure 2:
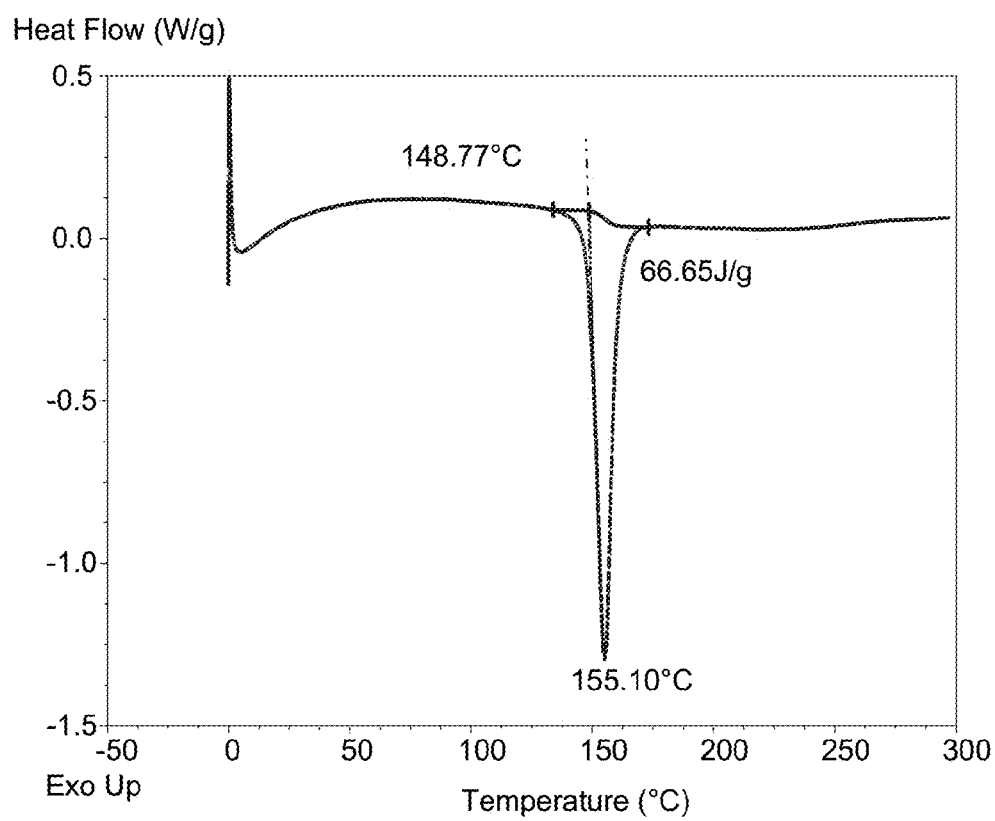
FIG. 2 is the differential scanning calorimetry graph of Example F1, crystalline anhydrous form

Unless specified otherwise, the term "compounds of the present invention" refers to compounds of formula (I) and subformulae thereof, salts of the compound, hydrates or solvates of the compounds and/or salts, as well as all stereoisomers (including diastereoisomers and enantiomers), tautomers and isotopically labeled compounds (including deuterium substitutions). Compounds of the present invention further comprise polymorphs of compounds of formula (I) (or subformulae thereof) and salts thereof. Where compounds of formula (I) are mentioned, this is meant to include also the tautomers and N-oxides of the compounds of formula (I).

The invention may be more fully appreciated by reference to the following description, including the following glossary of terms and the concluding examples. As used herein, the terms "including", "containing" and "comprising" are used herein in their open, non-limiting sense.

Tautomers, such as tautomers between keto- and enol form, lactam- and lactim form, amid form and imidic acid form or enamine form and imine form, can be present for example in the $R^1$ portion of compounds of formula (I). Nitrogen containing heterocyclyl and heteroaryl residues may form N-oxides.

Where the plural form is used for compounds, salts, and the like, this is taken to mean also a single compound, salt, or the like.

The general terms used hereinbefore and hereinafter preferably have within the context of this disclosure the following meanings, unless otherwise indicated:

As used herein, the term "alkyl" refers to a fully saturated branched, including single or multiple branching, or unbranched hydrocarbon moiety having up to 20 carbon atoms. Unless otherwise provided, alkyl refers to hydrocarbon moieties having 1 to 16 carbon atoms, 1 to 10 carbon atoms, 1 to 7 carbon atoms, or 1 to 4 carbon atoms.

Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. Typically, alkyl groups have 1-7, more preferably 1-4 carbons.

As used herein, the term "halo-alkyl" refers to an alkyl as defined herein, which is substituted by one or more halo groups as defined herein. The halo-alkyl can be mono-halo-alkyl, di-halo-alkyl or poly-halo-alkyl including per-halo-alkyl. A mono-halo-alkyl can have one iodo, bromo, chloro or fluoro within the alkyl group. Di-halo-alky and poly-halo-alkyl groups can have two or more of the same halo atoms or a combination of different halo groups within the alkyl. Typically the poly-halo-alkyl contains up to 12, or 10, or 8, or 6, or 4, or 3, or 2 halo groups. Non-limiting examples of halo-alkyl include fluoro-methyl, di-fluoro-methyl, tri-fluoro-methyl, chloro-methyl, di-chloro-methyl, tri-chloro-methyl, penta-fluoro-ethyl, hepta-fluoro-propyl, di-fluoro-chloro-methyl, di-chloro-fluoro-methyl, di-fluoro-ethyl, di-fluoro-propyl, di-chloro-ethyl and dichloro-propyl. A per-halo-alkyl refers to an alkyl having all hydrogen atoms replaced with halo atoms.

As used herein, the term "heterocyclyl" or "heterocyclic" refers to a 3 to 7 membered monocyclic or 7 to 10 membered saturated or partially saturated ring or ring system, which contains at least one heteroatom selected from N, O and S, where the N and S can also optionally be oxidized to various oxidation states. 'Heterocyclyl' can be attached at a heteroatom or a carbon atom. 'Heterocyclyl' can include fused or bridged rings as well as spirocyclic rings.

In the context of $R^4$, examples of heterocycles include oxiranyl, aziridinyl, oxetanyl, thiethanyl, acetitinyl, pyrrolidinyl, tetrahydrofuranyl, tetrahydrothiophenyl, 2,3-dihydrofuranyl, 2,5-dihydrofuranyl, 2,3-dihydrothiophenyl, 1-pyrrolinyl, 2-pyrrolinyl, 3-pyrrolinyl, tetrahydropyranyl, piperidinyl, tetrahydrothiopyranyl, morpholinyl, thiomorpholinyl, oxathianyl, dioxanyl, piperazinyl, dihydropyranyl, tetrahydropyridinyl, dihydrothiopyranyl, azepanyl, thiepanyl and oxepanyl.

In the context of $R^8$, examples of heterocycles include pyrrolinyl, piperidinyl, morpholinyl, thiomorpholinyl, piperazinyl, tetrahydropyridinyl and azepanyl.

As used herein, the term "heteroaryl" or "heteroarylic" refers to a 4-, 5-, 6-, or 7-membered monocyclic, 7-, 8-, 9-, 10-, 11-, or 12-membered bicyclic or 10-, 11-, 12-, 13-, 14- or 15-membered tricyclic unsaturated ring or ring system—carrying the highest possible number of conjugated double bonds in the ring(s), which contains at least one heteroatom selected from N, O and S, wherein the N and S can also optionally be oxidized to various oxidation states. 'Heteroaryl' can be attached at a heteroatom or a carbon atom. 'Heteroaryl' can include fused or bridged rings as well as spirocyclic rings. Examples of heteroaryl include furanyl, thiophenyl, pyrrolyl, imidazolyl, pyrazolyl, thiazolyl, isothiazolyl, oxazolyl, isoxazolyl, 1,2,5-oxadiazolyl, 1,2,4-oxadiazolyl, 1,2,3-oxadiazolyl, 1,3,4-oxadiazolyl, 1,2,5-thiadiazolyl, 1,2,4-thiadiazolyl, 1,2,3-thiadiazolyl, 1,3,4-thiadiazolyl, 1,2,3-triazolyl, 1,2,4-triazolyl, 1,2,5-triazolyl, pyridyl, pyrimidinyl, pyrazinyl, pyridazinyl, 1,2,3-triazinyl, 1,2,4-triazinyl and 1,3,5-triazinyl.

As used herein, the term "cycloalkyl" refers to saturated or partially unsaturated monocyclic, bicyclic or tricyclic hydrocarbon groups of 3-12 carbon atoms. Unless otherwise provided, cycloalkyl refers to cyclic hydrocarbon groups having between 3 and 10 ring carbon atoms or between 3 and 7 ring carbon atoms. Exemplary bicyclic hydrocarbon groups include octahydroindyl, decahydronaphthyl. Exemplary tricyclic hydrocarbon bicyclo[2.1.1]hexyl, bicyclo [2.2.1]heptyl, bicyclo[2.2.1]heptenyl, 6,6-dimethylbicyclo [3.1.1]heptyl, 2,6,6-trimethylbicyclo[3.1.1]heptyl, bicyclo [2.2.2]octy. Exemplary tetracyclic hydrocarbon groups include adamantyl.

As used herein, the term "oxy" refers to an —O— linking group.

As used herein, the term "carboxy" or "carboxyl" is —COOH.

As used herein, all substituents are written in a way to show the order of functional groups (groups) they are composed of. The functional groups are defined herein above.

Various enumerated embodiments of the invention are described herein. It will be recognized that features specified in each embodiment may be combined with other specified features to provide further embodiments of the present invention.

In one embodiment, the invention provides a compound of the formula (I) and/or a pharmaceutically acceptable salt and/or a solvate thereof, selected from a compound of the formula (I')

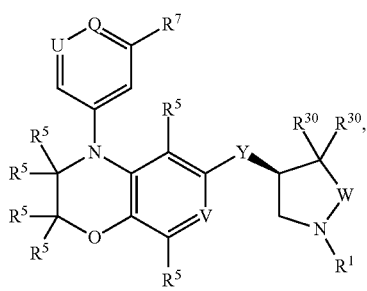

(I')

wherein $R^1$, $R^5$, $R^7$, $R^{30}$, Y, V, W, U and Q are as defined above.

In one embodiment, the invention provides a compound of the formula (I) and/or a pharmaceutically acceptable salt and/or a solvate thereof, selected from a compound of the formula (Ia)

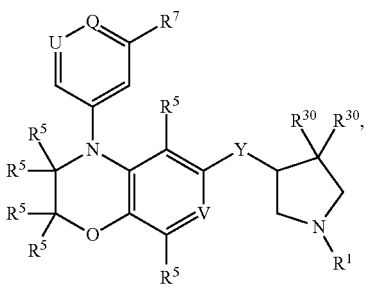

(Ia)

wherein $R^1$, $R^5$, $R^7$, $R^{30}$, Y, V, U and Q are as defined above.

In one embodiment, the invention provides a compound of the formula (I) and/or a pharmaceutically acceptable salt and/or a solvate thereof, selected from a compound of the formula (Ia')

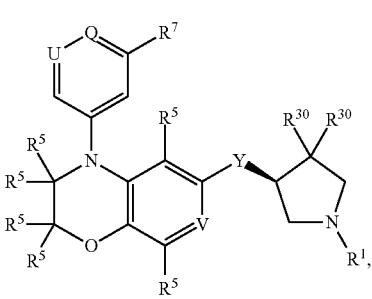

(Ia')

wherein $R^1$, $R^5$, $R^7$, $R^{30}$, Y, V, U and Q are as defined above.

In another embodiment, the invention provides a compound of the formula (I) and/or a pharmaceutically acceptable salt and/or a solvate thereof, selected from a compound of the formula (Ib)

(Ib)

wherein $R^1$, $R^5$, $R^7$, $R^{30}$, V, W, U and Q are as defined above.

In another embodiment, the invention provides a compound of the formula (I) and/or a pharmaceutically acceptable salt and/or a solvate thereof, selected from a compound of the formula (Ib')

(Ib')

wherein $R^1$, $R^5$, $R^7$, $R^{30}$, V, W, U and Q are as defined above.

In another embodiment, the invention provides a compound of the formula (I) and/or a pharmaceutically acceptable salt and/or a solvate thereof, selected from a compound of the formula (Ic)

(Ic)

wherein $R^1$, $R^5$, $R^7$, U and Q are as defined above.

In another embodiment, the invention provides a compound of the formula (I) and/or a pharmaceutically acceptable salt and/or a solvate thereof, selected from a compound of the formula (Ic')

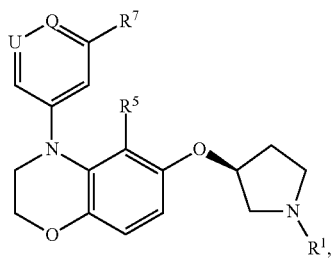

(Ic′)

wherein R¹, R⁵, R⁷, U and Q are as defined above.

In another embodiment, the invention provides a compound of the formula (I) and/or a pharmaceutically acceptable salt and/or a solvate thereof, selected from a compound of the formula (Id)

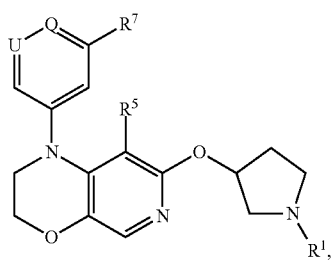

(Id)

wherein R¹, R⁵, R⁷, U and Q are as defined above.

In another embodiment, the invention provides a compound of the formula (I) and/or a pharmaceutically acceptable salt and/or a solvate thereof, selected from a compound of the formula (Id′)

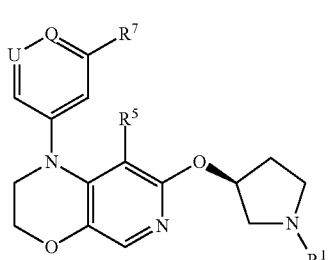

(Id′)

wherein R¹, R⁵, R⁷, U and Q are as defined above.

In another embodiment, the invention provides a compound of the formula (I) and/or a pharmaceutically acceptable salt and/or a solvate thereof, selected from a compound of the formula (Ie)

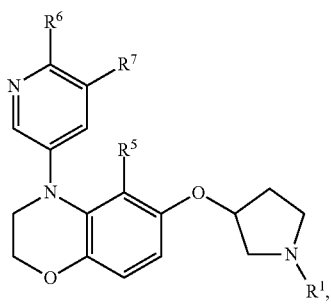

(Ie)

wherein R¹, R⁵, R⁶ and R⁷ are as defined above.

In another embodiment, the invention provides a compound of the formula (I) and/or a pharmaceutically acceptable salt and/or a solvate thereof, selected from a compound of the formula (Ie′)

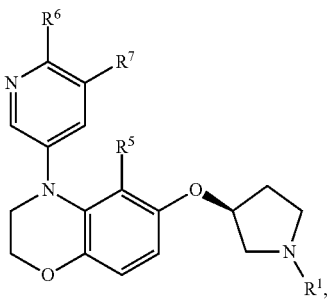

(Ie′)

wherein R¹, R⁵, R⁶ and R⁷ are as defined above.

In another embodiment, the invention provides a compound of the formula (I) and/or a pharmaceutically acceptable salt and/or a solvate thereof, selected from a compound of the formula (If)

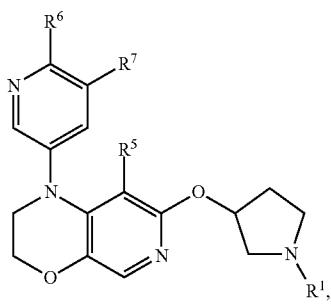

(If)

wherein R¹, R⁵, R⁶ and R⁷ are as defined above.

In another embodiment, the invention provides a compound of the formula (I) and/or a pharmaceutically acceptable salt and/or a solvate thereof, selected from a compound of the formula (If′)

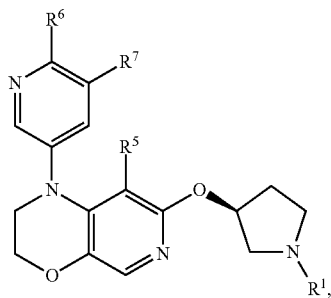
(If')

wherein $R^1$, $R^5$, $R^6$ and $R^7$ are as defined above.

In another embodiment, the invention provides a compound of the formula (I) and/or a pharmaceutically acceptable salt and/or a solvate thereof, selected from a compound of the formula (Ig)

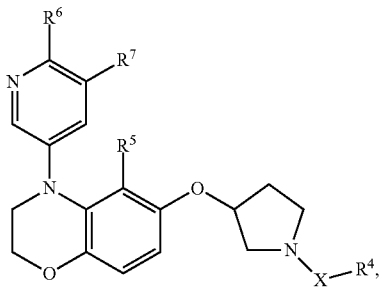
(Ig)

wherein X, $R^4$, $R^5$, $R^6$ and $R^7$ are as defined above.

In another embodiment, the invention provides a compound of the formula (I) and/or a pharmaceutically acceptable salt and/or a solvate thereof, selected from a compound of the formula (Ig')

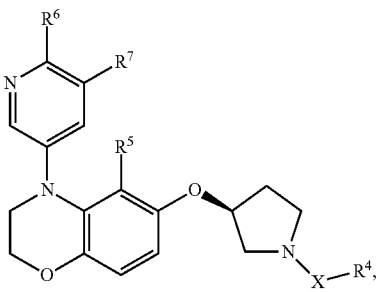
(Ig')

wherein X, $R^4$, $R^5$, $R^6$ and $R^7$ are as defined above.

In another embodiment, the invention provides a compound of the formula (I) and/or a pharmaceutically acceptable salt and/or a solvate thereof, selected from a compound of the formula (Ih)

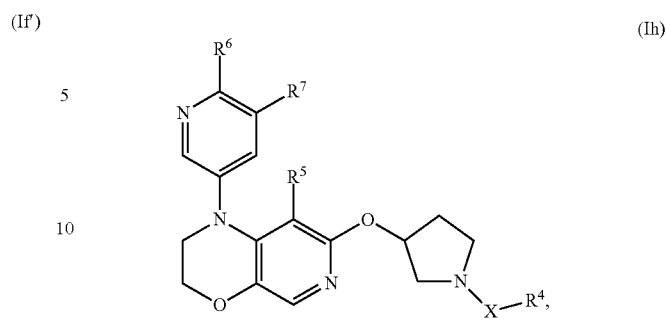
(Ih)

wherein X, $R^4$, $R^5$, $R^6$ and $R^7$ are as defined above.

In another embodiment, the invention provides a compound of the formula (I) and/or a pharmaceutically acceptable salt and/or a solvate thereof, selected from a compound of the formula (Ih')

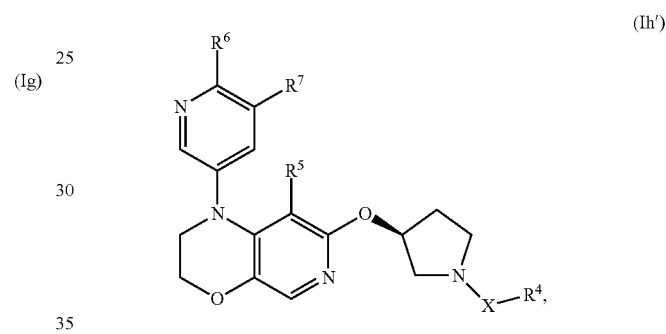
(Ih')

wherein X, $R^4$, $R^5$, $R^6$ and $R^7$ are as defined above.

In another embodiment, the invention provides a compound of the formula (I) and/or a pharmaceutically acceptable salt and/or a solvate thereof, selected from a compound of the formula (Ii)

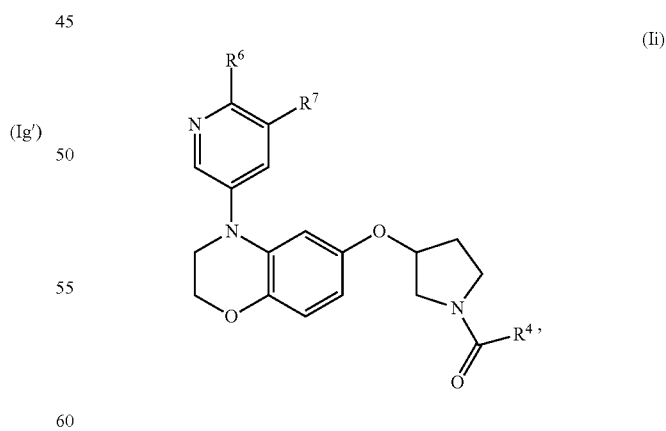
(Ii)

wherein $R^4$, $R^5$, $R^6$ and $R^7$ are as defined above.

In another embodiment, the invention provides a compound of the formula (I) and/or a pharmaceutically acceptable salt and/or a solvate thereof, selected from a compound of the formula (Ii')

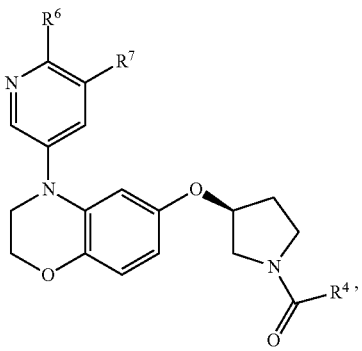

(Ii')

wherein $R^4$, $R^5$, $R^6$ and $R^7$ are as defined above.

In another embodiment, the invention provides a compound of the formula (I) and/or a pharmaceutically acceptable salt and/or a solvate thereof, selected from a compound of the formula (Ij)

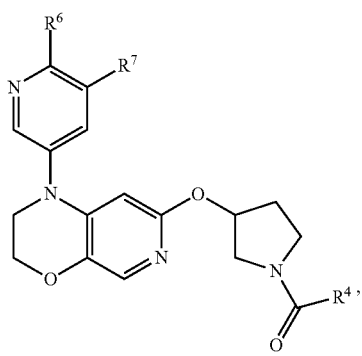

(Ij)

wherein $R^4$, $R^5$, $R^6$ and $R^7$ are as defined above.

In another embodiment, the invention provides a compound of the formula (I) and/or a pharmaceutically acceptable salt and/or a solvate thereof, selected from a compound of the formula (Ij')

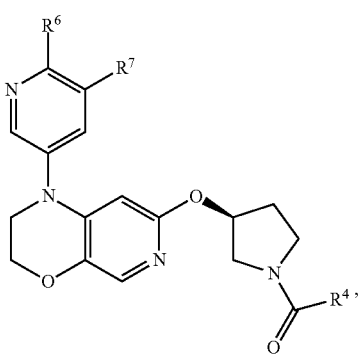

(Ij')

wherein $R^4$, $R^5$, $R^6$ and $R^7$ are as defined above.

In another embodiment, the invention provides a compound of the formulae (I), (I'), (Ia), (Ia'), (Ib), (Ib') (Ic), (Ic'), (Id), (Id'), (Ie), (Ie'), (If), (If'), (Ig), (Ig'), (Ih), (Ih'), (Ii), (Ii'), (Ij) or (Ij') and/or a pharmaceutically acceptable salt and/or a solvate thereof, wherein $R^4$ is selected from $C_1$-$C_8$-alkyl, hydroxy-$C_1$-$C_8$-alkyl, $C_1$-$C_8$-alkoxy-$C_1$-$C_8$-alkyl, cyano-$C_1$-$C_8$-alkyl, N,N-di-$C_1$-$C_4$-alkyl-amino-$C_1$-$C_8$-alkyl, $C_1$-$C_4$-alkyl-sulfonyl-$C_1$-$C_8$-alkyl, phenyl, heterocyclyl, heterocyclyl-$C_1$-$C_8$-alkyl, $C_3$-$C_{12}$-cycloalkyl, heteroaryl, heteroaryl-$C_1$-$C_8$-alkyl, $C_1$-$C_8$-alkoxy, wherein $C_1$-$C_8$-alkyl in N—$C_1$-$C_8$-alkyl-amino and in N,N-di-$C_1$-$C_8$-alkyl-amino may be unsubstituted or substituted by halogen, hydroxy or $C_1$-$C_4$-alkoxy, wherein $C_3$-$C_{12}$-cycloalkyl in $C_3$-$C_{12}$-cycloalkyl and in $C_3$-$C_{12}$-cycloalkyl-$C_1$-$C_8$-alkyl may be unsubstituted or substituted by halogen, hydroxy or $C_1$-$C_4$-alkoxy;

wherein 'heterocyclyl' is a 3 to 7 membered saturated or partially unsaturated monocyclic ring system containing 1 to 3 heteroatoms selected from N, O or S, which is unsubstituted or substituted by 1-5 substituents selected from oxo, halogen, $C_1$-$C_8$-alkyl, halo-$C_1$-$C_8$-alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, halo-$C_1$-$C_8$-alkyl-carbonyl, hydroxy-$C_1$-$C_8$-alkyl-carbonyl or $C_1$-$C_8$-alkoxy-$C_1$-$C_8$-alkyl-carbonyl; wherein 'heterocyclyl' can be attached at a heteroatom or a carbon atom and where the N and/or S heteroatoms can also optionally be oxidized to various oxidation states, wherein 'heteroaryl' is a 3 to 7 membered fully unsaturated monocyclic ring system containing 1 to 3 heteroatoms selected from N, O or S, or pyrazolo[1,5-a]pyrimidine or imidazo[2,1-b]thiazole, each of which is unsubstituted or substituted by 1-5 substituents selected from halogen, $C_1$-$C_8$-alkyl, halo-$C_1$-$C_8$-alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, halo-$C_1$-$C_8$-alkyl-carbonyl, hydroxy-$C_1$-$C_8$-alkyl-carbonyl or $C_1$-$C_8$-alkoxy-$C_1$-$C_8$-alkyl-carbonyl; wherein 'heteroaryl' can be attached at a heteroatom or a carbon atom and where the N and/or S heteroatoms can also optionally be oxidized to various oxidation states.

In another embodiment, the invention provides a compound of the formulae (I), (I'), (Ia), (Ia'), (Ib), (Ib') (Ic), (Ic'), (Id), (Id'), (Ie), (Ie'), (If), (If'), (Ig), (Ig'), (Ih), (Ih'), (Ii), (Ii'), (Ij) or (Ij') and/or a pharmaceutically acceptable salt and/or a solvate thereof, wherein $R^4$ is selected from $C_1$-$C_8$-alkyl, hydroxy-$C_1$-$C_8$-alkyl, $C_1$-$C_8$-alkoxy-$C_1$-$C_8$-alkyl, cyano-$C_1$-$C_5$-alkyl, N,N-di-$C_1$-$C_4$-alkyl-amino-$C_1$-$C_8$-alkyl, $C_1$-$C_4$-alkyl-sulfonyl-$C_1$-$C_8$-alkyl, phenyl, heterocyclyl, heterocyclyl-$C_1$-$C_8$-alkyl, $C_3$-$C_{12}$-cycloalkyl, heteroaryl, heteroaryl-$C_1$-$C_8$-alkyl, $C_1$-$C_8$-alkoxy, wherein $C_1$-$C_8$-alkyl in N—$C_1$-$C_8$-alkyl-amino and in N,N-di-$C_1$-$C_8$-alkyl-amino may be unsubstituted or substituted by halogen, hydroxy or $C_1$-$C_4$-alkoxy, wherein $C_3$-$C_{12}$-cycloalkyl in $C_3$-$C_{12}$-cycloalkyl and in $C_3$-$C_{12}$-cycloalkyl-$C_1$-$C_8$-alkyl may be unsubstituted or substituted by halogen, hydroxy or $C_1$-$C_4$-alkoxy;

wherein 'heterocyclyl' is selected from pyrrolidinyl, tetrahydrofuranyl, tetrahydrothiophenyl, tetrahydropyranyl, piperidinyl, tetrahydrothiopyranyl, morpholinyl, dioxanyl or dihydropyranyl, each of which is unsubstituted or substituted by 1-3 substituents selected from oxo, $C_1$-$C_8$-alkyl or $C_1$-$C_8$-alkyl-carbonyl; wherein 'heterocyclyl' can be attached at a heteroatom or a carbon atom and where the N and/or S heteroatoms can also optionally be oxidized to various oxidation states, wherein 'heteroaryl' is selected from imidazolyl, pyrazolyl, thiazolyl, oxazolyl, 1,2,5-oxadiazolyl, 1,3,4-oxadiazolyl, pyridyl, pyrimidinyl, pyrazinyl, pyrazolo[1, 5-a]pyrimidine or imidazo[2,1-b]thiazole, each of which is unsubstituted or substituted by 1-3 substituents selected from $C_1$-$C_8$-alkyl, hydroxyl or amino; wherein 'heteroaryl' can be attached at a heteroatom or a carbon atom and where the N and/or S heteroatoms can also optionally be oxidized to various oxidation states.

In another embodiment, the invention provides a compound of the formulae (I), (I'), (Ia), (Ia'), (Ib), (Ib') (Ic), (Ic'), (Id), (Id'), (Ie), (Ie'), (If), (If'), (Ig), (Ig'), (Ih), (Ih'), (Ii), (Ii'), (Ij) or (Ij') and/or a pharmaceutically acceptable salt and/or a solvate thereof, wherein $R^6$ is selected from halogen, $C_1$-$C_4$-alkoxy, $C_1$-$C_4$-alkyl-sulfonyl or halo-$C_1$-$C_4$-alkoxy.

In another embodiment, the invention provides a compound of the formulae (I), (I'), (Ia), (Ia'), (Ib), (Ib') (Ic), (Ic'), (Id), (Id'), (Ie), (Ie'), (If), (If'), (Ig), (Ig'), (Ih), (Ih'), (Ii), (Ii'), (Ij) or (Ij') and/or a pharmaceutically acceptable salt and/or a solvate thereof, wherein $R^7$ is selected from hydrogen, halogen, cyano, $C_1$-$C_4$-alkyl, halo-$C_1$-$C_4$-alkyl or $C_1$-$C_4$-alkoxy.

In another embodiment, the invention provides a compound of the formulae (I), (I'), (Ia), (Ia'), (Ib), (Ib') (Ic), (Ic'), (Id), (Id'), (Ie), (Ie'), (If), (If'), (Ig), (Ig'), (Ih), (Ih'), (Ii), (Ii'), (Ij) or (Ij') and/or a pharmaceutically acceptable salt and/or a solvate thereof, wherein $R^4$ is selected from $C_1$-$C_8$-alkyl, hydroxy-$C_1$-$C_8$-alkyl, $C_1$-$C_8$-alkoxy-$C_1$-$C_8$-alkyl, cyano-$C_1$-$C_8$-alkyl, N,N-di-$C_1$-$C_4$-alkyl-amino-$C_1$-$C_8$-alkyl, $C_1$-$C_4$-alkyl-sulfonyl-$C_1$-$C_8$-alkyl, phenyl, heterocyclyl, heterocyclyl-$C_1$-$C_8$-alkyl, $C_3$-$C_{12}$-cycloalkyl, heteroaryl, heteroaryl-$C_1$-$C_8$-alkyl, $C_1$-$C_8$-alkoxy, wherein $C_1$-$C_8$-alkyl in N—$C_1$-$C_8$-alkyl-amino and in N,N-di-$C_1$-$C_8$-alkyl-amino may be unsubstituted or substituted by halogen, hydroxy or $C_1$-$C_4$-alkoxy,
  wherein $C_3$-$C_{12}$-cycloalkyl in $C_3$-$C_{12}$-cycloalkyl and in $C_3$-$C_{12}$-cycloalkyl-$C_1$-$C_8$-alkyl may be unsubstituted or substituted by halogen, hydroxy or $C_1$-$C_4$-alkoxy;
  wherein 'heterocyclyl' is a 3 to 7 membered saturated or partially unsaturated monocyclic ring system containing 1 to 3 heteroatoms selected from N, O or S, which is unsubstituted or substituted by 1-5 substituents selected from oxo, halogen, $C_1$-$C_8$-alkyl, halo-$C_1$-$C_8$-alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, halo-$C_1$-$C_8$-alkyl-carbonyl, hydroxy-$C_1$-$C_8$-alkyl-carbonyl or $C_1$-$C_8$-alkoxy-$C_1$-$C_8$-alkyl-carbonyl; wherein 'heterocyclyl' can be attached at a heteroatom or a carbon atom and where the N and/or S heteroatoms can also optionally be oxidized to various oxidation states,
  wherein 'heteroaryl' is a 3 to 7 membered fully unsaturated monocyclic ring system containing 1 to 3 heteroatoms selected from N, O or S, or pyrazolo[1,5-a]pyrimidine or imidazo[2,1-b]thiazole, each of which is unsubstituted or substituted by 1-5 substituents selected from halogen, $C_1$-$C_8$-alkyl, halo-$C_1$-$C_8$-alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, halo-$C_1$-$C_8$-alkyl-carbonyl, hydroxy-$C_1$-$C_8$-alkyl-carbonyl or $C_1$-$C_8$-alkoxy-$C_1$-$C_8$-alkyl-carbonyl; wherein 'heteroaryl' can be attached at a heteroatom or a carbon atom and where the N and/or S heteroatoms can also optionally be oxidized to various oxidation states;
and $R^6$ is selected from halogen, $C_1$-$C_4$-alkoxy, $C_1$-$C_4$-alkyl-sulfonyl or halo-$C_1$-$C_4$-alkoxy.

In another embodiment, the invention provides a compound of the formulae (I), (I'), (Ia), (Ia'), (Ib), (Ib') (Ic), (Ic'), (Id), (Id'), (Ie), (Ie'), (If), (If'), (Ig), (Ig'), (Ih), (Ih'), (Ii), (Ii'), (Ij) or (Ij') and/or a pharmaceutically acceptable salt and/or a solvate thereof, wherein $R^4$ is selected from $C_1$-$C_8$-alkyl, hydroxy-$C_1$-$C_8$-alkyl, $C_1$-$C_8$-alkoxy-$C_1$-$C_8$-alkyl, cyano-$C_1$-$C_8$-alkyl, N,N-di-$C_1$-$C_4$-alkyl-amino-$C_1$-$C_8$-alkyl, $C_1$-$C_4$-alkyl-sulfonyl-$C_1$-$C_8$-alkyl, phenyl, heterocyclyl, heterocyclyl-$C_1$-$C_8$-alkyl, $C_3$-$C_{12}$-cycloalkyl, heteroaryl, heteroaryl-$C_1$-$C_8$-alkyl, $C_1$-$C_8$-alkoxy, wherein $C_1$-$C_8$-alkyl in N—$C_1$-$C_8$-alkyl-amino and in N,N-di-$C_1$-$C_8$-alkyl-amino may be unsubstituted or substituted by halogen, hydroxy or $C_1$-$C_4$-alkoxy,
  wherein $C_3$-$C_{12}$-cycloalkyl in $C_3$-$C_{12}$-cycloalkyl and in $C_3$-$C_{12}$-cycloalkyl-$C_1$-$C_8$-alkyl may be unsubstituted or substituted by halogen, hydroxy or $C_1$-$C_4$-alkoxy;
  wherein 'heterocyclyl' is a 3 to 7 membered saturated or partially unsaturated monocyclic ring system containing 1 to 3 heteroatoms selected from N, O or S, which is unsubstituted or substituted by 1-5 substituents selected from oxo, halogen, $C_1$-$C_8$-alkyl, halo-$C_1$-$C_8$- alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, hydroxy-$C_1$-$C_8$-alkyl-carbonyl, halo-$C_1$-$C_8$-alkyl-carbonyl, hydroxy-$C_1$-$C_8$-alkyl-carbonyl or $C_1$-$C_8$-alkoxy-$C_1$-$C_8$-alkyl-carbonyl; wherein 'heterocyclyl' can be attached at a heteroatom or a carbon atom and where the N and/or S heteroatoms can also optionally be oxidized to various oxidation states, wherein 'heteroaryl' is a 3 to 7 membered fully unsaturated monocyclic ring system containing 1 to 3 heteroatoms selected from N, O or S, or pyrazolo[1,5-a]pyrimidine or imidazo[2,1-b]thiazole, each of which is unsubstituted or substituted by 1-5 substituents selected from halogen, $C_1$-$C_8$-alkyl, halo-$C_1$-$C_8$-alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, halo-$C_1$-$C_8$-alkyl-carbonyl, hydroxy-$C_1$-$C_8$-alkyl-carbonyl or $C_1$-$C_8$-alkoxy-$C_1$-$C_8$-alkyl-carbonyl; wherein 'heteroaryl' can be attached at a heteroatom or a carbon atom and where the N and/or S heteroatoms can also optionally be oxidized to various oxidation states;

$R^6$ is selected from halogen, $C_1$-$C_4$-alkoxy, $C_1$-$C_4$-alkylsulfonyl or halo-$C_1$-$C_4$-alkoxy and $R^7$ is selected from hydrogen, halogen, cyano, $C_1$-$C_4$-alkyl, halo-$C_1$-$C_4$-alkyl or $C_1$-$C_4$-alkoxy.

In another embodiment individual compounds according to the invention are those listed in the Examples section below.

As used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$, $^{31}P$, $^{32}P$, $^{35}S$, $^{36}Cl$, $^{125}I$ respectively. The invention includes various isotopically labeled compounds as defined herein, for example those into which radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, DMSO-d6.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by PI3K or (ii) associated with PI3K activity, or (iii) characterized by activity (normal or abnormal) of PI3K or (2) reduce or inhibit the activity of PI3K or (3) reduce or inhibit the expression of PI3K. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of PI3K; or at least partially reducing or inhibiting the expression of PI3K. The meaning of the term "a therapeutically effective amount" as illustrated in the above embodiment for PI3K also applies by the same means to any other relevant proteins/peptides/enzymes.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

Typically, the compounds of formula (I) can be prepared according to the methods provided infra.

Scheme A

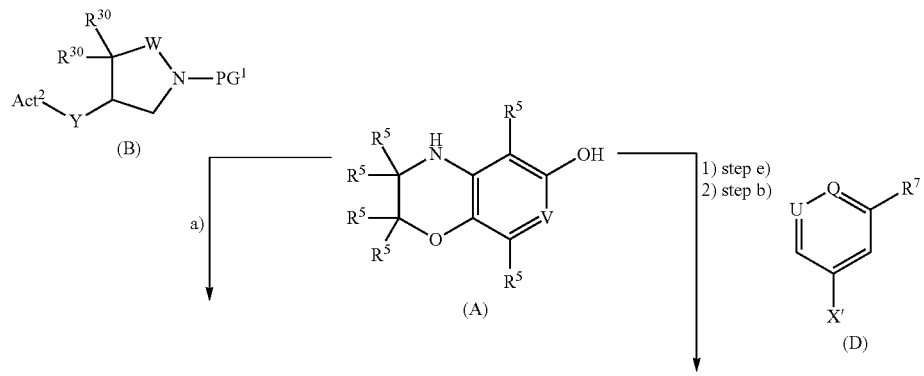

-continued

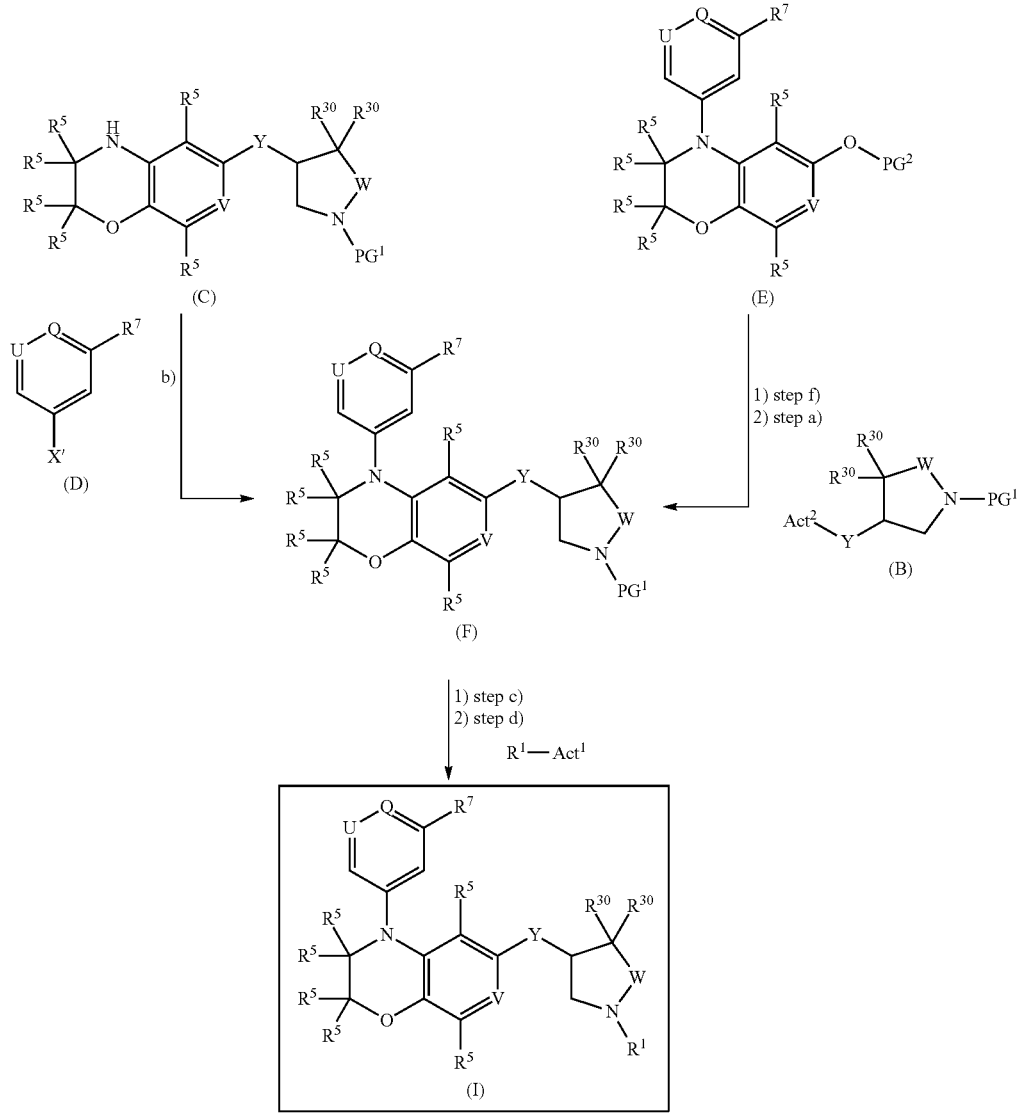

In one embodiment, the invention relates to a process for manufacturing a compound of formula (I) (Method A) comprising steps a, b, c, d.

The compound of formula (I) is obtained via the step c of deprotecting $PG^1$ from the compound of formula (F), wherein $PG^1$ represents a suitable protecting group, such as a Boc group, and the other substituents are as defined above,

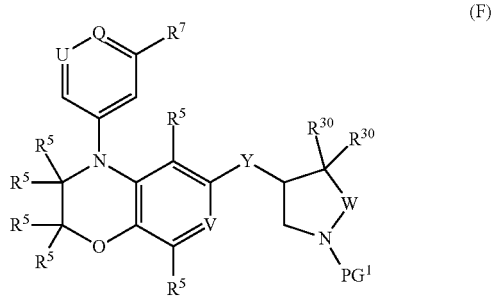

(F)

followed by coupling reaction step d with $R^1$-$Act^1$, step c1: Where $R^1$ is —C(O)—$R^4$, or —S(O)$_2$—$R^4$, wherein $R^4$ is defined above, and $Act^1$ represents an activating group or a hydroxy group: The coupling reaction is an amide, urea, carbamic ester or sulfonamid formation. There are many known ways of preparing amides, urea carbamic esters or sulfonamids. The coupling reaction step can be carried out with $Act^1$ representing an activating group, preferably in a one step procedure or with $Act^1$ representing a hydroxy group either involving a one or two step procedure. For examples of amide bond formations, see Mantalbetti, C. A. G. N and Falque, V., Amide bond formation and peptide coupling, Tetrahedron, 2005, 61(46), pp 10827-10852 and references cited therein. For examples of urea synthesis, see Sartori, G.; Maggi, R. Acyclic and cyclic ureas, Science of Synthesis (2005), 18, 665-758; Gallou, Isabelle. Unsymmetrical ureas Synthetic methodologies and application in drug design, Organic Preparations and Procedures International (2007), 39(4), 355-383. For examples of carbamate synthesis see Adams, Philip; Baron, Frank A. Esters of carbamic acid, Chemical Reviews (1965), 65(5), 567-602. The examples provided herein are thus not intended to be exhaustive, but merely illustrative;

step c2: Where $R^1$ is selected from phenyl, pyridyl, pyrimidinyl, pyrazinyl, pyridazinyl, 1,2,3-triazinyl, 1,2,4-triazinyl or 1,3,5-triazinyl and $Act^1$ represents halogen, particularly iodo or bromo: The coupling reaction is carried out in the presence of an amine base such as N,N-diisopropylethylamine. The reaction is carried out in the presence of an organic solvent or without a solvent under microwave heating. Alternatively, the reaction is carried out under customary Buchwald-Hartwig conditions such as the conditions described above. The reaction is preferably carried out under an inert gas such as nitrogen or argon.

The compound of formula (F) is obtained via the step b of coupling the compound of formula (C), wherein $PG^1$ represents a suitable protecting group, such as a Boc, and the other substituents are as defined above,

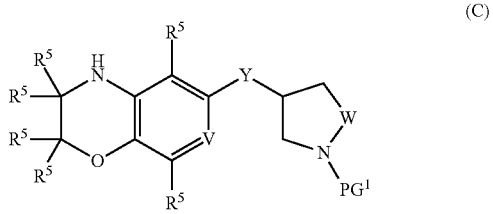

(C)

with a compound of formula (D), wherein X' represents halogen, such as iodo or bromo and the other substituents are as defined above,

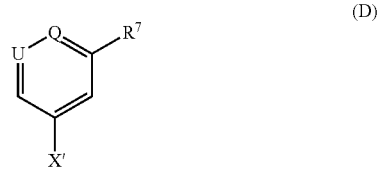

(D)

under customary Buchwald-Hartwig conditions using a suitable Pd catalyst/ligand combination such as $Pd_2(dba)_3$/2-(dicyclohexylphosphino)biphenyl or $Pd_2(dba)_3$/2-dicyclohexylphosphino-2',4',6'-triisopropyl-biphenyl, $Pd_2(dba)_3$/X-Phos, $Pd_2(dba)_3$/(rac)-BINAP, $Pd(OAc)_2$/(rac)-BINAP or bis(tri-t-butylphosphine)palladium and a suitable base, such as NaOtBu, $Cs_2CO_3$ or $K_3PO_4$ and organic solvent such as toluene, dioxane or THF. The reaction is stirred at a temperature of approximately 60-140° C., for example at 100° C. to 110° C. and is optionally performed in a microwave reactor. The reaction is preferably carried out under an inert gas such as nitrogen or argon.

The compound of formula (C) is obtained via the step a of coupling the compound of formula (A), wherein the substituents are as defined above with a compound of formula (B), wherein $PG^1$ represents a suitable protecting group, such as a Boc group and $Act^2$ is an activating group or H, and the other substituents are as defined above,

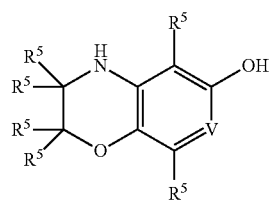

(A)

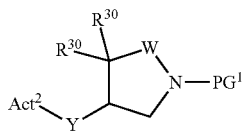

(B)

step a1: Where Y is O and $Act^2$ represents an activating group such as a mesylate: The reaction takes place in the presence of a suitable base such as sodium hydroxide (NaH), $K_2CO_3$ or potassium t-butoxide (tBuOK) in a suitable polar organic solvent such as DMF, THF, 2-methyltetrahydrofuran or Dioxane at a suitable temperature such as rt—100° C.

step a2: Where Y is O and $Act^2$ represents H: The reaction takes place using customary Mitsunobu conditions, for example using $Ph_3P$ and DEAD in organic solvent such as THF under inert gas conditions at elevated temperature such as 70° C.

step a3: Where Y is NH and $Act^2$ represents H: A base promoted phosphonium coupling reaction is employed, whereby a compound of the formula (A) in a suitable solvent such as acetonitrile is reacted with a phosphonium salt such as benzotriazol-1-yloxytris(dimethylamino)phosphonium hexafluorophosphate (BOP) in the presence of a base such as 1,8-diaza-7-bicyclo[5.4.0]undecene (DBU) followed by addition of a compound of the formula (B). The reaction mixture is stirred at a temperature of 20° C. to 100° C.

In another embodiment, the invention relates to a process for manufacturing a compound of formula (I) (Method A-a) comprising steps a and b as defined above for Method A, using a compound of formula (B) wherein $PG^1$ represents $R^1$.

In another embodiment, the invention relates to a process for manufacturing a compound of formula (I) (Method B) comprising steps e, b, f, a, c and d.

The compound of formula (I) is obtained via the steps c and d as described above for Method A from the compound of formula (F).

The compound of formula (F) is obtained via the step f of deprotecting $PG^2$ from the compound of formula (E), wherein $PG^2$ is a suitable protecting group, such as a silyl protecting group, and the other substituents are as defined above

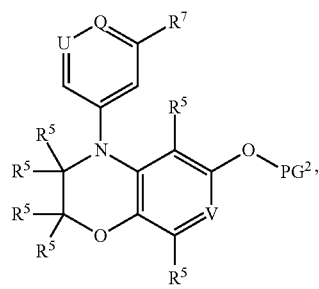

(E)

followed by coupling reaction step a, as described above for Method A, with the compound of formula (B).

The compound of formula (E) is obtained via the step e of protecting the compound of formula (A) with a suitable protecting group $PG^2$, followed by from the compound of formula (E), wherein $PG^2$ is a suitable protecting group, such as a silyl protecting group, followed by coupling reaction step b, as described above for Method A with the compound of formula (D).

In another embodiment, the invention relates to a process for manufacturing a compound of formula (I) (Method B-a) comprising steps e, b and f as defined above for Method B, using a compound of formula (B) wherein PG$^1$ represents R$^1$.

In another embodiment, the invention relates to a process for manufacturing a compound of formula (I) (Method C) using a compound of formula (A'), wherein X" represents halogen and the other substituents are as defined above

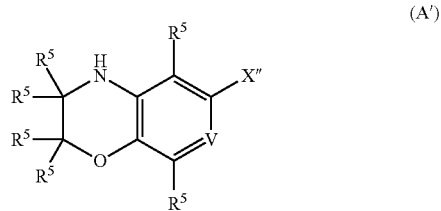

(A')

comprising steps b, c and d as defined above for Method B, using a compound of formula (B) and a modified step a4:

step a4: Where Y is NH and Act$^2$ is H: The reaction takes place in the presence of a suitable base such as for example potassium carbonate or a suitable amine base such as triethylamine or N,N-diisopropylethylamine at elevated temperature such as 100° C. to 140° C. Alternatively, the reaction is carried out under customary Buchwald-Hartwig conditions such as the conditions described above. The reaction is preferably carried out under an inert gas such as nitrogen or argon.

In another embodiment, the invention relates to a process for manufacturing a compound of formula (I) (Method C-a) comprising steps b, a4, c and d as defined above for Method B$^1$, using a compound of formula (B) wherein PG$^1$ represents R$^1$.

The term "activating group" as used herein relates to a group that can activate a carboxylic acid, carbonic acid or carbamic acid derivative, for coupling with an amine moiety to form an amide, urea or carbamic ester moiety, respectively (Act$^1$) or to a group that can activate a hydroxy group for coupling with another hydroxy moiety to form an ether (Act$^2$).

Groups that can activate a carboxylic acid, carbonic acid or carbamic acid derivative, for coupling with an amine moiety to form an amide, urea or carbamic ester moiety are chlorides, or groups resulting from the reaction of the acid derivative with an activating agent. Suitable activating agents are known to the skilled person, examples of such activating reagents are carbodiimide derivatives, pentafluorophenyl ester derivatives, triazole derivatives, imidazole derivatives.

Groups that can activate a hydroxy group for coupling with another hydroxy moiety to form an ether are groups are known to the skilled person, examples of such activating groups are mesylates and tosylates.

The term "protecting group" as used herein relates to a group that protects a functional group which is present in the starting materials and is not intended to take part in the reaction. In additional process steps, carried out as desired, functional groups of the starting compounds which should not take part in the reaction may be present in unprotected form or may be protected for example by one or more protecting groups. The protecting groups are then wholly or partly removed according to one of the known methods. Protecting groups, and the manner in which they are introduced and removed are described, for example, in "Protective Groups in Organic Chemistry", Plenum Press, London, New York 1973, and in "Methoden der organischen Chemie", Houben-Weyl, 4th edition, Vol. 15/1, Georg-Thieme-Verlag, Stuttgart 1974 and in Theodora W. Greene, "Protective Groups in Organic Synthesis", John Wiley & Sons, New York 1981. A characteristic of protecting groups is that they can be removed readily, i.e. without the occurrence of undesired secondary reactions, for example by solvolysis, reduction, photolysis or alternatively under physiological conditions.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Compounds of the invention and intermediates can also be converted into each other according to methods generally known to those skilled in the art.

Intermediates and final products can be worked up and/or purified according to standard methods, e.g. using chromatographic methods, distribution methods, (re-) crystallization, and the like.

The following applies in general to all processes mentioned herein before and hereinafter.

All the above-mentioned process steps can be carried out under reaction conditions that are known to those skilled in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about –100° C. to about 190° C., including, for example, from approximately –80° C. to approximately 150° C., for example at from –80 to –60° C., at room temperature, at from –20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described herein above.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

In another aspect, the present invention provides a pharmaceutical composition comprising a compound of the present invention, or a pharmaceutically acceptable salt thereof, and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compounds of formula I in free form or in salt form, exhibit valuable pharmacological properties, e.g. PI3K modulating properties, e.g. as indicated in in vitro and in vivo tests as provided in the next sections, and are therefore indicated for therapy or for use as research chemicals, e.g. as tool compounds.

Compounds of the invention may be useful in the treatment of conditions, diseases or disorders including disease or infection associated immunopathology in which one or more of the functions of B cells such as antibody production, antigen presentation, cytokine production or lymphoid organogenesis are abnormal or are undesirable including rheumatoid arthritis, pemphigus vulgaris and related diseases, idiopathic thrombocytopenia purpura, systemic lupus erythematosus, multiple sclerosis, myasthenia gravis, Sjögren's syndrome, autoimmune hemolytic anemia, ANCA-associated vasculitides, cryoglobulinemia, thrombotic thrombocytopenic purpura, chronic autoimmune urticaria, allergy (atopic dermatitis, contact dermatitis, allergic rhinitis), goodpasture's syndrome, AMR (antibody-mediated transplant rejection), B cell-mediated hyperacute, acute and chronic transplant rejection and cancers of haematopoietic origin including but not limited to multiple myeloma; acute myelogenous leukemia; chronic myelogenous leukemia; lymphocytic leukemia; myeloid leukemia; non-Hodgkin lymphoma; lymphomas; polycythemia vera; essential thrombocythemia; myelofibrosis with myeloid metaplasia; and Walden stroem disease.

The invention includes methods of treating conditions, diseases or disorders in which one or more of the functions of neutrophils, such as superoxide release, stimulated exocytosis, or chemoatractic migration are abnormal or are undesirable including rheumatoid arthritis, sepsis, pulmonary or respiratory disorders such as asthma, inflammatory dermatoses such as psoriasis, as well as in disease or infection associated immunopathology and others.

The invention includes methods of treating conditions, diseases or disorders in which one or more of the functions of basophil and mast cells such as chemoatractic migration or allergen-IgE-mediated degranulation are abnormal or are undesirable including allergic diseases (atopic dermatitis, contact dermatitis, allergic rhinitis) as well as other disorders such as COPD, asthma or emphysema.

The invention includes methods of treating conditions, diseases or disorders in which one or more of the functions of T cells such as cytokine production or cell-mediated cytotoxicity abnormal or are undesirable including rheumatoid arthritis, multiple sclerosis, acute or chronic rejection of cell tissue or organ grafts or cancers of haematopoietic origin as well as in disease or infection associated immunopathology.

Further, the invention includes methods of treating neurodegenerative diseases, cardiovascular diseases and platelet aggregation.

Further, the invention includes methods of treating skin diseases such as porphyria cutanea tarda, polymorphous light eruption, dermatomyositis, solar urticaria, oral lichen planus, panniculitis, scleroderma, urticarial vasculitis.

Further, the invention includes methods of treating chronic inflammatory diseases such as sarcoidosis, granuloma annulare.

In other embodiments, the condition or disorder (e.g. PI3K-mediated) is selected from the group consisting of: polycythemia vera, essential thrombocythemia, myelofibrosis with myeloid metaplasia, asthma, COPD, ARDS, Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma, eosinophil-related disorders affecting the airways occasioned by drug-reaction, psoriasis, contact dermatitis, atopic dermatitis, alopecia areata, erythema multiforme, dermatitis herpetiformis, scleroderma, vitiligo, hypersensitivity angiitis, urticaria, bullous pemphigoid, lupus erythematosus, pemphigus, epidermolysis bullosa acquisita, autoimmune haematogical disorders (e.g. haemolytic anaemia, aplastic anaemia, pure red cell anaemia and idiopathic thrombocytopenia), systemic lupus erythematosus, polychondritis, scleroderma, Wegener granulomatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), interstitial lung fibrosis, psoriatic arthritis, glomerulonephritis, cardiovascular diseases, atherosclerosis, hypertension, deep venous thrombosis, stroke, myocardial infarction, unstable angina, thromboembolism, pulmonary embolism, thrombolytic diseases, acute arterial ischemia, peripheral thrombotic occlusions, and coronary artery disease, reperfusion injuries, retinopathy, such as diabetic retinopathy or hyperbaric oxygen-induced retinopathy, and conditions characterized by elevated intraocular pressure or secretion of ocular aqueous humor, such as glaucoma.

In another embodiment, the compounds of the present invention are useful in the treatment, prevention, or amelioration of autoimmune disease and of inflammatory conditions, in particular inflammatory conditions with an aetiology including an autoimmune component such as arthritis (for example rheumatoid arthritis, arthritis chronica progrediente and arthritis deformans) and rheumatic diseases, including inflammatory conditions and rheumatic diseases involving bone loss, inflammatory pain, spondyloarhropathies including ankolsing spondylitis, Reiter syndrome, reactive arthritis, psoriatic arthritis, and enterophathics arthritis, hypersensitivity (including both airways hypersensitivity and dermal hypersensitivity) and allergies. Specific auto-immune diseases for which antibodies of the invention may be employed include autoimmune haematological disorders (including e.g. hemolytic anaemia, aplastic anaemia, pure red cell anaemia and idiopa-thic thrombocytopenia), acquired hemophilia A, cold agglutinin disease, cryoglobulinemia, thrombotic thrombocytopenic purpura, Sjögren's syndrome, systemic lupus erythematosus, inflammatory muscle disorders, polychondritis, sclerodoma, anti-neutrophil cytoplasmic antibody-associated vasculitis, IgM mediated neuropathy, opsoclonus myoclonus syndrome, Wegener granulomatosis, dermatomyositis, chronic active hepatitis, myasthenia gravis, psoriasis, Steven-Johnson syndrome, pemphigus vulgaris, pemphigus foliacius, idio-pathic sprue, autoimmune inflammatory bowel disease (including e.g. ulcerative colitis, Crohn's disease and Irritable Bowel Syndrome), endocrine ophthalmopathy, Graves' disease, sarcoidosis, multiple sclerosis, neuromyelitis optica, primary biliary cirrhosis, juvenile diabetes (diabetes mellitus type I), uveitis (anterior, intermediate and posterior as well as panuveitis), keratoconjunctivitis sicca and vernal keratoconjunctivitis, interstitial lung fibrosis, psoriatic arthritis and glomerulonephritis (with and without nephrotic syndrome, e.g. including idiopathic nephro-tic syndrome or minimal change nephropathy), tumors, inflammatory disease of skin and cornea, myositis, loosening of bone implants, metabolic disorders, such as atherosclerosis, diabetes, and dislipidemia.

In another embodiment, the compounds of the present invention are useful in the treatment of conditions or disorders selected from the group consisting of, primary cutaneous B-cell lymphoma, immunobullous disease, pemphigus vulgaris, pemphigus foliaceus, endemic form of Brazilian pemphigus (Fogo selvagem), paraneoplastic pemphigus, bullous pemphigoid, mucous membrane pemphigoid, epidermolysis bullosa acquisita, chronic graft versus host disease, dermatomyositis, systemic lupus erythematosus, vasculitis, small vessel vasculitis, hypocomplementemic urticarial vasculitis, antineutrophil cytoplasmic antibody-vasculitis, cryoglobulinemia, Schnitzler syndrome, Waldenstrom's macroglobulinemia, angioedema, vitiligo, systemic lupus erythematosus, idiopathic thrombocytopenic purpura, multiple sclerosis, cold agglutinin disease, autoimmune hemolytic anemia, antineutrophil cytoplasmic antibody-associated vasculitis, graft versus host disease, cryoglobulinemia and thrombotic thrombocytopenic.

Thus, as a further embodiment, the present invention provides the use of a compound of formulae (I), (I'), (Ia), (Ia'), (Ib), (Ib') (Ic), (Ic'), (Id), (Id'), (Ie), (Ie'), (If), (If'), (Ig), (Ig'), (Ih), (Ih'), (Ii), (Ii'), (Ij) or (Ij') in therapy. In a further embodiment, the therapy is selected from a disease which may be treated by inhibition of PI3K. In another embodiment, the disease is selected from the afore-mentioned list, suitably from autoimmune disorders, inflammatory diseases, allergic diseases, airway diseases, such as asthma and COPD, transplant rejection; antibody production, antigen presentation, cytokine production or lymphoid organogenesis are abnormal or are undesirable including rheumatoid arthritis, pemphigus vulgaris, idiopathic thrombocytopenia purpura, systemic lupus erythematosus, multiple sclerosis, myasthenia gravis, Sjögren's syndrome, autoimmune hemolytic anemia, ANCA-associated vasculitides, cryoglobulinemia, thrombotic thrombocytopenic purpura, chronic autoimmune urticaria, allergy (atopic dermatitis, contact dermatitis, allergic rhinitis), goodpasture's syndrome, AMR (antibody-mediated transplant rejection), B cell-mediated hyperacute, acute and chronic transplant rejection and cancers of haematopoietic origin including but not limited to multiple myeloma; a leukaemia; acute myelogenous leukemia; chronic myelogenous leukemia; lymphocytic leukemia; myeloid leukemia; non-Hodgkin lymphoma; lymphomas; polycythemia vera; essential thrombocythemia; myelofibrosis with myeloid metaplasia; and Walden stroem disease; more suitably from rheumatoid arthritis (RA), pemphigus vulgaris (PV), idiopathic thrombocytopenia purpura (ITP), thrombotic thrombocytopenic purpura (TTP), autoimmune hemolytic anemia (AIHA), acquired hemophilia type A (AHA), systemic lupus erythematosus (SLE), multiple sclerosis (MS), myasthenia gravis (MG), Sjögren's syndrome (SS), ANCA-associated vasculitides, cryoglobulinemia, chronic autoimmune urticaria (CAU), allergy (atopic dermatitis, contact dermatitis, allergic rhinitis), goodpasture's syndrome, transplant rejection and cancers of haematopoietic origin as well as in disease or infection associated immunopathology, for example in severe and cerebral malaria, trypanosomiasis, leishmaniasis, toxoplasmosis and neurocysticercosis.

In another embodiment, the invention provides a method of treating a disease which is treated by inhibition of PI3K comprising administration of a therapeutically acceptable amount of a compound of formulae (I), (I'), (Ia), (Ia'), (Ib), (Ib') (Ic), (Ic'), (Id), (Id'), (Ie), (Ie'), (If), (If'), (Ig), (Ig'), (Ih), (Ih'), (Ii), (Ii'), (Ij) or (Ij'). In a further embodiment, the disease is selected from the afore-mentioned list, suitably from autoimmune disorders, inflammatory diseases, allergic diseases, airway diseases, such as asthma and COPD, transplant rejection; antibody production, antigen presentation, cytokine production or lymphoid organogenesis are abnormal or are undesirable including rheumatoid arthritis, pemphigus vulgaris, idiopathic thrombocytopenia purpura, systemic lupus erythematosus, multiple sclerosis, myasthenia gravis, Sjögren's syndrome, autoimmune hemolytic anemia, ANCA-associated vasculitides, cryoglobulinemia, thrombotic thrombocytopenic purpura, chronic autoimmune urticaria, allergy (atopic dermatitis, contact dermatitis, allergic rhinitis), goodpasture's syndrome, AMR (antibody-mediated transplant rejection), B cell-mediated hyperacute, acute and chronic transplant rejection and cancers of haematopoietic origin including but not limited to multiple myeloma; a leukaemia; acute myelogenous leukemia; chronic myelogenous leukemia; lymphocytic leukemia; myeloid leukemia; non-Hodgkin lymphoma; lymphomas; polycythemia vera; essential thrombocythemia; myelofibrosis with myeloid metaplasia; and Walden stroem disease; more suitably from rheumatoid arthritis (RA), pemphigus vulgaris (PV), idiopathic thrombocytopenia purpura (ITP), thrombotic thrombocytopenic purpura (TTP), autoimmune hemolytic anemia (AIHA), acquired hemophilia type A (AHA), systemic lupus erythematosus (SLE), multiple sclerosis (MS), myasthenia gravis (MG), Sjögren's syndrome (SS), ANCA-associated vasculitides, cryoglobulinemia, chronic autoimmune urticaria (CAU), allergy (atopic dermatitis, contact dermatitis, allergic rhinitis), goodpasture's syndrome, transplant rejection and cancers of haematopoietic origin as well as in disease or infection associated immunopathology, for example in severe and cerebral malaria, trypanosomiasis, leishmaniasis, toxoplasmosis and neurocysticercosis.

Thus, as a further embodiment, the present invention provides the use of a compound of formulae (I), (I'), (Ia), (Ia'), (Ib), (Ib') (Ic), (Ic'), (Id), (Id'), (Ie), (Ie'), (If), (If'), (Ig), (Ig'), (Ih), (Ih'), (Ii), (Ii'), (Ij) or (Ij') for the manufacture of a medicament. In a further embodiment, the medicament is for treatment of a disease which may be treated inhibition of PI3K. In another embodiment, the disease is selected from the afore-mentioned list, suitably from autoimmune disorders, inflammatory diseases, allergic diseases, airway diseases, such as asthma and COPD, transplant rejection; antibody production, antigen presentation, cytokine production or lymphoid organogenesis are abnormal or are undesirable including rheumatoid arthritis, pemphigus vulgaris, idiopathic thrombocytopenia purpura, systemic lupus erythematosus, multiple sclerosis, myasthenia gravis, Sjögren's syndrome, autoimmune hemolytic anemia, ANCA-associated vasculitides, cryoglobulinemia, thrombotic thrombocytopenic purpura, chronic autoimmune urticaria, allergy (atopic dermatitis, contact dermatitis, allergic rhinitis), goodpasture's syndrome, AMR (antibody-mediated transplant rejection), B cell-mediated hyperacute, acute and chronic transplant rejection and cancers of haematopoietic origin including but not limited to multiple myeloma; a leukaemia; acute myelogenous leukemia; chronic myelogenous leukemia; lymphocytic leukemia; myeloid leukemia; non-Hodgkin lymphoma; lymphomas; polycythemia vera; essential thrombocythemia; myelofibrosis with myeloid metaplasia; and Walden stroem disease; more suitably from rheumatoid arthritis (RA), pemphigus vulgaris (PV), idiopathic thrombocytopenia purpura (ITP), thrombotic thrombocytopenic purpura (TTP), autoimmune hemolytic anemia (AIHA), acquired hemophilia type A (AHA), systemic lupus erythematosus (SLE), multiple sclerosis (MS), myasthenia gravis (MG), Sjögren's syndrome (SS), ANCA-associated vasculitides, cryoglobulinemia, chronic autoimmune urticaria (CAU), allergy (atopic dermatitis, contact dermatitis, allergic rhinitis), goodpasture's syndrome, transplant rejection and cancers of haematopoietic origin as well as in disease or infection associated immunopathology, for example in severe and cerebral malaria, trypanosomiasis, leishmaniasis, toxoplasmosis and neurocysticercosis.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by the activity of the PI3K enzymes. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable carrier, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition mediated by the activity of the PI3K enzymes, wherein the medicament is prepared for administration with another therapeutic agent. The invention also provides the use of another therapeutic agent for treating a disease or condition mediated by the activity of the PI3K enzymes, wherein the medicament is administered with a compound of formula (I).

The invention also provides a compound of formula (I) for use in a method of treating a disease or condition mediated by the activity of the PI3K enzymes, wherein the compound of formula (I) is prepared for administration with another therapeutic agent. The invention also provides another therapeutic agent for use in a method of treating a disease or condition mediated by the activity of the PI3K enzymes, wherein the other therapeutic agent is prepared for administration with a compound of formula (I). The invention also provides a compound of formula (I) for use in a method of treating a disease or condition mediated by the activity of the PI3K enzymes wherein the compound of formula (I) is administered with another therapeutic agent. The invention also provides another therapeutic agent for use in a method of treating a disease or condition mediated by the activity of the PI3K enzymes wherein the other therapeutic agent is administered with a compound of formula (I).

The invention also provides the use of a compound of formula (I) for treating a disease or condition mediated by the activity of the PI3K enzymes, wherein the patient has previously (e.g. within 24 hours) been treated with another therapeutic agent. The invention also provides the use of another therapeutic agent for treating a disease or condition mediated by the activity of the PI3K enzymes, wherein the patient has previously (e.g. within 24 hours) been treated with a compound of formula (I).

The compounds of formula I may be administered as the sole active ingredient or in conjunction with, e.g. as an adjuvant to, other drugs e.g. immunosuppressive or immunomodulating agents or other anti-inflammatory agents, e.g. for the treatment or prevention of allo- or xenograft acute or chronic rejection or inflammatory or autoimmune disorders, or a chemotherapeutic agent, e.g. a malignant cell antiproliferative agent. For example, the compounds of formula I may be used in combination with a calcineurin inhibitor, e.g. cyclosporin A or FK 506; a mTOR inhibitor, e.g. rapamycin, 40-O-(2-hydroxyethyl)-rapamycin, CCI1779, ABT578, AP23573, TAFA-93, biolimus-7 or biolimus-9; an ascomycin having immuno-suppressive properties, e.g. ABT-281, ASM981, etc.; corticosteroids; cyclophosphamide; azathioprene; methotrexate; leflunomide; mizoribine; mycophenolic acid or salt; mycophenolate mofetil; 15-deoxyspergualine or an immunosuppressive homologue, analogue or derivative thereof; a PKC inhibitor, e.g. as disclosed in WO 02/38561 or WO 03/82859, e.g. the compound of Example 56 or 70; a JAK3 kinase inhibitor, e.g. N-benzyl-3,4-dihydroxy-benzylidene-cyanoacetamide α-cyano-(3,4-dihydroxy)-]N-benzylcinnamamide (Tyrphostin AG 490), prodigiosin 25-C (PNU156804), [4-(4'-hydroxyphenyl)-amino-6,7-dimethoxyquinazoline] (WHI-P131), [4-(3'-bromo-4'-hydroxylphenyl)-amino-6,7-dimethoxyquinazoline] (WHI-P154), [4-(3',5'-dibromo-4'-hydroxylphenyl)-amino-6,7-dimethoxyquinazoline] WHI-P97, KRX-211, 3-{(3R,4R)-4-methyl-3-[methyl-(7H-pyrrolo[2,3-d]pyrimidin-4-yl)-amino]-piperidin-1-yl}-3-oxo-propionitrile, in free form or in a pharmaceutically acceptable salt form, e.g. mono-citrate (also called CP-690, 550), or a compound as disclosed in WO 04/052359 or WO 05/066156; immunosuppressive monoclonal antibodies, e.g., monoclonal antibodies to leukocyte receptors, e.g., MHC, CD2, CD3, CD4, CD7, CD8, CD25, CD28, CD40, CD45, CD52, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists; or antihistamines; or antitussives, or a bronchodilatory agent; or an angiotensin receptor blockers; or an anti-infectious agent.

Where the compounds of formula I are administered in conjunction with other immunosuppressive/immunomodulatory, anti-inflammatory, chemotherapeutic or anti-infectious therapy, dosages of the co-administered immunosuppressant, immunomodulatory, anti-inflammatory, chemotherapeutic or anti-infectious compound will of course vary depending on the type of co-drug employed, e.g. whether it is a steroid or a calcineurin inhibitor, on the specific drug employed, on the condition being treated and so forth.

A compound of the formula (I) may also be used to advantage in combination with each other or in combination with other therapeutic agents, especially other antiproliferative agents. Such antiproliferative agents include, but are not limited to, aromatase inhibitors; antiestrogens; topoisomerase I inhibitors; topoisomerase II inhibitors; microtubule active agents; alkylating agents; histone deacetylase inhibitors; compounds, which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; agents used in the treatment of hematologic malignancies; compounds which target, decrease or inhibit the activity of Flt-3; Hsp90 inhibitors; temozolomide (TEMODAL®); and leucovorin.

The term "aromatase inhibitor", as used herein, relates to a compound which inhibits the estrogen production, i.e., the conversion of the substrates androstenedione and testosterone to estrone and estradiol, respectively. The term includes, but is not limited to, steroids, especially atamestane, exemestane and formestane; and, in particular, non-steroids, especially aminoglutethimide, roglethimide, pyridoglutethimide, trilostane, testolactone, ketoconazole, vorozole, fadrozole, anastrozole and letrozole. Exemestane can be administered, e.g., in the form as it is marketed, e.g., under the trademark AROMASIN. Formestane can be administered, e.g., in the form as it is marketed, e.g., under the trademark LENTARON. Fadrozole can be administered, e.g., in the form as it is marketed, e.g., under the trademark AFEMA. Anastrozole can be administered, e.g., in the form as it is marketed, e.g., under the trademark ARIMIDEX. Letrozole can be administered, e.g., in the form as it is marketed, e.g., under the trademark FEMARA or FEMAR. Aminoglutethimide can be administered, e.g., in the form as it is marketed, e.g., under the trademark ORIMETEN. A combination of the invention comprising a chemotherapeutic agent which is an aromatase inhibitor is particularly useful for the treatment of hormone receptor positive tumors, e.g., breast tumors.

The term "anti-estrogen", as used herein, relates to a compound which antagonizes the effect of estrogens at the estrogen receptor level. The term includes, but is not limited to, tamoxifen, fulvestrant, raloxifene and raloxifene hydrochloride. Tamoxifen can be administered, e.g., in the form as it is marketed, e.g., under the trademark NOLVADEX. Raloxifene hydrochloride can be administered, e.g., in the form as it is marketed, e.g., under the trademark EVISTA. Fulvestrant can be formulated as disclosed in U.S. Pat. No. 4,659,516 or it can be administered, e.g., in the form as it is marketed, e.g., under the trademark FASLODEX. A combination of the invention comprising a chemotherapeutic agent which is an antiestrogen is particularly useful for the treatment of estrogen receptor positive tumors, e.g., breast tumors.

The term "anti-androgen", as used herein, relates to any substance which is capable of inhibiting the biological effects of androgenic hormones and includes, but is not limited to, bicalutamide (CASODEX), which can be formulated, e.g., as disclosed in U.S. Pat. No. 4,636,505.

The term "gonadorelin agonist", as used herein, includes, but is not limited to, abarelix, goserelin and goserelin acetate. Goserelin is disclosed in U.S. Pat. No. 4,100,274 and can be administered, e.g., in the form as it is marketed, e.g., under the trademark ZOLADEX. Abarelix can be formulated, e.g., as disclosed in U.S. Pat. No. 5,843,901.

The term "topoisomerase I inhibitor", as used herein, includes, but is not limited to, topotecan, gimatecan, irinotecan, camptothecian and its analogues, 9-nitrocamptothecin and the macromolecular camptothecin conjugate PNU-166148 (compound A1 in WO 99/17804). Irinotecan can be administered, e.g., in the form as it is marketed, e.g., under the trademark CAMPTOSAR. Topotecan can be administered, e.g., in the form as it is marketed, e.g., under the trademark HYCAMTIN.

The term "topoisomerase II inhibitor", as used herein, includes, but is not limited to, the anthracyclines, such as doxorubicin, including liposomal formulation, e.g., CAELYX; daunorubicin; epirubicin; idarubicin; nemorubicin; the anthraquinones mitoxantrone and losoxantrone; and the podophillotoxines etoposide and teniposide. Etoposide can be administered, e.g., in the form as it is marketed, e.g., under the trademark ETOPOPHOS. Teniposide can be administered, e.g., in the form as it is marketed, e.g., under the trademark VM 26-BRISTOL. Doxorubicin can be administered, e.g., in the form as it is marketed, e.g., under the trademark ADRIBLASTIN or ADRIAMYCIN. Epirubicin can be administered, e.g., in the form as it is marketed, e.g., under the trademark FARMORUBICIN. Idarubicin can be administered, e.g., in the form as it is marketed, e.g., under the trademark ZAVEDOS. Mitoxantrone can be administered, e.g., in the form as it is marketed, e.g., under the trademark NOVANTRON.

The term "microtubule active agent" relates to microtubule stabilizing, microtubule destabilizing agents and microtublin polymerization inhibitors including, but not limited to, taxanes, e.g., paclitaxel and docetaxel; vinca alkaloids, e.g., vinblastine, especially vinblastine sulfate; vincristine, especially vincristine sulfate and vinorelbine; discodermolides; cochicine; and epothilones and derivatives thereof, e.g., epothilone B or D or derivatives thereof. Paclitaxel may be administered, e.g., in the form as it is marketed, e.g., TAXOL. Docetaxel can be administered, e.g., in the form as it is marketed, e.g., under the trademark TAXOTERE. Vinblastine sulfate can be administered, e.g., in the form as it is marketed, e.g., under the trademark VINBLASTIN R.P. Vincristine sulfate can be administered, e.g., in the form as it is marketed, e.g., under the trademark FARMISTIN. Discodermolide can be obtained, e.g., as disclosed in U.S. Pat. No. 5,010,099. Also included are epothilone derivatives which are disclosed in WO 98/10121, U.S. Pat. No. 6,194,181, WO 98/25929, WO 98/08849, WO 99/43653, WO 98/22461 and WO 00/31247. Especially preferred are epothilone A and/or B.

The term "alkylating agent", as used herein, includes, but is not limited to, cyclophosphamide, ifosfamide, melphalan or nitrosourea (BCNU or Gliadel). Cyclophosphamide can be administered, e.g., in the form as it is marketed, e.g., under the trademark CYCLOSTIN. Ifosfamide can be administered, e.g., in the form as it is marketed, e.g., under the trademark HOLOXAN.

The term "histone deacetylase inhibitors" or "HDAC inhibitors" relates to compounds which inhibit the histone deacetylase and which possess antiproliferative activity. This includes compounds disclosed in WO 02/22577, especially N-hydroxy-3-[4-[[(2-hydroxyethyl)[2-(1H-indol-3-yl)ethyl]-amino]methyl]phenyl]-2E-2-propenamide, N-hydroxy-3-[4-[[[2-(2-methyl-1H-indol-3-yl)-ethyl]-amino] methyl]phenyl]-2E-2-propenamide and pharmaceutically acceptable salts thereof. It further especially includes suberoylanilide hydroxamic acid (SAHA).

The term "antineoplastic antimetabolite" includes, but is not limited to, 5-fluorouracil or 5-FU; capecitabine; gemcitabine; DNA demethylating agents, such as 5-azacytidine and decitabine; methotrexate and edatrexate; and folic acid antagonists, such as pemetrexed. Capecitabine can be administered, e.g., in the form as it is marketed, e.g., under the trademark XELODA. Gemcitabine can be administered, e.g., in the form as it is marketed, e.g., under the trademark GEMZAR. Also included is the monoclonal antibody trastuzumab which can be administered, e.g., in the form as it is marketed, e.g., under the trademark HERCEPTIN.

The term "platin compound", as used herein, includes, but is not limited to, carboplatin, cis-platin, cisplatinum and oxaliplatin. Carboplatin can be administered, e.g., in the form as it is marketed, e.g., under the trademark CARBOPLAT. Oxaliplatin can be administered, e.g., in the form as it is marketed, e.g., under the trademark ELOXATIN.

The term "compounds targeting/decreasing a protein or lipid kinase activity; or a protein or lipid phosphatase activity; or further anti-angiogenic compounds", as used herein, includes, but is not limited to, protein tyrosine kinase and/or serine and/or threonine kinase inhibitors or lipid kinase inhibitors, e.g., a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g., a N-phenyl-2-pyrimidine-amine derivative, e.g., imatinib, SU101, SU6668 and GFB-111;

b) compounds targeting, decreasing or inhibiting the activity of the fibroblast growth factor-receptors (FGFR);

c) compounds targeting, decreasing or inhibiting the activity of the insulin-like growth factor receptor I (IGF-IR), such as compounds which target, decrease or inhibit the activity of IGF-IR, especially compounds which inhibit the IGF-IR receptor, such as those compounds disclosed in WO 02/092599;

d) compounds targeting, decreasing or inhibiting the activity of the Trk receptor tyrosine kinase family;

e) compounds targeting, decreasing or inhibiting the activity of the Axl receptor tyrosine kinase family;

f) compounds targeting, decreasing or inhibiting the activity of the c-Met receptor;

g) compounds targeting, decreasing or inhibiting the activity of the Kit/SCFR receptor tyrosine kinase;

h) compounds targeting, decreasing or inhibiting the activity of the C-kit receptor tyrosine kinases—(part of the PDGFR family), such as compounds which target, decrease or inhibit the activity of the c-Kit receptor tyrosine kinase family, especially compounds which inhibit the c-Kit receptor, e.g., imatinib;

i) compounds targeting, decreasing or inhibiting the activity of members of the c-Abl family and their gene-fusion products, e.g., BCR-Abl kinase, such as compounds which target decrease or inhibit the activity of c-Abl family members and their gene fusion products, e.g., a N-phenyl-2-pyrimidine-amine derivative, e.g., imatinib, PD180970, AG957, NSC 680410 or PD173955 from ParkeDavis;

j) compounds targeting, decreasing or inhibiting the activity of members of the protein kinase C (PKC) and Raf family of serine/threonine kinases, members of the MEK, SRC, JAK, FAK, PDK and Ras/MAPK family members, or PI(3) kinase family, or of the PI(3)-kinase-related kinase family, and/or members of the cyclin-dependent kinase family (CDK) and are especially those staurosporine derivatives disclosed in U.S. Pat. No. 5,093,330, e.g., midostaurin; examples of further compounds include, e.g., UCN-01; safingol; BAY 43-9006; Bryostatin 1; Perifosine; Ilmofosine; RO 318220 and RO 320432; GO 6976; Isis 3521; LY333531/LY379196; isochinoline compounds, such as those disclosed in WO 00/09495; FTIs; PD184352; or QAN697 (a PI3K inhibitor);

k) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC) or tyrphostin. A tyrphostin is preferably a low molecular weight (Mr<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810, AG 99, Tyrphostin AG 213, Tyrphostin AG 1748, Tyrphostin AG 490, Tyrphostin B44, Tyrphostin B44 (+) enantiomer, Tyrphostin AG 555, AG 494, Tyrphostin AG 556, AG957 and adaphostin (4-{[(2,5-dihydroxyphenyl)methyl]amino}-benzoic acid adamantyl ester, NSC 680410, adaphostin; and l) compounds targeting, decreasing or inhibiting the activity of the epidermal growth factor family of receptor tyrosine kinases (EGFR, ErbB2, ErbB3, ErbB4 as homo- or hetero-dimers), such as compounds which target, decrease or inhibit the activity of the epidermal growth factor receptor family are especially compounds, proteins or antibodies which inhibit members of the EGF receptor tyrosine kinase family, e.g., EGF receptor, ErbB2, ErbB3 and ErbB4 or bind to EGF or EGF related ligands, and are in particular those compounds, proteins or monoclonal antibodies generically and specifically disclosed in WO 97/02266, e.g., the compound of Example 39, or in EP 0 564 409; WO 99/03854; EP 0520722; EP 0 566 226; EP 0 787 722; EP 0 837 063; U.S. Pat. No. 5,747,498; WO 98/10767; WO 97/30034; WO 97/49688; WO 97/38983 and, especially, WO 96/30347, e.g., compound known as CP 358774; WO 96/33980, e.g., compound ZD 1839; and WO 95/03283, e.g., compound ZM105180, e.g., trastuzumab (HERCEPTIN), cetuximab, Iressa, Tarceva, OSI-774, CI-1033, EKB-569, GW-2016, E1.1, E2.4, E2.5, E6.2, E6.4, E2.11, E6.3 or E7.6.3; and 7H-pyrrolo-[2,3-d]pyrimidine derivatives which are disclosed in WO 03/013541.

Further anti-angiogenic compounds include compounds having another mechanism for their activity, e.g., unrelated to protein or lipid kinase inhibition, e.g., thalidomide (THALOMID) and TNP-470.

Compounds which target, decrease or inhibit the activity of a protein or lipid phosphatase are, e.g., inhibitors of phosphatase 1, phosphatase 2A, PTEN or CDC25, e.g., okadaic acid or a derivative thereof.

Compounds which induce cell differentiation processes are e.g. retinoic acid, α- γ- or δ-tocopherol or α- γ- or δ-tocotrienol.

The term cyclooxygenase inhibitor, as used herein, includes, but is not limited to, e.g., Cox-2 inhibitors, 5-alkyl substituted 2-arylaminophenylacetic acid and derivatives, such as celecoxib (CELEBREX), rofecoxib (VIOXX), etoricoxib, valdecoxib or a 5-alkyl-2-arylaminophenylacetic acid, e.g., 5-methyl-2-(2'-chloro-6'-fluoroanilino)phenyl acetic acid or lumiracoxib.

The term "bisphosphonates", as used herein, includes, but is not limited to, etridonic, clodronic, tiludronic, pamidronic, alendronic, ibandronic, risedronic and zoledronic acid. "Etridonic acid" can be administered, e.g., in the form as it is marketed, e.g., under the trademark DIDRONEL. "Clodronic acid" can be administered, e.g., in the form as it is marketed, e.g., under the trademark BONEFOS. "Tiludronic acid" can be administered, e.g., in the form as it is marketed, e.g., under the trademark SKELID. "Pamidronic acid" can be administered, e.g., in the form as it is marketed, e.g., under the trademark AREDIA™. "Alendronic acid" can be administered, e.g., in the form as it is marketed, e.g., under the trademark FOSAMAX. "IIbandronic acid" can be administered, e.g., in the form as it is marketed, e.g., under the trademark BONDRANAT. "Risedronic acid" can be administered, e.g., in the form as it is marketed, e.g., under the trademark ACTONEL. "Zoledronic acid" can be administered, e.g., in the form as it is marketed, e.g., under the trademark ZOMETA.

The term "mTOR inhibitors" relates to compounds which inhibit the mammalian target of rapamycin (mTOR) and which possess antiproliferative activity, such as sirolimus (Rapamune®), everolimus (Certican™), CCI-779 and ABT578.

The term "heparanase inhibitor", as used herein, refers to compounds which target, decrease or inhibit heparin sulphate degradation. The term includes, but is not limited to, PI-88.

The term "biological response modifier", as used herein, refers to a lymphokine or interferons, e.g., interferon γ.

The term "inhibitor of Ras oncogenic isoforms", e.g., H-Ras, K-Ras or N-Ras, as used herein, refers to compounds which target, decrease or inhibit the oncogenic activity of Ras, e.g., a "farnesyl transferase inhibitor", e.g., L-744832, DK8G557 or R115777 (Zarnestra).

The term "telomerase inhibitor", as used herein, refers to compounds which target, decrease or inhibit the activity of telomerase. Compounds which target, decrease or inhibit the activity of telomerase are especially compounds which inhibit the telomerase receptor, e.g., telomestatin.

The term "methionine aminopeptidase inhibitor", as used herein, refers to compounds which target, decrease or inhibit the activity of methionine aminopeptidase. Compounds which target, decrease or inhibit the activity of methionine aminopeptidase are, e.g., bengamide or a derivative thereof.

The term "proteasome inhibitor", as used herein, refers to compounds which target, decrease or inhibit the activity of the proteasome. Compounds which target, decrease or inhibit the activity of the proteasome include, e.g., PS-341 and MLN 341.

The term "matrix metalloproteinase inhibitor" or "MMP inhibitor", as used herein, includes, but is not limited to, collagen peptidomimetic and nonpeptidomimetic inhibitors, tetracycline derivatives, e.g., hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "agents used in the treatment of hematologic malignancies", as used herein, includes, but is not limited to, FMS-like tyrosine kinase inhibitors, e.g., compounds targeting, decreasing or inhibiting the activity of FMS-like tyrosine kinase receptors (Flt-3R); interferon, 1-b-D-arabinofuransylcytosine (ara-c) and bisulfan; and ALK inhibitors, e.g., compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, e.g., PKC412, midostaurin, a staurosporine derivative, SU11248 and MLN518.

The term "HSP90 inhibitors", as used herein, includes, but is not limited to, compounds targeting, decreasing or inhibiting the intrinsic ATPase activity of HSP90; degrading, targeting, decreasing or inhibiting the HSP90 client proteins via the ubiquitin proteasome pathway. Compounds targeting, decreasing or inhibiting the intrinsic ATPase activity of HSP90 are especially compounds, proteins or antibodies which inhibit the ATPase activity of HSP90, e.g., 17-allylamino, 17-demethoxygeldanamycin (17AAG), a geldanamycin derivative, other geldanamycin related compounds, radicicol and HDAC inhibitors.

The term "antiproliferative antibodies", as used herein, includes, but is not limited to, trastuzumab (Herceptin™), Trastuzumab-DM1, erlotinib (Tarceva™), bevacizumab (Avastin™), rituximab (Rituxan), PRO64553 (anti-CD40) and 2C4 antibody. By antibodies is meant, e.g., intact monoclonal antibodies, polyclonal antibodies, multispecific antibodies formed from at least two intact antibodies, and antibodies fragments so long as they exhibit the desired biological activity.

For the treatment of acute myeloid leukemia (AML), compounds of formula (I) can be used in combination with standard leukemia therapies, especially in combination with therapies used for the treatment of AML. In particular, compounds of formula (I) can be administered in combination with, e.g., farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

A compound of the formula (I) may also be used to advantage in combination with each other or in combination with other therapeutic agents, especially other anti-malarial agents. Such anti-malarial agents include, but are not limited to proguanil, chlorproguanil, trimethoprim, chloroquine, mefloquine, lumefantrine, atovaquone, pyrimethamine-sulfadoxine, pyrimethamine-dapsone, halofantrine, quinine, quinidine, amodiaquine, amopyroquine, sulphonamides, artemisinin, arteflene, artemether, artesunate, primaquine, inhaled NO, L-arginine, Dipropylenetri-amine NONOate (NO donor), Rosiglitzone (PPARγ agonist), activated charcoal, Erythropoietin, Levamisole, and pyronaridine.

A compound of the formula (I) may also be used to advantage in combination with each other or in combination with other therapeutic agents, such as used for the treatment of Leishmaniosis, Trypanosomiasis, Toxoplasmosis and Neurocysticercosis. Such agents include, but are not limited to chloroquine sulfate, atovaquone-proguanil, artemether-lumefantrine, quinine-sulfate, artesunate, quinine, doxycycline, clindamycin, meglumine antimoniate, sodium stibogluconate, miltefosine, ketoconazole, pentamidine, amphotericin B (AmB), liposomal-AmB, paromomycine, eflornithine, nifurtimox, suramin, melarsoprol, prednisolone, benznidazole, sulfadiazine, pyrimethamine, clindamycin, trimetropim, sulfamethoxazole, azitromycin, atovaquone, dexamethasone, praziquantel, albendazole, beta-lactams, fluoroquinolones, macrolides, aminoglycosides, sulfadiazine and pyrimethamine.

The structure of the active agents identified by code nos., generic or trade names may be taken from the actual edition of the standard compendium "The Merck Index" or from databases, e.g., Patents International, e.g., IMS World Publications.

The above-mentioned compounds, which can be used in combination with a compound of the formula (I), can be prepared and administered as described in the art, such as in the documents cited above.

A compound of the formula (I) may also be used to advantage in combination with known therapeutic processes, e.g., the administration of hormones or especially radiation.

A compound of formula (I) may in particular be used as a radiosensitizer, especially for the treatment of tumors which exhibit poor sensitivity to radiotherapy.

By "combination", there is meant either a fixed combination in one dosage unit form, or a kit of parts for the combined administration where a compound of the formula (I) and a combination partner may be administered independently at the same time or separately within time intervals that especially allow that the combination partners show a cooperative, e.g., synergistic, effect or any combination thereof. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g. a compound of formula I and a combination partner, are both administered to a patient simultaneously in the form of a single entity or dosage. The term "non-fixed combination" means that the active ingredients, e.g. a compound of formula (I) and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

EXAMPLES

Experimental Details

The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

ABBREVIATIONS

ACN acetonitrile
AcOH acetic acid aq. aqueous
Boc tert-butoxycarbonyl
Boc₂O di-tert-butyl dicarbonate
tBu tert-butyl
tBuOH tert-butanol
BrettPhos 2-(Dicyclohexylphosphino)-3,6-dimethoxy-2'-4'-6'-triisopropyl-1,1'-biphenyl
br s broad singlet
COMU (1-cyano-2-ethoxy-2-oxoethylidenaminooxy)dimethylamino-morpholino-carbenium hexafluorophosphate
conc. concentrated
d day(s)
d doublet
dd doublet of doublets
dba dibenzylideneacetone
DCM dichloromethane
DEA diethylamine
DEAD diethyl azodicarboxylate
DEAP diethylaminopyridine
DIPEA diisopropylethylamine
DMF dimethylformamide
DMME dimethoxymethane
DMSO dimethylsulfoxide
DPPA diphenylphosphoryl azide
DPPF 1,1'-bis(diphenylphosphino)ferrocene
EDC 1-(3-dimethylaminopropyl)-3-ethylcarbodiimide hydrochloride
eq. equivalent(s)
ESI electrospray ionisation
Et₃N triethylamine
Et₂O diethylether
EtOAc ethyl acetate
EtOH ethanol
h hour(s)
HATU O-(7-azabenzotriazol-1-yl)-N,N,NN',N'-tetramethyl-uronium hexafluorophosphate
HBTU O-(1H-benzotriazol-1-yl)-N,N,N',N'-tetramethyluronium hexafluorophosphate
HMDS hexamethyldisilazane
HOBT 1-hydroxy-benztriazole
HPLC high performance liquid chromatography
IPA isopropanol
LCMS liquid chromatography with mass spectrometry
mCPBA meta-chloroperoxybenzoic acid
MeOH methanol
m multiplet
min minute(s)
MS mass spectrometry
mw microwave
NMR nuclear magnetic resonance spectrometry
NaOtBu sodium tert-butoxide
NP normal phase
OBD optimum bed density
Pd₂(dba)₃ tris(dibenzylideneacetone)dipalladium
PL-HCO₃ MP SPE Polymer-supported bicarbonate cartridge for acid removal
prep. preparative
PPh₃ triphenylphosphine
q quartet
Rac-BINAP racemic 2,2'-bis(di-p-tolylphosphino)-1,1'-binaphthyl
RP reversed phase
Rt retention time
rt room temperature
RuPhos 2-dicyclohexylphosphino-2',6'-di-isopropoxy-1,1'-biphenyl
sat. saturated
SCX-2 polymer supported sulfonic acid macroporous polystyrene
soln. solution
t triplet
TBME tert-butyl methyl ether
TBAF tetrabutylammonium fluoride
TBDMSCl tert-butyldimethylsilylchloride
Tetramethyl-t-butyl
XPhos 2-di-t-butylphosphino-3,4,5,6-tetramethyl-2',4',6'-triisopropylbiphenyl
TFA trifluoroacetic acid
THF tetrahydrofuran
TLC thin layer chromatography
UPLC ultra performance liquid chromatography
XPhos 2-dicyclohexylphosphino-2',4',6'-triisopropylbiphenyl
Pd[RuPhos] (2-dicyclohexylphosphino-2'6'-diisopropyl-1 1'-biphenyl)(2-(2-aminoethyl)phenyl)palladium(II)
Microwave equipment used is a Biotage Initiator®
All compounds are named using AutoNom.

Preparation of Examples

General Procedures

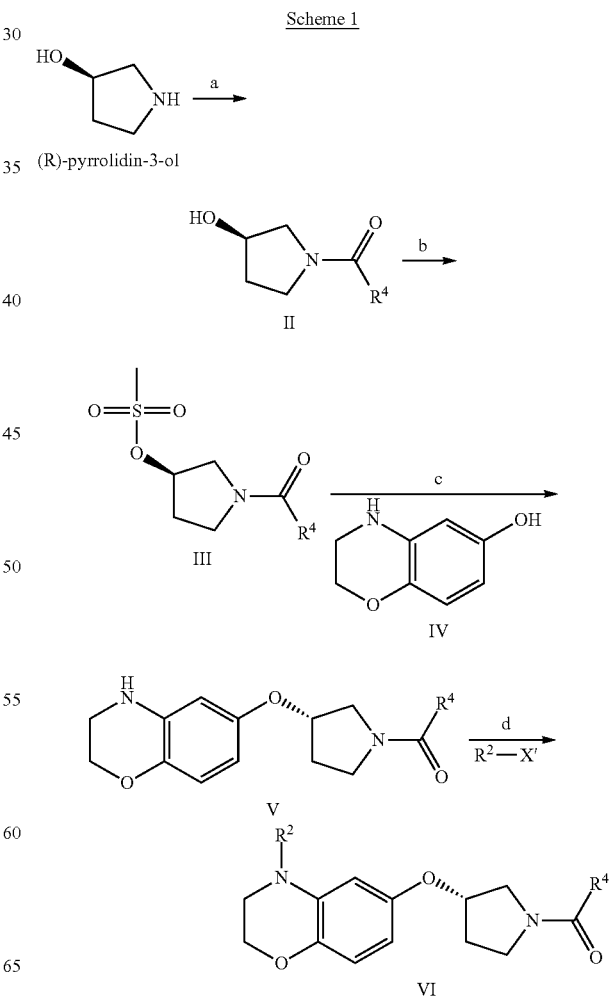

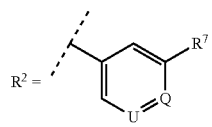

a) (R)-pyrrolidin-3-ol and an acid chloride of formula R⁴C(O)Cl or carboxylic acid of formula R⁴C(O)OH were reacted to prepare an amide of general formula II. Those skilled in the art will appreciate that there are many known ways of preparing amides. For example, see Mantalbetti, C. A. G. N and Falque, V., Amide bond formation and peptide coupling, Tetrahedron, 2005, 61(46), pp 10827-10852 and references cited therein. The following general methods i-ii have been used.

i. A soln. of the carboxylic acid and DMF (1 eq.) in DCM was treated with oxalyl chloride (1.5 eq.) for 1 h at 3° C. The reaction mixture was concentrated under reduced pressure, dissolved in DCM and added to a soln. of (R)-pyrrolidin-3-ol hydrochloride (1.0 eq.) and Et₃N (2.5 eq.) in DCM at 3° C. The resulting mixture was stirred vigorously at 3° C. for 1 h, then concentrated under reduced pressure. The residue was treated with EtOAc and filtered. The residue was washed with EtOAc, and the combined filtrates were concentrated under reduced pressure and purified by flash chromatography.

ii. A soln. of a commercial acid chloride (1.0 eq.) in DCM was added to a soln. of (R)-pyrrolidin-3-ol hydrochloride (1.0 eq.) and Et₃N (2.5 eq.) in DCM at 3° C. The resulting mixture was stirred vigorously at 3° C. for 1 h, then concentrated under reduced pressure. The residue was treated with EtOAc and filtered. The residue was washed with EtOAc, and the combined filtrates were concentrated under reduced pressure and purified by flash chromatography. Typical conditions for amid bond formation reactions are exemplified in the section B) Amide bond formation conditions below.

b) The mesylates of compounds of general formula II were prepared by customary conditions, preferably by reaction of II with methane sulfonyl chloride (2 eq.) and Et₃N (2 eq.) in DCM at 0° C.

c) Compounds of general formula V were prepared by reacting 3,4-dihydro-2H-benzo[1,4]oxazin-6-ol IV with compounds of general formula III in the presence of a suitable base such as sodium hydride (NaH) and polar organic solvent such as DMF under inert gas conditions at 50° C. Typical conditions for such reactions are exemplified in the section C) Side chain introduction conditions below.

d) Buchwald-Hartwig cross-coupling between V and an aryl halogenide of the general formula R²—X' where X'=bromo or iodo was performed under customary Buchwald-Hartwig conditions using a Pd catalyst/ligand combination such as preferably Pd₂(dba)₃/2-(dicyclohexylphosphino)biphenyl or Pd₂(dba)₃/2-dicyclohexylphosphino-2',4',6'-triisopropyl-biphenyl or bis(tri-t-butylphosphine) palladium and a base, such as preferably NaOtBu, and organic solvent such as preferably toluene. The reaction was preferably stirred at a temperature of approximately 80-120° C., preferably 110° C. and was preferably performed in a microwave reactor. The reaction was preferably carried out under an inert gas such as nitrogen or argon. The final compounds were purified by normal or reversed phase chromatography. Typical conditions for Buchwald-Hartwig cross-coupling reactions are exemplified in the section A) Buchwald aminations or hydroxylations below.

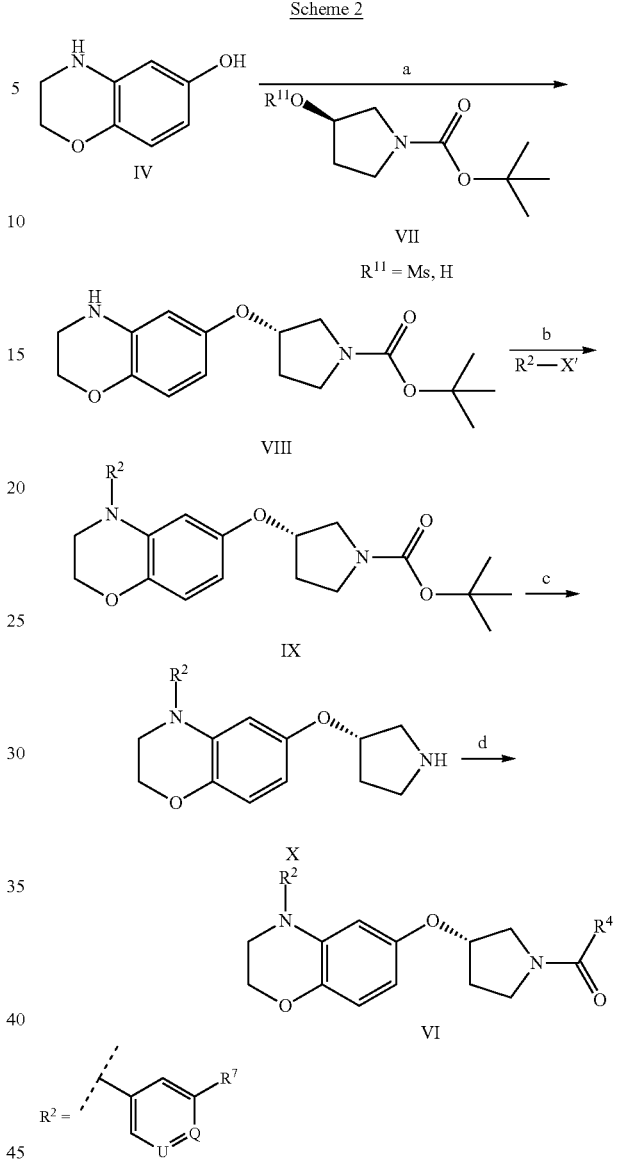

Scheme 2 a) (S)-tert-butyl 3-((3,4-dihydro-2H-benzo[b][1,4]oxazin-6-yl)oxy)pyrrolidine-1-carboxylate (compound VIII) was prepared by reacting 3,4-dihydro-2H-benzo[1,4]oxazin-6-ol IV with a compound of general formula VII by one of the following methods 1) for X=mesylate, compounds IV and VII were reacted in the presence of a suitable base such as sodium hydride (NaH) and a polar organic solvent DMF under inert gas conditions at room temperature ii) for X=H, compounds of general formula IV and VII were reacted using customary Mitsunobu conditions, preferably using Ph₃P (1.4 eq.) and DEAD (1.4 eq.) in organic solvent such as THF under inert gas conditions at a temperature of preferably 70° C. Typical conditions for such reactions are exemplified in the section C) Side chain introduction conditions below.

b) Buchwald-Hartwig cross-coupling between VIII and an aryl halogenide of the general formula R²—X' where X'=bromo or iodo was performed under customary Buchwald-Hartwig conditions using a Pd catalyst/ligand combination such as preferably Pd₂(dba)₃/X-Phos, Pd₂(dba)₃/

(rac)-BINAP, Pd(OAc)$_2$/(rac)-BINAP or bis(tri-t-butylphosphine)palladium and a base, such as preferably NaOtBu, Cs$_2$CO$_3$ or K$_3$PO$_4$ and an organic solvent such as preferably toluene, dioxane or THF. The reaction was preferably stirred at a temperature of approximately 60-120° C. and was preferably be performed in a microwave reactor. The reaction was preferably carried out under an inert gas such as nitrogen or argon. Typical conditions for Buchwald-Hartwig cross-coupling reactions are exemplified in the section A) Buchwald aminations or hydroxylations below.

c) N—BOC deprotection of compounds of general formula IX was performed under customary BOC deprotection conditions using among the possible acids preferably trifluoro-acetic acid and organic solvent, preferably DCM. The reaction was preferably performed at room temperature.

d) A compound of the general formula X and an acid chloride of formula R$^4$C(O)Cl or a carboxylic acid of formula R$^4$C(O)OH were are reacted to prepare an amide of general formula VI using customary amide coupling conditions: in addition to the methods described in Scheme 1, step a) preferred coupling reagents were HBTU, HOBt/EDC, COMU/DIPEA. The couplings were performed in an organic solvent such as preferably DMF or DCM and the final compounds were purified by normal or reversed phase chromatography. Typical conditions for amid bond formation reactions are exemplified in the section B) Amide bond formation conditions below.

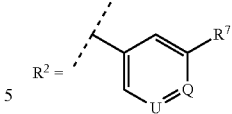

a) 3,4-Dihydro-2H-benzo[1,4]oxazin-6-ol IV was O-protected using standard silylation procedures, using a silylating reagent, preferably TBDMSCl and a base, preferably NaH, in an organic solvent, preferably THF at room temperature.

b) Buchwald-Hartwig cross-coupling between XI and an aryl halogenide of the general formula R$^2$—X' where X'=bromo or iodo was performed under customary Buchwald-Hartwig conditions using a Pd catalyst/ligand combination such as preferably Pd$_2$(dba)$_3$/X-Phos, Pd$_2$(dba)$_3$/dicyclohexylphosphino-2',4',6'-triisopropylbiphenyl or bis(tri-t-butylphosphine)-palladium and a base, such as preferably NaOtBu and an organic solvent such as preferably toluene. The reaction was preferably stirred at a temperature of approximately 110-140° C. and was preferably performed in a microwave reactor. The reaction was preferably carried out under an inert gas such as nitrogen or argon. Typical conditions for Buchwald-Hartwig cross-coupling reactions are exemplified in the section A) Buchwald aminations or hydroxylations below.

c) O-TBDMS deprotection of compounds of general formula XII was performed under customary deprotection conditions using preferably TBAF and an organic solvent, preferably THF. The reaction was preferably performed at room temperature d) Compounds of general formula XIII were coupled with mesylates of general formula III using a suitable base such as preferably sodium hydride (NaH) or K$_2$CO$_3$ and polar organic solvent such as DMF under inert gas conditions at room temperature or elevated temperatures up to 100° C. The final compounds were purified by normal or reversed phase chromatography. Typical conditions for such reactions are exemplified in the section C) Side chain introduction conditions below.

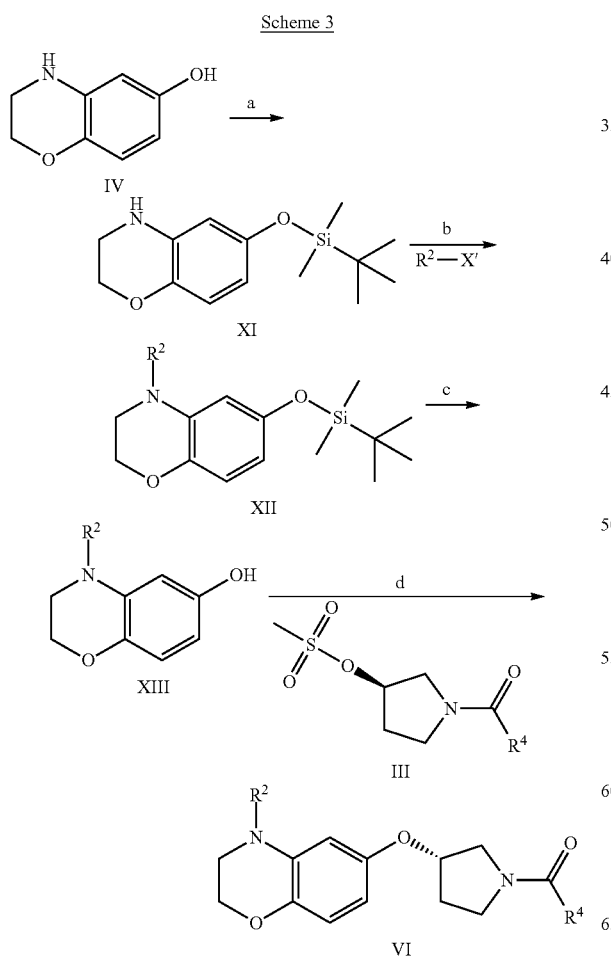

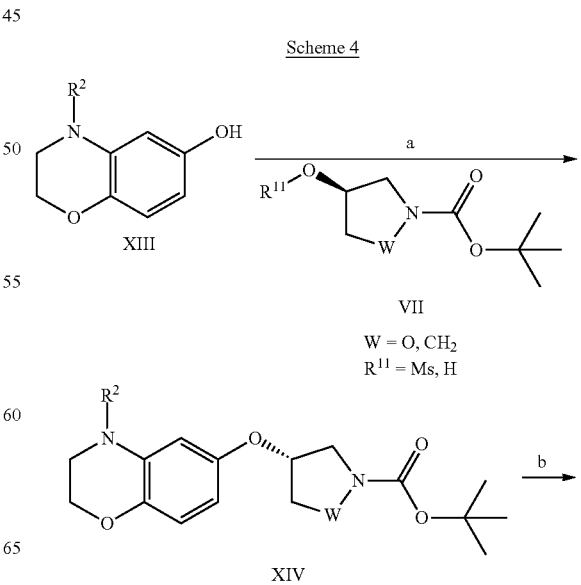

-continued

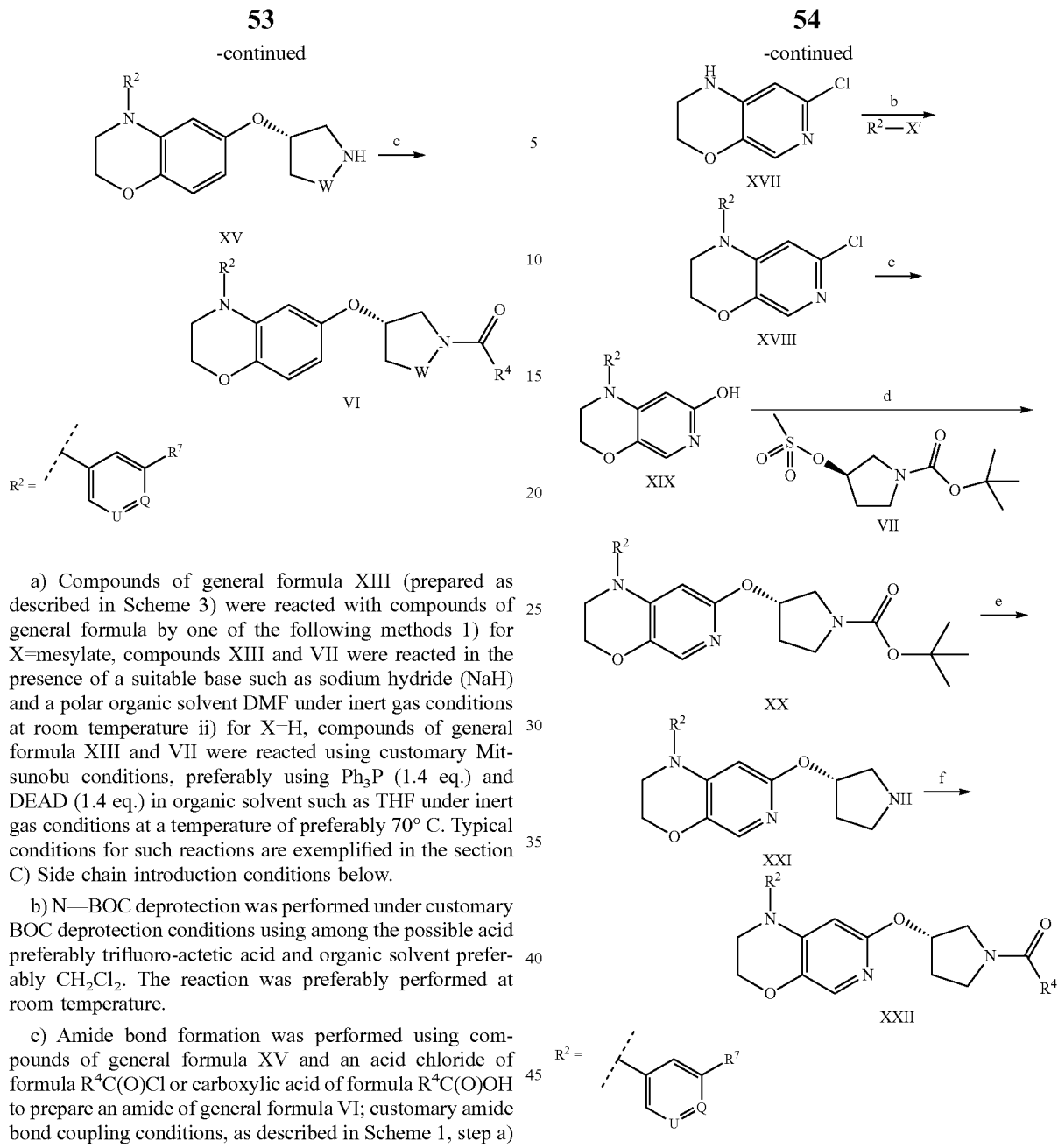

a) Compounds of general formula XIII (prepared as described in Scheme 3) were reacted with compounds of general formula by one of the following methods 1) for X=mesylate, compounds XIII and VII were reacted in the presence of a suitable base such as sodium hydride (NaH) and a polar organic solvent DMF under inert gas conditions at room temperature ii) for X=H, compounds of general formula XIII and VII were reacted using customary Mitsunobu conditions, preferably using Ph₃P (1.4 eq.) and DEAD (1.4 eq.) in organic solvent such as THF under inert gas conditions at a temperature of preferably 70° C. Typical conditions for such reactions are exemplified in the section C) Side chain introduction conditions below.

b) N—BOC deprotection was performed under customary BOC deprotection conditions using among the possible acid preferably trifluoro-actetic acid and organic solvent preferably CH₂Cl₂. The reaction was preferably performed at room temperature.

c) Amide bond formation was performed using compounds of general formula XV and an acid chloride of formula R⁴C(O)Cl or carboxylic acid of formula R⁴C(O)OH to prepare an amide of general formula VI; customary amide bond coupling conditions, as described in Scheme 1, step a) have been used. In addition to the methods described in Scheme 1, step a), coupling of carboxylic acids using HOBt/EDC or coupling using chloroformates or carbamic chlorides were used. The couplings were performed in an organic solvent such as preferably DMF or DCM and the final compounds were purified by normal or reversed phase chromatography. Typical conditions for amid bond formation reactions are exemplified in the section B) Amide bond formation conditions below.

Scheme 5

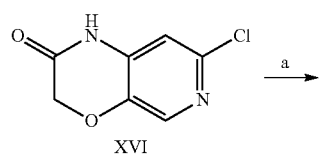

a) 7-Chloro-2,3-dihydro-1H-pyrido[3,4-b][1,4]oxazine XVII was prepared from 7-chloro-1H-pyrido[3,4-b][1,4]oxazin-2-one XVI by customary reduction methods, using as reducing agent preferably BH₃*THF and as solvent preferably THF. XVI is available via flow nitration of 2-chloro-5-(2-methoxy-2-oxoethoxy)pyridine-1-oxide, followed by reduction and cyclisation.

b) Cross-coupling between XVII and an aryl halogenide of the general formula R²—X' where X'=bromo or iodo was performed under customary Buchwald-Hartwig conditions using a Pd catalyst/ligand combination such as preferably Pd₂(dba)₃/X-Phos, and a base, such as preferably Cs₂CO₃ and an organic solvent such as preferably dioxane. The reaction was preferably stirred at a temperature of approximately 100° C. and could be performed in a microwave reactor. The reaction was preferably carried out under an inert gas such as nitrogen or argon. Typical conditions for Buchwald-Hartwig cross-coupling reactions are exemplified in the section A) Buchwald aminations or hydroxylations below.

c) Hydroxylation of XVIII was performed using aq. KOH and a Pd catalyst/ligand combination such as preferably Pd₂(dba)₃/tetramethyl-tert-butyl-Xphos and an organic solvent such as preferably dioxane. The reaction was preferably stirred at a temperature of approximately 100° C. The reaction was preferably carried out under an inert gas such as nitrogen or argon.

d) Coupling of a compound of general formula XIX with a compound of general formula VII was performed using a suitable base such as sodium hydride (NaH, Cs₂CO₃, K₂CO₃) and polar organic solvent such as DMF under inert gas conditions at a temperature of preferably 60-80° C. Typical conditions for such reactions are exemplified in the section C) Side chain introduction conditions below.

e) N—BOC deprotection was performed under customary BOC deprotection conditions using among the possible acid preferably trifluoro-actetic acid and organic solvent preferably CH₂Cl₂. The reaction was preferably performed at room temperature.

f) Amide bond formation was performed using compounds of general formula XXI and an acid chloride of formula R⁴C(O)Cl or carboxylic acid of formula R⁴C(O)OH to prepare an amide of general formula XXII; customary amide bond coupling conditions, as described in Scheme 1, step a) have been used, in addition coupling of carboxylic acids using HOBt/EDC was applied. The couplings were performed in an organic solvent such as preferably DMF or DCM and the final compounds were purified by normal or reversed phase chromatography. Typical conditions for amid bond formation reactions are exemplified in the section B) Amide bond formation conditions below.

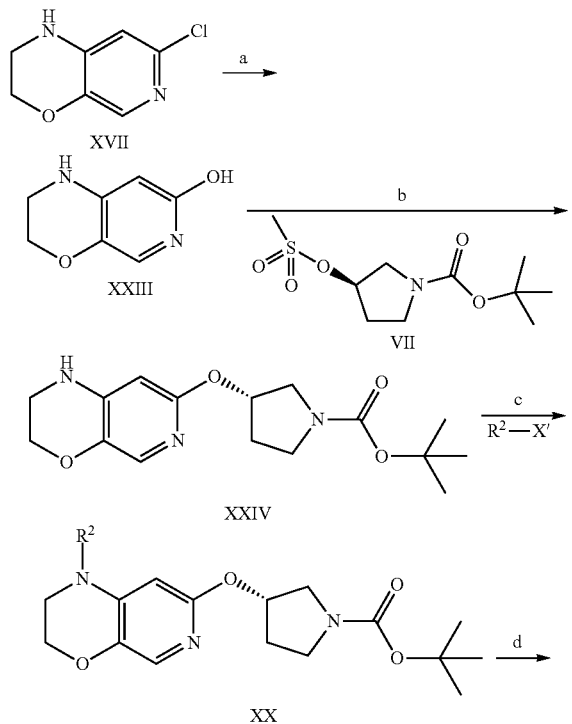

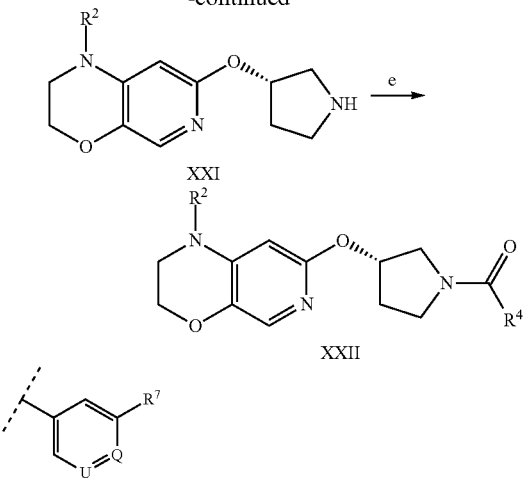

a) Hydroxylation of 7-chloro-2,3-dihydro-1H-pyrido[3,4-b][1,4]oxazine XVII to give 2,3-dihydro-1H-pyrido[3,4-b][1,4]oxazin-7-ol XXIII was performed using aq. KOH and a Pd catalyst/ligand combination such as preferably Pd₂(dba)₃/tetramethyl-tert-butyl-Xphos and an organic solvent such as preferably dioxane. The reaction was preferably stirred at a temperature of approximately 100° C. The reaction was preferably carried out under an inert gas such as nitrogen or argon.

b) Coupling of compound XXIII with mesylate VII was effected using a suitable base such as sodium hydride (NaH) and polar organic solvent such as DMF under inert gas conditions at a temperature of preferably 80° C. Typical conditions for such reactions are exemplified in the section C) Side chain introduction conditions below.

c) Cross-coupling between XXIV and an aryl halogenide of the general formula R²—X' where X'=bromo or iodo was performed under customary Buchwald-Hartwig conditions using a Pd catalyst/ligand combination such as preferably Pd₂(dba)₃/X-Phos or Pd₂(dba)₃/(rac)-BINAP, and a base, such as preferably Cs₂CO₃ or NaOtBu and an organic solvent such as preferably dioxane or toluene. The reaction was preferably stirred at a temperature of approximately 100° C. and could be performed in a microwave reactor. The reaction was preferably carried out under an inert gas such as nitrogen or argon. Typical conditions for Buchwald-Hartwig cross-coupling reactions are exemplified in the section A) Buchwald aminations or hydroxylations below.

d) N—BOC deprotection was performed under customary BOC deprotection conditions using among the possible acid preferably trifluoro-actetic acid and organic solvent preferably CH₂Cl₂. The reaction was preferably performed at room temperature e) Amide bond formation was performed using compounds of general formula XXI and an acid chloride of formula R⁴C(O)Cl or carboxylic acid of formula R⁴C(O)OH to prepare an amide of general formula XXII; customary amide bond coupling conditions, as described in Scheme 1, step a) have been used or coupling of carboxylic acids using HBTU, HOBt/EDC or HATU was applied. The couplings were performed in an organic solvent such as preferably DMF or DCM and the final compounds were purified by normal or reversed phase chromatography. Typical conditions for amid bond formation reactions are exemplified in the section B) Amide bond formation conditions below.

General Chromatography Information
LCMS Method M1 ($Rt_{M1}$)
HPLC-column dimensions: 2.1×50 mm
HPLC-column type: Acquity UPLC HSS T3, 1.8 μm
HPLC-eluent: A) water+0.05 Vol.-% formic acid+3.75 mM ammonium acetate B) ACN+0.04 Vol.-% formic acid
HPLC-gradient: 2-98% B in 1.4 min, 98% B 0.45 min, flow=1.2 ml/min
HPLC-column temperature: 50° C.
LCMS Method M2 ($Rt_{M2}$)
HPLC-column dimensions: 2.1×30 mm
HPLC-column type: Ascentis Express C18, 2.7 μm
HPLC-eluent A) water+0.05 Vol.-% formic acid+3.75 mM ammonium acetate B) ACN+0.04 Vol.-% formic acid
HPLC-gradient: 2-98% B in 1.4 min, 0.75 min 98% B, flow=1.2 ml/min
HPLC-column temperature: 50° C.
LCMS Method M3 ($Rt_{M3}$)
HPLC-column dimensions: 2.1×30 mm
HPLC-column type: Ascentis Express C18, 2.7 μm
HPLC-eluent A) water+0.05 Vol.-% formic acid+3.75 mM ammonium acetate B) ACN+0.04 Vol.-% formic acid
HPLC-gradient: 2-98% B in 8.5 min, 1 min 98% B, flow=1.2 ml/min
HPLC-column temperature: 50° C.
LCMS Method M4 ($Rt_{M4}$)
HPLC-column dimensions: 4.6×50 mm
HPLC-column type: SunFire C18, 5 μm
HPLC-eluent A) water+0.1 Vol.-% TFA, B) ACN+0.1 Vol.-% TFA
HPLC-gradient: 5-100% B in 8.0 min B, flow=2 ml/min
HPLC-column temperature: 40° C.
LCMS Method M5 ($Rt_{M5}$)
HPLC-column dimensions: 0.46×25 cm
HPLC-column type: Chiralcel OJ-H (1189)
HPLC-eluent EtOH/MeOH 60:40
HPLC-gradient: isocratic, flow=0.5 ml/min
Detector: UV 220 nm
LCMS Method M6 ($Rt_{M6}$)
HPLC-column dimensions: 2.1×30 mm
HPLC-column type: Ascentis Express C18, 2.7 μm
HPLC-eluent A) water+0.05% TFA, B) ACN+0.04% TFA
HPLC-gradient: 2-98% B in 1.4 min, 0.75 min 98% B, flow=1.2 ml/min
HPLC-column temperature: 50° C.
LCMS Method M7 ($Rt_{M7}$)
HPLC-column dimensions: 2.1×30 mm
HPLC-column type: Ascentis Express C18, 2.7 μm
HPLC-eluent A) water+0.05% TFA, B) ACN+0.04% TFA
HPLC-gradient: 10-95% B in 3.0 min, 1 min 95% B, flow=1.2 ml/min
HPLC-column temperature: 50° C.
LCMS Method M8 ($Rt_{M8}$)
HPLC-column dimensions: 2.1×30 mm
HPLC-column type: Ascentis Express C18 2.7 μm
HPLC-eluent: A) water+0.05% formic acid+3.75 mM ammonium acetate, B) acetonitrile+0.04% formic acid
HPLC-gradient: 10-95% B in 3.0 min, flow=1.2 ml/min
LCMS Method M9 ($Rt_{M9}$)
HPLC-column dimensions: 2.1×30 mm
HPLC-column type: Ascentis Express C18 2.7 μm
HPLC-eluent: A) water+0.05 formic acid+3.75 mM ammonium acetate, B) acetonitrile+0.04% formic acid
HPLC-gradient: 10% B from 0.0 to 0.5 min then from 0.5 min to 3.0 min gradient 10-95% B, flow=1.2 ml/min
LCMS Method M10 ($Rt_{M10}$)
HPLC-column dimensions: 2.1×50 mm
HPLC-column type: Acquity UPLC BEH C18 1.7 μm
HPLC-eluent: A) water+0.1 Vol.-% formic acid, B) acetonitrile
HPLC-gradient: 20-25% B in 1.00 min, then 25-95% B in 3.20 min, then 95-100% B in 0.10 min, then 100% for 0.20 min, flow=0.7 ml/min
LCMS Method M11 ($Rt_{M11}$)
HPLC-column dimensions: 2.1×50 mm
HPLC-column type: Acquity UPLC BEH C18 1.7 μm
HPLC-eluent: A) water+0.1 Vol.-% formic acid, B) acetonitrile
HPLC-gradient: 5-10% B in 1.00 min, then 10-90% B in 3.00 min, then 90-100% B in 0.10 min, then 100% for 0.40 min, flow=0.7 ml/min
LCMS Method M12 ($Rt_{M12}$)
HPLC-column dimensions: 2.1×30 mm
HPLC-column type: Ascentis Express C18 2.7 μm
HPLC-eluent: A) water+0.1 Vol.-% TFA, B) acetonitrile
HPLC-gradient: 10-95% B over 1.7 min and 1.2 mL/min as solvent flow and then 95 5 B over 0.7 min, flow=1.4 mL/min.
LCMS Method M13 ($Rt_{M13}$)
HPLC-column dimensions: 2.1×30 mm
HPLC-column type: Ascentis Express C18 2.7 μm
HPLC-eluent: A) water+0.05% formic acid+3.75 mM ammonium acetate, B) acetonitrile+0.04% formic acid
HPLC-gradient: 10-95% B in 3.7 min, flow=1.2 ml/min
LCMS Method M14 ($Rt_{M14}$)
HPLC-column dimensions: 2.1×30 mm
HPLC-column type: Ascentis Express C18, 2.7 μm
HPLC-eluent A) water+0.05% formic acid+3.75 mM ammonium acetate, B) acetonitrile+0.04% formic acid
HPLC-gradient: 10-95% B in 1.5 min, 1 min 95% B, flow=1.2 ml/min
LCMS Method M15 ($Rt_{M15}$)
HPLC-column dimensions: 0.46×25 cm
HPLC-column type: Chiralcel OD-H (1194)
HPLC-eluent Hexan/EtOH 50:50+0.05% DEA
HPLC-gradient: isocratic, flow=0.5 ml/min
Detector: UV 220 nm
LCMS Method M16 ($Rt_{M16}$)
HPLC-column dimensions: 2.1×50 mm
HPLC-column type: Acquity UPLC HSS T3, 1.8 μm
HPLC-eluent: A) water+0.05 Vol.-% formic acid+3.75 mM ammonium acetate B) ACN+0.04 Vol.-% formic acid
HPLC-gradient: 5-98% B in 1.4 min, 98% B 0.4 min, flow=1.0 ml/min
HPLC-column temperature: 60° C.
X-Ray Powder Diffraction
Instrumentation:
Method X1
Instrument Bruker D8 GADDS Discover
Irradiation CuKα (40 kV, 40 mA)
Detector HI-STAR Area detector
Scan range 6°-39° (2 theta value)
Melting Point Determination:
Melting point was determined by Differential Scanning calorimetry (DSC). DSC was as recorded on a TA Instruments DSC Q2000 using a heating rate of 10° C./min. A sample of 0.6 mg was weighed into standard aluminium pan (pan+lid, TA 900786.901, 900779.901). The instrument was operated using the Thermal Advantage Q-Series software V.2.6.0.367 and the Thermal Advantage software V4.6.9. Thermal events were characterized using Universal Analysis V4.3A Build 4.3.0.6. The samples was measured against sample pan without pin hole. The sample was treated according to the protocol below:

Step 1: EQUILIBRATE AT 0° C.
Step 2: Ramp 10° C./min to 300° C.

Preparation of Examples

Where it is stated that compounds were prepared in the manner described for an earlier example, the skilled person will appreciate that reaction times, number of equivalents of reagents and reaction temperatures may be modified for each specific reaction, and that it may nevertheless be necessary or desirable to employ different work-up or purification conditions.

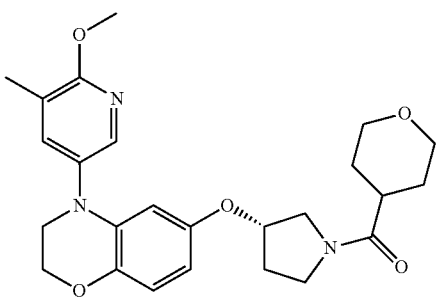 [SMILES: COc1ncc(N2CCOc3ccc(O[C@H]4CCN(C(=O)C5CCOCC5)C4)cc32)cc1C]

Example A1

(S)-(3-((4-(6-methoxy-5-methylpyridin-3-yl)-3,4-dihydro-2H-benzo[b][1,4]oxazin-6-yl)oxy)pyrrolidin-1-yl)(tetrahydro-2H-pyran-4-yl)methanone (according to Scheme 1)

a1) (R)-(3-hydroxypyrrolidin-1-yl)(tetrahydro-2H-pyran-4-yl)methanone

A stirred solution of tetrahydro-2H-pyran-4-carboxylic acid (CAS registry 5337-03-1) (0.200 g, 1.537 mmol) and DMF (0.012 ml, 0.154 mmol) in DCM (3 ml) was treated with oxalyl chloride (0.202 ml, 2.305 mmol) at 3° C. After 1 h at 3° C., the reaction mixture was concentrated under reduced pressure. The residue was then dissolved in DCM (2 ml), and added to a stirred solution of (R)-pyrrolidin-3-ol hydrochloride (CAS registry 104706-47-0) (0.190 g, 1.537 mmol), Et$_3$N (0.535 ml, 3.84 mmol) in DCM (3 ml) at 3° C. After 1 h at 3° C., the reaction mixture was concentrated under reduced pressure. The residue was treated with EtOAc (10 ml) and filtered. The residue was washed with EtOAc, and the combined filtrates were concentrated under reduced pressure. The crude product was purified by flash chromatography on silica gel (DCM/methanol gradient) to provide the title compound as a white solid.

ESIMS: 200 [(M+H)$^+$].

$^1$H NMR (400 MHz, CDCl$_3$): δ 4.61-4.50 (m, 1H), 4.10-4.02 (m, 2H), 3.77-3.40 (m, 6H), 2.70-2.53 (m, 1H), 2.20-1.85 (m, 4H), 1.75-1.69 (m, 3H).

alternative method a2: instead of preparing the acid chloride in situ, a commercially available acid chloride like propanoyl chloride (CAS registry 79-03-8) was used.

b1) (R)-1-(tetrahydro-2H-pyran-4-carbonyl)pyrrolidin-3-yl methanesulfonate

A stirred solution of (R)-(3-hydroxypyrrolidin-1-yl)(tetrahydro-2H-pyran-4-yl)methanone (0.245 g, 1.230 mmol) in DCM (10 ml) was treated with Et$_3$N (0.343 ml, 2.459 mmol) and methanesulfonyl chloride (0.192 ml, 2.459 mmol) at 0° C. After 1 h at 0° C., water (20 ml) was added. The organic layer was washed with a saturated NaCl solution (20 ml), dried with MgSO$_4$, filtered and concentrated under reduced pressure. The crude product was purified by trituration with diethyl ether to provide the title compound as a white solid.

ESIMS: 278 [(M+H)$^+$].

$^1$H NMR (400 MHz, CDCl$_3$): δ 5.40-5.29 (m, 1H), 4.10-4.02 (m, 2H), 3.94-3.87 (m, 1H), 3.82-3.56 (m. 3H), 3.52-3.41 (m, 2H), 3.11-3.04 (m, 3H), 2.70-2.10 (m, 3H), 2.02-2.87 (m, 2H), 1.72-1.57 (m, 2H).

c1) (S)-(3-((3,4-dihydro-2H-benzo[b][1,4]oxazin-6-yl)oxy)pyrrolidin-1-yl)(tetrahydro-2H-pyran-4-yl)methanone A stirred solution of 3,4-dihydro-2H-benzoxazin-6-ol (CAS registry 26021-57-8) (0.140 g, 0.926 mmol) in DMF (3 ml) was treated with sodium hydride (60% in mineral oil, 0.445 g, 1.111 mmol) at rt. After 10 min at rt, (R)-1-(tetrahydro-2H-pyran-4-carbonyl)pyrrolidin-3-yl methanesulfonate (0.283 g, 1.019 mmol) was added. The vial was capped and heated to 50° C. for 3 h. After this time, the reaction mixture was concentrated under reduced pressure. The residue was dissolved in EtOAc (50 ml), and water (50 ml) was added. The organic layer was washed with a saturated NaCl solution (20 ml), dried with MgSO$_4$, filtered and concentrated under reduced pressure. The crude product was purified by flash chromatography on silica gel (DCM/methanol gradient) to provide the title compound as a grey amorphous solid.

HPLC Rt$_{M10}$=2.07 min; ESIMS: 333 [(M+H)$^+$].

$^1$H NMR (400 MHz, DMSO-d$_6$): δ 6.55-6.50 (m, 1H), 6.15-6.11 (m, 1H), 6.07-6.00 (m, 1H), 5.77 (br s, 1H), 4.88-4.74 (m, 1H), 4.06-4.01 (m, 2H), 3.90-3.22 (m, 10H), 2.75-2.58 (m, 1H), 2.15-1.95 (m, 2H), 1.65-1.45 (m, 4H).

d1) (S)-(3-((4-(6-methoxy-5-methylpyridin-3-yl)-3,4-dihydro-2H-benzo[b][1,4]oxazin-6-yl)oxy)pyrrolidin-1-yl)(tetrahydro-2H-pyran-4-yl)methanone A stirred solution of (S)-(3-((3,4-dihydro-2H-benzo[b][1,4]oxazin-6-yl)oxy)pyrrolidin-1-yl)(tetrahydro-2H-pyran-4-yl)methanone (0.050 g, 0.150 mmol) in toluene (1 ml) was treated with 5-bromo-2-methoxy-3-methylpyridine (CAS registry 760207-87-2) (0.030 g, 0.150 mmol), NaOtBu (0.022 g, 0.226 mmol), 2-(dicyclohexylphosphino)biphenyl (CAS registry 247940-06-3) and Pd$_2$(dba)$_3$ (0.004 g, 0.005 mmol) at rt under argon. The reaction vial was capped and heated to 110° C. in a microwave reactor for 3 h. After this time, the reaction mixture was concentrated under reduced pressure. The crude product was purified by flash chromatography on silica gel (cyclohexane/EtOAc gradient) to provide the title compound as an off-white solid.

HPLC Rt$_{M10}$=2.85 min; ESIMS: 454 [(M+H)$^+$].

$^1$H NMR (400 MHz, CD$_3$OD): δ 7.90-7.85 (m, 1H), 7.49-7.44 (m, 1H), 6.76-6.69 (m, 1H), 6.32-6.24 (m, 1H), 6.07-6.02 (m, 1H), 4.86-4.73 (m, 1H), 4.29-4.23 (m, 2H), 4.02-3.92 (m, 5H), 3.80-3.40 (m, 8H), 2.85-2.60 (m, 1H), 2.25-1.91 (m, 5H), 1.85-1.50 (m, 4H).

alternative method d2: 2-(dicyclohexylphosphino)biphenyl (CAS registry 247940-06-3) was replaced with 2-dicyclohexylphosphino-2',4',6'-triisopropylbiphenyl (CAS registry 564483-18-7)

alternative method d3: 2-(dicyclohexylphosphino)biphenyl (CAS registry 247940-06-3) and Pd₂(dba)₃ was replaced with bis(tri-t-butylphosphine)palladium (CAS registry 53199-31-8)

Examples A2 to A43

The compounds listed in Table 1 were prepared by a procedure analogous to that used in Example A1.

TABLE 1

| Example | Compound | HPLC Rt [min] (method) | MS [m/z; (M + 1)⁺] |
|---|---|---|---|
| A2 | 5-{6-[(S)-1-(Tetrahydro-pyran-4-carbonyl)-pyrrolidin-3-yloxy]-2,3-dihydro-benzo[1,4]oxazin-4-yl}-pyridine-3-sulfonic acid dimethylamide<br>Synthetic route used: a1, b1, c1, d1<br>(intermediate IA13) | 2.50 (M10) | 517 |
| A3 | ((S)-3-{4-[5-(Morpholine-4-sulfonyl)-pyridin-3-yl]-3,4-dihydro-2H-benzo[1,4]oxazin-6-yloxy}-pyrrolidin-1-yl)-(tetrahydro-pyran-4-yl)-methanone<br>Synthetic route used: a1, b1, c1, d1<br>(intermediate IA14) | 1.10 (M12) | 560 |
| A4 | {(S)-3-[4-(6-Methyl-5-nitro-pyridin-3-yl)-3,4-dihydro-2H-benzo[1,4]oxazin-6-yloxy]-pyrrolidin-1-yl}-(tetrahydro-pyran-4-yl)-methanone<br>Synthetic route used: a1, b1, c1, d1<br>(intermediate IA15) | 1.78 (M10) | 469 |

TABLE 1-continued

| Example | Compound | HPLC Rt [min] (method) | MS [m/z; (M + 1)+] |
|---|---|---|---|
| A5 | 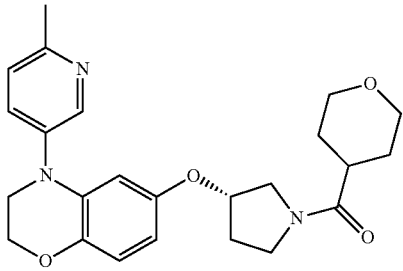 {(S)-3-[4-(6-Methyl-pyridin-3-yl)-3,4-dihydro-2H-benzo[1,4]oxazin-6-yloxy]-pyrrolidin-1-yl}-(tetrahydro-pyran-4-yl)-methanone Synthetic route used: a1, b1, c1, d1 (intermediate IA16) | 1.03 (M10) | 425 |
| A6 | 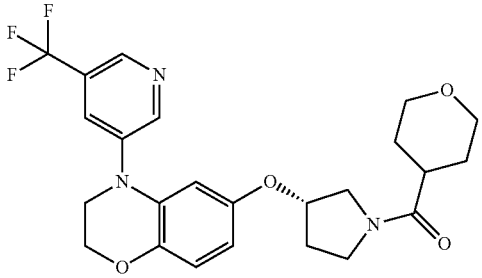 (Tetrahydro-pyran-4-yl)-{(S)-3-[4-(5-trifluoromethyl-pyridin-3-yl)-3,4-dihydro-2H-benzo[1,4]oxazin-6-yloxy]-pyrrolidin-1-yl}-methanone Synthetic route used: a1, b1, c1, d1 (intermediate IA18) | 1.21 (M12) | 479 |
| A7 | 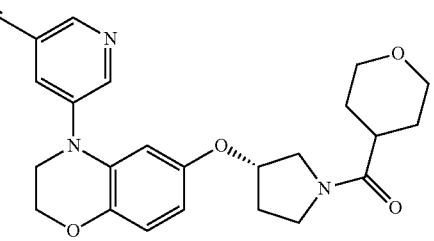 5-{6-[(S)-1-(Tetrahydro-pyran-4-carbonyl)-pyrrolidin-3-yloxy]-2,3-dihydro-benzo[1,4]oxazin-4-yl}-nicotinonitrile Synthetic route used: a1, b1, c1, d2 (intermediate IA17) | 2.44 (M10) | 435 |

TABLE 1-continued

| Example | Compound | HPLC Rt [min] (method) | MS [m/z; (M + 1)+] |
|---|---|---|---|
| A8 | 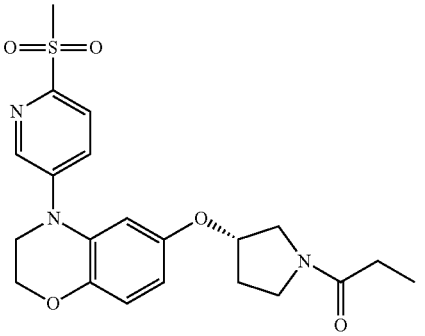 1-{(S)-3-[4-(6-Methanesulfonyl-pyridin-3-yl)-3,4-dihydro-2H-benzo[1,4]oxazin-6-yloxy]-pyrrolidin-1-yl}-propan-1-one<br>Synthetic route used: a2, b1, c1, d2<br>(intermediate IA40) | 1.46 (M8) | 432 |
| A9 | 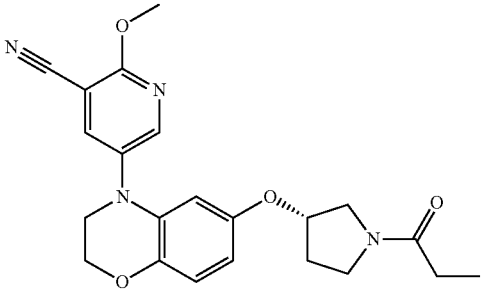 2-Methoxy-5-[6-((S)-1-propionyl-pyrrolidin-3-yloxy)-2,3-dihydro-benzo[1,4]oxazin-4-yl]-nicotinonitrile<br>Synthetic route used: a2, b1, c1, d2<br>(intermediate IA12) | 2.80 (M10) | 409 |
| A10 | 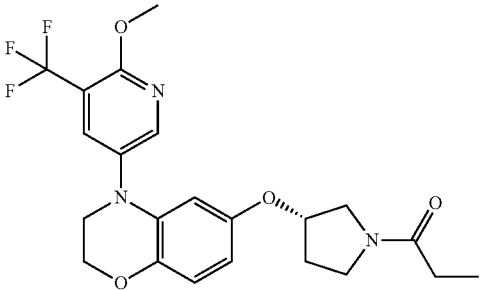 1-{(S)-3-[4-(6-Methoxy-5-trifluoromethyl-pyridin-3-yl)-3,4-dihydro-2H-benzo[1,4]oxazin-6-yloxy]-pyrrolidin-1-yl}-propan-1-one<br>Synthetic route used: a2, b1, c1, d2<br>(intermediate IA21) | 2.74 (M11) | 452 |

TABLE 1-continued

| Example | Compound | HPLC Rt [min] (method) | MS [m/z; (M + 1)+] |
|---|---|---|---|
| A11 | 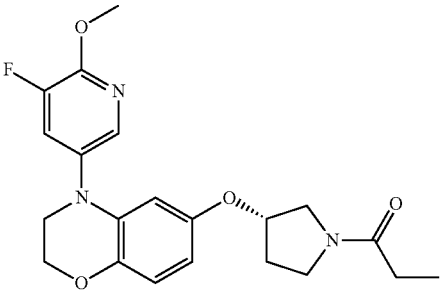1-{(S)-3-[4-(5-Fluoro-6-methoxy-pyridin-3-yl)-3,4-dihydro-2H-benzo[1,4]oxazin-6-yloxy]-pyrrolidin-1-yl}-propan-1-one<br>Synthetic route used: a2, b1, c1, d2<br>(intermediate IA10) | 2.86 (M10) | 402 |
| A12 | 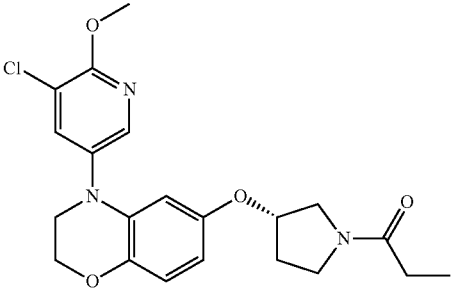1-{(S)-3-[4-(5-Chloro-6-methoxy-pyridin-3-yl)-3,4-dihydro-2H-benzo[1,4]oxazin-6-yloxy]-pyrrolidin-1-yl}-propan-1-one<br>Synthetic route used: a2, b1, c1, d2<br>(intermediate IA11) | 3.00 (M10) | 418 |
| A13 | 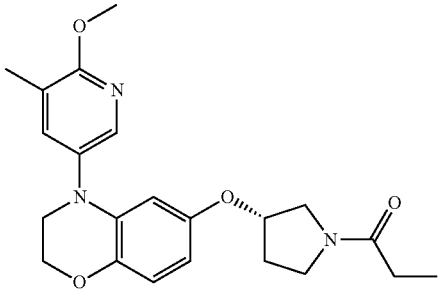1-{(S)-3-[4-(6-Methoxy-5-methyl-pyridin-3-yl)-3,4-dihydro-2H-benzo[1,4]oxazin-6-yloxy]-pyrrolidin-1-yl}-propan-1-one<br>Synthetic route used: a2, b1, c1, d2<br>(intermediate IA9) | 2.93 (M10) | 398 |

TABLE 1-continued

| Example | Compound | HPLC Rt [min] (method) | MS [m/z; (M + 1)+] |
|---|---|---|---|
| A14 | 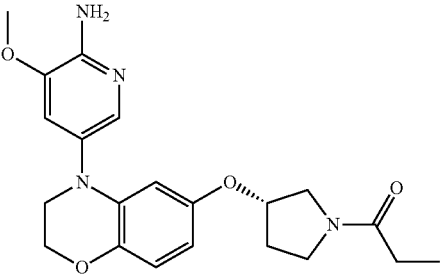<br>1-{(S)-3-[4-(6-Amino-5-methoxy-pyridin-3-yl)-3,4-dihydro-2H-benzo[1,4]oxazin-6-yloxy]-pyrrolidin-1-yl}-propan-1-one<br>Synthetic route used: a2, b1, c1, d2<br>(intermediate IA46) | 1.98 (M10) | 399 |
| A15 | 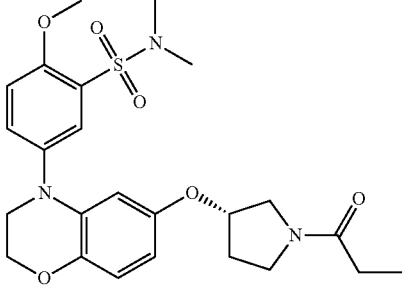<br>2-Methoxy-N,N-dimethyl-5-[6-((S)-1-propionyl-pyrrolidin-3-yloxy)-2,3-dihydro-benzo[1,4]oxazin-4-yl]-benzenesulfonamide<br>Synthetic route used: a2, b1, c1, d2<br>(intermediate IA60) | 2.76 (M10) | 490 |
| A16 | 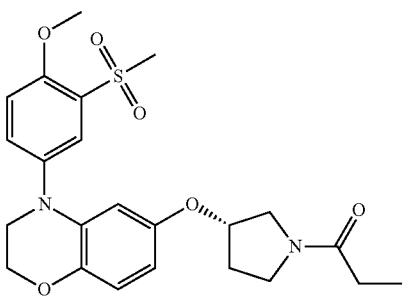<br>1-{(S)-3-[4-(3-Methanesulfonyl-4-methoxy-phenyl)-3,4-dihydro-2H-benzo[1,4]oxazin-6-yloxy]-pyrrolidin-1-yl}-propan-1-one<br>Synthetic route used: a2, b1, c1, d2<br>(intermediate IA59) | 2.56 (M10) | 461 |

TABLE 1-continued

| Example | Compound | HPLC Rt [min] (method) | MS [m/z; (M + 1)+] |
|---|---|---|---|
| A17 | 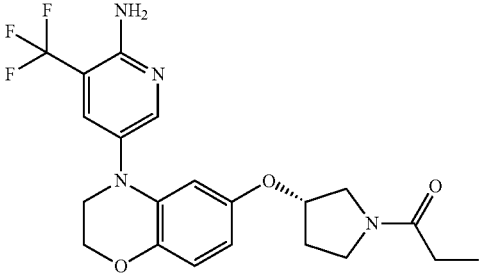 1-{(S)-3-[4-(6-Amino-5-trifluoromethyl-pyridin-3-yl)-3,4-dihydro-2H-benzo[1,4]oxazin-6-yloxy]-pyrrolidin-1-yl}-propan-1-one<br>Synthetic route used: a2, b1, c1, d2<br>(intermediate IA23) | 2.67 (M10) | 437 |
| A18 | 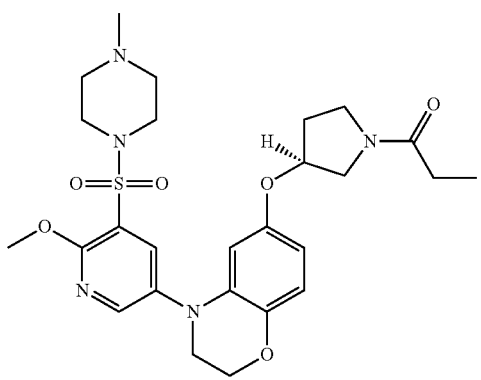 1-((S)-3-{4-[6-Methoxy-5-(4-methyl-piperazine-1-sulfonyl)-pyridin-3-yl]-3,4-dihydro-2H-benzo[1,4]oxazin-6-yloxy}-pyrrolidin-1-yl)-propan-1-one<br>Synthetic route used: a2, b1, c1, d3<br>(intermediate IA24) | 1.60 (M9) | 546 |
| A19 | 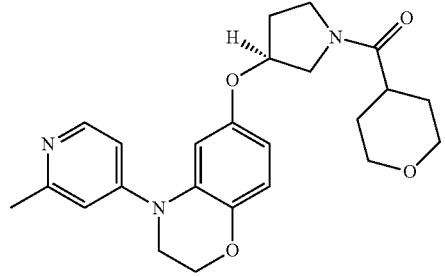 {(S)-3-[4-(2-Methyl-pyridin-4-yl)-3,4-dihydro-2H-benzo[1,4]oxazin-6-yloxy]-pyrrolidin-1-yl}-(tetrahydro-pyran-4-yl)-methanone<br>Synthetic route used: a1, b1, c1, d3<br>(intermediate IA61) | 1.32 (M9) | 424 |

TABLE 1-continued

| Example | Compound | HPLC Rt [min] (method) | MS [m/z; (M + 1)+] |
|---|---|---|---|
| A20 | 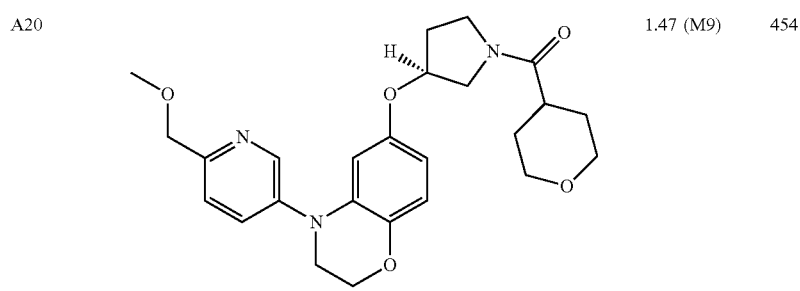{(S)-3-[4-(6-Methoxymethyl-pyridin-3-yl)-3,4-dihydro-2H-benzo[1,4]oxazin-6-yloxy]-pyrrolidin-1-yl}-(tetrahydro-pyran-4-yl)-methanone<br>Synthetic route used: a1, b1, c1, d3<br>(intermediate IA25) | 1.47 (M9) | 454 |
| A21 | 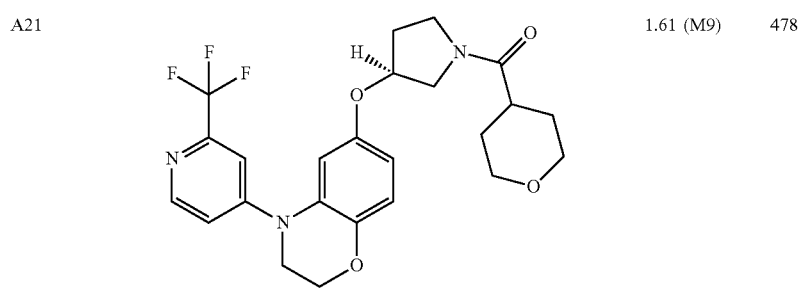(Tetrahydro-pyran-4-yl)-{(S)-3-[4-(2-trifluoromethyl-pyridin-4-yl)-3,4-dihydro-2H-benzo[1,4]oxazin-6-yloxy]-pyrrolidin-1-yl}-methanone<br>Synthetic route used: a1, b1, c1, d3<br>(intermediate IA63) | 1.61 (M9) | 478 |
| A22 | 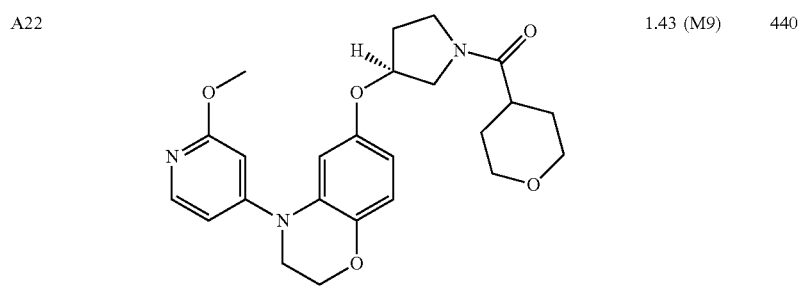{(S)-3-[4-(2-Methoxy-pyridin-4-yl)-3,4-dihydro-2H-benzo[1,4]oxazin-6-yloxy]-pyrrolidin-1-yl}-(tetrahydro-pyran-4-yl)-methanone<br>Synthetic route used: a1, b1, c1, d3<br>(intermediate IA62) | 1.43 (M9) | 440 |

TABLE 1-continued

| Example | Compound | HPLC Rt [min] (method) | MS [m/z; (M + 1)+] |
|---|---|---|---|
| A23 | 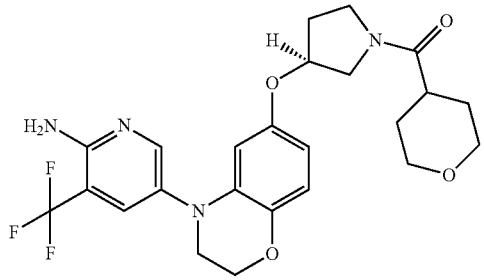<br>{(S)-3-[4-(6-Amino-5-trifluoromethyl-pyridin-3-yl)-3,4-dihydro-2H-benzo[1,4]oxazin-6-yloxy]-pyrrolidin-1-yl}-(tetrahydro-pyran-4-yl)-methanone<br>Synthetic route used: a1, b1, c1, d3<br>(intermediate IA23) | 1.57 (M9) | 493 |
| A24 | 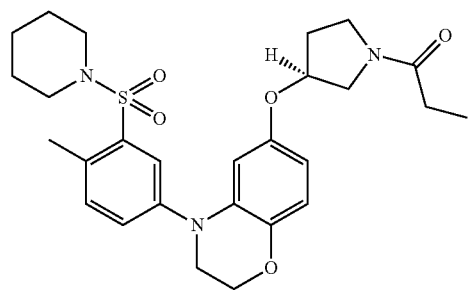<br>1-((S)-3-{4-[4-Methyl-3-(piperidine-1-sulfonyl)-phenyl]-3,4-dihydro-2H-benzo[1,4]oxazin-6-yloxy}-pyrrolidin-1-yl)-propan-1-one<br>Synthetic route used: a2, b1, c1, d3<br>(intermediate IA31) | 2.04 (M9) | 514 |
| A25 | 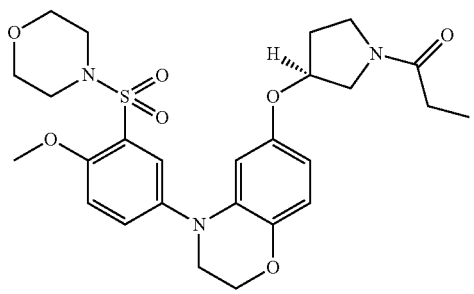<br>1-((S)-3-{4-[4-Methoxy-3-(morpholine-4-sulfonyl)-phenyl]-3,4-dihydro-2H-benzo[1,4]oxazin-6-yloxy}-pyrrolidin-1-yl)-propan-1-oneSynthetic route used: a2, b1, c1, d3 (intermediate IA32) | 1.83 (M9) | 532 |

TABLE 1-continued

| Example | Compound | HPLC Rt [min] (method) | MS [m/z; (M + 1)+] |
|---|---|---|---|
| A26 | 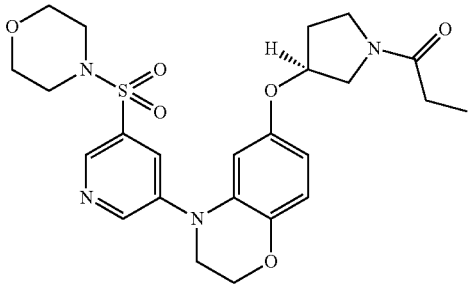 1-((S)-3-{4-[5-(Morpholine-4-sulfonyl)-pyridin-3-yl]-3,4-dihydro-2H-benzo[1,4]oxazin-6-yloxy}-pyrrolidin-1-yl)-propan-1-one<br>Synthetic route used: a2, b1, c1, d3<br>(intermediate IA33) | 1.83 (M9) | 503 |
| A27 | 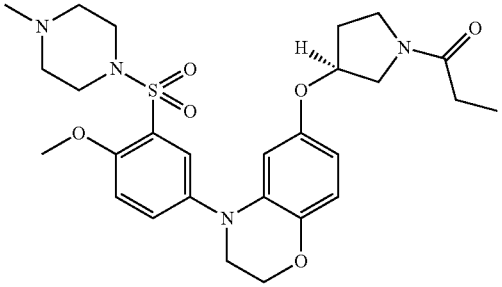 1-((S)-3-{4-[4-Methoxy-3-(4-methyl-piperazine-1-sulfonyl)-phenyl]-3,4-dihydro-2H-benzo[1,4]oxazin-6-yloxy}-pyrrolidin-1-yl)-propan-1-one<br>Synthetic route used: a2, b1, c1, d3<br>(intermediate IA34) | 2.22 (M9) | 545 |
| A28 | 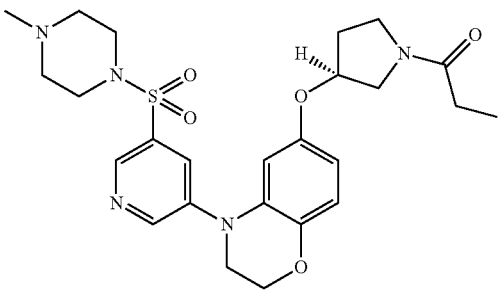 1-((S)-3-{4-[5-(4-Methyl-piperazine-1-sulfonyl)-pyridin-3-yl]-3,4-dihydro-2H-benzo[1,4]oxazin-6-yloxy}-pyrrolidin-1-yl)-propan-1-one<br>Synthetic route used: a2, b1, c1, d3<br>(intermediate IA35) | 2.08 (M9) | 516 |

TABLE 1-continued

| Example | Compound | HPLC Rt [min] (method) | MS [m/z; (M + 1)+] |
|---|---|---|---|
| A29 | 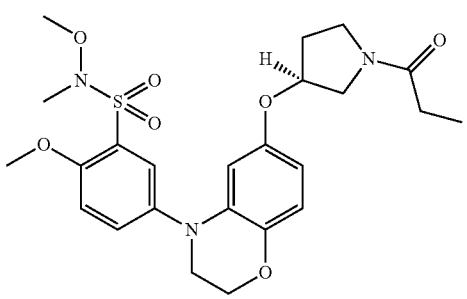<br>2,N-Dimethoxy-N-methyl-5-[6-((S)-1-propionyl-pyrrolidin-3-yloxy)-2,3-dihydro-benzo[1,4]oxazin-4-yl]-benzenesulfonamide<br>Synthetic route used: a2, b1, c1, d3<br>(intermediate IA36) | 2.82 (M9) | 506 |
| A30 | 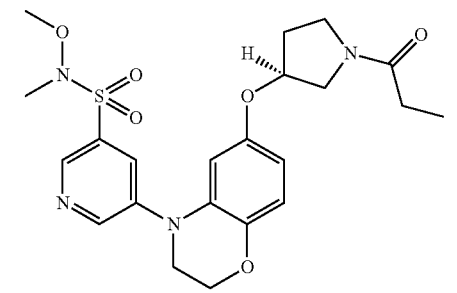<br>5-[6-((S)-1-Propionyl-pyrrolidin-3-yloxy)-2,3-dihydro-benzo[1,4]oxazin-4-yl]-pyridine-3-sulfonic acid methoxy-methyl-amide<br>Synthetic route used: a2, b1, c1, d3<br>(intermediate IA37) | 2.69 (M9) | 477 |
| A31 | 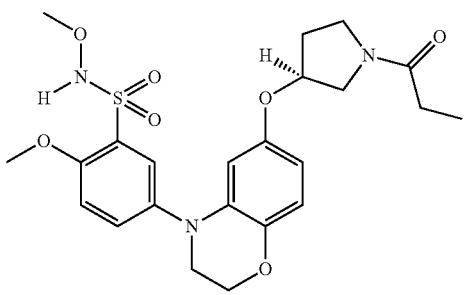<br>2,N-Dimethoxy-5-[6-((S)-1-propionyl-pyrrolidin-3-yloxy)-2,3-dihydro-benzo[1,4]oxazin-4-yl]-benzenesulfonamide<br>Synthetic route used: a2, b1, c1, d3<br>(intermediate IA65) | 2.72 (M9) | 492 |

TABLE 1-continued

| Example | Compound | HPLC Rt [min] (method) | MS [m/z; (M + 1)+] |
|---|---|---|---|
| A32 | 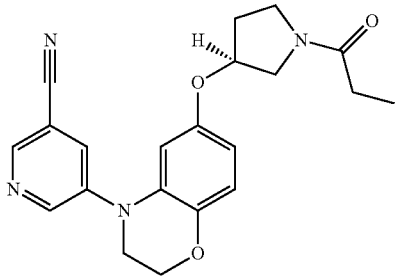 5-[6-((S)-1-Propionyl-pyrrolidin-3-yloxy)-2,3-dihydro-benzo[1,4]oxazin-4-yl]-nicotinonitrile Synthetic route used: a2, b1, c1, d3 (intermediate IA17) | 2.49 (M9) | 379 |
| A33 | 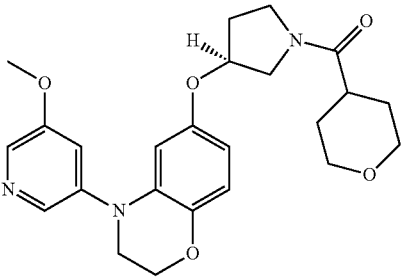 {(S)-3-[4-(5-Methoxy-pyridin-3-yl)-3,4-dihydro-2H-benzo[1,4]oxazin-6-yloxy]-pyrrolidin-1-yl}-(tetrahydro-pyran-4-yl)-methanone Synthetic route used: a1, b1, c1, d3 (intermediate IA38) | 1.54 (M9) | 440 |
| A34 | 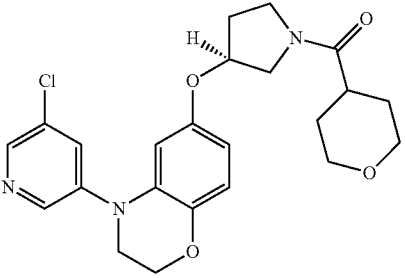 {(S)-3-[4-(5-Chloro-pyridin-3-yl)-3,4-dihydro-2H-benzo[1,4]oxazin-6-yloxy]-pyrrolidin-1-yl}-(tetrahydro-pyran-4-yl)-methanone Synthetic route used: a1, b1, c1, d3 (intermediate IA39) | 1.76 (M9) | 444 |

TABLE 1-continued

| Example | Compound | HPLC Rt [min] (method) | MS [m/z; (M + 1)+] |
|---|---|---|---|
| A35 | 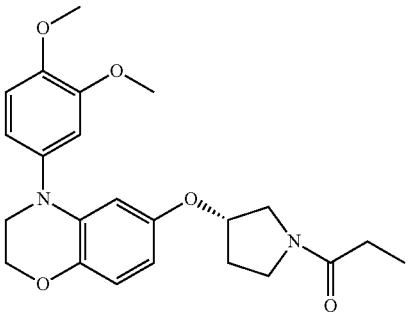 1-{(S)-3-[4-(3,4-Dimethoxy-phenyl)-3,4-dihydro-2H-benzo[1,4]oxazin-6-yloxy]-pyrrolidin-1-yl}-propan-1-one Synthetic route used: a1, b1, c1, d3 (intermediate IA66) | 1.24 (M6) | 413 |
| A36 | 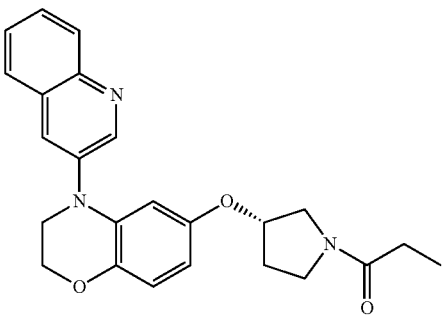 1-[(S)-3-(4-Quinolin-3-yl-3,4-dihydro-2H-benzo[1,4]oxazin-6-yloxy)-pyrrolidin-1-yl]-propan-1-one Synthetic route used: a1, b1, c1, d3 (intermediate IA54) | 1.02 (M6) | 404 |
| A37 | 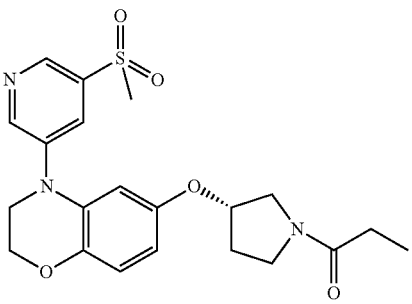 1-{(S)-3-[4-(5-Methanesulfonyl-pyridin-3-yl)-3,4-dihydro-2H-benzo[1,4]oxazin-6-yloxy]-pyrrolidin-1-yl}-propan-1-one Synthetic route used: a1, b1, c1, d3 (intermediate IA55) | 1.03 (M6) | 432 |

TABLE 1-continued

| Example | Compound | HPLC Rt [min] (method) | MS [m/z; (M + 1)+] |
|---|---|---|---|
| A38 | 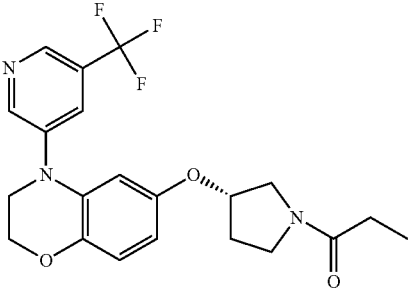1-{(S)-3-[4-(5-Trifluoromethyl-pyridin-3-yl)-3,4-dihydro-2H-benzo[1,4]oxazin-6-yloxy]-pyrrolidin-1-yl}-propan-1-one<br>Synthetic route used: a1, b1, c1, d3<br>(intermediate IA18) | 1.24 (M6) | 422 |
| A39 | 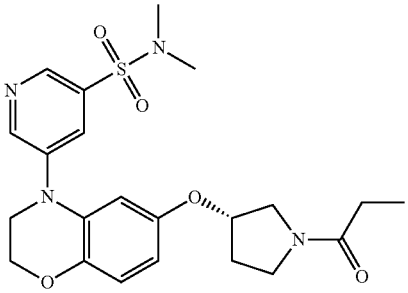5-[6-((S)-1-Propionyl-pyrrolidin-3-yloxy)-2,3-dihydro-benzo[1,4]oxazin-4-yl]-pyridine-3-sulfonic acid dimethylamide<br>Synthetic route used: a1, b1, c1, d3<br>(intermediate IA13) | 1.13 (M6) | 461 |
| A40 | 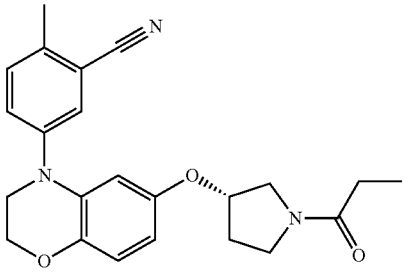2-Methyl-5-[6-((S)-1-propionyl-pyrrolidin-3-yloxy)-2,3-dihydro-benzo[1,4]oxazin-4-yl]-benzonitrile<br>Synthetic route used: a1, b1, c1, d3<br>(intermediate IA56) | 1.33 (M6) | 392 |

TABLE 1-continued

| Example | Compound | HPLC Rt [min] (method) | MS [m/z; (M + 1)+] |
|---|---|---|---|
| A41 | 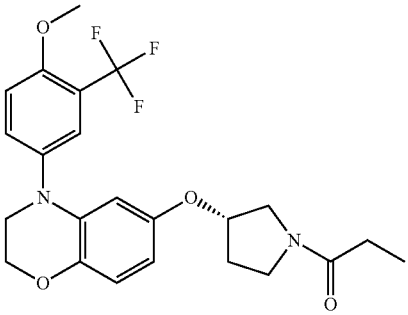 1-{(S)-3-[4-(4-Methoxy-3-trifluoromethyl-phenyl)-3,4-dihydro-2H-benzo[1,4]oxazin-6-yloxy]-pyrrolidin-1-yl}-propan-1-one<br>Synthetic route used: a1, b1, c1, d3<br>(intermediate IA57) | 1.44 (M6) | 451 |
| A42 | 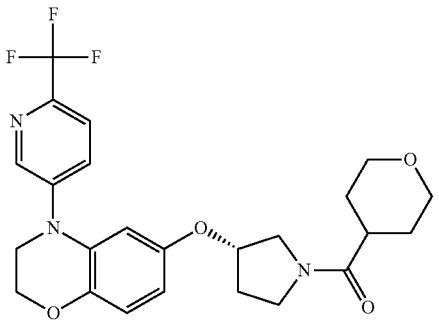 (Tetrahydro-pyran-4-yl)-{(S)-3-[4-(6-trifluoromethyl-pyridin-3-yl)-3,4-dihydro-2H-benzo[1,4]oxazin-6-yloxy]-pyrrolidin-1-yl}-methanone<br>Synthetic route used: a1, b1, c1, d3<br>(intermediate IA26) | 1.82 (M6) | 478 |
| A43 | 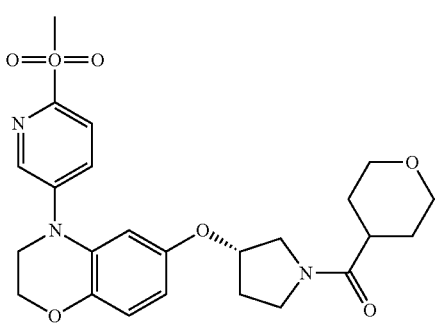 {(S)-3-[4-(6-Methanesulfonyl-pyridin-3-yl)-3,4-dihydro-2H-benzo[1,4]oxazin-6-yloxy]-pyrrolidin-1-yl}-(tetrahydro-pyran-4-yl)-methanone<br>Synthetic route used: a1, b1, c1, d3<br>(intermediate IA40) | 1.44 (M6) | 488 |

Example B1

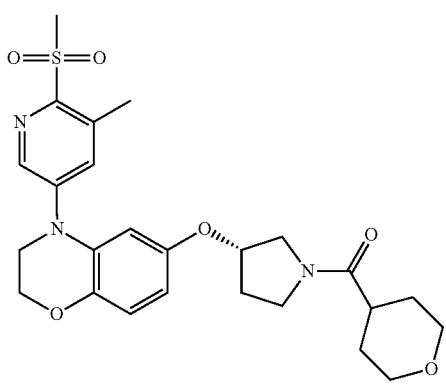 [SMILES: Cc1cc(N2CCOc3ccc(O[C@H]4CCN(C(=O)C5CCOCC5)C4)cc32)cnc1S(C)(=O)=O]

{(S)-3-[4-(6-Methanesulfonyl-5-methyl-pyridin-3-yl)-3,4-dihydro-2H-benzo[1,4]oxazin-6-yloxy]-pyrrolidin-1-yl}-(tetrahydro-pyran-4-yl)-methanone (according to Scheme 2)

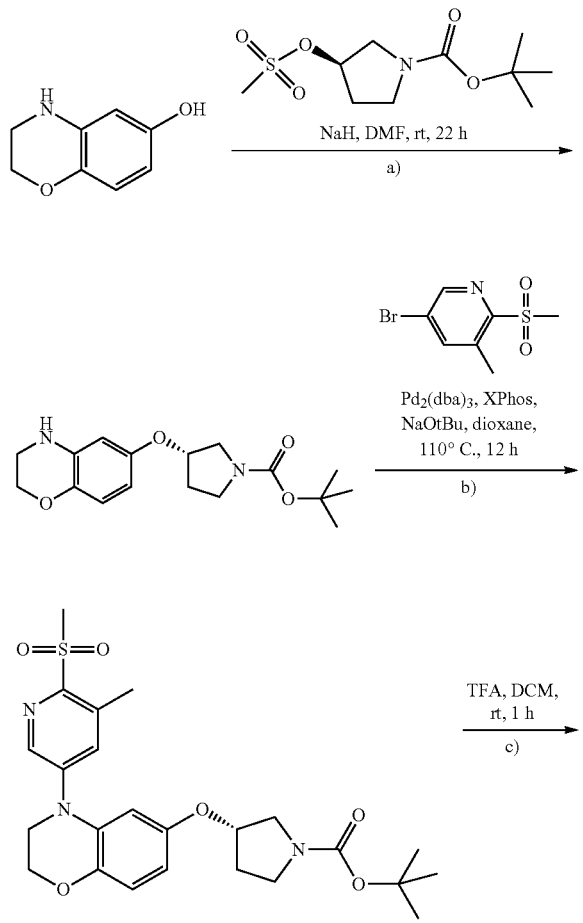

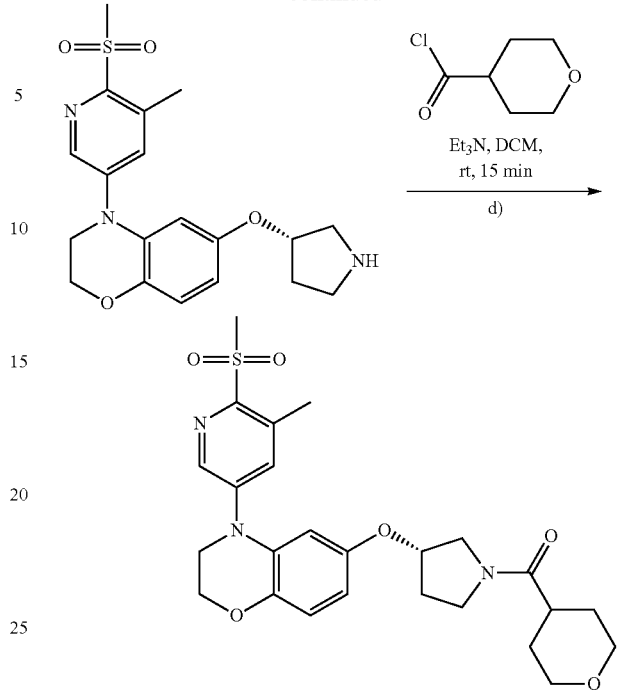

a) (S)-3-(3,4-Dihydro-2H-benzo[1,4]oxazin-6-yloxy)-pyrrolidine-1-carboxylic acid tert-butyl ester A solution of 3,4-dihydro-2H-benzo[1,4]oxazin-6-ol (CAS registry 26021-57-8) (4.0 g, 26.5 mmol) in DMF (150 ml) was treated with NaH (2.117 g, 52.9 mmol) for 20 min at 20° C. (R)-3-Methanesulfonyloxy-pyrrolidine-1-carboxylic acid tert-butyl ester (CAS registry 127423-61-4) (9.13 g, 34.4 mmol) was added. After stirring for 22 h at rt the reaction mixture was concentrated to dryness, then taken up with EtOAc, filtered through hyflo and the filtrate was washed with sat. aq. $Na_2CO_3$ solution. Combined organic layers were washed with brine, dried over $Na_2SO_4$, filtered and evaporated. The crude product was purified by flash chromatography on silica gel (cyclohexane/isopropanol 100:0 to 85:15 in 40 min) to provide the title compound as a yellow oil.

HPLC $Rt_{MS}$=1.84 min; ESIMS: 321 [(M+H)$^+$].

$^1$H NMR (400 MHz, DMSO): 6.52 (d, 1H), 6.12 (d, 1H), 6.02 (m, 1H), 5.76 (m, 1H), 4.75 (br s, 1H), 4.01-40.5 (m, 2H), 3.27-3.50 (m, 4H), 3.22-3.26 (m, 2H), 1.95-2.08 (m, 2H), 1.39 (m, 9H).

b) (S)-3-[4-(6-Methanesulfonyl-5-methyl-pyridin-3-yl)-3,4-dihydro-2H-benzo[1,4]oxazin-6-yloxy]-pyrrolidine-1-carboxylic acid tert-butyl ester A mixture of (S)-3-(3,4-dihydro-2H-benzo[1,4]oxazin-6-yloxy)-pyrrolidine-1-carboxylic acid tert-butyl ester (2.12 g, 6.62 mmol), 5-bromo-2-methanesulfonyl-3-methyl-pyridine (Intermediate IA1) (2.091 g, 7.94 mmol), NaOtBu (1.272 g, 13.23 mmol), XPhos ligand (0.158 g, 0.331 mmol) and $Pd_2(dba)_3$ (0.303 g, 0.331 mmol) in dioxane (3.5 ml) was degassed and stirred for 12 h at 110° C. Sat. aq. $NaHCO_3$ solution was added and the reaction mixture was extracted with EtOAc. Combined organic layers were washed with brine, dried over $Na_2SO_4$, filtered and evaporated. The crude product was purified by flash chromatography on silica gel (cyclohexane/EtOAc 100:0 to 50:50) to provide the title compound.

HPLC $Rt_{M14}$=1.25 min; ESIMS: 490 [(M+H)$^+$].
$^1$H NMR (400 MHz, CDCl$_3$): δ 8.33 (d, 1H), 7.43 (d, 1H), 6.86 (d, 1H), 6.59 (d, 1H), 6.47 (m, 1H), 4.69-4.73 (m, 12H), 4.23-4.28 (m, 2H), 3.73-3.78 (m, 2H), 3.41-3.58 (m, 4H), 3.34 (s, 3H), 2.69 (s, 3H), 1.96-2.17 (m, 2H), 1.46 (s, 9H).

c) 4-(6-Methanesulfonyl-5-methyl-pyridin-3-yl)-6-((S)-pyrrolidin-3-yloxy)-3,4-dihydro-2H-benzo[1,4]oxazine A solution of (S)-3-[4-(6-methanesulfonyl-5-methyl-pyridin-3-yl)-3,4-dihydro-2H-benzo[1,4]oxazin-6-yloxy]-pyrrolidine-1-carboxylic acid tert-butyl ester (1.5 g, 3.06 mmol) and TFA (0.236 ml, 3.06 mmol) in DCM (15 ml) was stirred for 1 h at rt. The reaction mixture was cooled down to 0° C., sat. Na$_2$CO$_3$ solution was added and the reaction mixture was extracted with DCM. Combined organic layers were dried over Na$_2$SO$_4$, filtered and evaporated to provide the title compound.

HPLC $Rt_{M2}$=0.66 min; ESIMS: 390 [(M+H)$^+$].
$^1$H NMR (400 MHz, CDCl$_3$): δ 8.33 (d, 1H), 7.43 (d, 1H), 6.86 (d, 1H), 6.58 (d, 1H), 6.47 (m, 1H), 4.68 (m, 1H), 4.22-4.27 (m, 2H), 3.73-3.78 (m, 2H), 3.33 (s, 3H), 3.12-3.22 (m, 2H), 2.86-3.04 (m, 2H), 2.68 (s, 3H), 1.88-2.08 (m, 2H).

d) {(S)-3-[4-(6-Methanesulfonyl-5-methyl-pyridin-3-yl)-3,4-dihydro-2H-benzo[1,4]oxazin-6-yloxy]-pyrrolidin-1-yl}-(tetrahydro-pyran-4-yl)-methanone A mixture of 4-(6-methanesulfonyl-5-methyl-pyridin-3-yl)-6-((S)-pyrrolidin-3-yloxy)-3,4-dihydro-2H-benzo[1,4]oxazine (0.085 g, 0.218 mmol), tetrahydro-2H-pyran-4-carbonyl chloride (CAS registry 40191-32-0) (0.049 mg, 0.327 mmol) and Et$_3$N (0.046 ml, 0.327 mmol) in DCM (4 ml) was stirred at rt for 15 min. The reaction mixture was concentrated to dryness. The crude product was purified by prep. RP-HPLC (column SunFire C18, H$_2$O+0.1% TFA/ACN+ 0.1% TFA 90:10 to 30:70 in 12 min) to provide the title compound as a white solid.

HPLC $Rt_{M7}$=1.62 min; ESIMS: 502 [(M+H)$^+$].
$^1$H NMR (400 MHz, DMSO): δ 8.38-8.42 (m, 1H), 7.72 (m, 1H), 6.84 (d, 1H), 6.67 (m, 1H), 6.50-6.57 (m, 1H), 4.82-4.94 (m, 1H), 4.20 (m, 2H), 3.31 (s, 3H), 3.28-3.88 (m, 10H), 2.59-2.73 (m, 1H), 2.56 (s, 3H), 1.95-2.13 (m, 2H), 1.44-1.62 (m, 4H).

Examples B2 to B122

The compounds listed in Table 2 were prepared by a procedure analogous to that used in Example B1.

TABLE 2

| Example | Compound/ Reaction Conditions | HPLC Rt [min] (method) | MS [m/z; (M + 1)$^+$] |
| --- | --- | --- | --- |
| B2 | 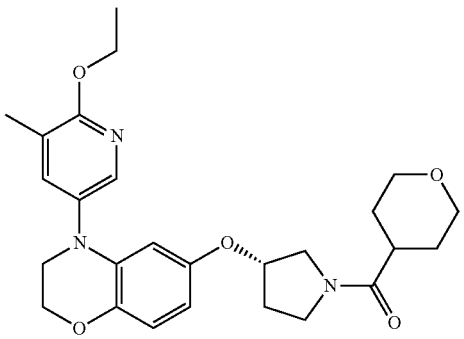<br>{(S)-3-[4-(6-Ethoxy-5-methyl-pyridin-3-yl)-3,4dihydro-2H-benzo[1,4]oxazin-6-yloxy]-pyrrolidin-1-yl}-(tetrahydro-pyran-4-yl)-methanone<br>Buchwald amination condition: CA6<br>Amide bond condition: CB6<br>Side chain introduction condition: CC2<br>Precursors used: CAS 26021-57-8, 127423-61-4, IA19, 40191-32-0 | 2.00 (M8) | 468 |

TABLE 2-continued

| Example | Compound/Reaction Conditions | HPLC Rt [min] (method) | MS [m/z; (M + 1)+] |
|---|---|---|---|
| B3 | 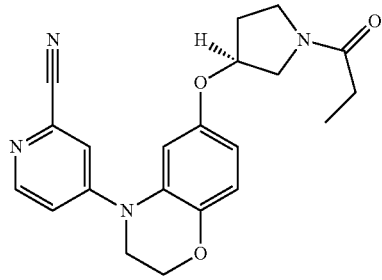<br>4-[6-((S)-1-Propionyl-pyrrolidin-3-yloxy)-2,3-dihydro-benzo[1,4]oxazin-4-yl]-pyridine-2-carbonitrile<br>Buchwald amination condition: CA12<br>Amide bond condition: CB6<br>Side chain introduction condition:<br>Precursors used: CAS 26021-57-8 ,127423-61-4, IA30, 79-03-8 | 1.53 (M8) | 379 |
| B4 | 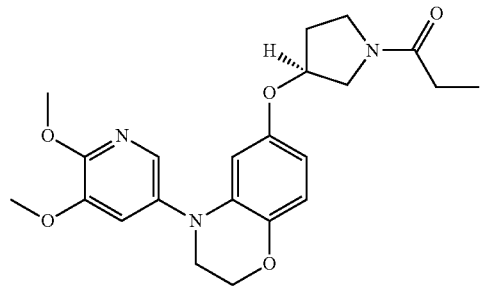<br>1-{(S)-3-[4-(5,6-Dimethoxy-pyridin-3-yl)-3,4-dihydro-2H-benzo[1,4]oxazin-6-yloxy]-pyrrolidin-1-yl}-propan-1-one<br>Buchwald amination condition: CA8<br>Amide bond condition: CB6<br>Side chain introduction condition: CC2<br>Precursors used: CAS 26021-57-8 ,127423-61-4, IA31, 79-03-8 | 1.58 (M9) | 414 |
| B5 | 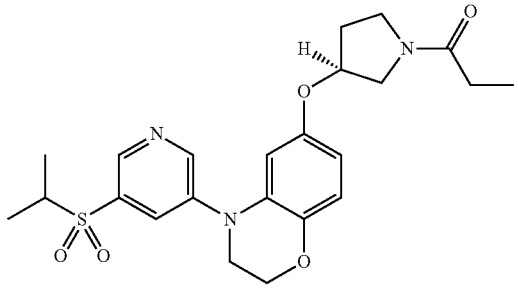<br>1-((S)-3-{4-[5-(Propane-2-sulfonyl)-pyridin-3-yl]-3,4-dihydro-2H-benzo[1,4]oxazin-6-yloxy}-pyrrolidin-1-yl)-propan-1-one<br>Buchwald amination condition: CA8<br>Amide bond condition: CB6<br>Side chain introduction condition: CC2<br>Precursors used: CAS 26021-57-8 ,127423-61-4, IA30, 79-03-8 | 2.61 (M10) | 460 |

TABLE 2-continued

| Example | Compound/Reaction Conditions | HPLC Rt [min] (method) | MS [m/z; (M + 1)+] |
|---|---|---|---|
| B6 | 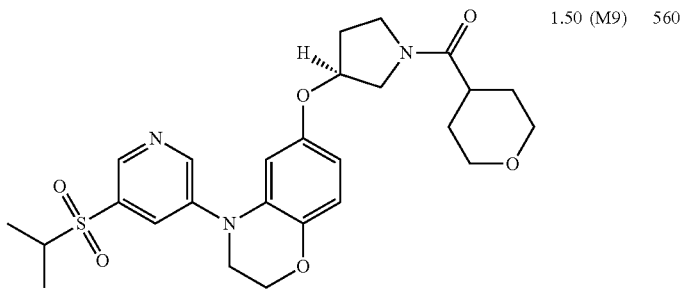((S)-3-{4-[5-(Propane-2-sulfonyl)-pyridin-3-yl]-3,4-dihydro-2H-benzo[1,4]oxazin-6-yloxy}-pyrrolidin-1-yl)-(tetrahydro-pyran-4-yl)-methanone<br>Buchwald amination condition: CA8<br>Amide bond condition: CB6<br>Side chain introduction condition: CC2<br>Precursors used: CAS 26021-57-8, 127423-61-4, IA30, 40191-32-0 | 1.50 (M9) | 560 |
| B7 | 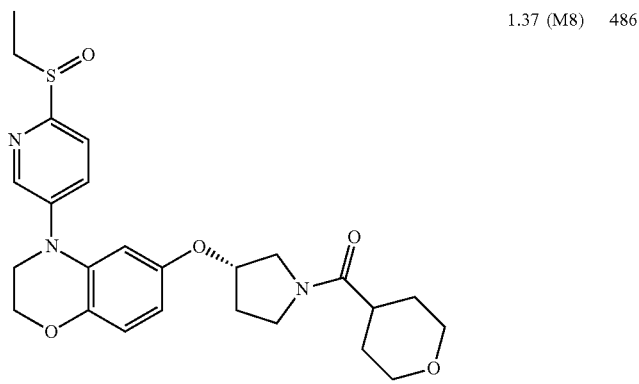{(S)-3-[4-(6-Ethanesulfinyl-pyridin-3-yl)-3,4-dihydro-2H-benzo[1,4]oxazin-6-yloxy]-pyrrolidin-1-yl}-(tetrahydro-pyran-4-yl)-methanone<br>Buchwald amination condition: CA13<br>Amide bond condition: CB6<br>Side chain introduction condition: CC2<br>Precursors used: CAS 26021-57-8, 127423-61-4, IA58, 40191-32-0 | 1.37 (M8) | 486 |

TABLE 2-continued

| Example | Compound/Reaction Conditions | HPLC Rt [min] (method) | MS [m/z; (M + 1)+] |
|---|---|---|---|
| B8 | 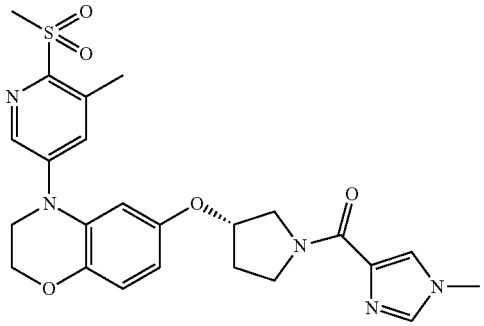<br>{(S)-3-[4-(6-Methanesulfonyl-5-methyl-pyridin-3-yl)-3,4-dihydro-2H-benzo[1,4]oxazin-6-yloxy]-pyrrolidin-1-yl}-(1-methyl-1H-imidazol-4-yl)-methanone<br>Buchwald amination condition: CA14<br>Amide bond condition: CB1<br>Side chain introduction condition: CC2<br>Precursors used: CAS 26021-57-8 ,127423-61-4, IA1, 41716-18-1 | 1.27 (M8) | 498 |
| B9 | 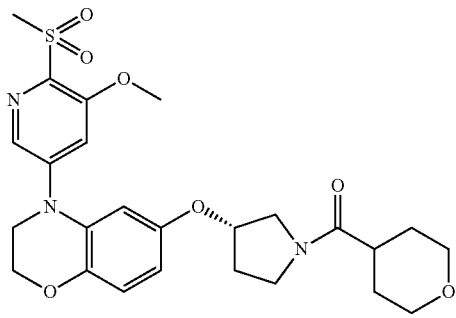<br>{(S)-3-[4-(6-Methanesulfonyl-5-methoxy-pyridin-3-yl)-3,4-dihydro-2H-benzo[1,4]oxazin-6-yloxy]-pyrrolidin-1-yl}-(tetrahydro-pyran-4-yl)-methanone<br>Buchwald amination condition: CA14<br>Amide bond condition: CB6<br>Side chain introduction condition: CC2<br>Precursors used: CAS 26021-57-8 ,127423-61-4, IA45, 40191-32-0 | 1.34 (M8) | 518 |

TABLE 2-continued

| Example | Compound/Reaction Conditions | HPLC Rt [min] (method) | MS [m/z; (M + 1)+] |
|---|---|---|---|
| B10 | 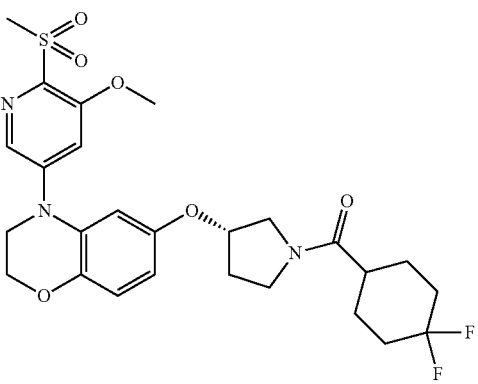 (4,4-Difluoro-cyclohexyl)-{(S)-3-[4-(6-methanesulfonyl-5-methoxy-pyridin-3-yl)-3,4-dihydro-2H-benzo[1,4]oxazin-6-yloxy]-pyrrolidin-1-yl}-methanone<br>Buchwald amination condition: CA14<br>Amide bond condition: CB6<br>Side chain introduction condition: CC2<br>Precursors used: CAS 26021-57-8, 127423-61-4, IA45, 122665-97-8 | 1.68 (M8) | 522 |
| B11 | 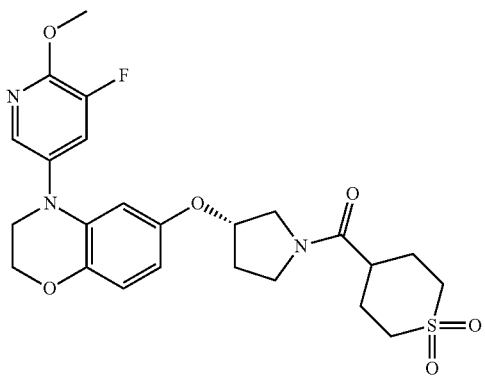 (1,1-Dioxo-hexahydro-1lambda*6*-thiopyran-4-yl)-{(S)-3-[4-(5-fluoro-6-methoxy-pyridin-3-yl)-3,4-dihydro-2H-benzo[1,4]oxazin-6-yloxy]-pyrrolidin-1-yl}-methanone<br>Buchwald amination condition: CA6<br>Amide bond condition: CB1<br>Side chain introduction condition: CC2<br>Precursors used: CAS 26021-57-8/127423-61-4/IA10/64096-87-3 | 1.67 (M8) | 506 |

TABLE 2-continued

| Example | Compound/Reaction Conditions | HPLC Rt [min] (method) | MS [m/z; (M + 1)+] |
|---|---|---|---|
| B12 | 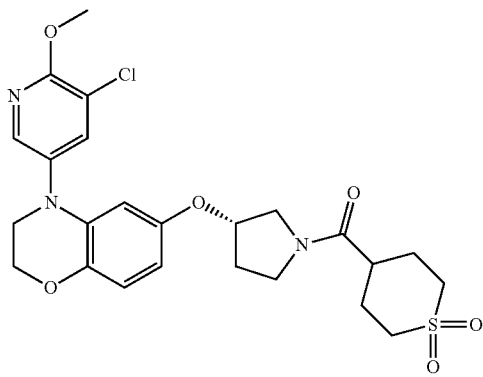<br>{(S)-3-[4-(5-Chloro-6-methoxy-pyridin-3-yl)-3,4-dihydro-2H-benzo[1,4]oxazin-6-yloxy]-pyrrolidin-1-yl}-(1,1-dioxo-hexahydro-1lambda*6*-thiopyran-4-yl)-methanone<br>Buchwald amination condition: CA6<br>Amide bond condition: CB1<br>Side chain introduction condition: CC2<br>Precursors used: CAS 26021-57-8/127423-61-4/IA11/64096-87-3 | 1.80 (M8) | 522, 524 |
| B13 | 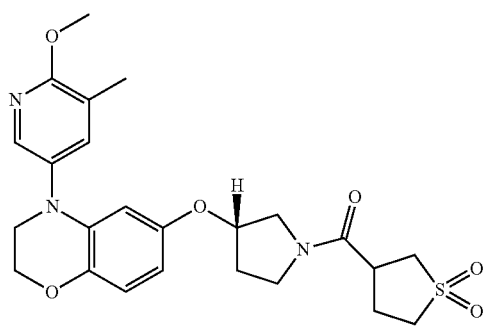<br>(1,1-Dioxo-tetrahydro-1lambda*6*-thiophen-3-yl)-{(S)-3-[4-(6-methoxy-5-methyl-pyridin-3-yl)-3,4-dihydro-2H-benzo[1,4]oxazin-6-yloxy]-pyrrolidin-1-yl}-methanone<br>Buchwald amination condition: CA16<br>Amide bond condition: CB1<br>Side chain introduction condition: CC2<br>Precursors used: CAS 26021-57-8/127423-61-4/IA9/4785-67-5 | 1.74 (M8) | 488 |

TABLE 2-continued

| Example | Compound/Reaction Conditions | HPLC Rt [min] (method) | MS [m/z; (M + 1)+] |
|---|---|---|---|
| B14 | 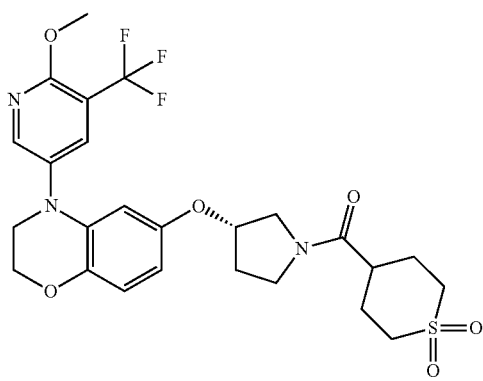<br>(1,1-Dioxo-hexahydro-1lambda*6*-thiopyran-4-yl)-{(S)-3-[4-(6-methoxy-5-trifluoromethyl-pyridin-3-yl)-3,4-dihydro-2H-benzo[1,4]oxazin-6-yloxy]-pyrrolidin-1-yl}-methanone<br>Buchwald amination condition: CA6<br>Amide bond condition: CB1<br>Side chain introduction condition: CC2<br>Precursors used: CAS 26021-57-8/127423-61-4/IA21/64096-87-3 | 1.95 (M8) | 556 |
| B15 | 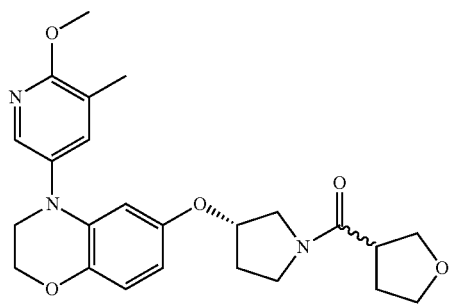<br>{(S)-3-[4-(6-Methoxy-5-methyl-pyridin-3-yl)-3,4-dihydro-2H-benzo[1,4]oxazin-6-yloxy]-pyrrolidin-1-yl}-(tetrahydro-furan-3-yl)-methanone<br>Buchwald amination condition: CA6<br>Amide bond condition: CB1<br>Side chain introduction condition: CC2<br>Precursors used: CAS 26021-57-8/127423-61-4/IA9/89364-31-8<br>Chiral separation: CD9 | 1.89 (M7) | 440 |

TABLE 2-continued

| Example | Compound/Reaction Conditions | HPLC Rt [min] (method) | MS [m/z; (M + 1)⁺] |
|---------|------------------------------|------------------------|--------------------|
| B16 | 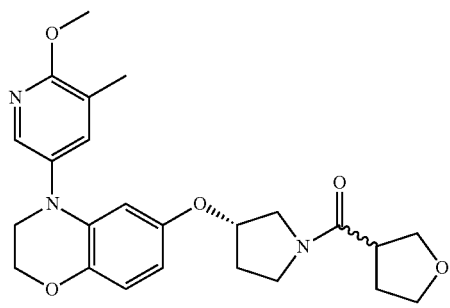{(S)-3-[4-(6-Methoxy-5-methyl-pyridin-3-yl)-3,4-dihydro-2H-benzo[1,4]oxazin-6-yloxy]-pyrollidin-1-yl}-(tetrahydro-furan-3-yl)-methanone<br>Buchwald amination condition: CA6<br>Amide bond condition: CB1<br>Side chain introduction condition: CC2<br>Precursors used: CAS 26021-57-8/127423-614/IA9/89364-31-8<br>Chiral separation: CD9 | 1.89 (M7) | 440 |
| B17 | 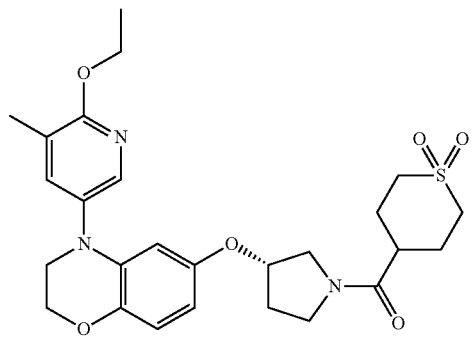(1,1-Dioxo-hexahydro-1lambda*6*-thiopyran-4-yl)-{(S)-3-[4-(6-ethoxy-5-methyl-pyridin-3-yl)-3,4-dihydro-2H-benzo[1,4]oxazin-6-yloxy]-pyrrolidin-1-yl}-methanone<br>Buchwald amination condition: CA6<br>Amide bond condition: CB7<br>Side chain introduction condition: CC2<br>Precursors used: CAS 26021-57-8/127423-61-4/IA19/64096-87-3 | 1.88 (M8) | 516 |

TABLE 2-continued

| Example | Compound/Reaction Conditions | HPLC Rt [min] (method) | MS [m/z; (M + 1)$^+$] |
|---|---|---|---|
| B18 | 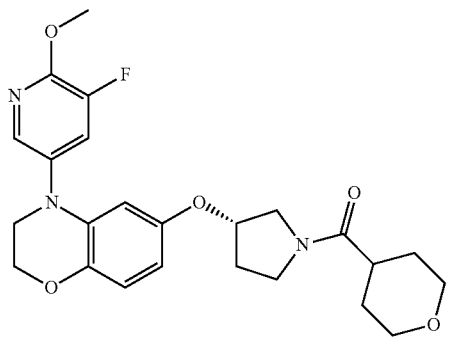<br>({(S)-3-[4-(5-Fluoro-6-methoxy-pyridin-3-yl)-3,4-dihydro-2H-benzo[1,4]oxazin-6-yloxy]-pyrrolidin-1-yl}-(tetrahydro-pyran-4-yl)-methanone<br>Buchwald amination condition: CA6<br>Amide bond condition: CB6<br>Side chain introduction condition: CC2<br>Precursors used: CAS 26021-57-8/127423-61-4/IA10/40191-32-0 | 1.86 (M7) | 458 |
| B19 | 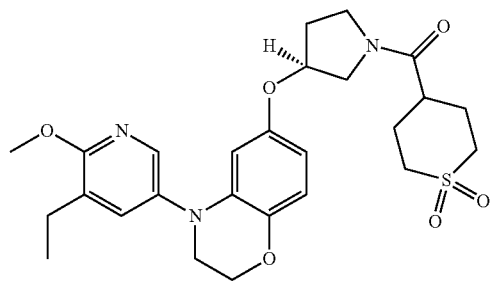<br>(1,1-Dioxo-hexahydro-1lambda*6*-thiopyran-4-yl)-{(S)-3-[4-(5-ethyl-6-methoxy-pyridin-3-yl)-3,4-dihydro-2H-benzo[1,4]oxazin-6-yloxy]-pyrrolidin-1-yl}-methanone<br>Buchwald amination condition: CA8<br>Amide bond condition: CB1<br>Side chain introduction condition: CC2<br>Precursors used: CAS 26021-57-8/127423-61-4/IA48/64096-87-3 | 1.04 (M2) | 516 |

TABLE 2-continued

| Example | Compound/Reaction Conditions | HPLC Rt [min] (method) | MS [m/z; (M + 1)+] |
|---|---|---|---|
| B20 | 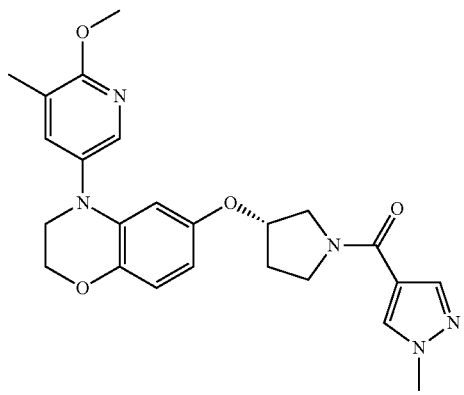<br>{(S)-3-[4-(6-Methoxy-5-methyl-pyridin-3-yl)-3,4-dihydro-2H-benzo[1,4]oxazin-6-yloxy]-pyrrolidin-1-yl}-(1-methyl-1H-pyrazol-4-yl)-methanone<br>Buchwald amination condition: CA6<br>Amide bond condition: CB4<br>Side chain introduction condition: CC2<br>Precursors used: CAS 26021-57-8/127423-61-4/IA9/5952-92-1 | 1.70 (M8) | 450 |
| B21 | 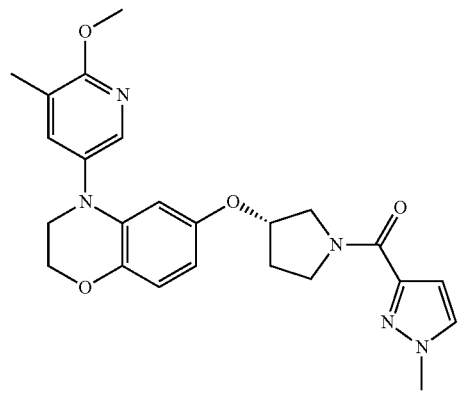<br>{(S)-3-[4-(6-Methoxy-5-methyl-pyridin-3-yl)-3,4-dihydro-2H-benzo[1,4]oxazin-6-yloxy]-pyrrolidin-1-yl}-(1-methyl-1H-pyrazol-3-yl)-methanone<br>Buchwald amination condition: CA6<br>Amide bond condition: CB4<br>Side chain introduction condition: CC2<br>Precursors used: CAS 26021-57-8/127423-61-4/IA9/25016-20-0 | 1.87 (M8) | 450 |

TABLE 2-continued

| Example | Compound/Reaction Conditions | HPLC Rt [min] (method) | MS [m/z; (M + 1)+] |
|---|---|---|---|
| B22 | 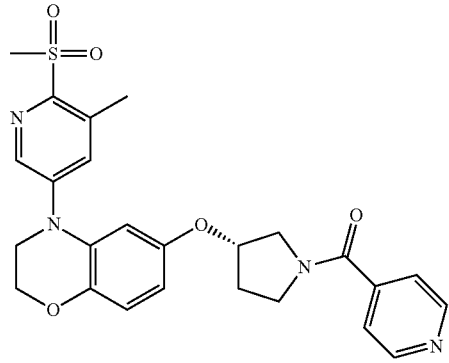<br>{(S)-3-[4-(6-Methanesulfonyl-5-methyl-pyridin-3-yl)-3,4-dihydro-2H-benzo[1,4]oxazin-6-yloxy]-pyrrolidin-1-yl}-pyridin-4-yl-methanone<br>Buchwald amination condition: CA6<br>Amide bond condition: CB4<br>Side chain introduction condition: CC2<br>Precursors used: CAS 26021-57-8/127423-61-4/IA1/55-22-1 | 0.85 (M6) | 495 |
| B23 | 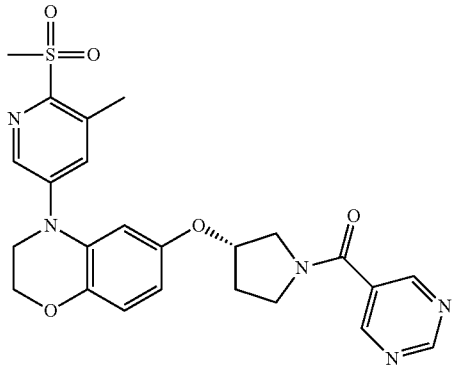<br>{(S)-3-[4-(6-Methanesulfonyl-5-methyl-pyridin-3-yl)-3,4-dihydro-2H-benzo[1,4]oxazin-6-yloxy]-pyrrolidin-1-yl}-pyrimidin-5-yl-methanone<br>Buchwald amination condition: CA6<br>Amide bond condition: CB4<br>Side chain introduction condition: CC2<br>Precursors used: CAS 26021-57-8/127423-61-4/IA1/4595-61-3 | 0.92 (M6) | 496 |

TABLE 2-continued

| Example | Compound/Reaction Conditions | HPLC Rt [min] (method) | MS [m/z; (M + 1)+] |
|---|---|---|---|
| B24 | 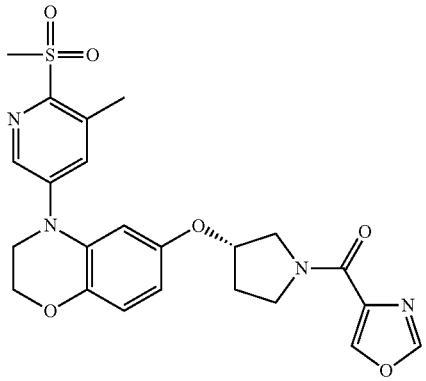<br>{(S)-3-[4-(6-Methanesulfonyl-5-methyl-pyridin-3-yl)-3,4-dihydro-2H-benzo[1,4]oxazin-6-yloxy]-pyrrolidin-1-yl}-oxazol-4-yl-methanone<br>Buchwald amination condition: CA6<br>Amide bond condition: CB4<br>Side chain introduction condition: CC2<br>Precursors used: CAS 26021-57-8/127423-61-4/IA1/23012-13-7 | 0.95 (M6) | 485 |
| B25 | 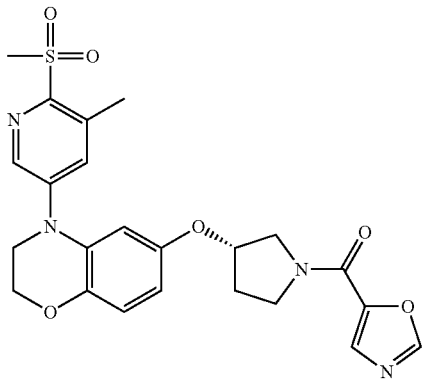<br>{(S)-3-[4-(6-Methanesulfonyl-5-methyl-pyridin-3-yl)-3,4-dihydro-2H-benzo[1,4]oxazin-6-yloxy]-pyrrolidin-1-yl}-oxazol-5-yl-methanone<br>Buchwald amination condition: CA6<br>Amide bond condition: CB4<br>Side chain introduction condition: CC2<br>Precursors used: CAS 26021-57-8/127423-61-4/IA1/118994-90-4 | 0.94 (M6) | 485 |

TABLE 2-continued

| Example | Compound/Reaction Conditions | HPLC Rt [min] (method) | MS [m/z; (M + 1)+] |
|---|---|---|---|
| B26 | 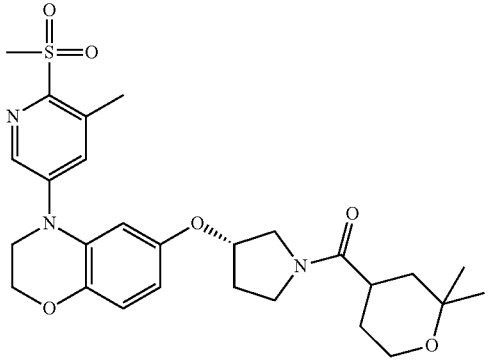<br>(2,2-Dimethyl-tetrahydro-pyran-4-yl)-{(S)-3-[4-(6-methanesulfonyl-5-methyl-pyridin-3-yl)-3,4-dihydro-2H-benzo[1,4]oxazin-6-yloxy]-pyrrolidin-1-yl}-methanone<br>Buchwald amination condition: CA6<br>Amide bond condition: CB4<br>Side chain introduction condition: CC2<br>Precursors used: CAS 26021-57-8/127423-61-4/IA1/52916-16-2 | 1.01 (M6) | 530 |
| B27 | 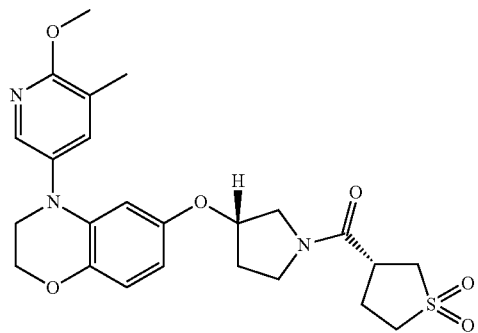<br>(1,1-Dioxo-tetrahydro-1lambda*6*-thiophen-3-yl)-{(S)-3-[4-(6-methoxy-5-methyl-pyridin-3-yl)-3,4-dihydro-2H-benzo[1,4]oxazin-6-yloxy]-pyrrolidin-1-yl}-methanone<br>Buchwald amination condition: CA6<br>Amide bond condition: CB1<br>Side chain introduction condition: CC2<br>Precursors used: CAS 26021-57-8/127423-61-4/IA9/4785-67-5<br>Chiral separation : CD8 | 1.62 (M2) | 488 |

TABLE 2-continued

| Example | Compound/Reaction Conditions | HPLC Rt [min] (method) | MS [m/z; (M + 1)+] |
|---|---|---|---|
| B28 | 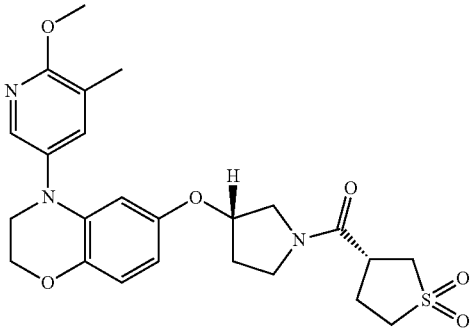<br>(1,1-Dioxo-tetrahydro-1lambda*6*-thiophen-3-yl)-{(S)-3-[4-(6-methoxy-5-methyl-pyridin-3-yl)-3,4-dihydro-2H-benzo[1,4]oxazin-6-yloxy]-pyrrolidin-1-yl}-methanone<br>Buchwald amination condition: CA6<br>Amide bond condition: CB1<br>Side chain introduction condition: CC2<br>Precursors used: CAS 26021-57-8 /127423-61-4 /IA9/4785-67-5<br>Chiral separation: CD8 | 1.62 (M2) | 488 |
| B29 | 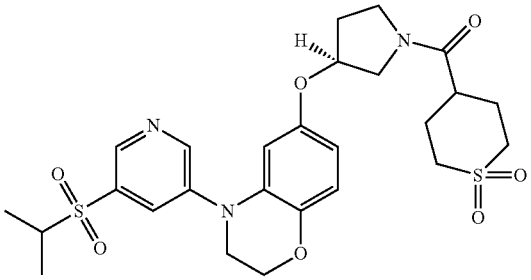<br>(1,1-Dioxo-hexahydro-1lambda*6*-thiopyran-4-yl)-((S)-3-{4-[5-(propane-2-sulfonyl)-pyridin-3-yl]-3,4-dihydro-2H-benzo[1,4]oxazin-6-yloxy}-pyrrolidin-1-yl)-methanone<br>Buchwald amination condition: CA8<br>Amide bond condition: CB5<br>Side chain introduction condition: CC2<br>Precursors used: CAS 26021-57-8/127423-61-4/IA30/64096-87-3 | 1.53 (M6) | 564 |

TABLE 2-continued

| Example | Compound/Reaction Conditions | HPLC Rt [min] (method) | MS [m/z; (M + 1)$^+$] |
|---|---|---|---|
| B30 | 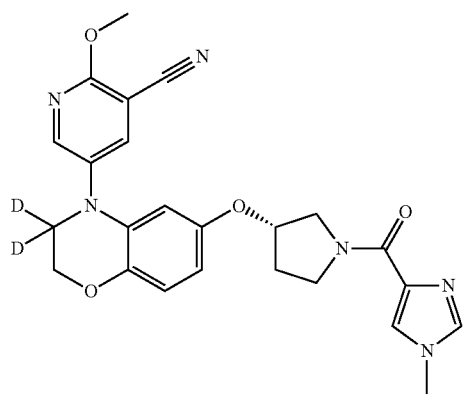

2-Methoxy-5-{6-[(S)-1-(1-methyl-1H-imidazole-4-carbonyl)-pyrrolidin-3-yloxy]-3,3-dideutero-2,3-dihydro-benzo[1,4]oxazin-4-yl}-nicotinonitrile
Buchwald amination condition: CA15
Amide bond condition: CB5
Side chain introduction condition: CC2
Precursors used: ID1, CAS 127423-61-4, IA12, CAS 41716-18-1 | 1.50 (M9) | 464 |
| B31 | 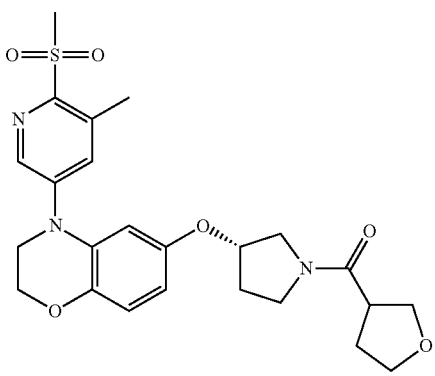

{(S)-3-[4-(6-Methanesulfonyl-5-methyl-pyridin-3-yl)-3,4-dihydro-2H-benzo[1,4]oxazin-6-yloxy]-pyrrolidin-1-yl}-(tetrahydro-furan-3-yl)-methanone
Buchwald amination condition: CA6
Amide bond condition: CB4
Side chain introduction condition: CC2
Precursors used: CAS 26021-57-8, CAS 127423-61-4, IA1, CAS 89364-31-8 | 0.94 (M6) | 488 |

TABLE 2-continued

| Example | Compound/Reaction Conditions | HPLC Rt [min] (method) | MS [m/z; (M + 1)+] |
|---|---|---|---|
| B32 | 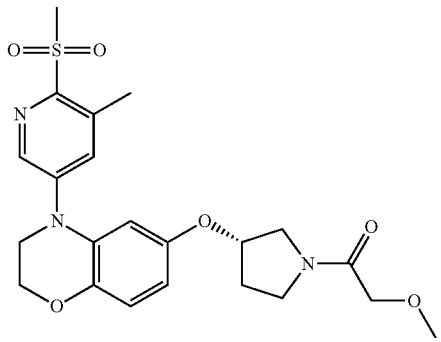<br>1-{(S)-3-[4-(6-Methanesulfonyl-5-methyl-pyridin-3-yl)-3,4-dihydro-2H-benzo[1,4]oxazin-6-yloxy]-pyrrolidin-1-yl}-2-methoxy-ethanone<br>Buchwald amination condition: CA6<br>Amide bond condition: CB4<br>Side chain introduction condition: CC2<br>Precursors used: CAS 26021-57-8, CAS 127423-61-4, IA1, CAS 625-45-6 | 0.92 (M6) | 462 |
| B33 | 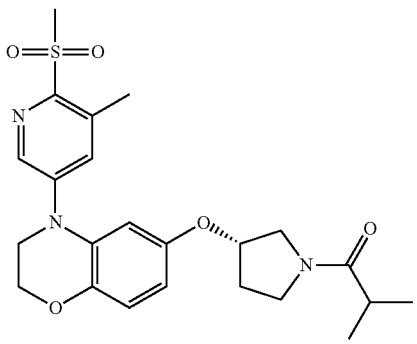<br>1-{(S)-3-[4-(6-Methanesulfonyl-5-methyl-pyridin-3-yl)-3,4-dihydro-2H-benzo[1,4]oxazin-6-yloxy]-pyrrolidin-1-yl}-2-methyl-propan-1-one<br>Buchwald amination condition: CA6<br>Amide bond condition: CB4<br>Side chain introduction condition: CC2<br>Precursors used: CAS 26021-57-8, CAS 127423-61-4, IA1, CAS 79-31-2 | 1.01 (M6) | 460 |

TABLE 2-continued

| Example | Compound/Reaction Conditions | HPLC Rt [min] (method) | MS [m/z; (M + 1)$^+$] |
|---|---|---|---|
| B34 | 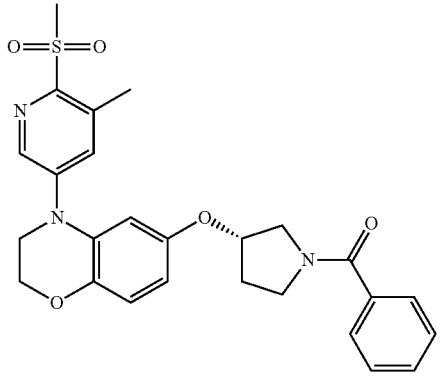<br>{(S)-3-[4-(6-Methanesulfonyl-5-methyl-pyridin-3-yl)-3,4-dihydro-2H-benzo[1,4]oxazin-6-yloxy]-pyrrolidin-1-yl}-phenyl-methanone<br>Buchwald amination condition: CA6<br>Amide bond condition: CB4<br>Side chain introduction condition: CC2<br>Precursors used: CAS 26021-57-8, CAS 127423-61-4, IA1, CAS 65-85-0 | 1.05 (M6) | 494 |
| B35 | 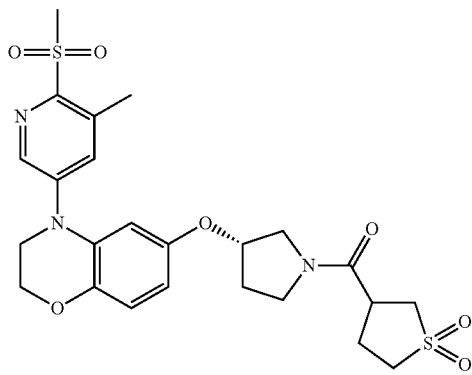<br>(1,1-Dioxo-tetrahydro-1lambda*6*-thiophen-3-yl)-{(S)-3-[4-(6-methanesulfonyl-5-methyl-pyridin-3-yl)-3,4-dihydro-2H-benzo[1,4]oxazin-6-yloxy]-pyrrolidin-1-yl}-methanone<br>Buchwald amination condition: CA6<br>Amide bond condition: CB4<br>Side chain introduction condition: CC2<br>Precursors used: CAS 26021-57-8, CAS 127423-61-4, IA1, CAS 4785-67-5 | 0.87 (M2) | 536 |

TABLE 2-continued

| Example | Compound/ Reaction Conditions | HPLC Rt [min] (method) | MS [m/z; (M + 1)+] |
|---|---|---|---|
| B36 | 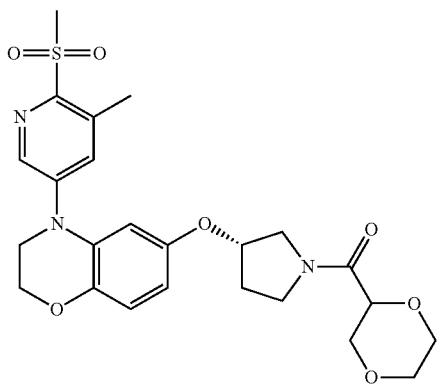[1,4]Dioxan-2-yl-{(S)-3-[4-(6-methanesulfonyl-5-methyl-pyridin-3-yl)-3,4-dihydro-2H-benzo[1,4]oxazin-6-yloxy]-pyrrolidin-1-yl}-methanone<br>Buchwald amination condition: CA6<br>Amide bond condition: CB4<br>Side chain introduction condition: CC2<br>Precursors used: CAS 26021-57-8, CAS 127423-61-4, IA1, CAS 89364-41-0 | 0.88 (M2) | 504 |
| B37 | 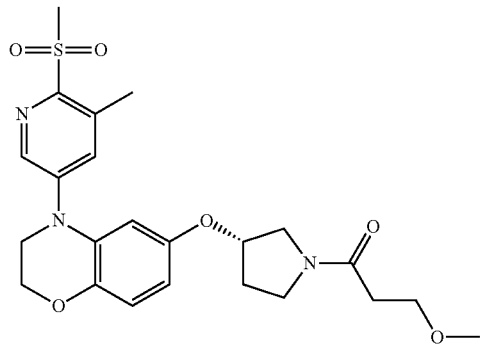1-{(S)-3-[4-(6-Methanesulfonyl-5-methyl-pyridin-3-yl)-3,4-dihydro-2H-benzo[1,4]oxazin-6-yloxy]-pyrrolidin-1-yl}-3-methoxy-propan-1-one<br>Buchwald amination condition: CA6<br>Amide bond condition: CB4<br>Side chain introduction condition: CC2<br>Precursors used: CAS 26021-57-8, CAS 127423-61-4, IA1, CAS 2544-06-1 | 0.88 (M2) | 476 |

TABLE 2-continued

| Example | Compound/Reaction Conditions | HPLC Rt [min] (method) | MS [m/z; (M + 1)+] |
|---|---|---|---|
| B38 | 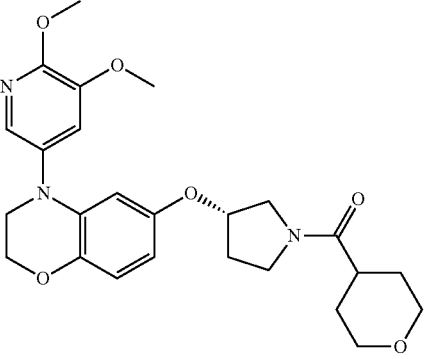 {(S)-3-[4-(5,6-Dimethoxy-pyridin-3-yl)-3,4-dihydro-2H-benzo[1,4]oxazin-6-yloxy]-pyrrolidin-1-yl}-(tetrahydro-pyran-4-yl)-methanone<br>Buchwald amination condition: CA8<br>Amide bond condition: CB6<br>Side chain introduction condition: CC2<br>Precursors used: CAS 26021-57-8, CAS 127423-61-4, IA29, acyl chloride 40191-32-0 | 0.93 (M2) | 470 |
| B39 | 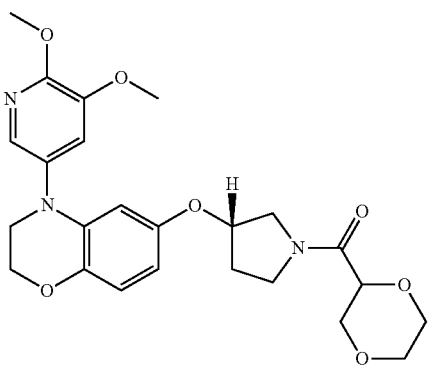 {(S)-3-[4-(5,6-Dimethoxy-pyridin-3-yl)-3,4-dihydro-2H-benzo[1,4]oxazin-6-yloxy]-pyrrolidin-1-yl}-[1,4]dioxan-2-yl-methanone<br>Buchwald amination condition: CA8<br>Amide bond condition: CB4<br>Side chain introduction condition: CC2<br>Precursors used: CAS 26021-57-8/127423-61-4/IA29/89364-41-0 | 0.91 (M2) | 472 |

TABLE 2-continued

| Example | Compound/Reaction Conditions | HPLC Rt [min] (method) | MS [m/z; (M + 1)+] |
|---|---|---|---|
| B40 | 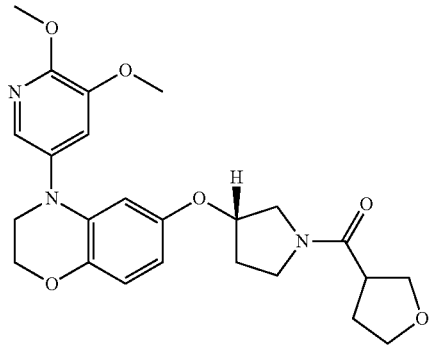{(S)-3-[4-(5,6-Dimethoxy-pyridin-3-yl)-3,4-dihydro-2H-benzo[1,4]oxazin-6-yloxy]-pyrrolidin-1-yl}-(tetrahydro-furan-3-yl)-methanone<br>Buchwald amination condition: CA8<br>Amide bond condition: CB4<br>Side chain introduction condition: CC2<br>Precursors used: CAS 26021-57-8 /127423-61-4 /IA29/89364-31-8 | 0.92 (M2) | 456 |
| B41 | 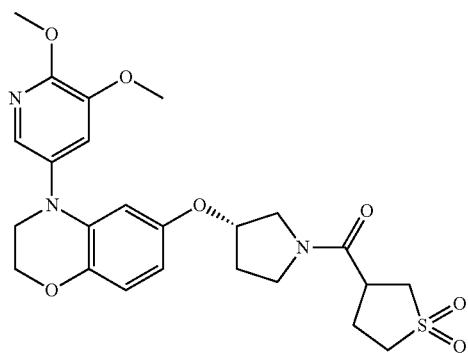{(S)-3-[4-(5,6-Dimethoxy-pyridin-3-yl)-3,4-dihydro-2H-benzo[1,4]oxazin-6-yloxy]-pyrrolidin-1-yl}-(1,1-dioxo-tetrahydro-1lambda*6*-thiophen-3-yl)-methanone<br>Buchwald amination condition: CA8<br>Amide bond condition: CB4<br>Side chain introduction condition: CC2<br>Precursors used: CAS 26021-57-8 /127423-61-4/IA29/4785-67-5 | 0.91 (M2) | 504 |

TABLE 2-continued

| Example | Compound/Reaction Conditions | HPLC Rt [min] (method) | MS [m/z; (M + 1)⁺] |
|---------|------------------------------|------------------------|---------------------|
| B42 | 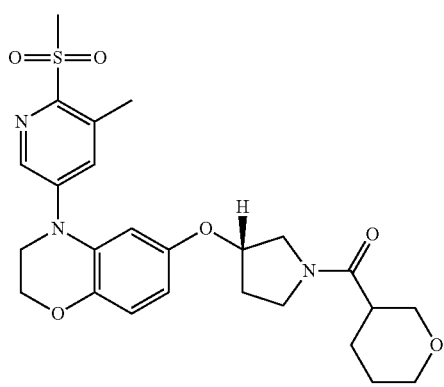<br>{(S)-3-[4-(6-Methanesulfonyl-5-methyl-pyridin-3-yl)-3,4-dihydro-2H-benzo[1,4]oxazin-6-yloxy]-pyrrolidin-1-yl}-(tetrahydro-pyran-3-yl)-methanone<br>Buchwald amination condition: CA6<br>Amide bond condition: CB4<br>Side chain introduction condition: CC2<br>Precursors used: CAS 26021-57-8 / 127423-61-4/IA1/873397-34-3 | 0.91 (M2) | 502 |
| B43 | 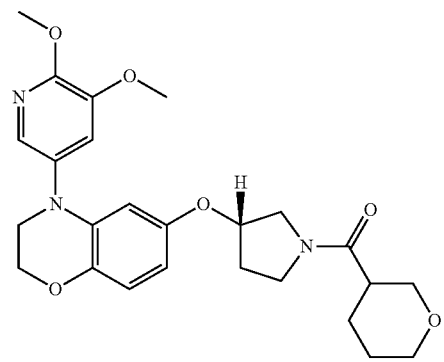<br>{(S)-3-[4-(5,6-Dimethoxy-pyridin-3-yl)-3,4-dihydro-2H-benzo[1,4]oxazin-6-yloxy]-pyrrolidin-1-yl}-(tetrahydro-pyran-3-yl)-methanone<br>Buchwald amination condition: CA8<br>Amide bond condition: CB4<br>Side chain introduction condition: CC2<br>Precursors used: CAS 26021-57-8/127423-61-4/IA29/873397-34-3 | 0.96 (M2) | 470 |

TABLE 2-continued

| Example | Compound/Reaction Conditions | HPLC Rt [min] (method) | MS [m/z; (M + 1)$^+$] |
|---|---|---|---|
| B44 | 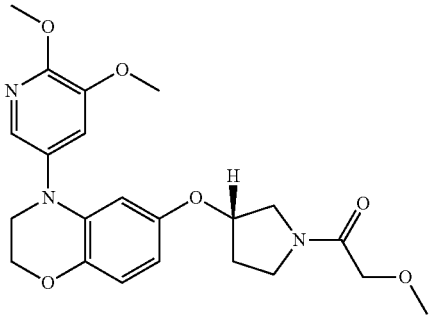<br>1-{(S)-3-[4-(5,6-Dimethoxy-pyridin-3-yl)-3,4-dihydro-2H-benzo[1,4]oxazin-6-yloxy]-pyrrolidin-1-yl}-2-methoxy-ethanone<br>Buchwald amination condition: CA8<br>Amide bond condition: CB4<br>Side chain introduction condition: CC2<br>Precursors used: CAS 26021-57-8/127423-61-4/IA29/625-45-6 | 0.90 (M2) | 430 |
| B45 | 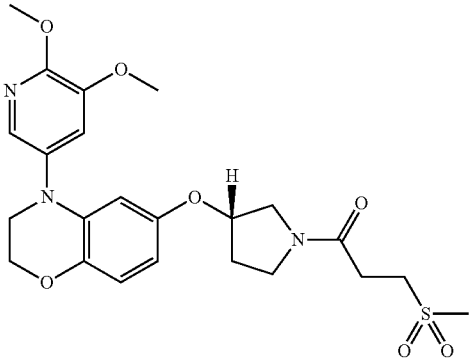<br>1-{(S)-3-[4-(5,6-Dimethoxy-pyridin-3-yl)-3,4-dihydro-2H-benzo[1,4]oxazin-6-yloxy]-pyrrolidin-1-yl}-3-methanesulfonyl-propan-1-one<br>Buchwald amination condition: CA8<br>Amide bond condition: CB4<br>Side chain introduction condition: CC2<br>Precursors used: CAS 26021-57-8/127423-61-4/IA29/645-83-0 | 0.89 (M2) | 492 |

TABLE 2-continued

| Example | Compound/Reaction Conditions | HPLC Rt [min] (method) | MS [m/z; (M + 1)$^+$] |
|---|---|---|---|
| B46 | 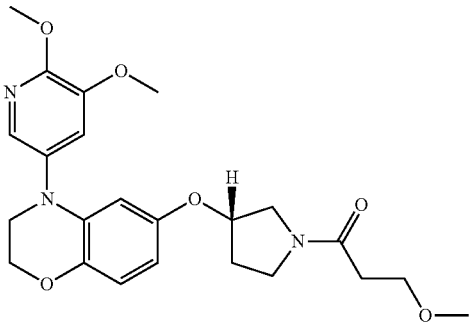  1-{(S)-3-[4-(5,6-Dimethoxy-pyridin-3-yl)-3,4-dihydro-2H-benzo[1,4]oxazin-6-yloxy]-pyrrolidin-1-yl}-3-methoxy-propan-1-one<br>Buchwald amination condition: CA8<br>Amide bond condition: CB4<br>Side chain introduction condition: CC2<br>Precursors used: CAS 26021-57-8/127423-61-4/IA29/2544-06-1 | 0.92 (M2) | 444 |
| B47 | 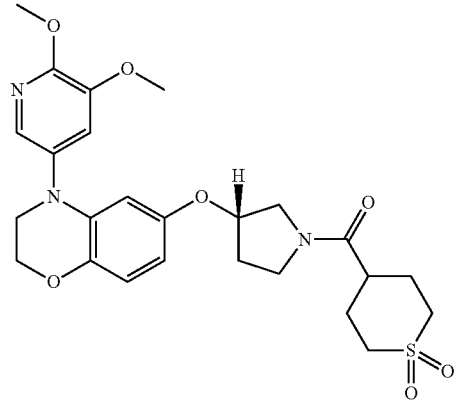  {(S)-3-[4-(5,6-Dimethoxy-pyridin-3-yl)-3,4-dihydro-2H-benzo[1,4]oxazin-6-yloxy]-pyrrolidin-1-yl}-(1,1-dioxo-hexahydro-1lambda*6*-thiopyran-4-yl)-methanone<br>Buchwald amination condition: CA8<br>Amide bond condition: CB4<br>Side chain introduction condition: CC2<br>Precursors used: CAS 26021-57-8/127423-61-4/IA29/64096-87-3 | 0.90 (M2) | 518 |

TABLE 2-continued

| Example | Compound/Reaction Conditions | HPLC Rt [min] (method) | MS [m/z; (M + 1)+] |
|---|---|---|---|
| B48 | 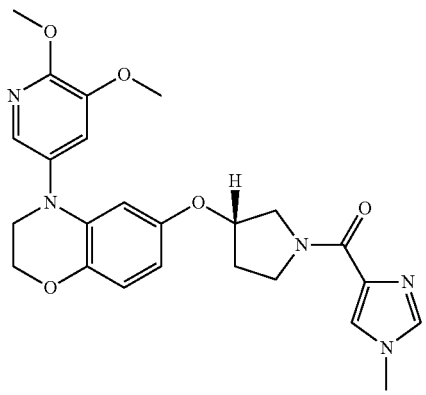<br>{(S)-3-[4-(5,6-Dimethoxy-pyridin-3-yl)-3,4-dihydro-2H-benzo[1,4]oxazin-6-yloxy]-pyrrolidin-1-yl}-(1-methyl-1H-imidazol-4-yl)-methanone<br>Buchwald amination condition: CA8<br>Amide bond condition: CB4<br>Side chain introduction condition: CC2<br>Precursors used: CAS 26021-57-8/127423-61-4/IA29/41716-18-1 | 0.85 (M2) | 466 |
| B49 | 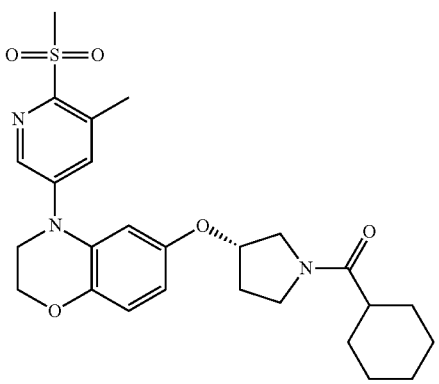<br>Cyclohexyl-{(S)-3-[4-(6-methanesulfonyl-5-methyl-pyridin-3-yl)-3,4-dihydro-2H-benzo[1,4]oxazin-6-yloxy]-pyrrolidin-1-yl}-methanone<br>Buchwald amination condition: CA6<br>Amide bond condition: CB4<br>Side chain introduction condition: CC2<br>Precursors used: CAS 26021-57-8 /127423-61-4/IA1/98-89-5 | 1.06 (M2) | 500 |

TABLE 2-continued

| Example | Compound/<br>Reaction Conditions | HPLC Rt<br>[min]<br>(method) | MS<br>[m/z;<br>$(M + 1)^+$] |
|---|---|---|---|
| B50 | 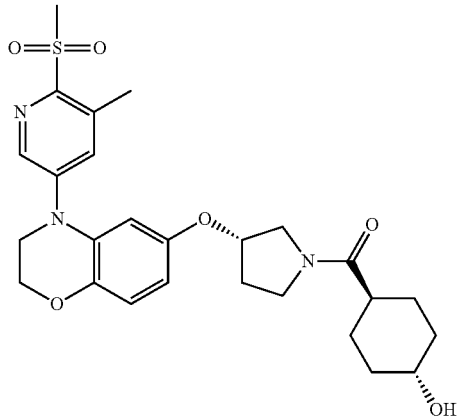<br>(4-Hydroxy-cyclohexyl)-{(S)-3-[4-(6-methanesulfonyl-5-methyl-pyridin-3-yl)-3,4-dihydro-2H-benzo[1,4]oxazin-6-yloxy]-pyrrolidin-1-yl}-methanone<br>Buchwald amination condition: CA6<br>Amide bond condition: CB1<br>Side chain introduction condition: CC2<br>Precursors used: CAS 26021-57-8/127423-61-4/IA1/3685-26-5 | 0.86 (M2) | 516 |
| B51 | 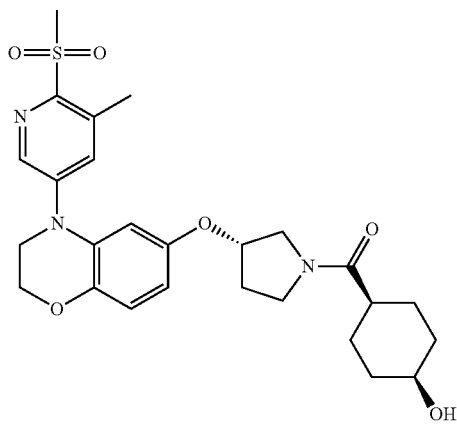<br>(4-Hydroxy-cyclohexyl)-{(S)-3-[4-(6-methanesulfonyl-5-methyl-pyridin-3-yl)-3,4-dihydro-2H-benzo[1,4]oxazin-6-yloxy]-pyrrolidin-1-yl}-methanone<br>Buchwald amination condition: CA6<br>Amide bond condition: CB1<br>Side chain introduction condition: CC2<br>Precursors used: CAS 26021-57-8/127423-61-4/IA1/3685-22-1 | 0.89 (M2) | 516 |

TABLE 2-continued

| Example | Compound/Reaction Conditions | HPLC Rt [min] (method) | MS [m/z; (M + 1)+] |
|---|---|---|---|
| B52 | 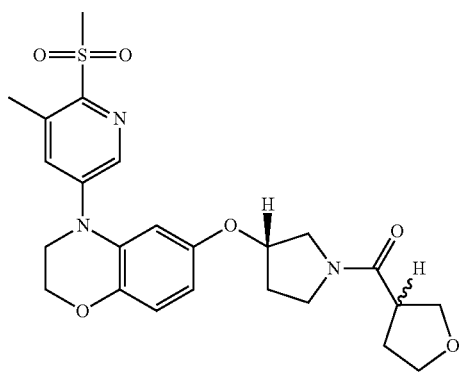<br>{(S)-3-[4-(6-Methanesulfonyl-5-methyl-pyridin-3-yl)-3,4-dihydro-2H-benzo[1,4]oxazin-6-yloxy]-pyrrolidin-1-yl}-(tetrahydro-furan-3-yl)-methanone<br>Buchwald amination condition: CA6<br>Amide bond condition: CB4<br>Side chain introduction condition: CC2<br>Precursors used: CAS 26021-57-8/127423-61-4/IA1/89364-31-8<br>Chiral separation: CD4 | 0.88 (M2)<br>15.13 (CD10) | 488 |
| B53 | 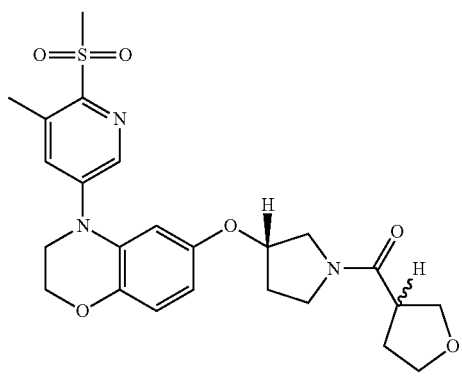<br>{(S)-3-[4-(6-Methanesulfonyl-5-methyl-pyridin-3-yl)-3,4-dihydro-2H-benzo[1,4]oxazin-6-yloxy]-pyrrolidin-1-yl}-(tetrahydro-furan-3-yl)-methanone<br>Buchwald amination condition: CA6<br>Amide bond condition: CB4<br>Side chain introduction condition: CC2<br>Precursors used: CAS 26021-57-8/127423-61-4/IA1/89364-31-8<br>Chiral separation: CD4 | 0.88 (M2)<br>18.70 (CD10) | 488 |

TABLE 2-continued

| Example | Compound/Reaction Conditions | HPLC Rt [min] (method) | MS [m/z; (M + 1)+] |
|---|---|---|---|
| B54 | {(S)-3-[4-(6-Chloro-5-methoxy-pyridin-3-yl)-3,4-dihydro-2H-benzo[1,4]oxazin-6-yloxy]-pyrrolidin-1-yl}-(tetrahydro-pyran-4-yl)-methanone<br>Buchwald amination condition: CA9<br>Amide bond condition: CB6<br>Side chain introduction condition: CC2<br>Precursors used: CAS 26021-57-8/127423-61-4/IA49/Acyl chloride: 40191-32-0 | 3.21 (M3) | 474, 476 |
| B55 | 1-{(S)-3-[4-(6-Chloro-5-methoxy-pyridin-3-yl)-3,4-dihydro-2H-benzo[1,4]oxazin-6-yloxy]-pyrrolidin-1-yl}-propan-1-one<br>Buchwald amination condition: CA9<br>Amide bond condition: CB6<br>Side chain introduction condition: CC2<br>Precursors used: CAS 26021-57-8/127423-61-4/IA49/Acyl chloride: 79-03-8 | 3.30 (M3) | 418, 420 |

TABLE 2-continued

| Example | Compound/Reaction Conditions | HPLC Rt [min] (method) | MS [m/z; (M + 1)⁺] |
|---|---|---|---|
| B56 | {(S)-3-[4-(6-Chloro-5-methoxy-pyridin-3-yl)-3,4-dihydro-2H-benzo[1,4]oxazin-6-yloxy]-pyrrolidin-1-yl}-(1,1-dioxo-hexahydro-1lambda*6*-thiopyran-4-yl)-methanone<br>Buchwald amination condition: CA9<br>Amide bond condition: CB5<br>Side chain introduction condition: CC2<br>Precursors used: CAS 26021-57-8/127423-61-4/IA49/64096-87-3 | 3.02 (M3) | 522, 524 |
| B57 | 1-{(S)-3-[4-(6-Chloro-5-methoxy-pyridin-3-yl)-3,4-dihydro-2H-benzo[1,4]oxazin-6-yloxy]-pyrrolidin-1-yl}-3-hydroxy-propan-1-one<br>Buchwald amination condition: CA9<br>Amide bond condition: CB5<br>Side chain introduction condition: CC2<br>Precursors used: CAS 26021-57-8/127423-61-4/IA49/503-66-2 | 0.88 (M2) | 434, 436 |

TABLE 2-continued

| Example | Compound/Reaction Conditions | HPLC Rt [min] (method) | MS [m/z; $(M + 1)^+$] |
|---|---|---|---|
| B58 | 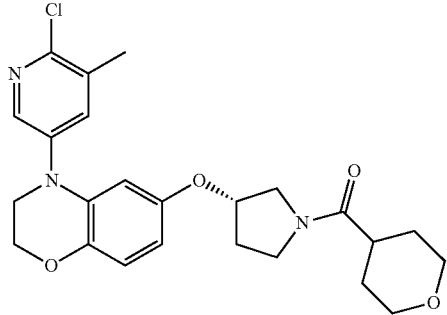<br>{(S)-3-[4-(6-Chloro-5-methyl-pyridin-3-yl)-3,4-dihydro-2H-benzo[1,4]oxazin-6-yloxy]-pyrrolidin-1-yl}-(tetrahydro-pyran-4-yl)-methanone<br>Buchwald amination condition: CA9<br>Amide bond condition: CB6<br>Side chain introduction condition: CC2<br>Precursors used: CAS 26021-57-8 /127423-61-4/IA50/Acyl chloride: 40191-32-0 | 3.36 (M3) | 458, 460 |
| B59 | 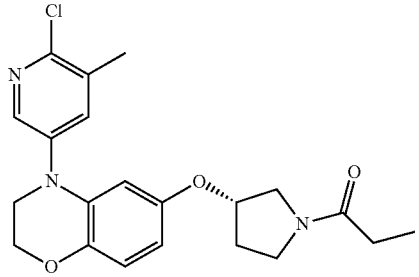<br>1-{(S)-3-[4-(6-Chloro-5-methyl-pyridin-3-yl)-3,4-dihydro-2H-benzo[1,4]oxazin-6-yloxy]-pyrrolidin-1-yl}-propan-1-one<br>Buchwald amination condition: CA9<br>Amide bond condition: CB6<br>Side chain introduction condition: CC2<br>Precursors used: CAS 26021-57-8/127423-61-4/IA50/Acyl chloride: 79-03-8 | 3.47 (M3) | 402, 404 |

| Example | Compound/ Reaction Conditions | HPLC Rt [min] (method) | MS [m/z; (M + 1)+] |
|---|---|---|---|
| B60 | 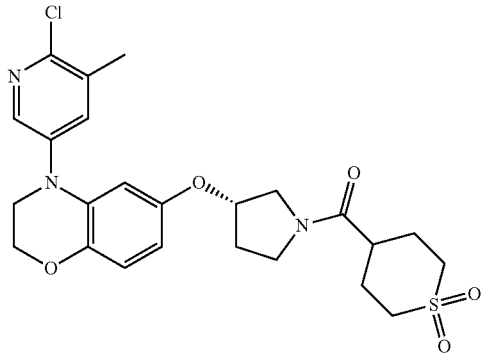<br>{(S)-3-[4-(6-Chloro-5-methyl-pyridin-3-yl)-3,4-dihydro-2H-benzo[1,4]oxazin-6-yloxy]-pyrrolidin-1-yl}-(1,1-dioxo-hexahydro-1lambda*6*-thiopyran-4-yl)-methanone<br>Buchwald amination condition: CA9<br>Amide bond condition: CB5<br>Side chain introduction condition: CC2<br>Precursors used: CAS 26021-57-8/127423-61-4/IA50/64096-87-3 | 3.17 (M3) | 506, 508 |
| B61 | 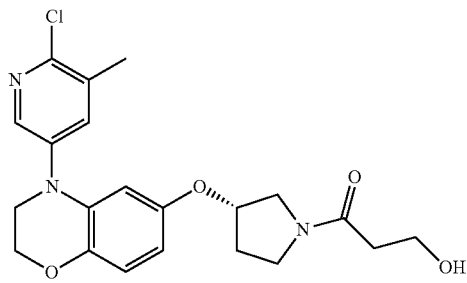<br>1-{(S)-3-[4-(6-Chloro-5-methyl-pyridin-3-yl)-3,4-dihydro-2H-benzo[1,4]oxazin-6-yloxy]-pyrrolidin-1-yl}-3-hydroxy-propan-1-one<br>Buchwald amination condition: CA9<br>Amide bond condition: CB5<br>Side chain introduction condition: CC2<br>Precursors used: CAS 26021-57-8/127423-61-4/IA50/503-66-2 | 0.91 (M2) | 418, 420 |

TABLE 2-continued

| Example | Compound/Reaction Conditions | HPLC Rt [min] (method) | MS [m/z; (M + 1)+] |
|---|---|---|---|
| B62 | 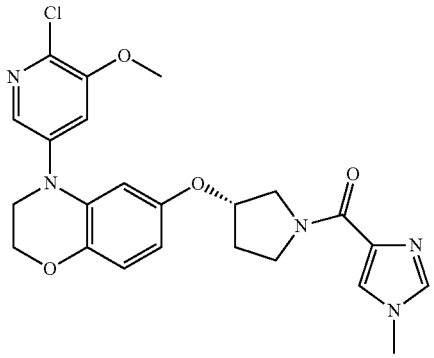<br>{(S)-3-[4-(6-Chloro-5-methoxy-pyridin-3-yl)-3,4-dihydro-2H-benzo[1,4]oxazin-6-yloxy]-pyrrolidin-1-yl}-(1-methyl-1H-imidazol-4-yl)-methanone<br>Buchwald amination condition: CA9<br>Amide bond condition: CB1<br>Side chain introduction condition: CC2<br>Precursors used: CAS 26021-57-8/127423-61-4/IA49/41716-18-1 | 2.59 (M3) | 469 |
| B63 | 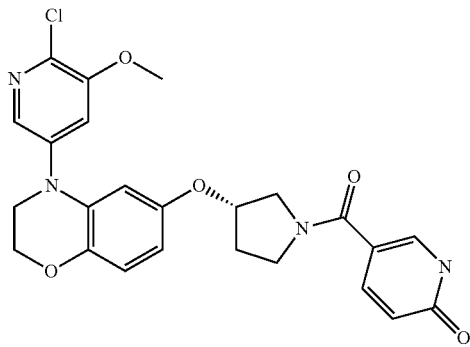<br>5-{(S)-3-[4-(6-Chloro-5-methoxy-pyridin-3-yl)-3,4-dihydro-2H-benzo[1,4]oxazin-6-yloxy]-pyrrolidine-1-carbonyl}-1H-pyridin-2-one<br>Buchwald amination condition: CA9<br>Amide bond condition: CB1<br>Side chain introduction condition: CC2<br>Precursors used: CAS 26021-57-8 /127423-61-4/IA49/5006-66-6 | 2.85 (M3) | 482, 483 |

TABLE 2-continued

| Example | Compound/Reaction Conditions | HPLC Rt [min] (method) | MS [m/z; (M + 1)+] |
|---------|------------------------------|------------------------|--------------------|
| B64 | 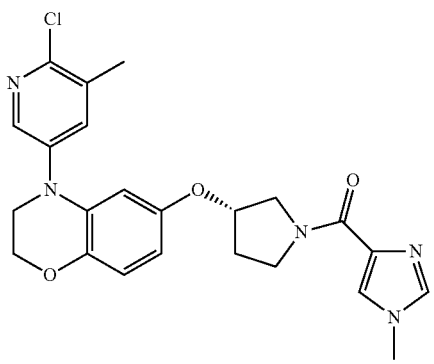{(S)-3-[4-(6-Chloro-5-methyl-pyridin-3-yl)-3,4-dihydro-2H-benzo[1,4]oxazin-6-yloxy]-pyrrolidin-1-yl}-(1-methyl-1H-imidazol-4-yl)-methanone<br>Buchwald amination condition: CA9<br>Amide bond condition: CB1<br>Side chain introduction condition: CC2<br>Precursors used: CAS 26021-57-8/127423-61-4/IA50/41716-18-1 | 2.71 (M3) | 453 |
| B65 | 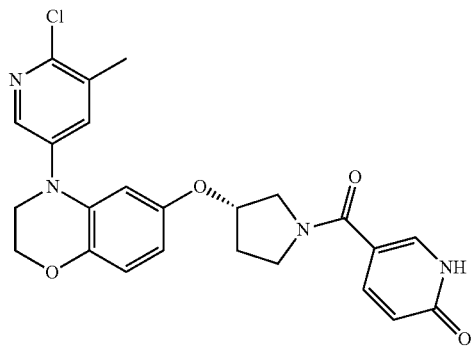5-{(S)-3-[4-(6-Chloro-5-methyl-pyridin-3-yl)-3,4-dihydro-2H-benzo[1,4]oxazin-6-yloxy]-pyrrolidine-1-carbonyl}-1H-pyridin-2-one<br>Buchwald amination condition: CA9<br>Amide bond condition: CB1<br>Side chain introduction condition: CC2<br>Precursors used: CAS 26021-57-8/127423-61-4/IA50/5006-66-6 | 2.97 (M3) | 466, 468 |

| Example | Compound/ Reaction Conditions | HPLC Rt [min] (method) | MS [m/z; (M + 1)+] |
|---|---|---|---|
| B66 | 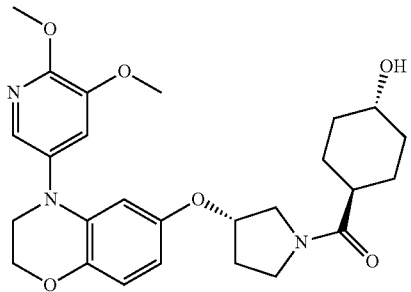 {(S)-3-[4-(5,6-Dimethoxy-pyridin-3-yl)-3,4-dihydro-2H-benzo[1,4]oxazin-6-yloxy]-pyrrolidin-1-yl}-(4-hydroxy-cyclohexyl)-methanone<br>Buchwald amination condition: CA8<br>Amide bond condition: CB4<br>Side chain introduction condition: CC2<br>Precursors used: CAS 26021-57-8/127423-61-4 /IA29/3685-26-5 | 0.88 (M2) | 484 |
| B67 | 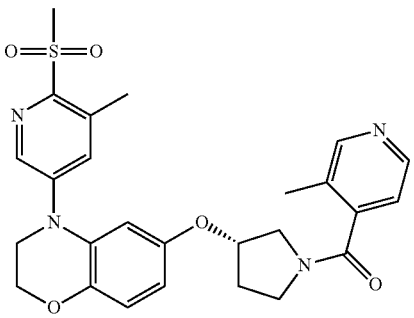 {(S)-3-[4-(6-Methanesulfonyl-5-methyl-pyridin-3-yl)-3,4-dihydro-2H-benzo[1,4]oxazin-6-yloxy]-pyrrolidin-1-yl}-(3-methyl-pyridin-4-yl)-methanone<br>Buchwald amination condition: CA6<br>Amide bond condition: CB5<br>Side chain introduction condition: CC2<br>Precursors used: CAS 26021-57-8/127423-61-4/IA1/4021-12-9 | 0.86 (M2) | 509 |

TABLE 2-continued

| Example | Compound/Reaction Conditions | HPLC Rt [min] (method) | MS [m/z; (M + 1)$^+$] |
|---|---|---|---|
| B68 | 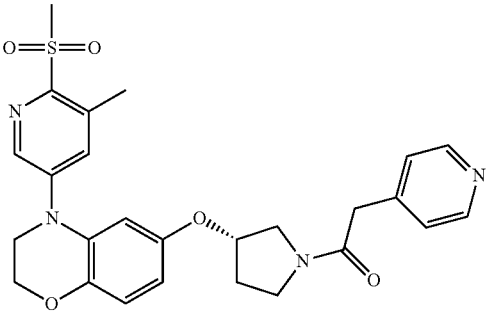<br>1-{(S)-3-[4-(6-Methanesulfonyl-5-methyl-pyridin-3-yl)-3,4-dihydro-2H-benzo[1,4]oxazin-6-yloxy]-pyrrolidin-1-yl}-2-pyridin-4-yl-ethanone<br>Buchwald amination condition: CA6<br>Amide bond condition: CB5<br>Side chain introduction condition: CC2<br>Precursors used: CAS 26021-57-8/127423-61-4/IA1/6622-91-9 | 0.77 (M2) | 509 |
| B69 | 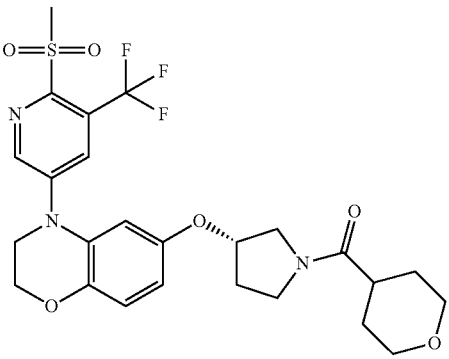<br>{(S)-3-[4-(6-Methanesulfonyl-5-trifluoromethyl-pyridin-3-yl)-3,4-dihydro-2H-benzo[1,4]oxazin-6-yloxy]-pyrrolidin-1-yl}-(tetrahydro-pyran-4-yl)-methanone<br>Buchwald amination condition: CA10<br>Amide bond condition: abbreviate: CB1<br>Side chain introduction condition: CC2<br>Precursors used: CAS 26021-57-8/127423-61-4/IA3/Acyl chloride: 40191-32-0 | 0.93 (M1) | 556 |

| Example | Compound/Reaction Conditions | HPLC Rt [min] (method) | MS [m/z; (M + 1)+] |
|---|---|---|---|
| B70 | 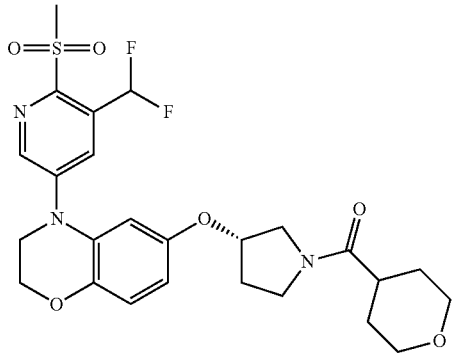<br>{(S)-3-[4-(5-Difluoromethyl-6-methanesulfonyl-pyridin-3-yl)-3,4-dihydro-2H-benzo[1,4]oxazin-6-yloxy]-pyrrolidin-1-yl}-(tetrahydro-pyran-4-yl)-methanone<br>Buchwald amination condition: CA10<br>Amide bond condition: CB1<br>Side chain introduction condition: CC2<br>Precursors used: CAS 26021-57-8/127423-61-4/IA4/Acyl chloride: 40191-32-0 | 0.91 (M1) | 538 |
| B71 | 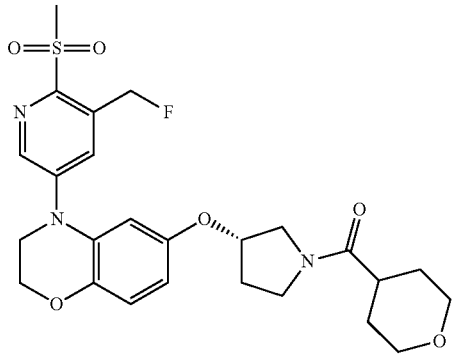<br>{(S)-3-[4-(5-Fluoromethyl-6-methanesulfonyl-pyridin-3-yl)-3,4-dihydro-2H-benzo[1,4]oxazin-6-yloxy]-pyrrolidin-1-yl}-(tetrahydro-pyran-4-yl)-methanone<br>Buchwald amination condition: CA10<br>Amide bond condition: CB1<br>Side chain introduction condition: CC2<br>Precursors used: CAS 26021-57-8/127423-61-4/IA5/Acyl chloride: 40191-32-0 | 0.88 (M1) | 520 |

TABLE 2-continued

| Example | Compound/Reaction Conditions | HPLC Rt [min] (method) | MS [m/z; (M + 1)+] |
|---|---|---|---|
| B72 | 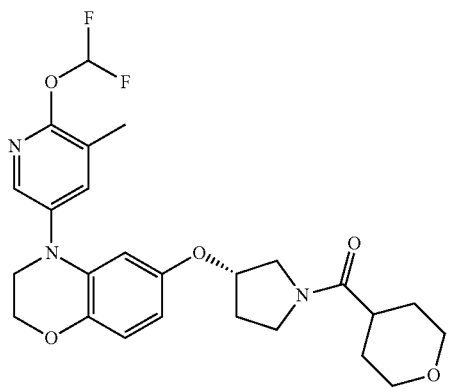<br>{(S)-3-[4-(6-Difluoromethoxy-5-methyl-pyridin-3-yl)-3,4-dihydro-2H-benzo[1,4]oxazin-6-yloxy]-pyrrolidin-1-yl)-(tetrahydro-pyran-4-yl)-methanone<br>Buchwald amination condition: CA2<br>Amide bond condition: CB6<br>Side chain introduction condition: CC4<br>Precursors used: CAS 26021-57-8/109431-87-0/IA8/Acyl chloride: 40191-32-0 | 1.07 (M1) | 490 |
| B73 | 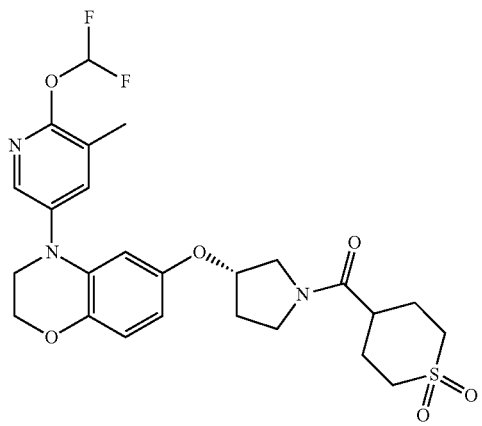<br>{(S)-3-[4-(6-Difluoromethoxy-5-methyl-pyridin-3-yl)-3,4-dihydro-2H-benzo[1,4]oxazin-6-yloxy]-pyrrolidin-1-yl}-(1,1-dioxo-hexahydro-6-thiopyran-4-yl)-methanone<br>Buchwald amination condition: CA2<br>Amide bond condition: CB3<br>Side chain introduction condition: CC4<br>Precursors used: CAS 26021-57-8/109431-87-0/IA8/64096-87-3 | 1.01 (M1) | 538 |

TABLE 2-continued

| Example | Compound/Reaction Conditions | HPLC Rt [min] (method) | MS [m/z; (M + 1)+] |
|---|---|---|---|
| B74 | 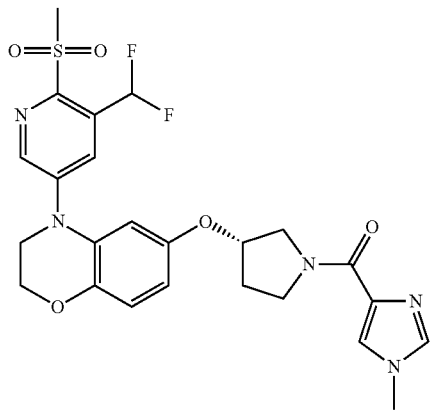<br>{(S)-3-[4-(6-Methanesulfonyl-5-methyl-pyridin-3-yl)-3,4-dihydro-2H-benzo[1,4]oxazin-6-yloxy]-pyrrolidin-1-yl}-(1-methyl-1H-imidazol-4-yl)-methanone<br>Buchwald amination condition: CA10<br>Amide bond condition: CB3<br>Side chain introduction condition: CC4<br>Precursors used: CAS 26021-57-8/109431-87-0/IA4/41716-18-1 | 0.81 (M1) | 534 |
| B75 | 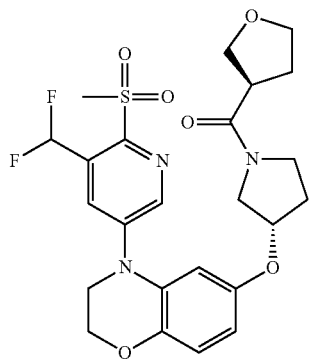<br>{(S)-3-[4-(5-Difluoromethyl-6-methanesulfonyl-pyridin-3-yl)-3,4-dihydro-2H-benzo[1,4]oxazin-6-yloxy]-pyrrolidin-1-yl}-(R)-tetrahydro-furan-3-yl-methanone Buchwald amination condition: CA10<br>Amide bond condition: CB4<br>Side chain introduction condition: CC4<br>Precursors used: CAS 26021-57-8/109431-87-0/IA4/IB1 | 0.88 (M1) | 524 |

TABLE 2-continued

| Example | Compound/Reaction Conditions | HPLC Rt [min] (method) | MS [m/z; (M + 1)+] |
|---|---|---|---|
| B76 | 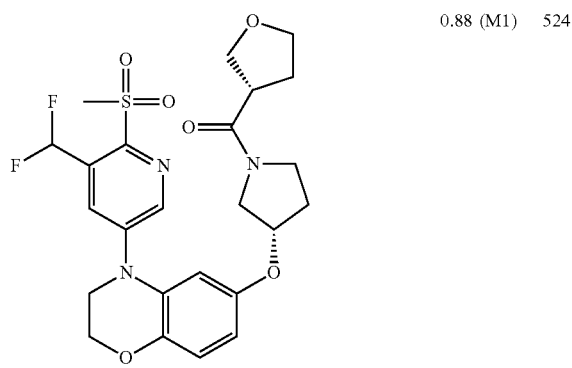<br>{(S)-3-[4-(5-Difluoromethyl-6-methanesulfonyl-pyridin-3-yl)-3,4-dihydro-2H-benzo[1,4]oxazin-6-yloxy]-pyrrolidin-1-yl}-(S)-tetrahydro-furan-3-yl-methanone<br>Buchwald amination condition: CA10<br>Amide bond condition: CB4<br>Side chain introduction condition: CC4<br>Precursors used: CAS 26021-57-8/109431-87-0/IA4/IB2 | 0.88 (M1) | 524 |
| B77 | 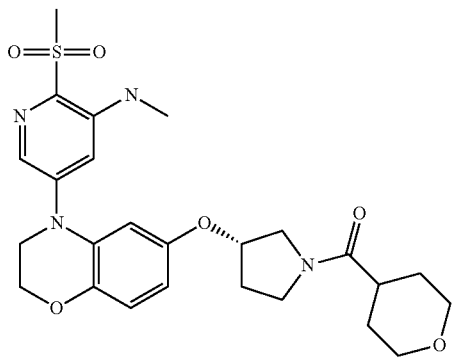<br>{(S)-3-[4-(6-Methanesulfonyl-5-methylamino-pyridin-3-yl)-3,4-dihydro-2H-benzo[1,4]oxazin-6-yloxy]-pyrrolidin-1-yl}-(tetrahydro-pyran-4-yl)-methanone<br>Buchwald amination condition: CA10<br>Amide bond condition: CB6<br>Side chain introduction condition: CC4<br>Precursors used: CAS 26021-57-8/109431-87-0/IA51/Acyl chloride: 40191-32-0 | 0.85 (M1) | 517 |

TABLE 2-continued

| Example | Compound/Reaction Conditions | HPLC Rt [min] (method) | MS [m/z; (M + 1)+] |
|---|---|---|---|
| B78 | 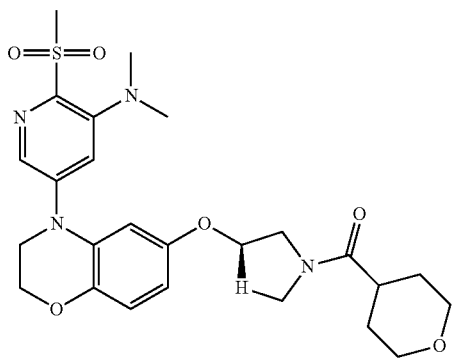<br>{(S)-3-[4-(5-Dimethylamino-6-methanesulfonyl-pyridin-3-yl)-3,4-dihydro-2H-benzo[1,4]oxazin-6-yloxy]-pyrrolidin-1-yl}-(tetrahydro-pyran-4-yl)-methanone<br>Buchwald amination condition: CA10<br>Amide bond condition: CB6<br>Side chain introduction condition: CC4<br>Precursors used: CAS 26021-57-8/109431-87-0/IA52/Acyl chloride: 40191-32-0 | 0.86 (M1) | 531 |
| B79 | 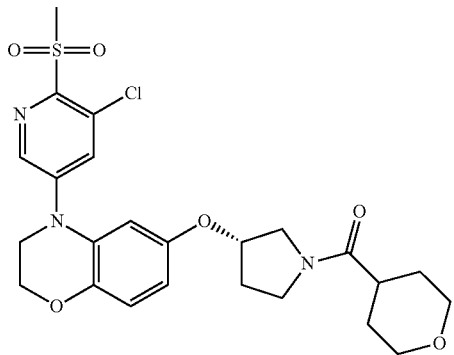<br>{(S)-3-[4-(5-Chloro-6-methanesulfonyl-pyridin-3-yl)-3,4-dihydro-2H-benzo[1,4]oxazin-6-yloxy]-pyrrolidin-1-yl}-(tetrahydro-pyran-4-yl)-methanone<br>Buchwald amination condition: CA10<br>Amide bond condition: CB6<br>Side chain introduction condition: CC2<br>Precursors used: CAS 26021-57-8, 127423-61-4, IA53, acyl chloride 40191-32-0 | 0.98 (M1) | 522 |

| Example | Compound/Reaction Conditions | HPLC Rt [min] (method) | MS [m/z; (M + 1)+] |
|---|---|---|---|
| B80 | 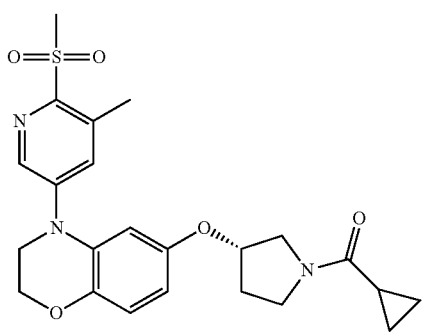<br>Cyclopropyl-{(S)-3-[4-(6-methanesulfonyl-5-methyl-pyridin-3-yl)-3,4-dihydro-2H-benzo[1,4]oxazin-6-yloxy]-pyrrolidin-1-yl}-methanone<br>Buchwald amination condition: CA4<br>Amide bond condition: CB6<br>Side chain introduction condition: CC2<br>Precursors used: CAS 26021-57-8, 127423-61-4, IA1, acyl chloride 4023-34-1 | 0.94 (M1) | 458 |
| B81 | 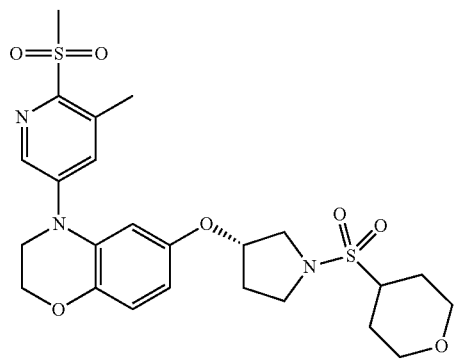<br>4-(6-Methanesulfonyl-5-methyl-pyridin-3-yl)-6-[(S)-1-(tetrahydro-pyran-4-sulfonyl)-pyrrolidin-3-yloxy]-3,4-dihydro-2H-benzo[1,4]oxazine<br>Buchwald amination condition: CA4<br>Amide bond condition: CB6<br>Side chain introduction condition: CC2<br>Precursors used: CAS 26021-57-8, 127423-61-4, IA1, sulfonyl chloride 338453-21-7 | 0.95 (M1) | 538 |

TABLE 2-continued

| Example | Compound/Reaction Conditions | HPLC Rt [min] (method) | MS [m/z; (M + 1)+] |
|---|---|---|---|
| B82 | <br>4-(6-Methanesulfonyl-5-methyl-pyridin-3-yl)-6-[(S)-1-(propane-2-sulfonyl)-pyrrolidin-3-yloxy]-3,4-dihydro-2H-benzo[1,4]oxazine<br>Buchwald amination condition: CA4<br>Amide bond condition: CB6<br>Side chain introduction condition: CC2<br>Precursors used: CAS 26021-57-8, 127423-61-4, IA1, sulfonyl chloride 10147-37-2 | 0.99 (M1) | 496 |
| B83 | 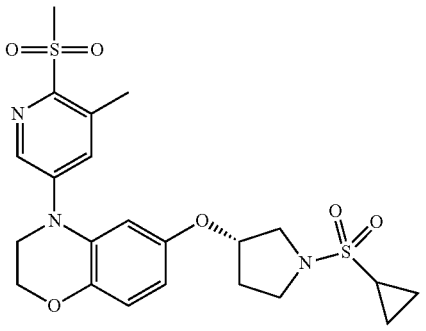<br>6-((S)-1-Cyclopropanesulfonyl-pyrrolidin-3-yloxy)-4-(6-methanesulfonyl-5-methyl-pyridin-3-yl)-3,4-dihydro-2H-benzo[1,4]oxazine<br>Buchwald amination condition: CA4<br>Amide bond condition: CB6<br>Side chain introduction condition: CC2<br>Precursors used: CAS 26021-57-8, 127423-61-4, IA1, sulfonyl chloride 139631-62-2 | 0.96 (M1) | 494 |

| Example | Compound/Reaction Conditions | HPLC Rt [min] (method) | MS [m/z; (M + 1)+] |
|---|---|---|---|
| B84 | 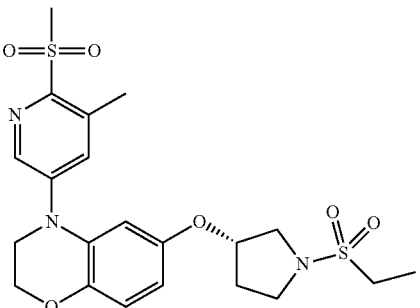<br>6-((S)-1-Ethanesulfonyl-pyrrolidin-3-yloxy)-4-(6-methanesulfonyl-5-methyl-pyridin-3-yl)-3,4-dihydro-2H-benzo[1,4]oxazine<br>Buchwald amination condition: CA4<br>Amide bond condition: CB6<br>Side chain introduction condition: CC2<br>Precursors used: CAS 26021-57-8, 127423-61-4, IA1, sulfonyl chloride 594-44-5 | 0.94 (M1) | 482 |
| B85 | 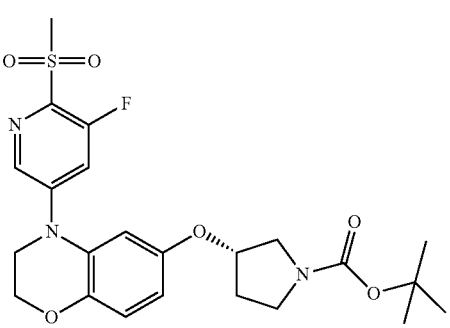<br>(S)-3-[4-(5-Fluoro-6-methanesulfonyl-pyridin-3-yl)-3,4-dihydro-2H-benzo[1,4]oxazin-6-yloxy]-pyrrolidine-1-carboxylic acid tert-butyl ester<br>Buchwald amination condition: CA10<br>Side chain introduction condition: CC2<br>Precursors used: CAS 26021-57-8, 127423-61-4, IA2 | 1.08 (M1) | 494 |

TABLE 2-continued

| Example | Compound/Reaction Conditions | HPLC Rt [min] (method) | MS [m/z; (M + 1)+] |
|---|---|---|---|
| B86 | 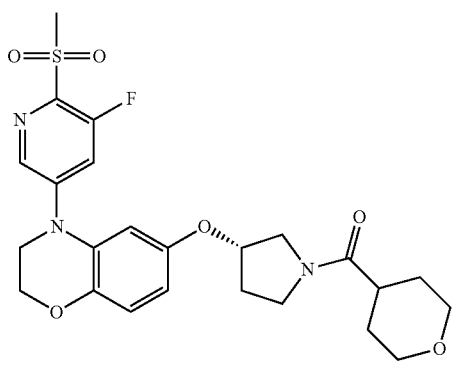 {(S)-3-[4-(5-Fluoro-6-methanesulfonyl-pyridin-3-yl)-3,4-dihydro-2H-benzo[1,4]oxazin-6-yloxy]-pyrrolidin-1-yl}-(tetrahydro-pyran-4-yl)-methanone<br>Buchwald amination condition: CA10<br>Amide bond condition: CB6<br>Side chain introduction condition: CC2<br>Precursors used: CAS 26021-57-8, 127423-61-4, IA2, acyl chloride 40191-32-0<br>BOC cleavage with HCl in dioxane instead of TFA | 0.80 (M1) | 506 |
| B87 | 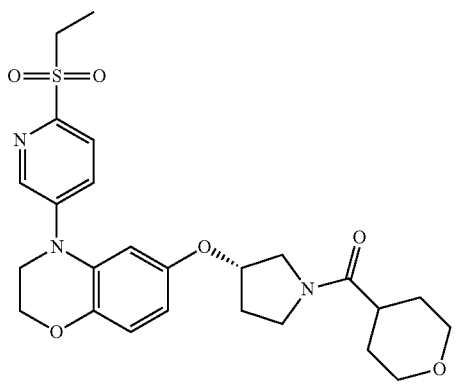 {(S)-3-[4-(6-Ethanesulfonyl-pyridin-3-yl)-3,4-dihydro-2H-benzo[1,4]oxazin-6-yloxy]-pyrrolidin-1-yl}-(tetrahydro-pyran-4-yl)-methanone<br>Buchwald amination condition: CA13<br>Amide bond condition: CB6<br>Side chain introduction condition: CC2<br>Precursors used: CAS 26021-57-8, 127423-61-4, IA58, acyl chloride 40191-32-0 | 1.57 (M7) | 502 |

TABLE 2-continued

| Example | Compound/Reaction Conditions | HPLC Rt [min] (method) | MS [m/z; (M + 1)+] |
|---|---|---|---|
| B88 | 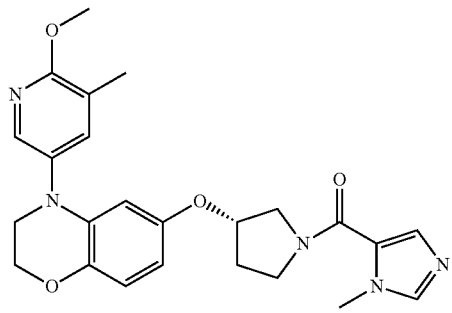 {(S)-3-[4-(6-Methoxy-5-methyl-pyridin-3-yl)-3,4-dihydro-2H-benzo[1,4]oxazin-6-yloxy]-pyrrolidin-1-yl}-(3-methyl-3H-imidazol-4-yl)-methanone<br>Buchwald amination condition: CA6<br>Amide bond condition: CB1<br>Side chain introduction condition: CC2<br>Precursors used: CAS 26021-57-8, 127423-61-4, IA9, 41806-40-0 | 1.45 (M8) | 450 |
| B89 | 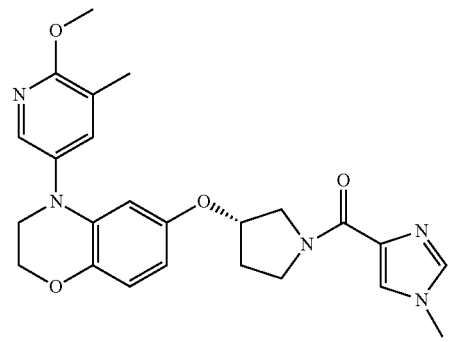 {(S)-3-[4-(6-Methoxy-5-methyl-pyridin-3-yl)-3,4-dihydro-2H-benzo[1,4]oxazin-6-yloxy]-pyrrolidin-1-yl}-(1-methyl-1H-imidazol-4-yl)-methanone<br>Buchwald amination condition: CA6<br>Amide bond condition: CB1<br>Side chain introduction condition: CC2<br>Precursors used: CAS 26021-57-8, 127423-61-4, IA9, 41716-18-1 | 1.52 (M8) | 450 |

TABLE 2-continued

| Example | Compound/Reaction Conditions | HPLC Rt [min] (method) | MS [m/z; (M + 1)+] |
|---|---|---|---|
| B90 | 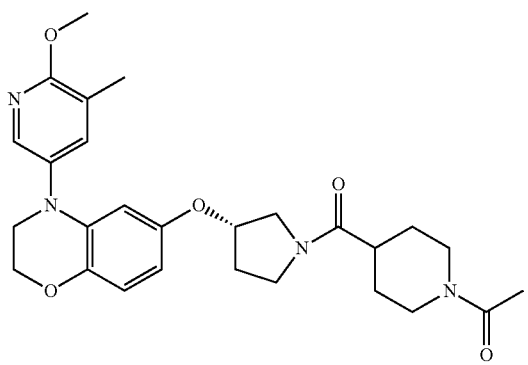<br>1-(4-{(S)-3-[4-(6-Methoxy-5-methyl-pyridin-3-yl)-3,4-dihydro-2H-benzo[1,4]oxazin-6-yloxy]-pyrrolidine-1-carbonyl}-piperidin-1-yl)-ethanone<br>Buchwald amination condition: CA6<br>Amide bond condition: CB1<br>Side chain introduction condition: CC2<br>Precursors used: CAS 26021-57-8, 127423-61-4, IA9, 25503-90-6 | 1.69 (M8) | 495 |
| B91 | 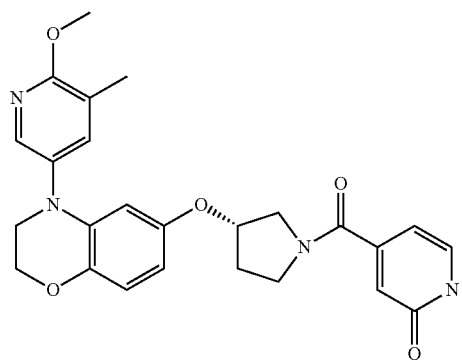<br>4-{(S)-3-[4-(6-Methoxy-5-methyl-pyridin-3-yl)-3,4-dihydro-2H-benzo[1,4]oxazin-6-yloxy]-pyrrolidine-1-carbonyl}-1H-pyridin-2-one<br>Buchwald amination condition: CA6<br>Amide bond condition: CB1<br>Side chain introduction condition: CC2<br>Precursors used: CAS 26021-57-8, 127423-61-4, IA9, 22282-72-0 | 1.53 (M8) | 463 |

TABLE 2-continued

| Example | Compound/Reaction Conditions | HPLC Rt [min] (method) | MS [m/z; (M + 1)+] |
|---|---|---|---|
| B92 | 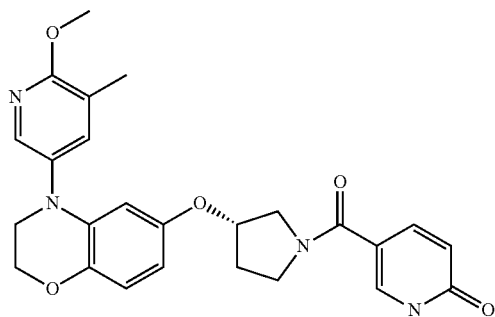<br>5-{(S)-3-[4-(6-Methoxy-5-methyl-pyridin-3-yl)-3,4-dihydro-2H-benzo[1,4]oxazin-6-yloxy]-pyrrolidine-1-carbonyl}-1H-pyridin-2-one<br>Buchwald amination condition: CA6<br>Amide bond condition: CB1<br>Side chain introduction condition: CC2<br>Precursors used: CAS 26021-57-8, 127423-61-4, IA9, 5006-66-6? | 1.54 (M8) | 463 |
| B93 | 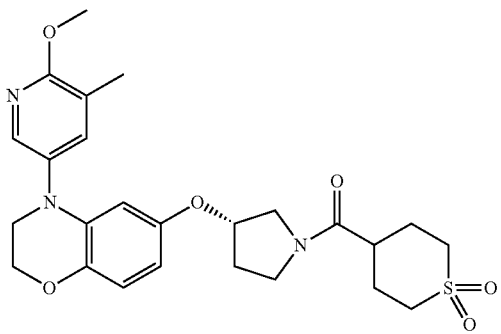<br>(1,1-Dioxo-hexahydro-1lambda*6*-thiopyran-4-yl)-{(S)-3-[4-(6-methoxy-5-methyl-pyridin-3-yl)-3,4-dihydro-2H-benzo[1,4]oxazin-6-yloxy]-pyrrolidin-1-yl}-methanone<br>Buchwald amination condition: CA6<br>Amide bond condition: CB1<br>Side chain introduction condition: CC2<br>Precursors used: CAS 26021-57-8, 127423-61-4, IA9, 64096-87-3 | 1.71 (M8) | 502 |

TABLE 2-continued

| Example | Compound/Reaction Conditions | HPLC Rt [min] (method) | MS [m/z; (M + 1)+] |
|---|---|---|---|
| B94 | 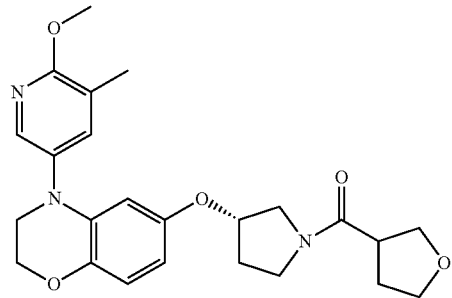<br>{(S)-3-[4-(6-Methoxy-5-methyl-pyridin-3-yl)-3,4-dihydro-2H-benzo[1,4]oxazin-6-yloxy]-pyrrolidin-1-yl}-(tetrahydro-furan-3-yl)-methanone<br>Buchwald amination condition: CA6<br>Amide bond condition: CB1<br>Side chain introduction condition: CC2<br>Precursors used: CAS 26021-57-8, 127423-61-4, IA9, 89364-31-8 | 1.88 (M8) | 440 |
| B95 | 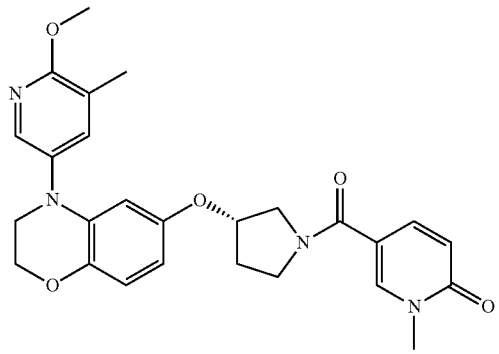<br>5-{(S)-3-[4-(6-Methoxy-5-methyl-pyridin-3-yl)-3,4-dihydro-2H-benzo[1,4]oxazin-6-yloxy]-pyrrolidine-1-carbonyl}-1-methyl-1H-pyridin-2-one<br>Buchwald amination condition: CA6<br>Amide bond condition: CB1<br>Side chain introduction condition: CC2<br>Precursors used: CAS 26021-57-8, 127423-61-4, IA9, 3719-45-7 | 1.59 (M8) | 477 |

TABLE 2-continued

| Example | Compound/Reaction Conditions | HPLC Rt [min] (method) | MS [m/z; (M + 1)+] |
|---|---|---|---|
| B96 | 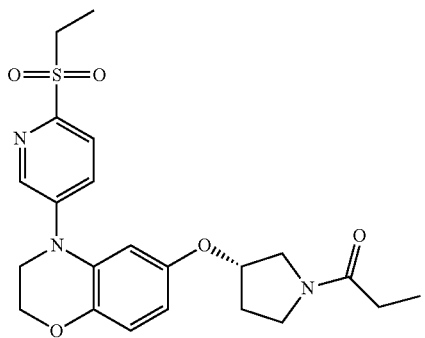<br>1-{(S)-3-[4-(6-Ethanesulfonyl-pyridin-3-yl)-3,4-dihydro-2H-benzo[1,4]oxazin-6-yloxy]-pyrrolidin-1-yl}-propan-1-one<br>Buchwald amination condition: CA13<br>Amide bond condition: CB6<br>Side chain introduction condition: CC2<br>Precursors used: CAS 26021-57-8, 127423-61-4, IA58, acyl chloride 79-03-8 | 1.50 (M7) | 446 |
| B97 | 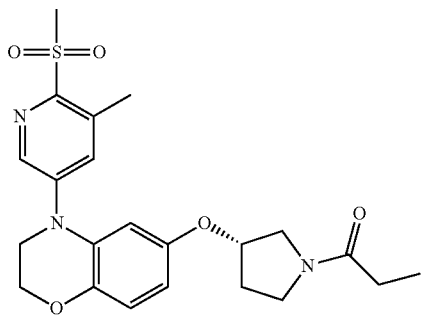<br>1-{(S)-3-[4-(6-Methanesulfonyl-5-methyl-pyridin-3-yl)-3,4-dihydro-2H-benzo[1,4]oxazin-6-yloxy]-pyrrolidin-1-yl}-propan-1-one<br>Buchwald amination condition: CA6<br>Amide bond condition: CB6<br>Side chain introduction condition: CC2<br>Precursors used: CAS 26021-57-8, 127423-61-4, IA1, acyl chloride 79-03-8 | 1.53 (M8) | 446 |

TABLE 2-continued

| Example | Compound/Reaction Conditions | HPLC Rt [min] (method) | MS [m/z; (M + 1)+] |
|---|---|---|---|
| B98 | 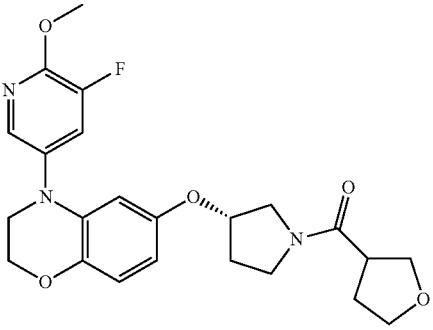<br>{(S)-3-[4-(5-Fluoro-6-methoxy-pyridin-3-yl)-3,4-dihydro-2H-benzo[1,4]oxazin-6-yloxy]-pyrrolidin-1-yl}-(tetrahydro-furan-3-yl)-methanone<br>Buchwald amination condition: CA6<br>Amide bond condition: CB5<br>Side chain introduction condition: CC2<br>Precursors used: CAS 26021-57-8/127423-61-4/IA10/89364-31-8 | 1.83 (M7) | 444 |
| B99 | 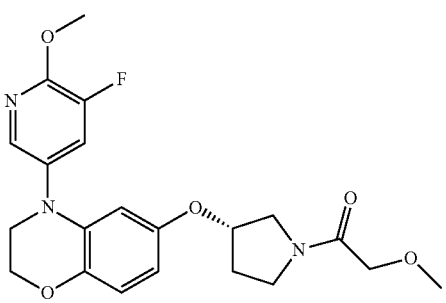<br>1-{(S)-3-[4-(5-Fluoro-6-methoxy-pyridin-3-yl)-3,4-dihydro-2H-benzo[1,4]oxazin-6-yloxy]-pyrrolidin-1-yl}-2-methoxy-ethanone<br>Buchwald amination condition: CA6<br>Amide bond condition: CB5<br>Side chain introduction condition: CC2<br>Precursors used: CAS 26021-57-8/127423-61-4/IA10/625-45-6 | 1.77 (M7) | 418 |

TABLE 2-continued

| Example | Compound/Reaction Conditions | HPLC Rt [min] (method) | MS [m/z; (M + 1)+] |
|---------|------------------------------|------------------------|---------------------|
| B100 | 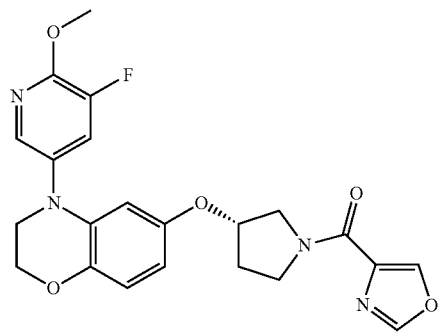<br>{(S)-3-[4-(5-Fluoro-6-methoxy-pyridin-3-yl)-3,4-dihydro-2H-benzo[1,4]oxazin-6-yloxy]-pyrrolidin-1-yl}-oxazol-4-yl-methanone<br>Buchwald amination condition: CA6<br>Amide bond condition: CB5<br>Side chain introduction condition: CC2<br>Precursors used: CAS 26021-57-8 / 127423-61-4/IA10/23012-13-7 | 1.87 (M7) | 441 |
| B101 | 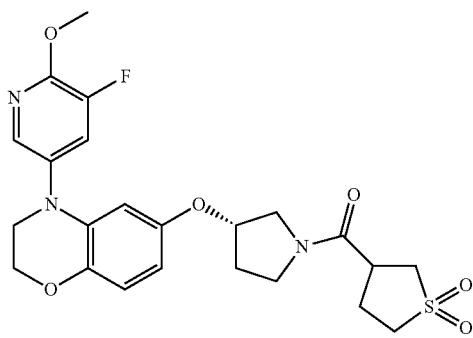<br>(1,1-Dioxo-tetrahydro-1lambda*6*-thiophen-3-yl)-{(S)-3-[4-(5-fluoro-6-methoxy-pyridin-3-yl)-3,4-dihydro-2H-benzo[1,4]oxazin-6-yloxy]-pyrrolidin-1-yl}-methanone<br>Buchwald amination condition: CA6<br>Amide bond condition: CB5<br>Side chain introduction condition: CC2<br>Precursors used: CAS 26021-57-8/127423-61-4/IA10/4785-67-5 | 1.81 (M7) | 492 |

TABLE 2-continued

| Example | Compound/<br>Reaction Conditions | HPLC Rt<br>[min]<br>(method) | MS<br>[m/z;<br>(M + 1)+] |
|---|---|---|---|
| B102 | 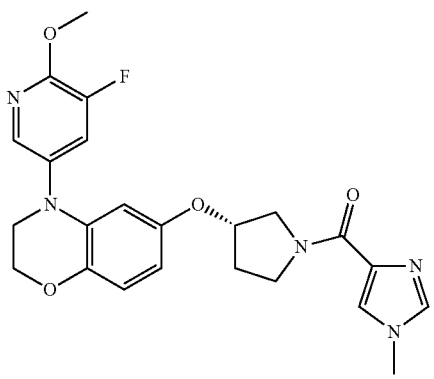<br>{(S)-3-[4-(5-Fluoro-6-methoxy-pyridin-3-yl)-3,4-<br>dihydro-2H-benzo[1,4]oxazin-6-yloxy]-pyrrolidin-<br>1-yl}-(1-methyl-1H-imidazol-4-yl)-methanone<br>Buchwald amination condition: CA6<br>Amide bond condition: CB5<br>Side chain introduction condition: CC2<br>Precursors used: CAS 26021-57-8/127423-61-<br>4/IA10/41716-18-1 | 1.48 (M7) | 453 |
| B103 | 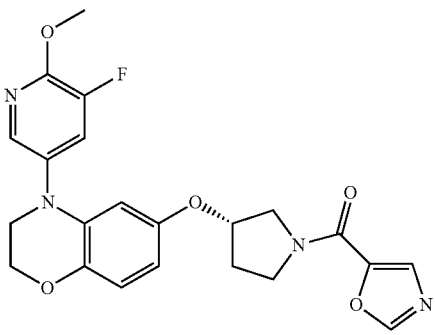<br>{(S)-3-[4-(5-Fluoro-6-methoxy-pyridin-3-yl)-3,4-<br>dihydro-2H-benzo[1,4]oxazin-6-yloxy]-pyrrolidin-<br>1-yl}-oxazol-5-yl-methanone<br>Buchwald amination condition: CA6<br>Amide bond condition: CB5<br>Side chain introduction condition: CC2<br>Precursors used: CAS 26021-57-8/127423-61-<br>4/IA10/118994-90-4 | 1.80 (M7) | 441 |

TABLE 2-continued

| Example | Compound/Reaction Conditions | HPLC Rt [min] (method) | MS [m/z; (M + 1)+] |
|---|---|---|---|
| B104 | 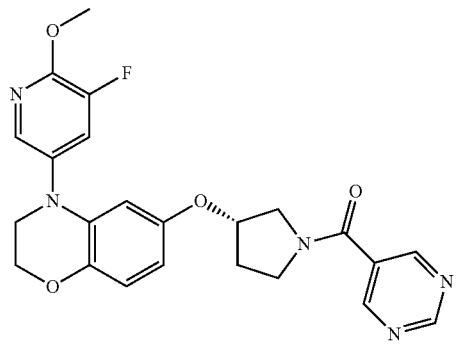 {(S)-3-[4-(5-Fluoro-6-methoxy-pyridin-3-yl)-3,4-dihydro-2H-benzo[1,4]oxazin-6-yloxy]-pyrrolidin-1-yl}-pyrimidin-5-yl-methanone<br>Buchwald amination condition: CA6<br>Amide bond condition: CB5<br>Side chain introduction condition: CC2<br>Precursors used: CAS 26021-57-8/127423-61-4/IA10/4595-61-3 | 1.75 (M7) | 452 |
| B105 | 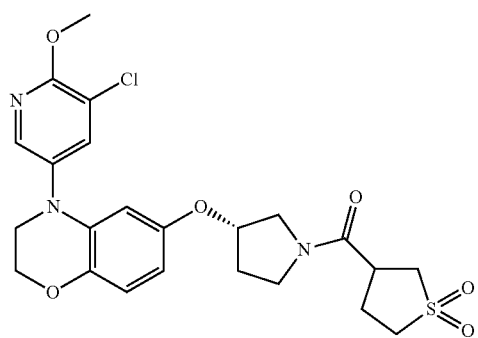 {(S)-3-[4-(5-Chloro-6-methoxy-pyridin-3-yl)-3,4-dihydro-2H-benzo[1,4]oxazin-6-yloxy]-pyrrolidin-1-yl}-(1,1-dioxo-tetrahydro-1lambda*6*-thiophen-3-yl)-methanone<br>Buchwald amination condition: CA6<br>Amide bond condition: CB5<br>Side chain introduction condition: CC2<br>Precursors used: CAS 26021-57-8/127423-61-4/IA11/4785-67-5 | 1.84 (M8) | 508, 510 |

TABLE 2-continued

| Example | Compound/Reaction Conditions | HPLC Rt [min] (method) | MS [m/z; (M + 1)+] |
|---|---|---|---|
| B106 | 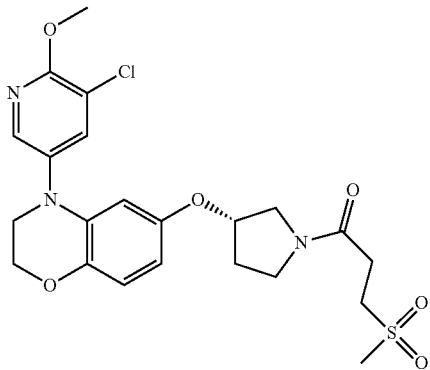<br>1-{(S)-3-[4-(5-Chloro-6-methoxy-pyridin-3-yl)-3,4-dihydro-2H-benzo[1,4]oxazin-6-yloxy]-pyrrolidin-1-yl}-3-methanesulfonyl-propan-1-one<br>Buchwald amination condition: CA6<br>Amide bond condition: CB5<br>Side chain introduction condition: CC2<br>Precursors used: CAS 26021-57-8/127423-61-4 /IA11/645-83-0 | 1.78 (M8) | 496, 498 |
| B107 | 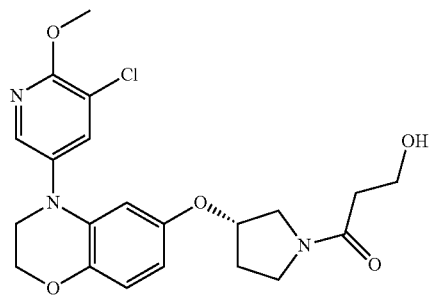<br>1-{(S)-3-[4-(5-Chloro-6-methoxy-pyridin-3-yl)-3,4-dihydro-2H-benzo[1,4]oxazin-6-yloxy]-pyrrolidin-1-yl}-3-hydroxy-propan-1-one<br>Buchwald amination condition: CA6<br>Amide bond condition: CB5<br>Side chain introduction condition: CC2<br>Precursors used: CAS 26021-57-8/127423-61-4/IA11/503-66-2 | 1.67 (M8) | 434, 436 |

TABLE 2-continued

| Example | Compound/Reaction Conditions | HPLC Rt [min] (method) | MS [m/z; (M + 1)⁺] |
|---|---|---|---|
| B108 | 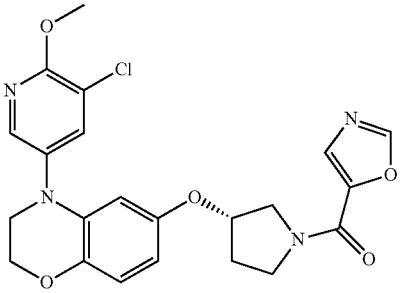<br>{(S)-3-[4-(5-Chloro-6-methoxy-pyridin-3-yl)-3,4-dihydro-2H-benzo[1,4]oxazin-6-yloxy]-pyrrolidin-1-yl}-oxazol-5-yl-methanone<br>Buchwald amination condition: CA6<br>Amide bond condition: CB5<br>Side chain introduction condition: CC2<br>Precursors used: CAS 26021-57-8/127423-61-4/IA11/118994-90-4 | 1.84 (M8) | 457, 459 |
| B109 | 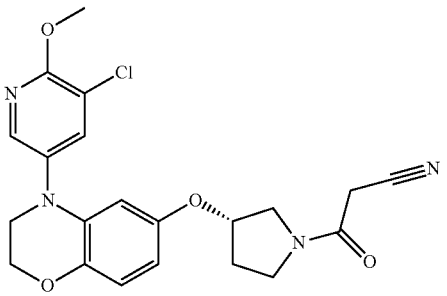<br>3-{(S)-3-[4-(5-Chloro-6-methoxy-pyridin-3-yl)-3,4-dihydro-2H-benzo[1,4]oxazin-6-yloxy]-pyrrolidin-1-yl}-3-oxo-propionitrile<br>Buchwald amination condition: CA6<br>Amide bond condition: CB5<br>Side chain introduction condition: CC2<br>Precursors used: CAS 26021-57-8/127423-61-4/IA11/372-09-8 | 1.88 (M8) | 429, 431 |
| B110 | 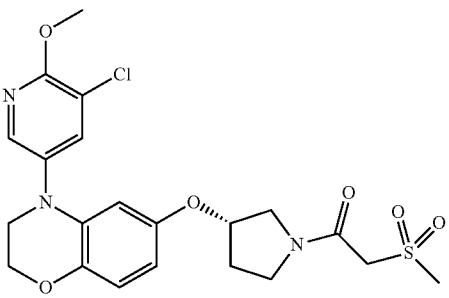<br>1-{(S)-3-[4-(5-Chloro-6-methoxy-pyridin-3-yl)-3,4-dihydro-2H-benzo[1,4]oxazin-6-yloxy]-pyrrolidin-1-yl}-2-methanesulfonyl-ethanone<br>Buchwald amination condition: CA6<br>Amide bond condition: CB5<br>Side chain introduction condition: CC2<br>Precursors used: CAS 26021-57-8/127423-61-4/IA11/2516-97-4 | 1.90 (M8) | 482 |

TABLE 2-continued

| Example | Compound/Reaction Conditions | HPLC Rt [min] (method) | MS [m/z; (M + 1)+] |
|---|---|---|---|
| B111 | 1-{(S)-3-[4-(5-Fluoro-6-methoxy-pyridin-3-yl)-3,4-dihydro-2H-benzo[1,4]oxazin-6-yloxy]-pyrrolidin-1-yl}-2-methanesulfonyl-ethanone<br>Buchwald amination condition: CA6<br>Amide bond condition: CB1<br>Side chain introduction condition: CC2<br>Precursors used: CAS 26021-57-8/127423-61-4/IA10/2516-97-4 | 1.70 (M8) | 466 |
| B112 | 1-{(S)-3-[4-(5-Fluoro-6-methoxy-pyridin-3-yl)-3,4-dihydro-2H-benzo[1,4]oxazin-6-yloxy]-pyrrolidin-1-yl}-3-methanesulfonyl-propan-1-one<br>Buchwald amination condition: CA6<br>Amide bond condition: CB1<br>Side chain introduction condition: CC2<br>Precursors used: CAS 26021-57-8/127423-61-4/IA10/645-83-0 | 1.77 (M8) | 480 |
| B113 | 1-{(S)-3-[4-(5-Fluoro-6-methoxy-pyridin-3-yl)-3,4-dihydro-2H-benzo[1,4]oxazin-6-yloxy]-pyrrolidin-1-yl}-3-hydroxy-propan-1-one<br>Buchwald amination condition: CA6<br>Amide bond condition: CB1<br>Side chain introduction condition: CC2<br>Precursors used: CAS 26021-57-8/127423-61-4/IA10/503-66-2 | 1.57 (M8) | 418 |

| Example | Compound/Reaction Conditions | HPLC Rt [min] (method) | MS [m/z; (M + 1)+] |
|---|---|---|---|
| B114 | 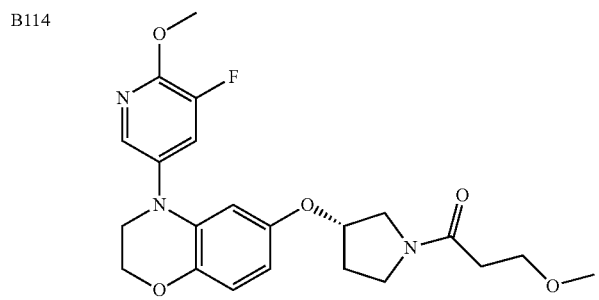<br>1-{(S)-3-[4-(5-Fluoro-6-methoxy-pyridin-3-yl)-3,4-dihydro-2H-benzo[1,4]oxazin-6-yloxy]-pyrrolidin-1-yl}-3-methoxy-propan-1-one<br>Buchwald amination condition: CA6<br>Amide bond condition: CB1<br>Side chain introduction condition: CC2<br>Precursors used: CAS 26021-57-8/127423-61-4/IA10/2544-06-1 | 1.84 (M8) | 432 |
| B115 | 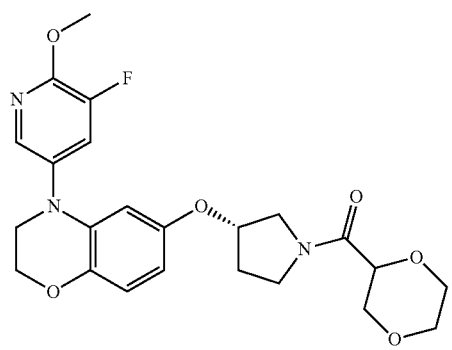<br>[1,4]Dioxan-2-yl-{(S)-3-[4-(5-fluoro-6-methoxy-pyridin-3-yl)-3,4-dihydro-2H-benzo[1,4]oxazin-6-yloxy]-pyrrolidin-1-yl}-methanone<br>Buchwald amination condition: CA6<br>Amide bond condition: CB1<br>Side chain introduction condition: CC2<br>Precursors used: CAS 26021-57-8/127423-61-4/IA10/89364-41-0 | 1.83 (M8) | 459 |

TABLE 2-continued

| Example | Compound/Reaction Conditions | HPLC Rt [min] (method) | MS [m/z; (M + 1)+] |
|---|---|---|---|

B116

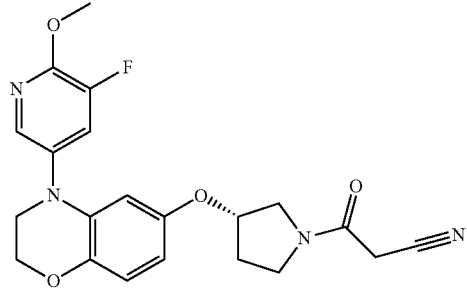

3-{(S)-3-[4-(5-Fluoro-6-methoxy-pyridin-3-yl)-
3,4-dihydro-2H-benzo[1,4]oxazin-6-yloxy]-
pyrrolidin-1-yl}-3-oxo-propionitrile
Buchwald amination condition: CA6
Amide bond condition: CB1
Side chain introduction condition: CC2
Precursors used: CAS 26021-57-8/127423-61-
4/IA10/372-09-8

1.85 (M8)   413

B117

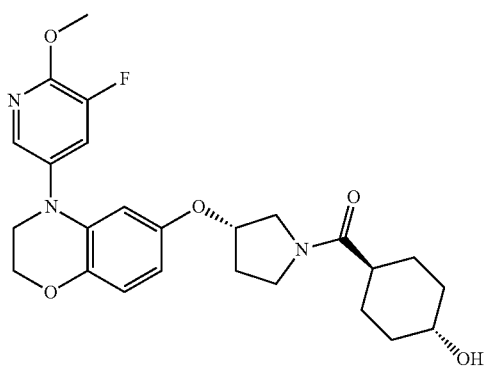

{(S)-3-[4-(5-Fluoro-6-methoxy-pyridin-3-yl)-3,4-
dihydro-2H-benzo[1,4]oxazin-6-yloxy]-pyrrolidin-
1-yl}-(4-hydroxy-cyclohexyl)-methanone
Buchwald amination condition: CA6
Amide bond condition: CB1
Side chain introduction condition: CC2
Precursors used: CAS 26021-57-8/127423-61-
4/IA10/3685-26-5

3.13 (M3)   472

TABLE 2-continued

| Example | Compound/Reaction Conditions | HPLC Rt [min] (method) | MS [m/z; (M + 1)+] |
|---|---|---|---|
| B118 | 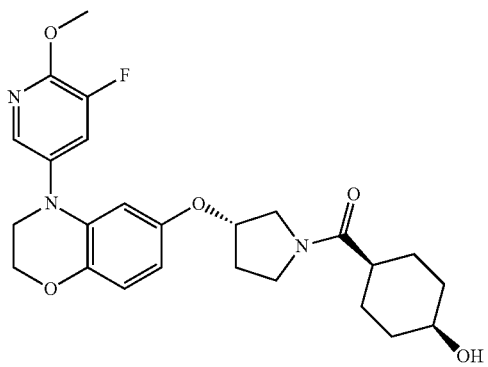<br>{(S)-3-[4-(5-Fluoro-6-methoxy-pyridin-3-yl)-3,4-dihydro-2H-benzo[1,4]oxazin-6-yloxy]-pyrrolidin-1-yl}-(4-hydroxy-cyclohexyl)-methanone<br>Buchwald amination condition: CA6<br>Amide bond condition: CB1<br>Side chain introduction condition: CC2<br>Precursors used: CAS 26021-57-8/127423-61-4/IA10/3685-22-1 | 3.40 (M3) | 472 |
| B119 | 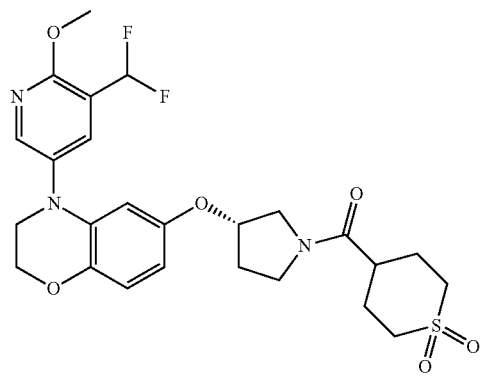<br>{(S)-3-[4-(5-Difluoromethyl-6-methoxy-pyridin-3-yl)-3,4-dihydro-2H-benzo[1,4]oxazin-6-yloxy]-pyrrolidin-1-yl}-(1,1-dioxo-hexahydro-6-thiopyran-4-yl)-methanone<br>Buchwald amination condition: CA2<br>Amide bond condition: CB3<br>Side chain introduction condition: CC2<br>Precursors used: CAS 928118-43-8/127423-61-4 /IA6/64096-87-3 | 0.97 (M1) | 538 |

TABLE 2-continued

| Example | Compound/Reaction Conditions | HPLC Rt [min] (method) | MS [m/z; (M + 1)+] |
|---|---|---|---|
| B120 | 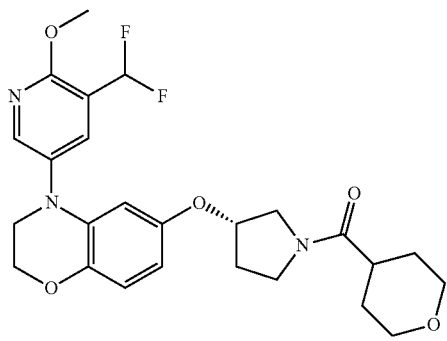<br>{(S)-3-[4-(5-Difluoro-6-methoxy-pyridin-3-yl)-3,4-dihydro-2H-benzo[1,4]oxazin-6-yloxy]-pyrrolidin-1-yl}-(tetrahydro-pyran-4-yl)-methanone<br>Buchwald amination condition: CA2<br>Amide bond condition: CB6<br>Side chain introduction condition: CC2<br>Precursors used: CAS 928118-43-8/127423-61-4/IA6/Acyl chloride 40191-32-0 | 1.03 (M1) | 490 |
| B121 | 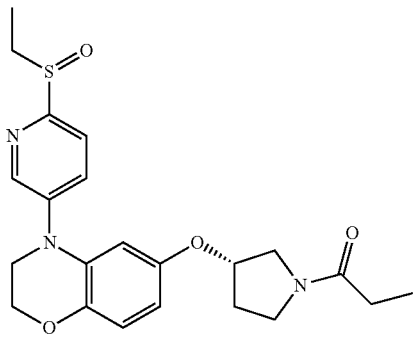<br>1-{(S)-3-[4-(6-Ethanesulfinyl-pyridin-3-yl)-3,4-dihydro-2H-benzo[1,4]oxazin-6-yloxy]-pyrrolidin-1-yl}-propan-1-one<br>Buchwald amination condition: CA14<br>Amide bond condition: CB6<br>Side chain introduction condition: CC2<br>Precursors used: CAS 26021-57-8/127423-61-4, IA44, acyl chloride CAS 79-03-8 | 1.42 (M8) | 430 |

TABLE 2-continued

| Example | Compound/<br>Reaction Conditions | HPLC Rt<br>[min]<br>(method) | MS<br>[m/z;<br>(M + 1)+] |
|---|---|---|---|
| B122 | 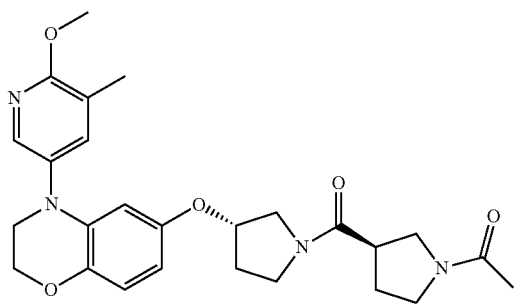  1-((R)-3-{(S)-3-[4-(6-Methoxy-5-methyl-pyridin-3-yl)-3,4-dihydro-2H-benzo[1,4]oxazin-6-yloxy]-pyrrolidine-1-carbonyl}-pyrrolidin-1-yl)-ethanone<br>Buchwald amination condition: CA6<br>Amide bond condition: CB1<br>Side chain introduction condition: CC2<br>Precursors used: CAS 26021-57-8/127423-61-4, IA9, CAS 72925-16-7, Product obtained after Deboc reaction using TFA in CH₂Cl₂ done in conventional way and final acylation in analogy to example J | 1.66 (M8) | 481 |

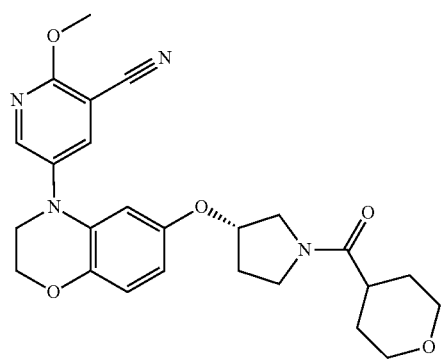 [SMILES: COc1ncc(N2CCOc3ccc(O[C@H]4CCN(C(=O)C5CCOCC5)C4)cc32)cc1C#N]

Example C1

2-Methoxy-5-{6-[(S)-1-(tetrahydro-pyran-4-carbonyl)-pyrrolidin-3-yloxy]-2,3-dihydro-benzo[1,4]oxazin-4-yl}-nicotinonitrile (according to Scheme 3)

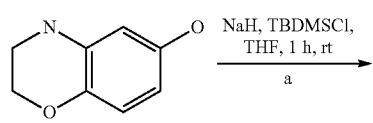

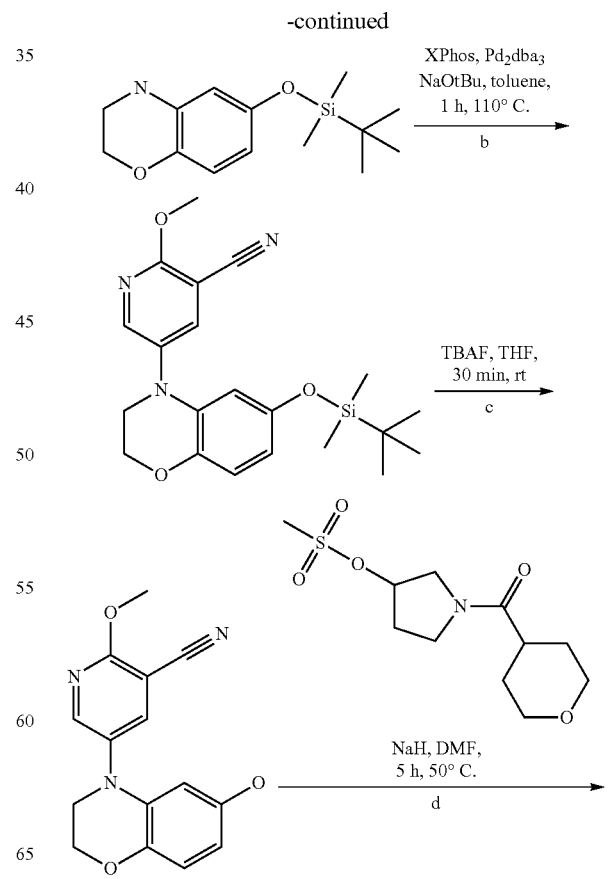

-continued

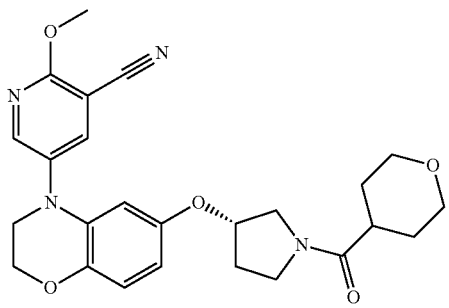

a) 6-(tert-Butyl-dimethyl-silanyloxy)-3,4-dihydro-2H-benzo[1,4]oxazine

Under argon, NaH (2.96 g, 74.1 mmol) was portionwise added to a solution of 3,4-dihydro-2H-benzo[1,4]oxazin-6-ol (CAS registry 26021-57-8) (5.60 g, 37.0 mmol) in THF (200 ml). After stirring at rt for 20 min, TBDMSCl (CAS registry 18162-48-6) (7.26 g, 48.2 mmol) was slowly added and stirring was continued for 1 h. The reaction mixture was diluted with Et$_2$O, washed with a sat. aq. NaHCO$_3$ soln. and brine. The organic phase was dried over MgSO$_4$, concentrated and the title compound was obtained after flash chromatography on silica gel (cyclohexane/EtOAc 100:0 to 60:40 over 15 min) as a yellow oil (9.20 g, 94% yield).

HPLC Rt$_{M10}$=3.65 min; ESIMS: 266 [(M+H)$^+$].

$^1$H NMR (400 MHz, DMSO-d$_6$): δ 6.46 (d, 1H), 6.08 (d, 1H), 5.91 (m, 1H), 5.71 (br s, 1H), 3.91-4.12 (m, 2H), 3.12-3.28 (m, 2H), 0.87-1.01 (s, 9H), 0.03-0.21 (s, 3H).

b) 5-[6-(tert-Butyl-dimethyl-silanyloxy)-2,3-dihydro-benzo[1,4]oxazin-4-yl]-2-methoxy nicotinonitrile Under argon, XPhos (CAS registry 564483-18-7) (0.79 g, 1.7 mmol) and Pd$_2$(dba)$_3$ (CAS registry 51364-51-3) (1.52 g, 1.7 mmol) were added to a suspension of 6-(tert-butyl-dimethyl-silanyloxy)-3,4-dihydro-2H-benzo[1,4]oxazine (9.00 g, 33.2 mmol), 5-bromo-2-methoxy-nicotinonitrile (CAS registry 941294-54-8) (7.79 g, 36.6 mmol), NaOtBu (4.79 g, 49.8 mmol) in toluene (270 ml). The reaction mixture was stirred at 110° C. for 1 h and was concentrated to afford a brown solid which was washed with a mixture of DCM/MeOH (8:2) and filtered off. The filtrate was concentrated, the obtained residue was dissolved in DCM/MeOH (8:2), filtered over hyflo, the filtrate was concentrated and triturated with MeOH to afford the title compound as yellow solid (10.14 g, 77% yield).

HPLC Rt$_{M11}$=3.89 min; ESIMS: 398 [(M+H)$^+$].

$^1$H NMR (400 MHz, DMSO-d$_6$): δ 8.35-8.51 (m, 1H), 8.16-8.31 (m, 1H), 6.60-6.79 (m, 1H), 6.15-6.32 (m, 1H), 5.92-6.09 (m, 1H), 4.00 (s, 3H), 3.51-3.74 (m, 2H), 0.87 (s, 9H), 0.07 (s, 6H).

c) 5-(6-hydroxy-2,3-dihydro-benzo[1,4]oxazin-4-yl)-2-methoxy-nicotinonitrile TBAF (1M in THF) (37.7 ml, 37.7 mmol) was added to a solution of 5-[6-(tert-butyl-dimethyl-silanyloxy)-2,3-dihydro-benzo[1,4]oxazin-4-yl]-2-methoxy-nicotinonitrile (10 g, 25.2 mmol) dissolved in THF (200 ml). The solution was stirred at rt for 30 min, diluted with EtOAc, washed with sat. aq. NaHCO$_3$ soln. and brine. The aqueous layers were back extracted with EtOAc, concentration of the organic phases after drying over MgSO$_4$ afforded a brown residue which was dissolved in DCM/MeOH (1:1) and filtered over hyflo. Concentration and trituration with Et$_2$O of the filtrate afforded the title compound as brown solid (6.63 g, 93% yield).

HPLC Rt$_{M10}$=2.56 min; ESIMS: 284 [(M+H)$^+$].

$^1$H NMR (400 MHz, DMSO-d$_6$): δ 8.70 (br. s, 1H), 8.44 (d, 1H), 8.28 (d, 1H), 6.62 (d, 1H), 6.12 (m, 1H), 6.01 (d, 1H), 4.11-4.32 (m, 2H), 4.01 (s, 3H), 3.54-3.68 (m, 2H).

d) 2-Methoxy-5-{6-[(S)-1-(tetrahydro-pyran-4-carbonyl)-pyrrolidin-3-yloxy]-2,3-dihydro-benzo[1,4]oxazin-4-yl}-nicotinonitrile Under argon, NaH (31 mg, 0.78 mmol) was added to a solution of 5-(6-hydroxy-2,3-dihydro-benzo[1,4]oxazin-4-yl)-2-methoxy-nicotinonitrile (100 mg, 0.35 mmol) in DMF (2 ml) and stirred at rt for 5 min. Methanesulfonic acid (R)-1-(tetrahydro-pyran-4-carbonyl)-pyrrolidin-3-yl ester (intermediate IC1) (98.0 mg, 0.35 mmol) was added and the reaction mixture was stirred at 50° C. for 4 h. After cooling, NaH (0.5 eq., 8.47 mg, 0.21 mmol) was added, the mixture was stirred at rt for 5 min and methanesulfonic acid (R)-1-(tetrahydro-pyran-4-carbonyl)-pyrrolidin-3-yl ester (intermediate IC1) (49.0 mg, 0.18 mmol) was added. The reaction mixture was stirred at 50° C. for 1 h. Concentration and purification by prep. RP-HPLC (Sunfire PrepC18 OBD 30×100 mm, 5 μm; solvent A: H$_2$O+0.1 Vol.-% TFA; solvent B: CH$_3$CN+0.1 Vol.-% TFA) afforded, after basification of the combined fractions and extraction with EtOAc, the title compound as a yellow solid (72 mg, 43% yield).

HPLC Rt$_{M10}$=2.72 min; ESIMS: 465 [(M+H)$^+$].

$^1$H NMR (400 MHz, CD$_3$OD): δ 8.36 (d, 1H), 8.06 (t, 1H), 6.78 (m, 1H), 6.37 (m, 1H), 6.17 (m, 1H), 4.81 (br s, 1H), 4.17-4.37 (m, 2H), 4.08 (s, 3H), 3.90-4.03 (m, 2H), 3.56-3.81 (m, 5H), 3.39-3.54 (m, 3H), 2.59-2.89 (m, 1H), 1.87-2.29 (m, 2H), 1.48-1.87 (m, 4H).

Examples C2 to C26

The compounds listed in Table 3 were prepared by a procedure analogous to that used in Example C1.

TABLE 3

| Example | Compound | UPLC Rt [min] (method) | MS [m/z; (M + 1)+] |
|---|---|---|---|
| C2 | 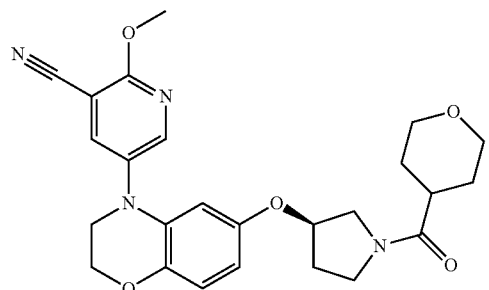<br>2-Methoxy-5-{6-[(R)-1-(tetrahydro-pyran-4-carbonyl)-pyrrolidin-3-yloxy]-2,3-dihydro-benzo[1,4]oxazin-4-yl}-nicotinonitrile<br>Buchwald amination condition: CA6<br>Side chain introduction condition: CC2<br>Precursors used: IC2 | 2.71 (M10) | 465 |
| C3 | 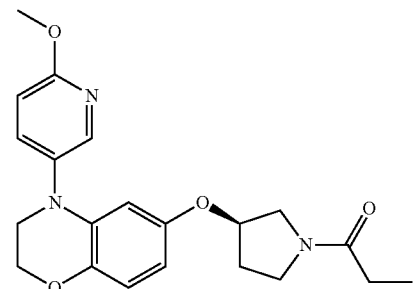<br>1-{(R)-3-[4-(6-Methoxy-pyridin-3-yl)-3,4-dihydro-2H-benzo[1,4]oxazin-6-yloxy]-pyrrolidin-1-yl}-propan-1-one<br>Buchwald amination condition: CA7<br>Side chain introduction condition: CC3<br>Precursors used: IC3 | 2.71 (M10) | 384 |
| C4 | 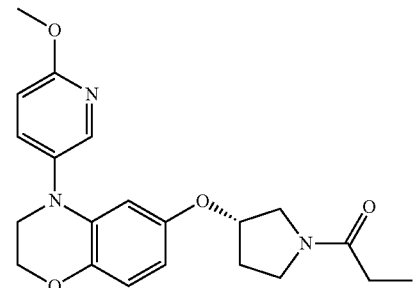<br>1-{(S)-3-[4-(6-Methoxy-pyridin-3-yl)-3,4-dihydro-2H-benzo[1,4]oxazin-6-yloxy]-pyrrolidin-1-yl}-propan-1-one<br>Buchwald amination condition: CA7<br>Side chain introduction condition: CC3<br>Precursors used: IC4 | 2.71 (M10) | 384 |

TABLE 3-continued

| Example | Compound | UPLC Rt [min] (method) | MS [m/z; (M + 1)+] |
|---|---|---|---|
| C5 | 2-Methoxy-5-{3-methyl-6-[(S)-1-(tetrahydro-pyran-4-carbonyl)-pyrrolidin-3-yloxy]-2,3-dihydro-benzo[1,4]oxazin-4-yl}-nicotinonitrile<br>Buchwald amination condition: CA6<br>Side chain introduction condition: CC2<br>Precursors used: CAS 704879-75-4, IC1<br>Chiral separation: CD3 | 2.83 (M10) 16.981 (M5) | 479 |
| C6 | 2-Methoxy-5-{3-methyl-6-[(S)-1-(tetrahydro-pyran-4-carbonyl)-pyrrolidin-3-yloxy]-2,3-dihydro-benzo[1,4]oxazin-4-yl}-nicotinonitrile<br>Buchwald amination condition: CA6<br>Side chain introduction condition: CC2<br>Precursors used: CAS 704879-75-4, IC1<br>Chiral separation: CD3 | 2.83 (M10) 19.957 (M5) | 479 |
| C7 | 5-{6-[(S)-1-(Furazan-3-carbonyl)-pyrrolidin-3-yloxy]-2,3-dihydro-benzo[1,4]oxazin-4-yl}-2-methoxy-nicotinonitrile<br>Buchwald amination condition: CA6<br>Amide bond condition: CB1<br>Side chain introduction condition: CC1<br>Precursors used: CAS 26021-57-8/127423-61-4/IA12/88598-08-7 | 4.13 (M4) | 449 |

TABLE 3-continued

| Example | Compound | UPLC Rt [min] (method) | MS [m/z; (M + 1)+] |
|---|---|---|---|
| C8 | 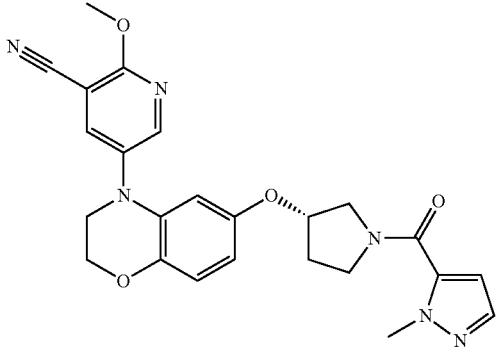 2-Methoxy-5-{6-[(S)-1-(2-methyl-2H-pyrazole-3-carbonyl)-pyrrolidin-3-yloxy]-2,3-dihydro-enzo[1,4]oxazin-4-yl}-nicotinonitrile<br>Buchwald amination condition: CA6<br>Amide bond condition: CB1<br>Side chain introduction condition: CC1<br>Precursors used: CAS 26021-57-8/127423-61-4/ IA12/16034-46-1 | 4.11 (M4) | 461 |
| C9 | 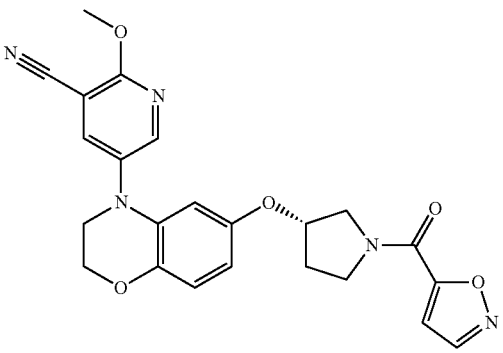 5-{6-[(S)-1-(Isoxazole-5-carbonyl)-pyrrolidin-3-yloxy]-2,3-dihydro-benzo[1,4]oxazin-4-yl}-2-methoxy-nicotinonitrile<br>Buchwald amination condition: CA6<br>Amide bond condition: CB1<br>Side chain introduction condition: CC1<br>Precursors used: CAS 26021-57-8/127423-61-4/ IA12/21169-71-1 | 4.17 (M4) | 448 |

TABLE 3-continued

| Example | Compound | UPLC Rt [min] (method) | MS [m/z; (M + 1)+] |
|---------|----------|------------------------|---------------------|
| C10 | 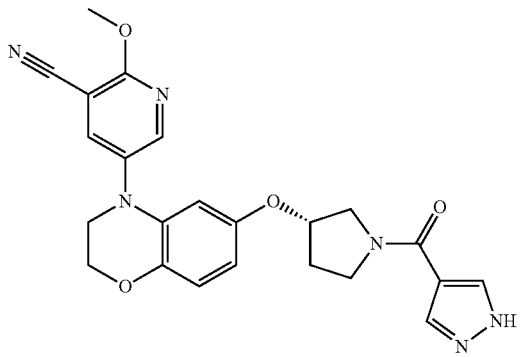<br>2-Methoxy-5-{6-[(S)-1-(1H-pyrazole-4-carbonyl)-pyrrolidin-3-yloxy]-2,3-dihydro-benzo[1,4]oxazin-4-yl}-nicotinonitrile<br>Buchwald amination condition: CA6<br>Amide bond condition: CB1<br>Side chain introduction condition: CC1<br>Precursors used: CAS 26021-57-8/127423-61-4/IA12/37718-11-9 | 3.60 (M4) | 447 |
| C11 | 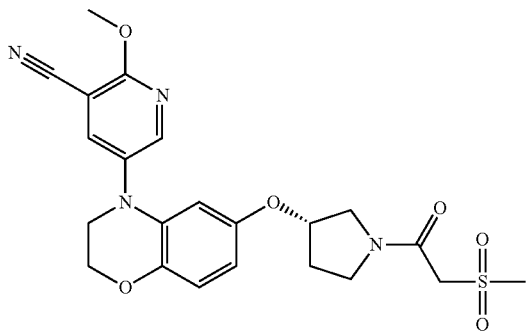<br>5-{6-[(S)-1-(2-Methanesulfonyl-acetyl)-pyrrolidin-3-yloxy]-2,3-dihydro-benzo[1,4]oxazin-4-yl}-2-methoxy-nicotinonitrile<br>Buchwald amination condition: CA6<br>Amide bond condition: CB1<br>Side chain introduction condition: CC1<br>Precursors used: CAS 26021-57-8/127423-61-4/IA12/2516-97-4 | 3.73 (M4) | 473 |

TABLE 3-continued

| Example | Compound | UPLC Rt [min] (method) | MS [m/z; (M + 1)+] |
|---|---|---|---|
| C12 | 2-Methoxy-5-{6-[(S)-1-(5-methyl-[1,3,4]oxadiazole-2-carbonyl)-pyrrolidin-3-yloxy]-2,3-dihydro-benzo[1,4]oxazin-4-yl}-nicotinonitrile<br>Buchwald amination condition: CA6<br>Amide bond condition: CB1<br>Side chain introduction condition: CC1<br>Precursors used: CAS 26021-57-8/127423-61-4/IA2/518048-06-1 | 4.02 (M4) | 463 |
| C13 | 2-Methoxy-5-{6-[(S)-1-(pyrimidine-5-carbonyl)-pyrrolidin-3-yloxy]-2,3-dihydro-benzo[1,4]oxazin-4-yl}-nicotinonitrile<br>Buchwald amination condition: CA6<br>Amide bond condition: CB1<br>Side chain introduction condition: CC1<br>Precursors used: CAS 26021-57-8/127423-61-4/IA12/4595-61-3 | 3.72 (M4) | 459 |

TABLE 3-continued

| Example | Compound | UPLC Rt [min] (method) | MS [m/z; (M + 1)+] |
|---|---|---|---|
| C14 | 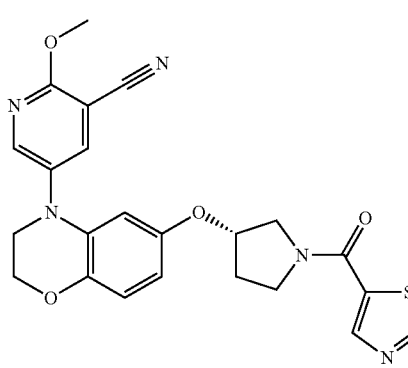<br>2-Methoxy-5-{6-[(S)-1-(thiazole-5-carbonyl)-pyrrolidin-3-yloxy]-2,3-dihydro-benzo[1,4]oxazin-4-yl}-nicotinonitrile<br>Buchwald amination condition: CA6<br>Amide bond condition: CB1<br>Side chain introduction condition: CC1<br>Precursors used: CAS 26021-57-8, IA12, 127423-61-4, 14527-41-4 | 4.02 (M4) | 464 |
| C15 | 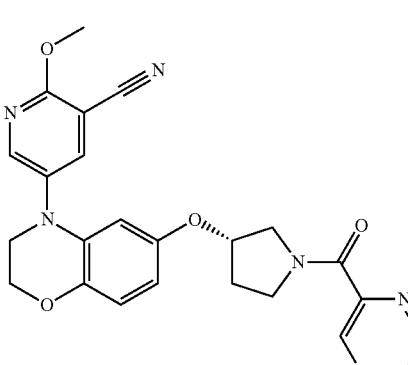<br>2-Methoxy-5-{6-[(S)-1-(pyrazine-2-carbonyl)-pyrrolidin-3-yloxy]-2,3-dihydro-benzo[1,4]oxazin-4-yl}-nicotinonitrile<br>Buchwald amination condition: CA6<br>Amide bond condition: CB1<br>Side chain introduction condition: CC1<br>Precursors used: CAS 26021-57-8, IA12, 127423-61-4, 1339899-95-4 | 4.03 (M3) | 459 |

TABLE 3-continued

| Example | Compound | UPLC Rt [min] (method) | MS [m/z; (M + 1)+] |
|---|---|---|---|
| C16 | 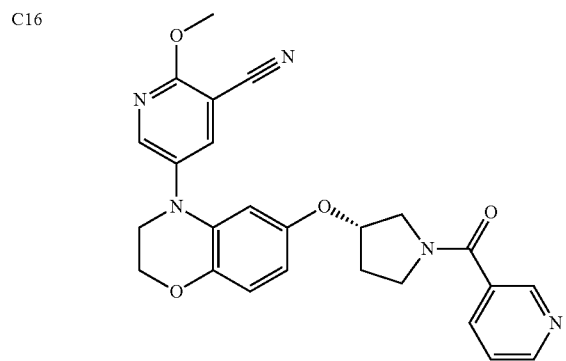<br>2-Methoxy-5-{6-[(S)-1-(pyridine-3-carbonyl)-pyrrolidin-3-yloxy]-2,3-dihydro-benzo[1,4]oxazin-4-yl}-nicotinonitrile<br>Buchwald amination condition: CA6<br>Amide bond condition: CB1<br>Side chain introduction condition: CC1<br>Precursors used: CAS 26021-57-8, IA12, 127423-61-4, 59-67-6 | 3.27 (M3) | 458 |
| C17 | 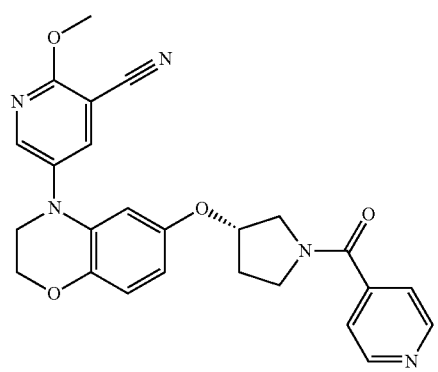<br>2-Methoxy-5-{6-[(S)-1-(pyridine-4-carbonyl)-pyrrolidin-3-yloxy]-2,3-dihydro-benzo[1,4]oxazin-4-yl}-nicotinonitrile<br>Buchwald amination: CA6<br>Amide bond condition: CB1<br>Side chain introduction condition: CC1<br>Precursors used: CAS 26021-57-8, IA12, 127423-61-4, 5-22-1 | 3.20 (M3) | 458 |

TABLE 3-continued

| Example | Compound | UPLC Rt [min] (method) | MS [m/z; (M + 1)+] |
|---|---|---|---|
| C18 | 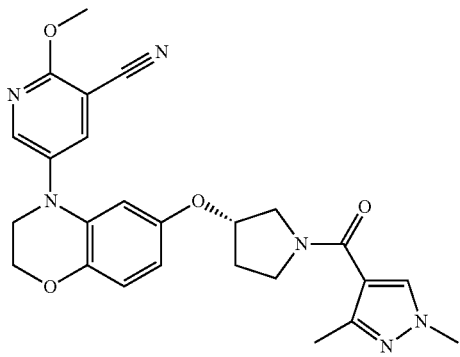<br>5-{6-[(S)-1-(1,3-Dimethyl-1H-pyrazole-4-carbonyl)-pyrrolidin-3-yloxy]-2,3-dihydro-benzo[1,4]oxazin-4-yl}-2-methoxy-nicotinonitrile<br>Buchwald amination condition: CA6<br>Amide bond condition: CB1<br>Side chain introduction condition: CC1<br>Precursors used: CAS 26021-57-8, IA12, 127423-61-4, 78703-53-4 | 3.91 (M3) | 475 |
| C19 | 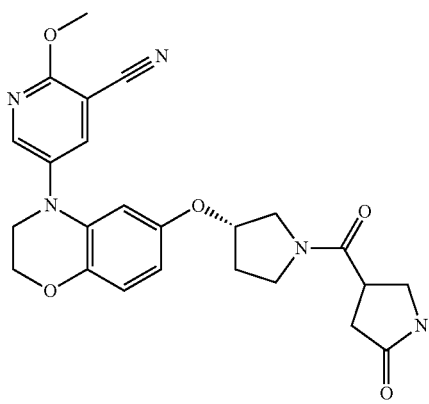<br>2-Methoxy-5-{6-[(S)-1-(5-oxo-pyrrolidine-3-carbonyl)-pyrrolidin-3-yloxy]-2,3-dihydro-benzo[1,4]oxazin-4-yl}-nicotinonitrile<br>Buchwald amination condition: CA6<br>Amide bond condition: CB1<br>Side chain introduction condition: CC1<br>Precursors used: CAS 26021-57-8, IA12, 127423-61-4, 7268-43-1 | 3.44 (M3) | 464 |

TABLE 3-continued

| Example | Compound | UPLC Rt [min] (method) | MS [m/z; (M + 1)+] |
|---|---|---|---|
| C20 | 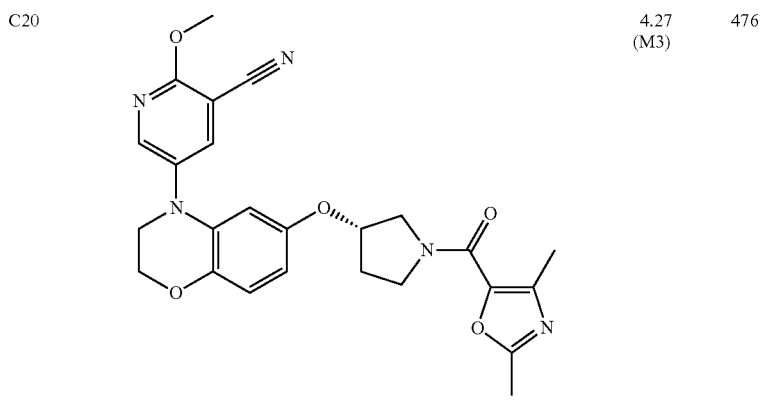<br>5-{6-[(S)-1-(2,4-Dimethyl-oxazole-5-carbonyl)-pyrrolidin-3-yloxy]-2,3-dihydro-benzo[1,4]oxazin-4-yl}-2-methoxy-nicotinonitrile<br>Buchwald amination condition: CA6<br>Amide bond condition: CB1<br>Side chain introduction condition: CC1<br>Precursors used: CAS 26021-57-8, IA12, 127423-61-4, 2510-37-4 | 4.27 (M3) | 476 |
| C21 | 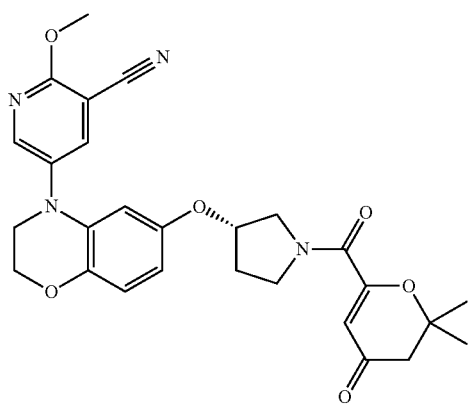<br>5-{6-[(S)-1-(6,6-Dimethyl-4-oxo-5,6-dihydro-4H-pyran-2-carbonyl)-pyrrolidin-3-yloxy]-2,3-dihydro-benzo[1,4]oxazin-4-yl}-2-methoxy-nicotinonitrile<br>Buchwald amination condition: CA6<br>Amide bond condition: CB1<br>Side chain introduction condition: CC1<br>Precursors used: CAS 26021-57-8, IA12, 127423-61-4, 80866-93-9 | 4.33 (M3) | 505 |

TABLE 3-continued

| Example | Compound | UPLC Rt [min] (method) | MS [m/z; (M + 1)+] |
|---|---|---|---|
| C22 | 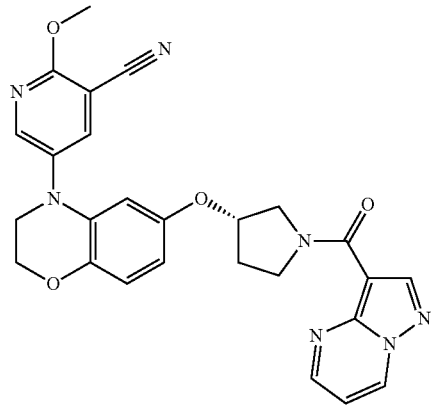 2-Methoxy-5-{6-[(S)-1-(pyrazolo[1,5-a]pyrimidine-3-carbonyl)-pyrrolidin-3-yloxy]-2,3-dihydro-benzo[1,4]oxazin-4-yl}-nicotinonitrile<br>Buchwald amination condition: CA6<br>Amide bond condition: CB1<br>Side chain introduction condition: CC1<br>Precursors used: CAS 26021-57-8, IA12, 127423-61-4, 25940-35-6 | 3.87 (M3) | 498 |
| C23 | 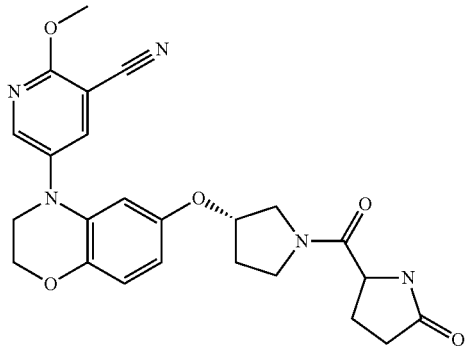 2-Methoxy-5-{6-[(S)-1-(5-oxo-pyrrolidine-2-carbonyl)-pyrrolidin-3-yloxy]-2,3-dihydro-benzo[1,4]oxazin-4-yl}-nicotinonitrile<br>Buchwald amination condition: CA6<br>Amide bond condition: CB1<br>Side chain introduction condition: CC1<br>Precursors used: CAS 26021-57-8, IA12, 127423-61-4, 149-87-1 | 3.47 (M3) | 464 |

TABLE 3-continued

| Example | Compound | UPLC Rt [min] (method) | MS [m/z; (M + 1)+] |
|---|---|---|---|
| C24 | 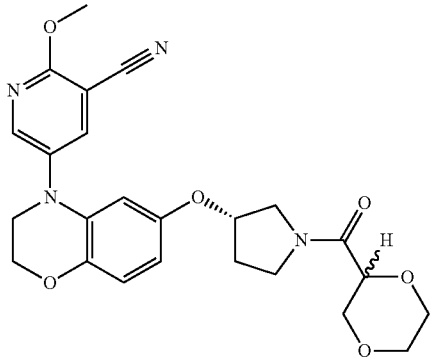<br>5-{6-[(S)-1-([1,4]Dioxane-2-carbonyl)-pyrrolidin-3-yloxy]-2,3-dihydro-benzo[1,4]oxazin-4-yl}-2-methoxy-nicotinonitrile<br>Buchwald amination condition: CA6<br>Amide bond condition: CB1<br>Side chain introduction condition: CC1<br>Precursors used: CAS 26021-57-8, IA12, 127423-61-4, 89364-41-0<br>Chiral separation: CD7 | 2.68 (M10) 22.58 (CD7) | 467 |
| C25 | 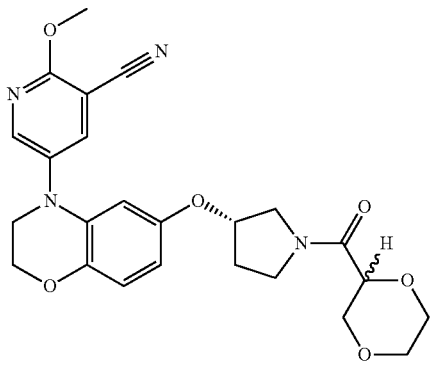<br>5-{6-[(S)-1-([1,4]Dioxane-2-carbonyl)-pyrrolidin-3-yloxy]-2,3-dihydro-benzo[1,4]oxazin-4-yl}-2-methoxy-nicotinonitrile<br>Buchwald amination condition: CA6<br>Amide bond condition: CB1<br>Side chain introduction condition: CC1<br>Precursors used: CAS 26021-57-8, IA12, 127423-61-4, 89364-41-0<br>Chiral separation: CD7 | 2.68 (M10) 33.80 (CD7) | 467 |

TABLE 3-continued

| Example | Compound | UPLC Rt [min] (method) | MS [m/z; (M + 1)+] |
|---|---|---|---|
| C26 | 2-Methoxy-5-{6-[(S)-1-(tetrahydro-pyran-3-carbonyl)-pyrrolidin-3-yloxy]-2,3-dihydro-benzo[1,4]oxazin-4-yl}-nicotinonitrile<br>Buchwald amination condition: CA6<br>Amide bond condition: CB4<br>Side chain introduction condition: CC2<br>Precursors used: CAS 26021-57-8, IA12, 127423-61-4, 873397-34-3 | 1.57 (M9) | 465 |

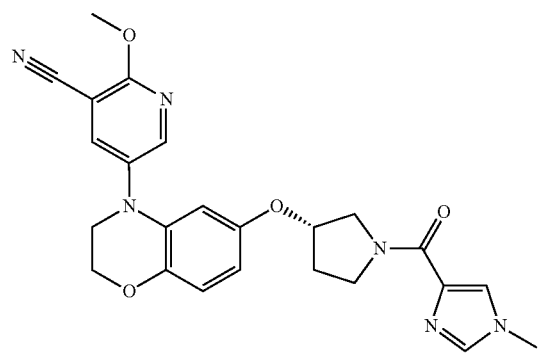 [SMILES: COc1ncc(N2CCOc3ccc(O[C@H]4CCN(C(=O)c5cn(C)cn5)C4)cc32)cc1C#N]

Example D1

(S)-2-methoxy-5-(6-((1-(1-methyl-1H-imidazole-4-carbonyl)pyrrolidin-3-yl)oxy)-2H-benzo[b][1,4]oxazin-4(3H)-yl)nicotinonitrile
(according to Scheme 4)

a1) 6-((tert-butyldimethylsilyl)oxy)-3,4-dihydro-2H-benzo[b][1,4]oxazine

A stirred solution of 3,4-dihydro-2H-1,4-benzoxazin-6-ol (CAS registry 226021-57-8) (6.00 g, 39.70 mmol) in THF (200 ml) was treated with sodium hydride (60% in mineral oil, 3.18 g, 79.00 mmol) at rt. After 20 min at rt, TBDMSCl (7.78 g, 51.6 mmol) was added, and the reaction mixture was stirred at rt for 1.5 h. After that time, diethyl ether (500 ml) and a sat. aq. NaHCO₃ soln. (100 ml) were added. The aq. layer was extracted with diethyl ether, and the combined organic extracts were dried with MgSO₄, filtered and concentrated under reduced pressure. The crude product was purified by flash chromatography on silica gel (cyclohexane/EtOAc gradient) to provide the title compound as a yellow oil.

HPLC Rt$_{M11}$=3.37 min; ESIMS: 266 [(M+H)+].
¹H NMR (400 MHz, DMSO-d₆): δ 6.48-6.44 (m, 1H), 6.09-6.05 (m, 1H), 5.94-5.89 (m, 1H), 5.76-5.70 (m, 1H), 4.06-4.00 (m, 2H), 3.25-3.19 (m, 2H), 0.92 (s, 9H), 0.12 (s, 6H).

b1) 5-(6-((tert-butyldimethylsilyl)oxy)-2H-benzo[b][1,4]oxazin-4(3H)-yl)-2-methoxynicotinonitrile A stirred solution of 6-((tert-butyldimethylsilyl)oxy)-3,4-dihydro-2H-benzo[b][1,4]oxazine (8.88 g, 32.80 mmol) in toluene (270 ml) was treated with 5-bromo-2-methoxynicotinonitrile (CAS registry 941294-54-8) (7.68 g, 36.10 mmol), NaOtBu (4.87 g, 49.2 mmol), 2-dicyclohexylphosphino-2',4',6'-triisopropylbiphenyl (CAS registry 564483-18-7) (0.806 g, 1.64 mmol), and Pd₂dba₃ (1.501 g, 1.64 mmol) at rt under argon. The reaction mixture was heated to 110° C. for 1.5 h. After that time, the reaction mixture was concentrated under reduced pressure. The residue was dissolved in DCM (200 ml), filtered through a pad of celite, and concentrated under reduced pressure. The residue was dissolved in MeOH, and sonicated several times to give a yellow/orange precipitate. The residue was filtered, washed with methanol, and dried under vacuum to provide the title compound as a yellow solid.

HPLC Rt$_{M11}$=3.90 min; ESIMS: 398 [(M+H)+].
¹H NMR (400 MHz, DMSO-d₆): δ 8.45-8.42 (m, 1H), 8.28-8.24 (m, 1H), 6.72-6.68 (m, 1H), 6.24-6.19 (m, 1H), 6.06-6.03 (m, 1H), 4.24-4.18 (m, 2H), 4.00 (s, 3H), 3.66-3.61 (m, 2H), 0.87 (s, 9H), 0.07 (s, 6H).

alternative method b2: dicyclohexylphosphino-2',4',6'-triisopropylbiphenyl (CAS registry 564483-18-7) and Pd₂

(dba)₃ were replaced with bis(tri-t-butylphosphine)palladium (CAS registry 53199-31-8)

c1) 5-(6-hydroxy-2H-benzo[b][1,4]oxazin-4(3H)-yl)-2-methoxynicotinonitrile

A stirred solution of 5-(6-(((tert-butyldimethylsilyl)oxy)-2H-benzo[b][1,4]oxazin-4(3H)-yl)-2-methoxynicotinonitrile (10.85 g, 27.30 mmol) in THF (220 ml) was treated with TBAF (1.0 M in THF, 40.9 ml, 40.90 mmol) at rt. After 40 min at rt, EtOAc (300 ml) and a sat. aq. NaHCO₃ soln. (200 ml) were added. The organic extracts were dried with MgSO₄, filtered and concentrated under reduced pressure. The crude product was purified by trituration with diethyl ether to provide the title compound as a pale brown solid.

HPLC Rt$_{M11}$=2.00 min; ESIMS: 284 [(M+H)⁺].
¹H NMR (400 MHz, DMSO-d₆): δ 8.71 (s, 1H), 8.44 (d, 1H), 8.29 (d, 1H), 6.61 (d, 1H), 6.12 (dd, 1H), 6.01 (d, 1H), 4.21-4.16 (m, 2H), 4.01 (s, 3H), 3.64-3.59 (m, 2H).

d1) (S)-tert-butyl 3-((4-(5-cyano-6-methoxypyridin-3-yl)-3,4-dihydro-2H-benzo[b][1,4]oxazin-6-yl)oxy)pyrrolidine-1-carboxylate A stirred solution of 5-(6-hydroxy-2H-benzo[b][1,4]oxazin-4(3H)-yl)-2-methoxynicotinonitrile (3.70 g, 13.06 mmol) in DMF (60 ml) was treated with sodium hydride (60% in mineral oil, 1.31 g, 32.70 mmol) at rt. The reaction mixture was stirred at rt for 15 min. After that time, (R)-1-Boc-3-methanesulfonyloxypyrrolidine (CAS registry 141699-57-2) (5.36 g, 19.59 mmol) was added, and the reaction mixture was stirred at 50° C. for 3 h. After that time, the reaction mixture was concentrated under reduced pressure. The crude product was purified by flash chromatography on silica gel (cyclohexane/acetone gradient) to provide the title compound as a yellow solid.

HPLC Rt$_{M11}$=3.13 min; ESIMS: 453 [(M+H)⁺].
¹H NMR (400 MHz, CDCl₃): δ 8.31 (d, 1H), 7.81 (d, 1H), 6.82 (d, 1H), 6.32 (dd, 1H), 6.14 (d, 1H), 4.74-4.68 (m, 1H), 4.32-4.28 (m, 2H), 4.09 (s, 3H), 3.67-3.62 (m, 2H), 3.59-3.39 (m, 4H), 2.17-1.92 (m, 2H), 1.47 (s, 9H).

alternative method d2: the mesylated alcohol, sodium hydride and DMF were replaced with the corresponding hydroxy-isoxazolidine, DEAD and THF using Mitsunobu conditions described in method CC4 e1) (S)-2-methoxy-5-(6-(pyrrolidin-3-yloxy)-2H-benzo[b][1,4]oxazin-4(3H)-yl)nicotinonitrile A stirred solution of (S)-tert-butyl 3-((4-(5-cyano-6-methoxypyridin-3-yl)-3,4-dihydro-2H-benzo[b][1,4]oxazin-6-yl)oxy)pyrrolidine-1-carboxylate (4.35 g, 9.32 mmol) in DCM (160 ml) was treated with TFA (35.9 ml, 466 mmol) at rt. The reaction mixture was stirred at rt for 2 h. After that time, the reaction mixture was concentrated under reduced pressure. The residue was dissolved in DCM (500 ml), and a saturated aqueous NaHCO₃ solution (500 ml) was added. The organic extracts were washed with a saturated aqueous NaCl solution (50 ml), dried with MgSO₄, filtered and concentrated under reduced pressure. The crude product (title compound, yellow solid) was used in the next step without further purification.

HPLC Rt$_{M10}$=2.06 min; ESIMS: 353 [(M+H)⁺].
¹H NMR (400 MHz, CDCl₃): δ 8.31 (d, 1H), 7.82 (d, 1H), 6.82 (d, 1H), 6.32 (dd, 1H), 6.12 (d, 1H), 4.71-4.65 (m, 1H), 4.32-4.27 (m, 2H), 4.09 (s, 3H), 3.67-3.62 (m, 2H), 3.22-2.90 (m, 4H), 2.08-1.88 (m, 2H).

f1) (S)-2-methoxy-5-(6-((1-(1-methyl-1H-imidazole-4-carbonyl)pyrrolidin-3-yl)oxy)-2H-benzo[b][1,4]oxazin-4(3H)-yl)nicotinonitrile A stirred solution of 1-methyl-1H-imidazole-4-carboxylic acid (CAS registry 41716-18-1) (0.578 g, 4.45 mmol) in DMF (40 ml) was treated with HOBT (0.695 g, 4.45 mmol), EDC (0.870 g, 4.45 mmol) and Et₃N (1.24 ml, 8.90 mmol) at rt. The reaction mixture was stirred at rt for 15 min. After that time, (S)-2-methoxy-5-(6-(pyrrolidin-3-yloxy)-2H-benzo[b][1,4]oxazin-4(3H)-yl)nicotinonitrile (1.10 g, 2.97 mmol) was added, and the reaction mixture was stirred for 3 h 15 min at rt. After that time, the reaction mixture was concentrated under reduced pressure. The residue was dissolved in DCM (200 ml), and a sat. aq. NaHCO₃ soln. (200 ml) was added. The organic extracts were dried with MgSO₄, filtered and concentrated under reduced pressure. The crude product was purified by flash chromatography on silica gel (DCM/methanol gradient) and preparative HPLC (SunFire C18 column, CH₃CN/1% TFA in H₂O gradient, pure fractions were treated with DCM and a saturated aqueous NaHCO₃ solution; the combined organic extracts were dried with MgSO₄, filtered and concentrated under reduced pressure) to provide the title compound as a yellow solid.

HPLC Rt$_{M10}$=2.27 min; ESIMS: 461 [(M+H)⁺].
¹H NMR (400 MHz, DMSO-d₆): δ 8.46-8.41 (m, 1H), 8.30-8.26 (m, 1H), 7.66-7.59 (m, 2H), 6.77-6.72 (m, 1H), 6.37-6.29 (m, 1H), 6.14-6.07 (m, 1H), 4.90-4.79 (m, 1H), 4.25-4.11 (m, 3H), 3.99 (s, 3H), 3.98-3.78 (m, 1H), 3.70-3.41 (m, 7H), 2.10-1.93 (m, 2H).

alternative method f2: the carboxylic acid, HOBT, EDC and DMF were replaced with the carboxylic acid chloride and DCM alternative method f3: the carboxylic acid, HOBT, EDC and DMF were replaced with a chloroformate and DCM alternative method f4: the carboxylic acid, HOBT and EDC were replaced with a carbamic chloride Examples D2 to D40

The compounds listed in Table 4 were prepared by a procedure analogous to that used in Example D1.

TABLE 4

| Example | Compound | HPLC Rt [min] (method) | MS [m/z; (M + 1)+] |
|---|---|---|---|
| D2 | 1-{(S)-3-[4-(6-Methoxy-pyridin-3-yl)-3,4-dihydro-2H-benzo[1,4]oxazin-6-yloxy]-pyrrolidin-1-yl}-2-morpholin-4-yl-ethanone<br>Synthetic route used: a1, b2 (intermediate: CAS registry 163129-79-1), c1, d1, e1, f1 (intermediate: CAS registry 89531-58-8) | 2.07 (M10) | 455 |
| D3 | 2-Dimethylamino-1-{(S)-3-[4-(6-methoxy-pyridin-3-yl)-3,4-dihydro-2H-benzo[1,4]oxazin-6-yloxy]-pyrrolidin-1-yl}-ethanone<br>Synthetic route used: a1, b2 (intermediate: CAS registry 163129-79-1), c1, d1, e1, f1 (intermediate: CAS registry 1118-68-9) | 2.08 (M10) | 413 |
| D4 | 2-Methoxy-5-{6-(S)-1-(tetrahydro-pyran-4-carbonyl)-pyrrolidin-3-yloxy]-2,3-dihydro-benzo[1,4]oxazin-4-yl}-nicotinonitrile<br>Synthetic route used: a1, b2 (intermediate IA12), c1, d1, e1, f2 (intermediate: CAS registry 40191-32-0) | 2.72 (M10) | 465 |

TABLE 4-continued

| Example | Compound | HPLC Rt [min] (method) | MS [m/z; (M + 1)+] |
|---|---|---|---|
| D5 | 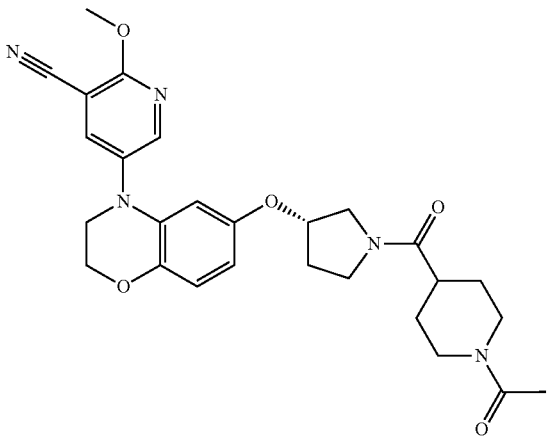<br>5-{6-[(S)-1-(1-Acetyl-piperidine-4-carbonyl)-pyrrolidin-3-yloxy]-2,3-dihydro-benzo[1,4]oxazin-4-yl}-2-methoxy-nicotinonitrile<br>Synthetic route used: a1, b1 (intermediate CAS registry 941294-54-8), c1, d1, e1, f1 (intermediate: CAS registry 25503-90-6) | 2.61 (M10) | 506 |
| D6 | 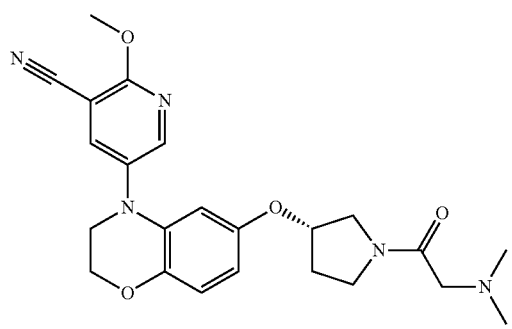<br>5-{6-[(S)-1-(2-Dimethylamino-acetyl)-pyrrolidin-3-yloxy]-2,3-dihydro-benzo[1,4]oxazin-4-yl}-2-methoxy-nicotinonitrile<br>Synthetic route used: a1, b1 (intermediate CAS registry 941294-54-8), c1, d1, e1, f1 (intermediate: CAS registry 1118-68-9) | 2.22 (M10) | 438 |
| D7 | 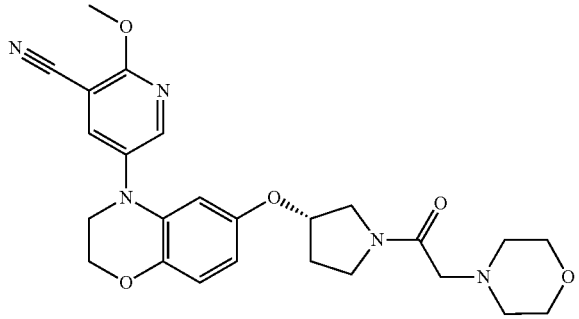<br>2-Methoxy-5-{6-[(S)-1-(2-morpholin-4-yl-acetyl)-pyrrolidin-3-yloxy]-2,3-dihydro-benzo[1,4]oxazin-4-yl}-nicotinonitrile<br>Synthetic route used: a1, b1 (intermediate CAS registry 941294-54-8), c1, d1, e1, f1 (intermediate: CAS registry 89531-58-8) | 2.14 (M10) | 480 |

TABLE 4-continued

| Example | Compound | HPLC Rt [min] (method) | MS [m/z; (M + 1)+] |
|---|---|---|---|
| D8 | 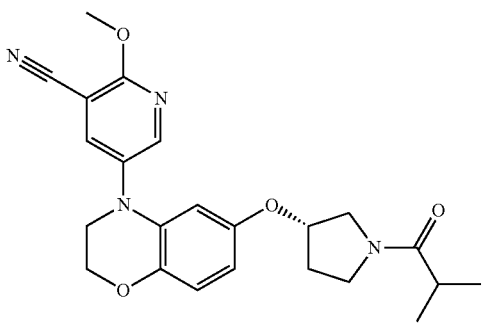<br>5-[6-((S)-1-Isobutyryl-pyrrolidin-3-yloxy)-2,3-dihydro-benzo[1,4]oxazin-4-yl]-2-methoxy-nicotinonitrile<br>Synthetic route used: a1, b1 (intermediate CAS registry 941294-54-8), c1, d1, e1, f2 (intermediate: CAS registry 89531-58-8) | 2.14 (M10) | 480 |
| D9 | 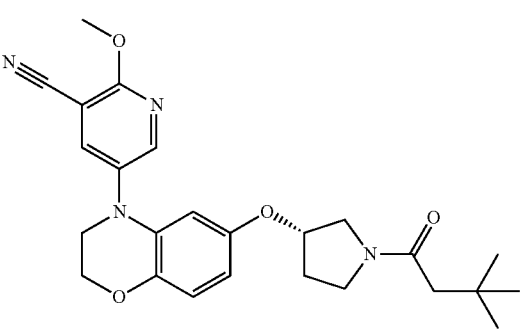<br>5-{6-[(S)-1-(3,3-Dimethyl-butyryl)-pyrrolidin-3-yloxy]-2,3-dihydro-benzo[1,4]oxazin-4-yl}-2-methoxy-nicotinonitrile<br>Synthetic route used: a1, b1 (intermediate CAS registry 941294-54-8), c1, d1, e1, f2 (intermediate: CAS registry 7065-46-5) | 3.19 (M10) | 451 |
| D10 | 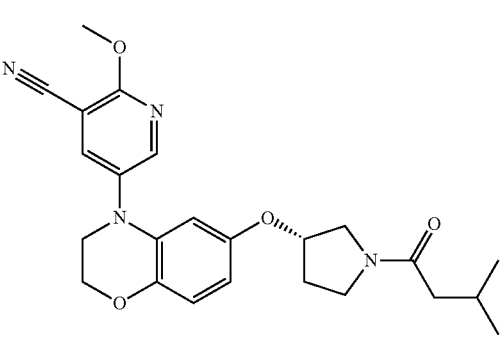<br>2-Methoxy-5-{6-[(S)-1-(3-methyl-butyryl)-pyrrolidin-3-yloxy]-2,3-dihydro-benzo[1,4]oxazin-4-yl}-nicotinonitrile<br>Synthetic route used: a1, b1 (intermediate CAS registry 941294-54-8), c1, d1, e1, f2 (intermediate: CAS registry 108-12-3) | 3.06 (M10) | 437 |

TABLE 4-continued

| Example | Compound | HPLC Rt [min] (method) | MS [m/z; (M + 1)+] |
|---|---|---|---|
| D11 | 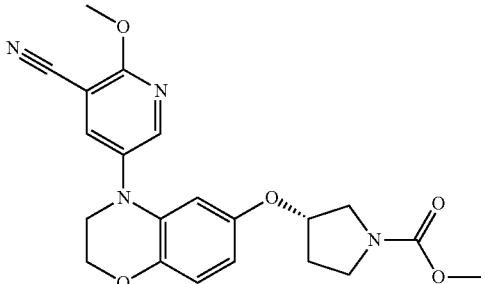<br>(S)-3-[4-(5-Cyano-6-methoxy-pyridin-3-yl)-3,4-dihydro-2H-benzo[1,4]oxazin-6-yloxy]-pyrrolidine-1-carboxylic acid methyl ester<br>Synthetic route used: a1, b1 (intermediate CAS registry 941294-54-8), c1, d1, e1, f3 (intermediate: CAS registry 79-22-1) | 2.96 (M10) | 411 |
| D12 | 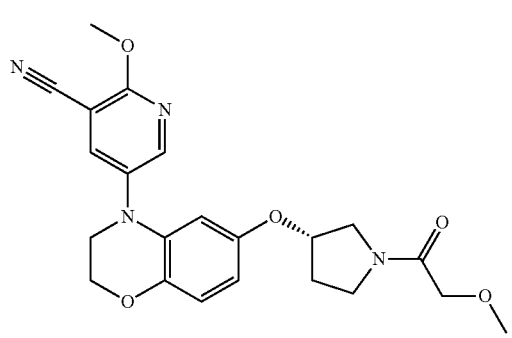<br>2-Methoxy-5-{6-[(S)-1-(2-methoxy-acetyl)-pyrrolidin-3-yloxy]-2,3-dihydro-benzo[1,4]oxazin-4-yl}-nicotinonitrile<br>Synthetic route used: a1, b1 (intermediate CAS registry 941294-54-8), c1, d1, e1, f2 (intermediate: CAS registry 38870-89-2) | 2.63 (M10) | 425 |
| D13 | 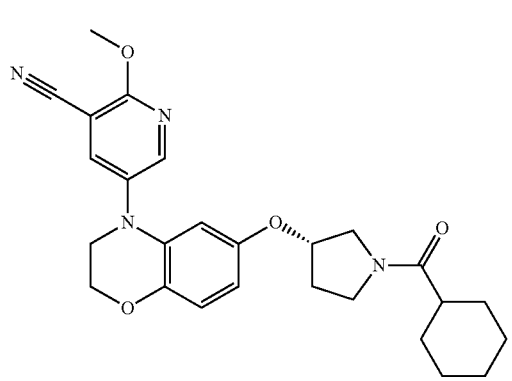<br>5-[6-((S)-1-Cyclohexanecarbonyl-pyrrolidin-3-yloxy)-2,3-dihydro-benzo[1,4]oxazin-4-yl]-2-methoxy-nicotinonitrile<br>Synthetic route used: a1, b1 (intermediate CAS registry 941294-54-8), c1, d1, e1, f2 (intermediate: CAS registry 2719-27-9) | 3.22 (M10) | 463 |

TABLE 4-continued

| Example | Compound | HPLC Rt [min] (method) | MS [m/z; (M + 1)+] |
|---|---|---|---|
| D14 | 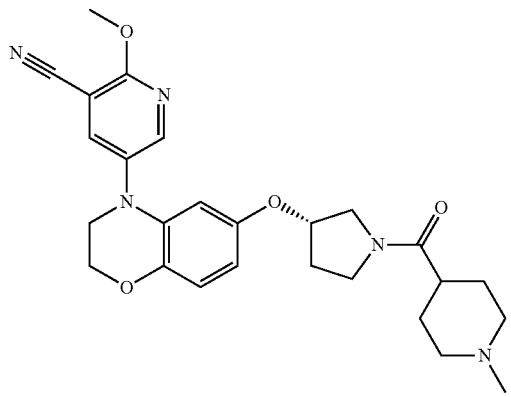<br>2-Methoxy-5-{6-[(S)-1-(1-methyl-piperidine-4-carbonyl)-pyrrolidin-3-yloxy]-2,3-dihydro-benzo[1,4]oxazin-4-yl}-nicotinonitrile<br>Synthetic route used: a1, b1 (intermediate CAS registry 941294-54-8), c1, d1, e1, f1 (intermediate: CAS registry 68947-43-3) | 2.23 (M10) | 478 |
| D15 | 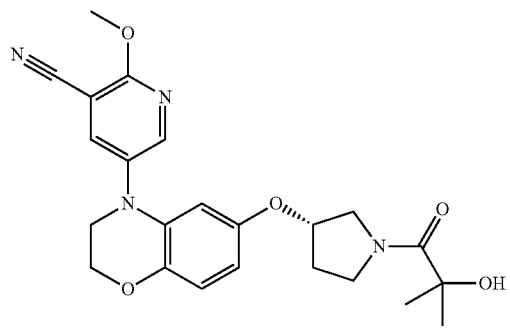<br>5-{6-[(S)-1-(2-Hydroxy-2-methyl-propionyl)-pyrrolidin-3-yloxy]-2,3-dihydro-benzo[1,4]oxazin-4-yl}-2-methoxy-nicotinonitrile<br>Synthetic route used: a1, b1 (intermediate CAS registry 941294-54-8), c1, d1, e1, f1 (intermediate: CAS registry 594-61-6) | 2.67 (M10) | 439 |

TABLE 4-continued

| Example | Compound | HPLC Rt [min] (method) | MS [m/z; (M + 1)+] |
|---|---|---|---|
| D16 | 5-{6-[(S)-1-(1,1-Dioxo-hexahydro-1lambda*6*-thiopyran-4-carbonyl)-pyrrolidin-3-yloxy]-2,3-dihydro-benzo[1,4]oxazin-4-yl}-2-methoxy-nicotinonitrile<br>Synthetic route used: a1, b1 (intermediate CAS registry 941294-54-8), c1, d1, e1, f1 (intermediate: CAS registry 64096-87-3) | 1.62 (M8) | 513 |
| D17 | 2-Methoxy-5-{6-[(S)-1-(1-methyl-6-oxo-1,6-dihydro-pyridine-3-carbonyl)-pyrrolidin-3-yloxy]-2,3-dihydro-benzo[1,4]oxazin-4-yl}-nicotinonitrile<br>Synthetic route used: a1, b1 (intermediate CAS registry 941295-54-8), c1, d1, e1, f1 (intermediate: CAS registry 3719-45-7) | 1.55 (M13) | 488 |
| D18 | 2-Methoxy-5-{6-[(S)-1-(oxazole-4-carbonyl)-pyrrolidin-3-yloxy]-2,3-dihydro-benzo[1,4]oxazin-4-yl}-nicotinonitrile<br>Synthetic route used: a1, b1 (intermediate CAS registry 941294-54-8), c1, d1, e1, f1 (intermediate: CAS registry 23012-13-7) | 1.75 (M13) | 448 |

TABLE 4-continued

| Example | Compound | HPLC Rt [min] (method) | MS [m/z; (M + 1)+] |
|---|---|---|---|
| D19 | 2-Methoxy-5-{6-[(S)-1-(1-methyl-2-oxo-1,2-dihydro-pyridine-4-carbonyl)-pyrrolidin-3-yloxy]-2,3-dihydro-benzo[1,4]oxazin-4-yl}-nicotinonitrile<br>Synthetic route used: a1, b1 (intermediate CAS registry 941294-54-8), c1, d1, e1, f1<br>(intermediate: CAS registry 33972-97-3) | 1.56 (M13) | 488 |
| D20 | 2-Methoxy-5-{6-[(S)-1-(6-oxo-1,6-dihydro-pyridine-3-carbonyl)-pyrrolidin-3-yloxy]-2,3-dihydro-benzo[1,4]oxazin-4-yl}-nicotinonitrile<br>Synthetic route used: a1, b1 (intermediate CAS registry 941294-54-8), c1, d1, e1, f1<br>(intermediate: CAS registry 5006-66-6) | 1.60 (M8) | 474 |
| D21 | 2-Methoxy-5-{6-[(S)-1-(2-oxo-1,2-dihydro-pyridine-4-carbonyl)-pyrrolidin-3-yloxy]-2,3-dihydro-benzo[1,4]oxazin-4-yl}-nicotinonitrile<br>Synthetic route used: a1, b1 (intermediate CAS registry 941294-54-8), c1, d1, e1, f1<br>(intermediate: CAS registry 22282-72-0) | 1.50 (M13) | 474 |

TABLE 4-continued

| Example | Compound | HPLC Rt [min] (method) | MS [m/z; (M + 1)+] |
|---|---|---|---|
| D22 | 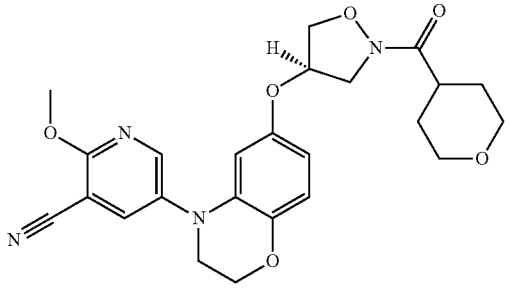<br>2-Methoxy-5-{6-[(R)-2-(tetrahydro-pyran-4-carbonyl)-isoxazolidin-4-yloxy]-2,3-dihydro-benzo[1,4]oxazin-4-yl}-nicotinonitrile<br>Synthetic route used: a1, b1 (intermediate CAS registry 941294-54-8), c1, d2 (intermediate CAS registry 878385-72-9), e1, f2 (intermediate: CAS registry 40191-32-0) | 3.01 (M10) | 467 |
| D23 | 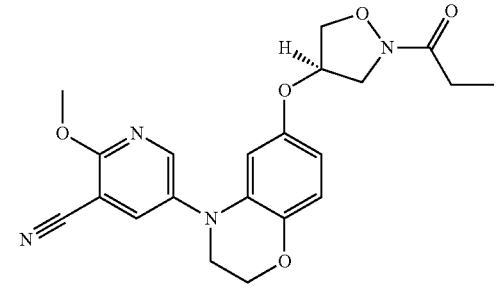<br>2-Methoxy-5-[6-((R)-2-propionyl-isoxazolidin-4-yloxy)-2,3-dihydro-benzo[1,4]oxazin-4-yl]-nicotinonitrile<br>Synthetic route used: a1, b1 (intermediate CAS registry 941294-54-8), c1, d2 (intermediate CAS registry 878385-72-9), e1, f2 (intermediate: CAS registry 79-03-8) | 3.11 (M10) | 411 |
| D24 | 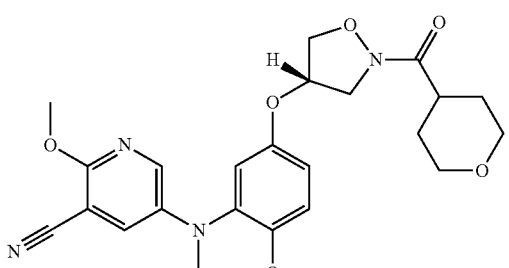<br>2-Methoxy-5-{6-[(S)-2-(tetrahydro-pyran-4-carbonyl)-isoxazolidin-4-yloxy]-2,3-dihydro-benzo[1,4]oxazin-4-yl}-nicotinonitrile<br>Synthetic route used: a1, b1 (intermediate CAS registry 941294-54-8), c1, d2 (intermediate CAS registry 1092454-84-6), e1, f2 (intermediate: CAS registry 40191-32-0) | 1.63 (M9) | 467 |

TABLE 4-continued

| Example | Compound | HPLC Rt [min] (method) | MS [m/z; (M + 1)+] |
|---|---|---|---|
| D25 | 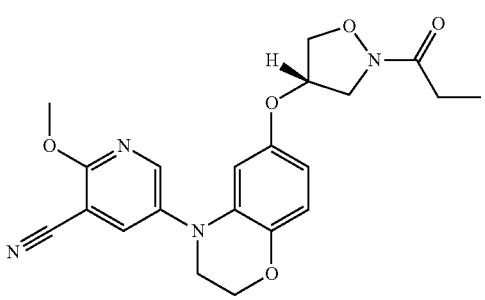2-Methoxy-5-[6-((S)-2-propionyl-isoxazolidin-4-yloxy)-2,3-dihydro-benzo[1,4]oxazin-4-yl]-nicotinonitrile<br>Synthetic route used: a1, b1 (intermediate CAS registry 941294-54-8), c1, d2 (intermediate CAS registry 1092454-84-6), e1, f2 (intermediate: CAS registry 79-03-8) | 1.66 (M9) | 411 |
| D26 | 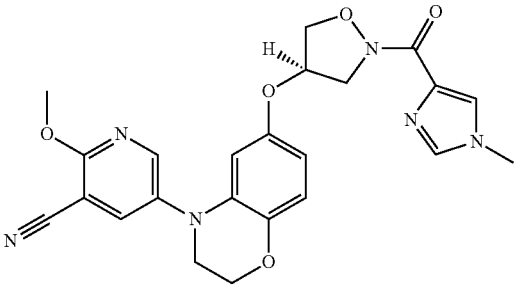2-Methoxy-5-{6-[(R)-2-(1-methyl-1H-imidazole-4-carbonyl)-isoxazolidin-4-yloxy]-2,3-dihydro-benzo[1,4]oxazin-4-yl}-nicotinonitrile<br>Synthetic route used: a1, b1 (intermediate CAS registry 941294-54-8), c1, d1, e1, f1 (intermediate: CAS registry 41716-18-1) | 2.31 (M10) | 463 |
| D27 | 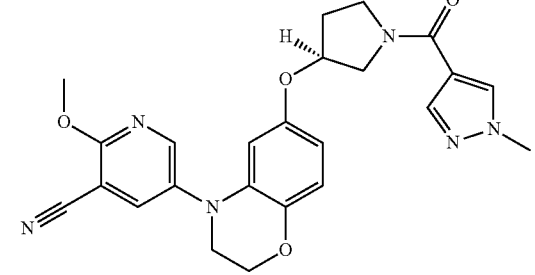2-Methoxy-5-{6-[(S)-1-(1-methyl-1H-pyrazole-4-carbonyl)-pyrrolidin-3-yloxy]-2,3-dihydro-benzo[1,4]oxazin-4-yl}-nicotinonitrile<br>Synthetic route used: a1, b1 (intermediate CAS registry 941294-54-8), c1, d1, e1, f1 (intermediate: CAS registry 5952-92-1) | 2.62 (M10) | 461 |

TABLE 4-continued

| Example | Compound | HPLC Rt [min] (method) | MS [m/z; (M + 1)+] |
|---|---|---|---|
| D28 | 2-Methoxy-5-{6-[(S)-1-(tetrahydro-furan-3-carbonyl)-pyrrolidin-3-yloxy]-2,3-dihydro-benzo[1,4]oxazin-4-yl}-nicotinonitrile<br>Synthetic route used: a1, b1 (intermediate CAS registry 941294-54-8), c1, d1, e1, f1 (intermediate: CAS registry 89364-31-8).<br>Isomer 1 | 2.68 (M10) | 451 |
| D29 | 2-Methoxy-5-{6-[(S)-1-(tetrahydro-furan-3-carbonyl)-pyrrolidin-3-yloxy]-2,3-dihydro-benzo[1,4]oxazin-4-yl}-nicotinonitrile<br>Synthetic route used: a1, b1 (intermediate CAS registry 941294-54-8), c1, d1, e1, f1 (intermediate: CAS registry 89364-31-8).<br>Isomer 2 | 2.68 (M10) | 451 |
| D30 | {(S)-3-[4-(6-Methoxy-pyridin-3-yl)-3,4-dihydro-2H-benzo[1,4]oxazin-6-yloxy]-pyrrolidin-1-yl}-(tetrahydro-pyran-4-yl)-methanone<br>Synthetic route used: a1, b2 (intermediate CAS registry 163129-79-1), c1, d1, e1, f2 (intermediate: CAS registry 40191-32-0) | 2.63 (M10) | 440 |

TABLE 4-continued

| Example | Compound | HPLC Rt [min] (method) | MS [m/z; (M + 1)+] |
|---|---|---|---|
| D31 | 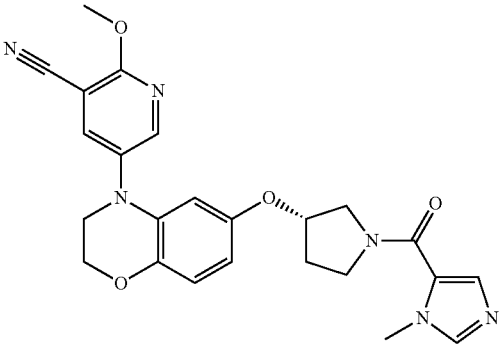2-Methoxy-5-{6-[(S)-1-(3-methyl-3H-imidazole-4-carbonyl)-pyrrolidin-3-yloxy]-2,3-dihydro-benzo[1,4]oxazin-4-yl}-nicotinonitrile Synthetic route used: a1, b1 (intermediate CAS registry 941294-54-8), c1, d1, e1, f1 (intermediate: CAS registry 41806-40-0) | 2.24 (M10) | 461 |
| D32 | 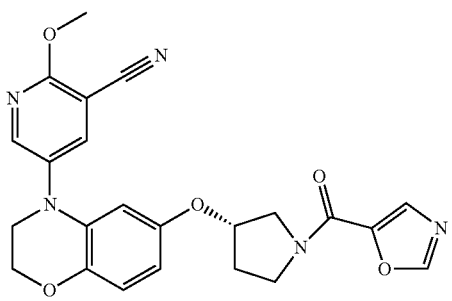2-Methoxy-5-{6-[(S)-1-(oxazole-5-carbonyl)-pyrrolidin-3-yloxy]-2,3-dihydro-benzo[1,4]oxazin-4-yl}-nicotinonitrile Synthetic route used: a1, b1 (intermediate CAS registry 941294-54-8), c1, d1, e1, f1 (intermediate: CAS registry 118994-90-4) | 1.69 (M13) | 448 |
| D33 | 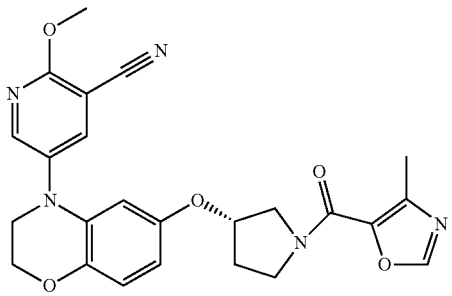2-Methoxy-5-{6-[(S)-1-(4-methyl-oxazole-5-carbonyl)-pyrrolidin-3-yloxy]-2,3-dihydro-benzo[1,4]oxazin-4-yl}-nicotinonitrile Synthetic route used: a1, b1 (intermediate CAS registry 941294-54-8), c1, d1, e1, f1 (intermediate: CAS registry 2510-32-9) | 1.80 (M13) | 462 |

TABLE 4-continued

| Example | Compound | HPLC Rt [min] (method) | MS [m/z; (M + 1)+] |
|---|---|---|---|
| D34 | 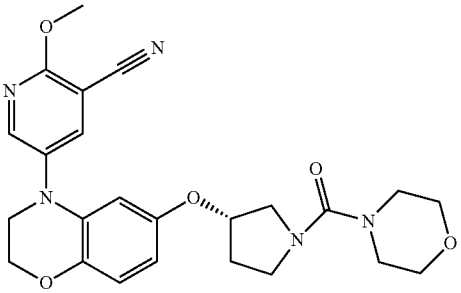<br>2-Methoxy-5-{6-[(S)-1-(morpholine-4-carbonyl)-pyrrolidin-3-yloxy]-2,3-dihydro-benzo[1,4]oxazin-4-yl}-nicotinonitrile<br>Synthetic route used: a1, b1 (intermediate CAS registry 941294-54-8), c1, d1, e1, f4 (intermediate: CAS registry 15159-40-7) | 1.77 (M13) | 466 |
| D35 | 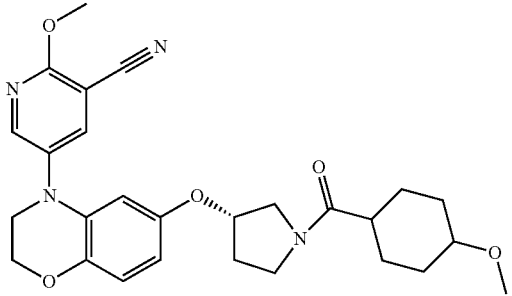<br>2-Methoxy-5-{6-[(S)-1-(4-methoxy-cyclohexanecarbonyl)-pyrrolidin-3-yloxy]-2,3-dihydro-benzo[1,4]oxazin-4-yl}-nicotinonitrile<br>Synthetic route used: a1, b1 (intermediate CAS registry 941294-54-8), c1, d1, e1, f1 (intermediate: CAS registry 95233-12-8)<br>Isomer 1 | 1.90 (M13) | 493 |
| D36 | 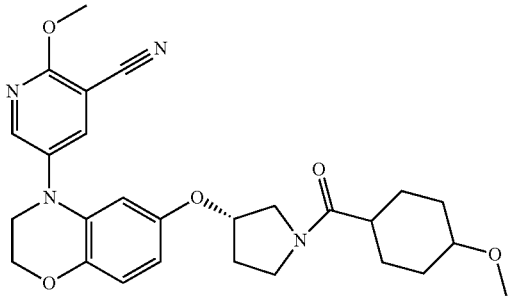<br>2-Methoxy-5-{6-[(S)-1-(4-methoxy-cyclohexanecarbonyl)-pyrrolidin-3-yloxy]-2,3-dihydro-benzo[1,4]oxazin-4-yl}-nicotinonitrile<br>Synthetic route used: a1, b1 (intermediate CAS registry 941294-54-8), c1, d1, e1, f1 (intermediate: CAS registry 95233-12-8)<br>Isomer 2 | 2.01 (M13) | 493 |

TABLE 4-continued

| Example | Compound | HPLC Rt [min] (method) | MS [m/z; (M + 1)+] |
|---|---|---|---|
| D37 | 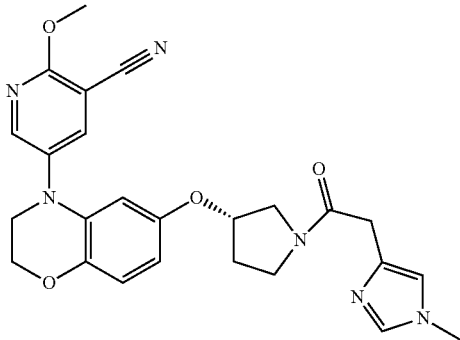<br>2-Methoxy-5-(6-{(S)-1-[2-(1-methyl-1H-imidazol-4-yl)-acetyl]-pyrrolidin-3-yloxy}-2,3-dihdyro-benzo[1,4]oxazin-4-yl)-nicotinonitrile<br>Synthetic route used: a1, b1 (intermediate CAS registry 941294-54-8), c1, d1, e1, f1 (intermediate: CAS registry 2625-49-2) | 1.28 (M13) | 475 |
| D38 | 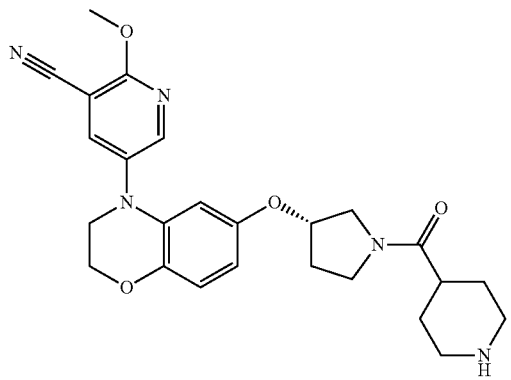<br>2-Methoxy-5-{6-[(S)-1-(piperidine-4-carbonyl)-pyrrolidin-3-yloxy]-2,3-dihydro-benzo[1,4]oxazin-4-yl}-nicotinonitrile<br>Synthetic route used: a1, b1 intermediate IA12, c1, d1 CAS registry 127423-61-4, f1 CAS registry 84358-13-4<br>last step: removal of Boc protecting group using TFA in a convention way. | 2.19 (M10) | 464 |

TABLE 4-continued

| Example | Compound | HPLC Rt [min] (method) | MS [m/z; (M + 1)+] |
|---|---|---|---|
| D39 | 2-Methoxy-5-{6-[(S)-1-((S)-pyrrolidine-3-carbonyl)-pyrrolidin-3-yloxy]-2,3-dihydro-benzo[1,4]oxazin-4-yl}-nicotinonitrile Synthetic route used: a1, b1 intermediate CAS registry IA12, c1, d1 CAS registry 127423-61-4, f1 CAS registry 140148-70-5 last step: removal of Boc protecting group using TFA in a conventional way. | 2.24 (M10) | 450 |
| D40 | 2-Methoxy-5-{6-[(S)-1-((R)-pyrrolidine-3-carbonyl)-pyrrolidin-3-yloxy]-2,3-dihydro-benzo[1,4]oxazin-4-yl}-nicotinonitrile Synthetic route used: a1, b1 intermediate IA12, c1, d1 CAS registry 127423-61-4, f1 CAS registry 72925-16-7, last step: removal of Boc protecting group using TFA in a conventional way. | 2.24 (M10) | 450 |

Example E1

{(S)-3-[1-(6-Methoxy-5-methyl-pyridin-3-yl)-2,3-dihydro-1H-pyrido[3,4-b][1,4]oxazin-7-yloxy]-pyrrolidin-1-yl}-(1-methyl-1H-imidazol-4-yl)-methanone (according to Scheme 5)

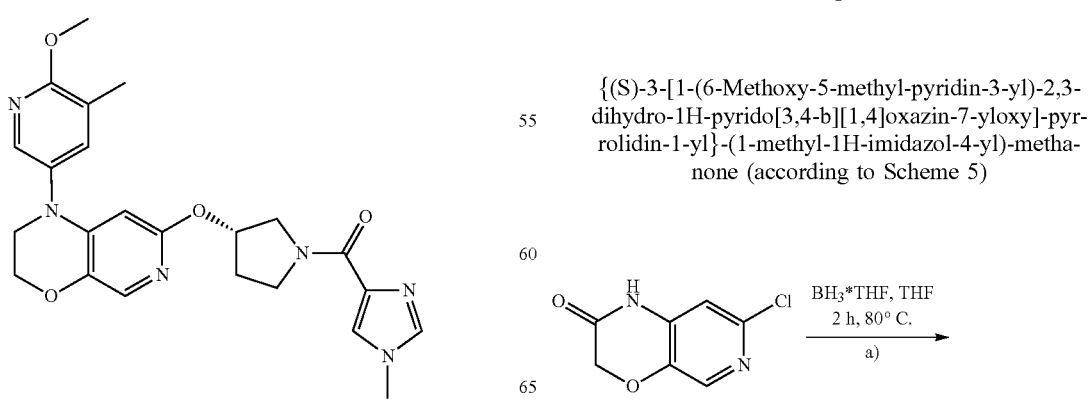

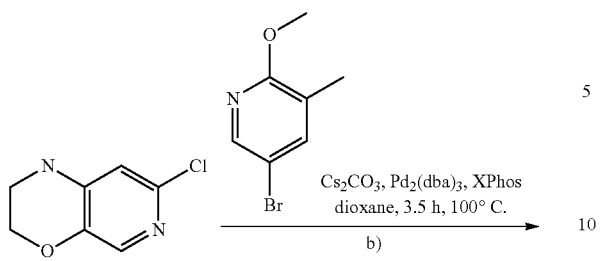

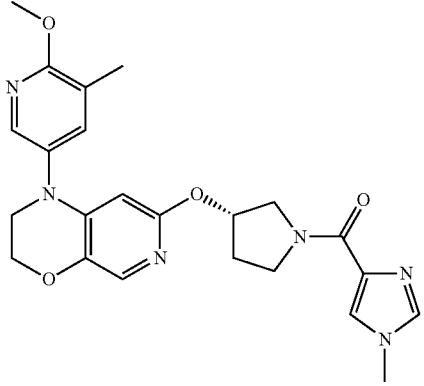

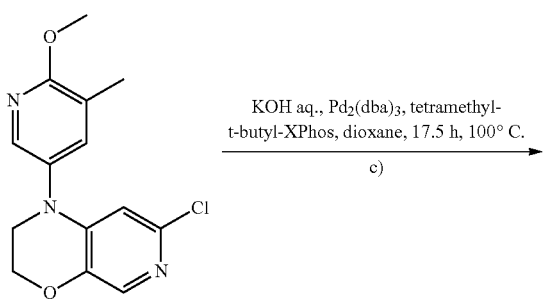

a) 7-Chloro-2,3-dihydro-1H-pyrido[3,4-b][1,4]oxazine

A mixture of 7-chloro-1H-pyrido[3,4-b][1,4]oxazin-2-one (CAS registry 928118-43-8) (630 mg, 3.41 mmol) and BH$_3$*THF (1 M in THF) (10.2 ml, 10.2 mmol) in THF (20 ml) was stirred for 2 h at 80° C. The reaction mixture was quenched with MeOH, NaOH aq. solution 1 M was added and the mixture was extracted with EtOAc. Combined organic layers were washed with brine, dried over Na$_2$SO$_4$, filtered and evaporated. The crude product was purified by flash chromatography on silica gel (heptane/EtOAc 100:0 to 50:50 in 12 min) to provide the title compound as a white solid (432 mg, 74% yield).

HPLC Rt$_{M1}$=0.47 min; ESIMS: 171 [(M+H)$^+$].

$^1$H NMR (400 MHz, CDCl$_3$): δ 7.74 (s, 1H), 6.46 (s, 1H), 4.43 (br s, 1H) 4.21-4.25 (m, 2H), 3.48-3.51 (m, 2H).

b) 7-Chloro-1-(6-methoxy-5-methyl-pyridin-3-yl)-2,3-dihydro-1H-pyrido[3,4-b][1,4]-oxazine

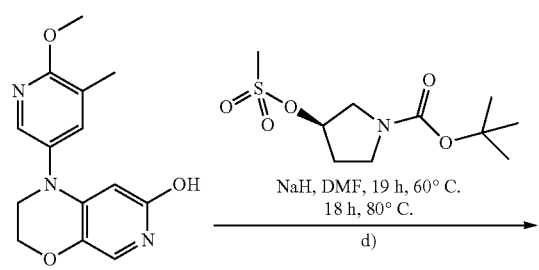

A mixture of 7-chloro-2,3-dihydro-1H-pyrido[3,4-b][1,4]oxazine (127 mg, 0.74 mmol), 5-bromo-2-methoxy-3-methylpyridine (CAS registry 760207-87-2) (0.196 g, 0.986 mmol), Cs$_2$CO$_3$ (534 mg, 1.64 mmol) and XPhos (28 mg, 0.06 mmol) in dioxane (3.5 ml) was degassed with argon and Pd$_2$(dba)$_3$ (27 mg, 0.03 mmol) was added. After stirring for 3.5 h at 100° C. the reaction mixture was filtered over hyflo, sat. aq. NaHCO$_3$ soln. was added and the mixture was extracted with EtOAc. Combined organic layers were washed with brine, dried over Na$_2$SO$_4$, filtered and evaporated. The crude product was purified by flash chromatography on silica gel (heptane/EtOAc 95:5 to 40:60 in 14 min) to provide the title compound as a pale colored solid (190 mg, 87% yield).

HPLC Rt$_{M1}$=1.04 min; ESIMS: 292 [(M+H)$^+$].

$^1$H NMR (400 MHz, CDCl$_3$): δ 7.94 (d, 1H), 7.80 (s, 1H), 7.31 (d, 1H), 6.31 (s, 1H), 4.34-4.37 (m, 2H), 4.01 (s, 3H), 3.68-3.72 (m, 2H), 2.24 (s, 3H).

c) 1-(6-Methoxy-5-methyl-pyridin-3-yl)-2,3-dihydro-1H-pyrido[3,4-b][1,4]oxazin-7-ol

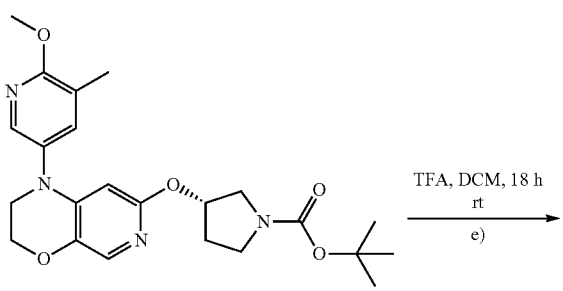

A mixture of 7-chloro-1-(6-methoxy-5-methyl-pyridin-3-yl)-2,3-dihydro-1H-pyrido[3,4-b][1,4]oxazine (190 mg, 0.65 mmol), tetramethyl-t-butyl-XPhos (13 mg, 0.03 mmol) in dioxane (3 ml) and 5M aq. KOH soln. (0.04 ml, 1.95 mmol) was degassed with argon and Pd$_2$(dba)$_3$ (6 mg, 0.01 mmol) was added. After stirring for 17.5 h at 100° C. the

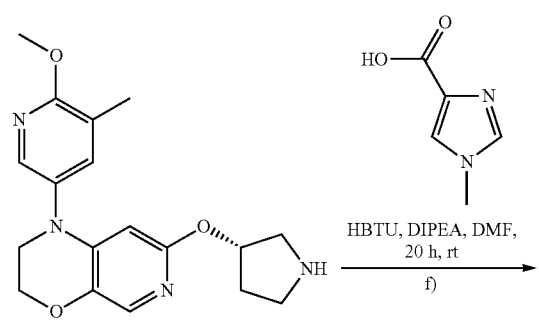

reaction mixture was filtered over hyflo, the filtrate was dried over Na$_2$SO$_4$, filtered and evaporated. The crude product was purified by flash chromatography on silica gel (EtOAc/MeOH 100:0 to 85:15 in 17 min) to provide the title compound as a white solid (111 mg, 62% yield).

HPLC Rt$_{M1}$=0.67 min; ESIMS: 274 [(M+H)$^+$].

$^1$H NMR (400 MHz, CDCl$_3$): δ 10.32 (brs, 1H), 8.02 (d, 1H), 7.62 (m, 1H), 6.89 (s, 1H), 4.84 (s, 1H), 4.17-4.21 (m, 2H), 3.91 (s, 3H), 3.61-3.66 (m, 2H), 2.17 (s, 3H).

d) (S)-3-[1-(6-Methoxy-5-methyl-pyridin-3-yl)-2,3-dihydro-1H-pyrido[3,4-b][1,4]oxazin-7-yloxy]-pyrrolidine-1-carboxylic acid tert-butyl ester A solution of 1-(6-methoxy-5-methyl-pyridin-3-yl)-2,3-dihydro-1H-pyrido[3,4-b][1,4]oxazin-7-ol (111 mg, 0.41 mmol) in DMF (3 ml) was treated with NaH (33 mg, 0.81 mmol) for 10 min at 20° C. (R)-3-Methanesulfonyloxy-pyrrolidine-1-carboxylic acid tert-butyl ester (CAS registry 127423-61-4) (162 mg, 0.61 mmol) was added. After stirring for 19 h at 60° C. and 18 h at 80° C. sat. aq. NaHCO$_3$ soln. was added and the reaction mixture was extracted with TBME. Combined organic layers were washed with brine, dried over Na$_2$SO$_4$, filtered and evaporated. The crude product was purified by flash chromatography on silica gel (heptane/EtOAc 93:7 to 40:60 in 13.5 min) to provide the title compound as a pale yellow oil (107 mg, 59% yield).

HPLC Rt$_{M1}$=1.21 min; ESIMS: 443 [(M+H)$^+$].

$^1$H NMR (400 MHz, CDCl$_3$): δ 7.93 (d, 1H), 7.61 (br s, 1H), 7.32 (br s 1H), 5.71 (s, 1H), 5.41 (br s, 1H), 4.32 (br s, 2H), 3.99 (s, 3H), 3.65-3.70 (m, 2H), 3.37-3.61 (m, 4H), 2.23 (s, 3H), 1.58 (s, 9H), 0.82-0.97 (m, 2H).

e) 1-(6-Methoxy-5-methyl-pyridin-3-yl)-7-((S)-pyrrolidin-3-yloxy)-2,3-dihydro-1H-pyrido[3,4-b][1,4]oxazine A solution of (S)-3-[1-(6-methoxy-5-methyl-pyridin-3-yl)-2,3-dihydro-1H-pyrido[3,4-b][1,4]-oxazin-7-yloxy]-pyrrolidine-1-carboxylic acid tert-butyl ester (103 mg, 0.23 mmol) and TFA (0.179 ml, 2.33 mmol) in DCM (1.8 ml) was stirred for 18 h at rt. Sat. aq. Na$_2$CO$_3$ soln. was added and the reaction mixture was extracted with DCM. Combined organic layers were washed with brine, dried over Na$_2$SO$_4$, filtered and evaporated, the title compound was as a pale yellow foam (72 mg, 90% yield).

HPLC Rt$_{M1}$=0.64 min; ESIMS: 343 [(M+H)$^+$].

$^1$H NMR (400 MHz, CDCl$_3$): δ 7.93 (d, 1H), 7.62 (s, 1H), 7.32 (m, 1H), 5.70 (s, 1H), 5.29-5.35 (m, 1H), 4.29-4.33 (m, 2H), 3.99 (s, 3H), 3.65-3.69 (m, 2H), 2.82-3.14 (m, 4H), 2.22 (s, 3H), 1.80-2.10 (m, 2H).

f) {(S)-3-[1-(6-Methoxy-5-methyl-pyridin-3-yl)-2,3-dihydro-1H-pyrido[3,4-b][1,4]oxazin-7-yloxy]-pyrrolidin-1-yl}-(1-methyl-1H-imidazol-4-yl)-methanone A mixture of 1-methyl-1H-imidazole-4-carboxylic acid (CAS registry 41716-18-1) (15 mg, 0.12 mmol), HBTU (53 mg, 0.14 mmol) and DIPEA (0.025 ml, 0.14 mmol) in DMF (0.6 ml) was stirred at rt for 5 min. A solution of 1-(6-methoxy-5-methyl-pyridin-3-yl)-7-((S)-pyrrolidin-3-yloxy)-2,3-dihydro-1H-pyrido[3,4-b][1,4]oxazine (0.037 g, 0.11 mmol) in DMF (0.6 ml) was added. After stirring for 20 h at rt water was added and the reaction mixture and was extracted with EtOAc. Combined organic layers were washed with brine, dried over Na$_2$SO$_4$, filtered and evaporated. The crude product was purified by prep. RP-HPLC (column SunFire C18, H$_2$O+0.1% TFA/ACN+0.1% TFA 90:10 to 60:40 in 16 min) to provide the title compound as a pale yellow foam (24 mg, 49% yield).

HPLC Rt$_{M1}$=0.74 min; ESIMS: 451 [(M+H)$^+$].

$^1$H NMR (400 MHz, DMSO): δ 8.00 (m, 1H), 7.58-7.63 (m, 3H), 7.53 (d, 1H), 5.51 (d, 1H), 5.29-5.40 (m, 1H), 4.23-4.29 (m, 2H), 3.99 (s, 3H), 3.77-4.19 (m, 2H), 3.66 (m, 5H), 3.39-3.63 (m, 2H), 2.15 (s, 3H), 1.89-2.11 (m, 2H).

Examples E2 to 11

The compounds listed in Table 5 were prepared by a procedure analogous to that used in Example E1.

TABLE 5

| Example | Compound/ Reaction Conditions | HPLC Rt [min] (method) | MS [m/z; (M + 1)$^+$] |
|---|---|---|---|
| E2 | (S)-3-[1-(6-Methoxy-5-methyl-pyridin-3-yl)-2,3-dihydro-1H-pyrido[3,4-b][1,4]oxazin-7-yloxy]-pyrrolidine-1-carboxylic acid tert-butyl ester<br>Buchwald amination condition: CA4<br>Side chain introduction condition: CC1<br>Precursors used: CAS 928118-43-8, IA9, 127423-61-4 | 1.19 (M1) | 443 |

TABLE 5-continued

| Example | Compound/Reaction Conditions | HPLC Rt [min] (method) | MS [m/z; (M + 1)+] |
|---|---|---|---|
| E3 | {(S)-3-[1-(6-Methoxy-5-methyl-pyridin-3-yl)-2,3-dihydro-1H-pyrido[3,4-b][1,4]oxazin-7-yloxy]-pyrrolidin-1-yl}-(tetrahydro-pyran-4-yl)-methanone<br>Buchwald amination condition: CA4<br>Amide bond condition: CB6<br>Side chain introduction condition: CC1<br>Precursors used: CAS 928118-43-8, 127423-61-4, IA9, acyl chloride 40191-32-0 | 0.84 (M1) | 455 |
| E4 | {(S)-3-[1-(6-Difluoromethoxy-5-methyl-pyridin-3-yl)-2,3-dihydro-1H-pyrido[3,4-b][1,4]oxazin-7-yloxy]-pyrrolidin-1-yl}-(1,1-dioxo-hexahydro-1lambda*6*-thiopyran-4-yl)-methanone<br>Buchwald amination condition: CA4<br>Amide bond condition: CB4<br>Side chain introduction condition: CC1<br>Precursors used: CAS 928118-43-8, IA8, 127423-61-4, 64096-87-3 | 1.09 (M1) | 328 |

TABLE 5-continued

| Example | Compound/Reaction Conditions | HPLC Rt [min] (method) | MS [m/z; (M + 1)+] |
|---|---|---|---|
| E5 | 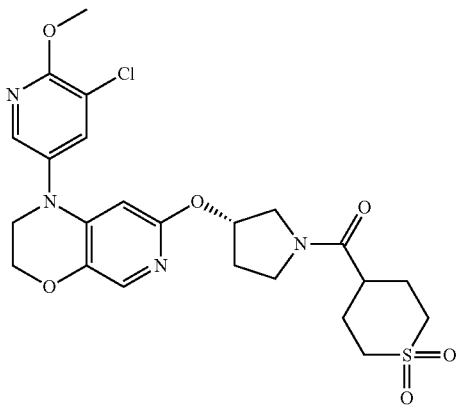 [SMILES: COc1ncc(N2CCOc3cnc(O[C@H]4CCN(C(=O)C5CCS(=O)(=O)CC5)C4)cc32)cc1Cl]<br>{(S)-3-[1-(5-Chloro-6-methoxy-pyridin-3-yl)-2,3-dihydro-1H-pyrido[3,4-b][1,4]oxazin-7-yloxy]-pyrrolidin-1-yl}-(1,1-dioxo-hexahydro-1lambda*6*-thiopyran-4-yl)-methanone<br>Buchwald amination condition: CA4<br>Amide bond condition: CB1<br>Side chain introduction condition: CC1<br>Precursors used: CAS 928118-43-8, 127423-61-4, IA11, 64096-87-3 | 0.79 (M1) | 523 |
| E6 | 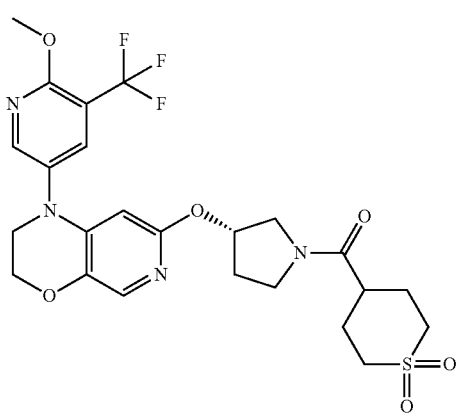 [SMILES: COc1ncc(N2CCOc3cnc(O[C@H]4CCN(C(=O)C5CCS(=O)(=O)CC5)C4)cc32)cc1C(F)(F)F]<br>(1,1-Dioxo-hexahydro-1lambda*6*-thiopyran-4-yl)-{(S)-3-[1-(6-methoxy-5-trifluoromethyl-pyridin-3-yl)-2,3-dihydro-1H-pyrido[3,4-b][1,4]oxazin-7-yloxy]-pyrrolidin-1-yl}-methanone<br>Buchwald amination condition: CA4<br>Amide bond condition: CB1<br>Side chain introduction condition: CC1<br>Precursors used: CAS 928118-43-8/127423-61-4/IA21/64096-87-3 | 0.92 (M1) | 557 |

TABLE 5-continued

| Example | Compound/Reaction Conditions | HPLC Rt [min] (method) | MS [m/z; (M + 1)+] |
|---|---|---|---|
| E7 | 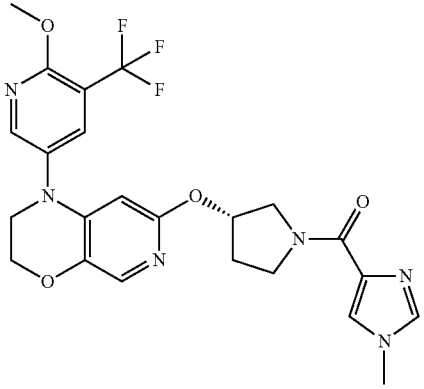 [SMILES: COc1ncc(N2CCOc3cnc(O[C@H]4CCN(C(=O)c5cn(C)cn5)C4)cc32)cc1C(F)(F)F]<br>{(S)-3-[1-(6-Methoxy-5-trifluoromethyl-pyridin-3-yl)-2,3-dihydro-1H-pyrido[3,4-b][1,4]oxazin-7-yloxy]-pyrrolidin-1-yl}-(1-methyl-1H-imidazol-4-yl)-methanone<br>Buchwald amination condition: CA4<br>Amide bond condition: CB1<br>Side chain introduction condition: CC1<br>Precursors used: CAS 928118-43-8/127423-61-4/IA21/41716-18-1 | 0.87 (M1) | 505 |
| E8 | 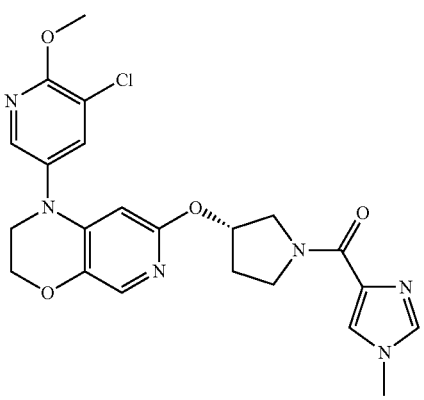<br>{(S)-3-[1-(5-Chloro-6-methoxy-pyridin-3-yl)-2,3-dihydro-1H-pyrido[3,4-b][1,4]oxazin-7-yloxy]-pyrrolidin-1-yl}-(1-methyl-1H-imidazol-4-yl)-methanone<br>Buchwald amination condition: CA4<br>Amide bond condition: CB1<br>Side chain introduction condition: CC1<br>Precursors used: CAS 928118-43-8, 127423-61-4, IA11, 41716-18-1 | 0.75 (M1) | 471 |

TABLE 5-continued

| Example | Compound/ Reaction Conditions | HPLC Rt [min] (method) | MS [m/z; (M + 1)+] |
|---|---|---|---|
| E9 | {(S)-3-[1-(6-Difluoromethoxy-5-methyl-pyridin-3-yl)-2,3-dihydro-1H-pyrido[3,4-b][1,4]oxazin-7-yloxy]-pyrrolidin-1-yl}-(tetrahydro-pyran-4-yl)-methanone<br>Buchwald amination condition: CA4<br>Amide bond condition: CB1<br>Side chain introduction condition: CC1<br>Precursors used: CAS 928118-43-8/127423-61-4/IA8/5337-03-1 | 0.95 (M1) | 491 |
| E10 | {(S)-3-[1-(6-Difluoromethoxy-5-methyl-pyridin-3-yl)-2,3-dihydro-1H-pyrido[3,4-b][1,4]oxazin-7-yloxy]-pyrrolidin-1-yl}-(1-methyl-1H-imidazol-4-yl)-methanone<br>Buchwald amination condition: CA4<br>Amide bond condition: CB1<br>Side chain introduction condition: CC1<br>Precursors used: CAS 928118-43-8/127423-61-4/IA8/41716-18-1 | 0.84 (M1) | 487 |

TABLE 5-continued

| Example | Compound/Reaction Conditions | HPLC Rt [min] (method) | MS [m/z; (M + 1)+] |
|---|---|---|---|
| E11 | 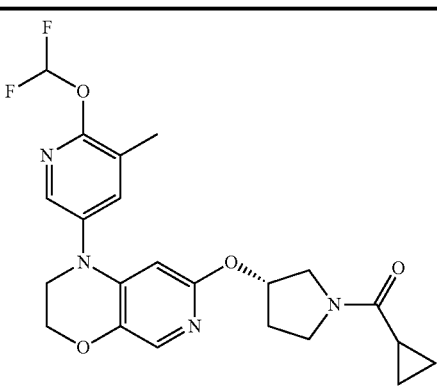<br>Cyclopropyl-{(S)-3-[1-(6-difluoromethoxy-5-methyl-pyridin-3-yl)-2,3-dihydro-1H-pyrido[3,4-b][1,4]oxazin-7-yloxy]-pyrrolidin-1-yl}-methanone<br>Buchwald amination condition: CA4<br>Amide bond condition: CB6<br>Side chain introduction condition: CC1<br>Precursors used: CAS 928118-43-8/127423-61-4/IA8/Acyl chloride: 4023-34-1 | 1.01 (M1) | 447 |

Reference Examples E12 to E13

The compounds listed in Table 5a were prepared by a procedure analogous to that used in Example E1, applying adequate protecting group strategies.

TABLE 5a

| Reference Example | Compound/Reaction Conditions | HPLC Rt [min] (method) | MS [m/z; (M + 1)+] |
|---|---|---|---|
| E12 | 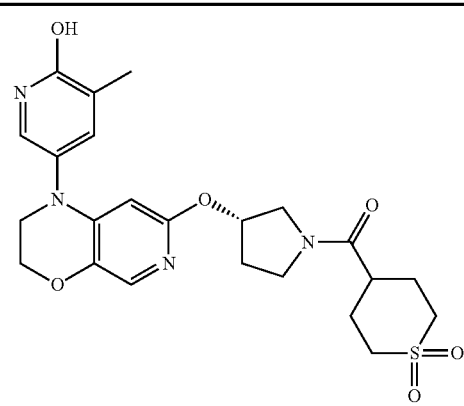<br>(1,1-Dioxo-hexahydro-1lambda*6*-thiopyran-4-yl)-{(S)-3-[1-(6-hydroxy-5-methyl-pyridin-3-yl)-2,3-dihydro-1H-pyrido[3,4-b][1,4]oxazin-7-yloxy]-pyrrolidin-1-yl}-methanone<br>Buchwald amination condition: CA2<br>Amide bond condition: CB7<br>Side chain introduction condition: CC1<br>Precursors used: CAS 928118-43-8/127423-61-4/IA69/64096-87-3 | 0.54 (M16) | 489 |

TABLE 5a-continued

| Reference Example | Compound/ Reaction Conditions | HPLC Rt [min] (method) | MS [m/z; (M + 1)+] |
|---|---|---|---|
| E13 | (1,1-Dioxo-hexahydro-1lambda*6*-thiopyran-4-yl)-{(S)-3-[1-(5-hydroxymethyl-6-methoxy-pyridin-3-yl)-2,3-dihydro-1H-pyrido[3,4-b][1,4]oxazin-7-yloxy]-pyrrolidin-1-yl}-methanone<br>Buchwald amination condition: CA2<br>Amide bond condition: CB7<br>Side chain introduction condition: CC1<br>Precursors used: CAS 928118-43-8/127423-61-4/IA70/64096-87-3 | 0.63 (M16) | 519 |

Example F1

(1,1-Dioxo-hexahydro-1lambda*6*-thiopyran-4-yl)-{(S)-3-[1-(6-methoxy-5-methyl-pyridin-3-yl)-2,3-dihydro-1H-pyrido[3,4-b][1,4]oxazin-7-yloxy]-pyrrolidin-1-yl}-methanone (according to Scheme 6)

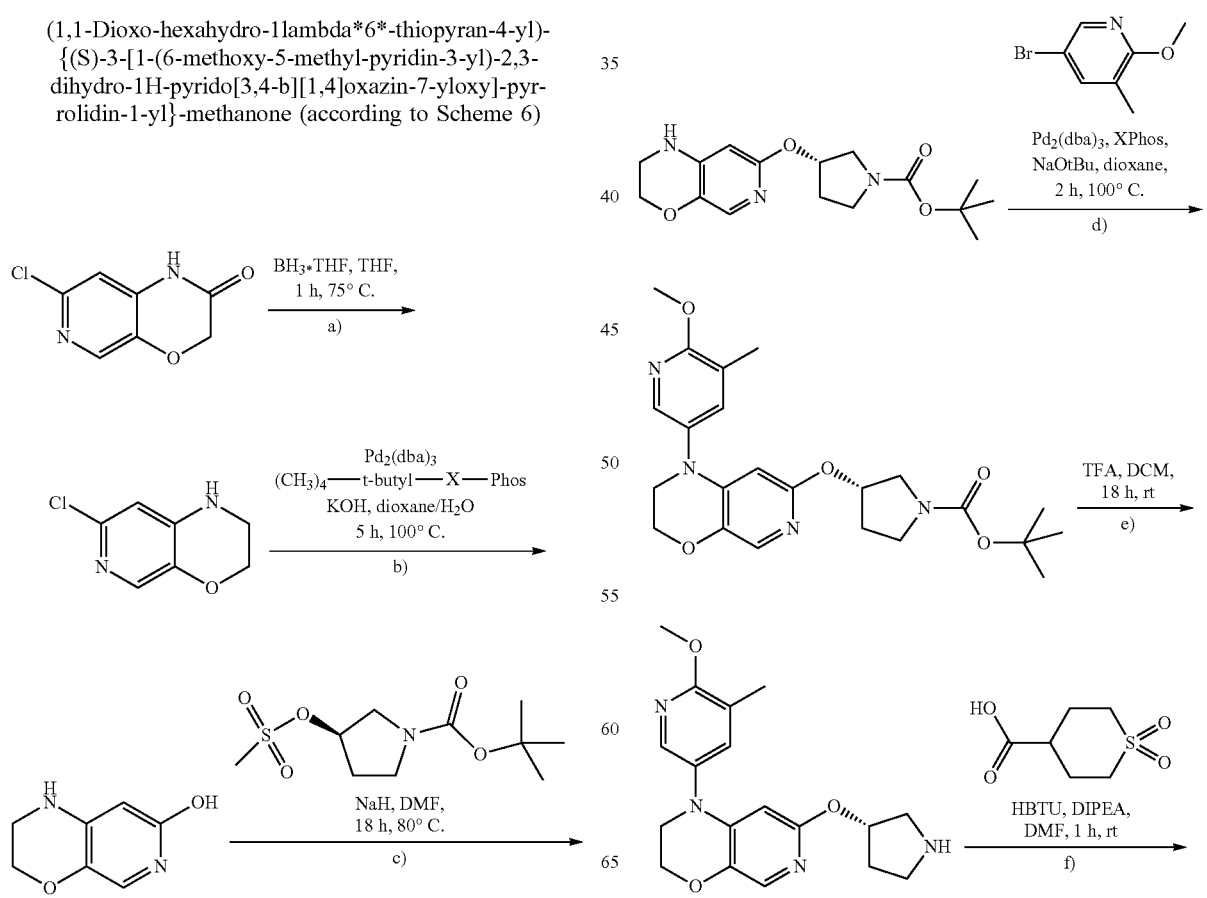

-continued

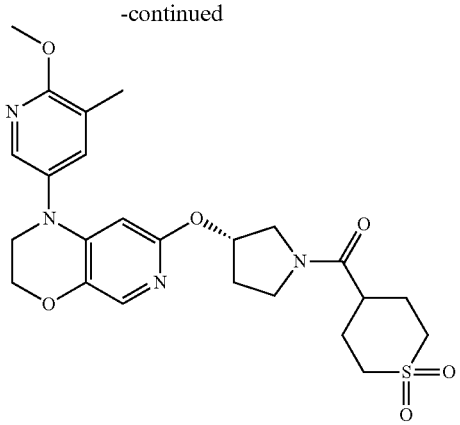

a) 7-Chloro-2,3-dihydro-1H-pyrido[3,4-b][1,4]oxazine

A solution of 7-chloro-1H-pyrido[3,4-b][1,4]oxazin-2-one (CAS registry 928118-43-8) (3.70 g, 20 mmol) in THF (63 ml) was treated with BH$_3$*THF (1M in THF, 47 ml, 47 mmol). The reaction mixture was stirred at 75° C. for 1 h, then cooled down to rt and quenched with methanol (24 ml, 600 mmol). The reaction mixture was concentrated under reduced pressure and the residue was taken up with EtOAc and washed with sat. aq. NaHCO$_3$ soln. The organic layer was dried over MgSO$_4$, filtered and concentrated under reduced pressure to afford the title product as a pale yellow solid (3.3 g, 96% yield).

UPLC Rt$_{M1}$=0.47 min; ESIMS: 171 [(M+H)$^+$].
$^1$H NMR (400 MHz, DMSO-d$_6$): δ 7.53 (s, 1H), 7.11 (br s, 1H), 6.47 (s, 1H), 4.09 (t, 2H), 3.17-3.38 (m, 2H).

b) 2,3-Dihydro-1H-pyrido[3,4-b][1,4]oxazin-7-ol

A mixture of 7-chloro-2,3-dihydro-1H-pyrido[3,4-b][1,4]oxazine (1.08 g, 6.33 mmol), aq. KOH soln. (1.07 g, 19 mmol KOH in 5.4 ml water), 2-di-t-butylphosphino-3,4,5,6-tetramethyl-2',4',6-tri-i-propylbiphenyl 98% (0.30 g, 0.63 mmol) and Pd$_2$(dba)$_3$ (0.29 g, 0.32 mmol) in dioxane (32.5 ml) was degassed three times with nitrogen, the tube was sealed and the reaction mixture was stirred at 100° C. for 5 h. After cooling to rt, the reaction mixture was filtered through hyflo, rinsed with EtOAc and methanol. The filtrates were concentrated and the title compound was obtained after flash chromatography on silica gel (DCM/MeOH, 98:2 to 75:25) as an orange residue (660 mg, 69% yield)

UPLC Rt$_{M1}$=0.34 min; ESIMS: 153 [(M+H)$^+$].
$^1$H NMR (400 MHz, DMSO-d$_6$): δ 10.33 (br s, 1H), 7.03 (br s, 1H), 6.71 (s, 1H), 5.15 (s, 1H), 3.95 (t, 2H), 3.25 (m, 2H).

c) (S)-3-(2,3-Dihydro-1H-pyrido[3,4-b][1,4]oxazin-7-yloxy)-pyrrolidine-1-carboxylic acid tert-butyl ester A dry solution of 2,3-dihydro-1H-pyrido[3,4-b][1,4]oxazin-7-ol (0.66 g, 4.34 mmol) and (R)-3-methanesulfonyloxy-pyrrolidine-1-carboxylic acid tert-butyl ester (CAS registry 127423-61-4) (1.73 g, 6.51 mmol) in DMF (40 ml) was treated with sodium hydride (60% in mineral oil, 0.21 g, 8.68 mmol) and the reaction mixture was stirred at 80° C. for 18 h. After cooling to rt, the reaction mixture was diluted with TBME and washed with sat. aq. NaHCO$_3$ soln. The organic layer was dried over MgSO$_4$, filtered, concentrated and the title compound was obtained after flash chromatography on silica gel (cyclohexane/EtOAc, 95:5 to 30:70) as a yellow oil (1.035 g, 75% purity, 56% yield)

UPLC Rt$_{M1}$=0.65 min; ESIMS: 322 [(M+H)$^+$].
$^1$H NMR (400 MHz, CDCl$_3$): δ 7.54 (s, 1H), 5.86 (s, 1H), 5.42 (br s, 1H), 4.25-4.41 (m, 1H), 4.19 (t, 2H), 3.38-3.66 (m, 6H), 2.00-2.18 (m, 2H), 1.46 (d, 9H).

d) (S)-3-[1-(6-Methoxy-5-methyl-pyridin-3-yl)-2,3-dihydro-1H-pyrido[3,4-b][1,4]oxazin-7-yloxy]-pyrrolidine-1-carboxylic acid tert-butyl ester A mixture of (S)-3-(2,3-dihydro-1H-pyrido[3,4-b][1,4]oxazin-7-yloxy)-pyrrolidine-1-carboxylic acid tert-butyl ester (254 mg, 0.79 mmol), 5-bromo-2-methoxy-3-methyl-pyridine (CAS registry 760207-87-2) (208 mg, 1.03 mmol), XPhos (30 mg, 0.06 mmol), and NaOtBu (167 mg, 1.74 mmol) in dioxane (6 ml) was degassed with argon for 5 min, then Pd$_2$(dba)$_3$ (29 mg, 0.03 mmol) was added. The tube was filled with argon, sealed and the reaction mixture was stirred at 100° C. for 2 h. After cooling to rt, the reaction mixture was filtered through hyflo, rinsed with EtOAc and the filtrates were washed with sat. aq. NaHCO$_3$ soln. The aq. layer was twice reextracted with EtOAc, the combined organic layers were dried over Na$_2$SO$_4$, filtered, concentrated and the title compound was obtained after flash chromatography on silica gel (heptane/EtOAc, 100:0 to 50:50) as a clear gum (274 mg, 78% yield). UPLC Rt$_{M1}$=1.20 min; ESIMS: 443 [(M+H)$^+$].
$^1$H NMR (400 MHz, CDCl$_3$): δ 7.93 (d, 1H), 7.61 (br s, 1H), 7.30-7.35 (m, 1H), 5.71 (s, 1H), 5.34-5.46 (m, 1H), 4.31 (br s, 2H), 3.99 (s, 3H), 3.68 (t, 2H), 3.34-3.62 (m, 4H), 2.23 (s, 3H), 2.01-2.09 (m, 2H), 1.44 (s, 9H).

e) 1-(6-Methoxy-5-methyl-pyridin-3-yl)-7-((S)-pyrrolidin-3-yloxy)-2,3-dihydro-1H-pyrido[3,4-b][1,4]oxazine A solution of (S)-3-[1-(6-methoxy-5-methyl-pyridin-3-yl)-2,3-dihydro-1H-pyrido[3,4-b][1,4]oxazin-7-yloxy]-pyrrolidine-1-carboxylic acid tert-butyl ester (364 mg, 0.82 mmol) in DCM (6 ml) was treated with TFA (0.63 ml, 8.23 mmol) and the reaction mixture was stirred at rt for 18 h, then quenched with sat. aq. NaHCO$_3$ soln. and extracted with DCM. The organic layer was dried over MgSO$_4$, filtered and concentrated under reduced pressure to afford the title product as a red oil, which was used in the next step without further purification (313 mg, 90% purity, quantitative yield).

UPLC Rt$_{M1}$=0.65 min; ESIMS: 343 [(M+H)$^+$].
$^1$H NMR (400 MHz, CDCl$_3$): δ 7.93 (d, 1H), 7.62 (s, 1H), 7.32 (d, 1H), 5.70 (s, 1H), 5.26-5.36 (m, 1H), 4.31 (t, 2H), 3.99 (s, 3H), 3.67 (t, 2H), 2.95-3.15 (m, 3H), 2.81-2.92 (m, 1H), 2.22 (s, 3H), 1.98-2.10 (m, 1H), 1.79-1.90 (m, 1H).

f) (1,1-Dioxo-hexahydro-1lambda*6*-thiopyran-4-yl)-{(S)-3-[1-(6-methoxy-5-methyl-pyridin-3-yl)-2,3-dihydro-1H-pyrido[3,4-b][1,4]oxazin-7-yloxy]-pyrrolidin-1-yl}-methanone A solution of 1,1-dioxo-hexahydro-1lambda*6*-thiopyran-4-carboxylic acid (CAS registry 64096-87-3) (106 mg, 0.59 mmol) in DMF (4 ml) was treated with HBTU (225 mg, 0.59 mmol) and DIPEA (0.24 ml, 1.37 mmol). The resulting orange solution was stirred at rt for 5 min, then a solution of 1-(6-methoxy-5-methyl-pyridin-3-yl)-7-((S)-pyrrolidin-3-yloxy)-2,3-dihydro-1H-pyrido[3,4-b][1,4]oxazine (156 mg, 0.46 mmol) in DMF (2 ml) was added. The reaction mixture was stirred at rt for 1 h then concentrated under reduced pressure and the residue was taken up with DCM and washed with sat. aq. NaHCO$_3$ soln. The organic layer was dried by passing it through a phase separating cartridge, concentrated and the title compound was obtained after SFC chromatography (column DEAP (250 mm×30 mm, 60 A, 5 μm) Princeton, gradient 11-16% of methanol in supercritical CO$_2$ in 6 min) as a slightly coloured solid (112 mg, 49% yield).

UPLC Rt$_{M1}$=0.81 min; ESIMS: 503 [(M+H)$^+$].

$^1$H NMR (400 MHz, DMSO-d$_6$): δ 8.01 (s, 1H), 7.61 (m, 1H), 7.52 (d, 1H), 5.52 (d, 1H), 5.24-5.43 (m, 1H), 4.26 (br s, 2H), 3.89 (s, 3H), 3.59-3.79 (m, 3H), 3.41-3.56 (m, 2H), 3.21-3.39 (m, 1H), 2.98-3.21 (m, 4H), 2.67-2.83 (m, 1H), 1.84-2.20 (m, 9H).

$^1$H NMR (600 MHz, DMSO-d$_6$): δ 8.01 (s, 1H), 7.63-7.59 (m, 1H), 7.55-7.51 (m, 1H), 5.55-5.51 (m, 1H), 5.43-5.24 (m, 1H), 4.29-4.22 (m, 2H), 3.90 (s, 3H), 3.80-3.60 (m, 2H), 3.56-3.37 (m, 3H), 3.28-2.99 (m, 5H), 2.89-2.66 (m, 1H), 2.19-2.09 (m, 4H), 2.08-1.98 (m, 2H), 1.98-1.86 (m, 3H).

Crystallization of Example F1 by Heating and Cooling in Isopropanol/Diethyl Ether 474 mg of amorphous Example F1 was suspended in 1.4 mL of isopropanol. The mixture was heated to 70° C. and stirred at 70° C. to allow complete dissolution of Example F1. The solution was cooled down to RT, a glue residue was formed. 2 mL of diethyl ether was added and the slurry was stirred for 48 h. A white suspension was formed. The suspension was filtered and the solid was dried at 40° C., 15 mbar. A fine, white powder was obtained. The material contains only slight residual solvent (<0.5%). A crystalline anhydrous form of Example F1 with an onset melting of 148.77° C. was obtained.

List of most significant 2-Theta peaks from X-ray Powder Diffraction Pattern with tolerances±0.5 of Example F1 anhydrous form (Method M1) (including low/weak peaks for information). Note: This list of peaks is not exhaustive but are only "inter alia".

| 2-Theta in deg | Intensity |
|---|---|
| 9.1 | Low |
| 10.2 | Medium |
| 11.9 | Medium |
| 13.0 | Low |
| 17.1 | Strong |
| 17.7 | Medium, unresolved |
| 18.7 | Medium |
| 20.3 | Medium, unresolved |
| 20.8 | Medium, unresolved |
| 26.0 | Medium/low |
| 26.7 | Medium |
| 23.2 | Medium/low |
| 24.1 | Medium/low |
| 24.8 | Medium/low |
| 29.3 | Medium/low |
| 27.4 | Medium/low |
| 21.4 | Medium/low |

Examples F2 to F15

The compounds listed in Table 6 were prepared by a procedure analogous to that used in Example F1.

TABLE 6

| Example | Compound/Reaction Conditions | HPLC Rt [min] (method) | MS [m/z; (M + 1)$^+$] |
|---|---|---|---|
| F2 | 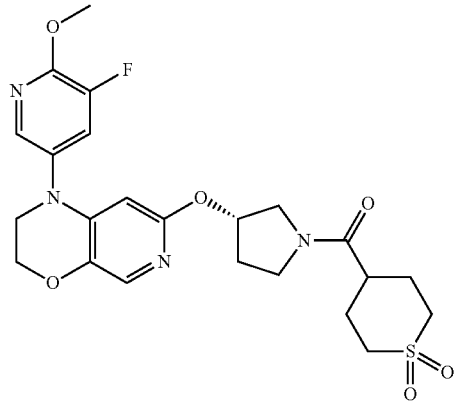 [SMILES: COc1ncc(N2CCOc3cnc(O[C@H]4CCN(C(=O)C5CCS(=O)(=O)CC5)C4)cc32)cc1F]<br>(1,1-Dioxo-hexahydro-1lambda*6*-thiopyran-4-yl)-{(S)-3-[1-(5-fluoro-6-methoxy-pyridin-3-yl)-2,3-dihydro-1H-pyrido[3,4-b][1,4]oxazin-7-yloxy]-pyrrolidin-1-yl}-methanone<br>Buchwald amination condition: CA2<br>Amide bond condition: CB2<br>Side chain introduction condition: CC1<br>Precursors used: CAS 928118-43-8/127423-61-4/IA10/64096-87-3 | 0.79 (M1) | 507 |

TABLE 6-continued

| Example | Compound/ Reaction Conditions | HPLC Rt [min] (method) | MS [m/z; (M + 1)+] |
|---|---|---|---|
| F3 | 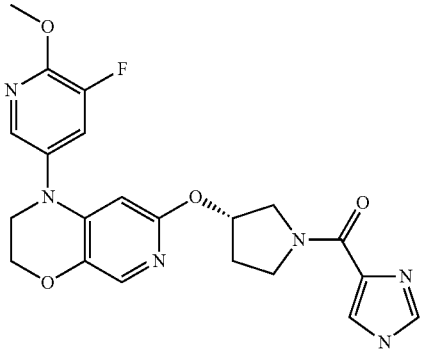<br>{(S)-3-[1-(5-Fluoro-6-methoxy-pyridin-3-yl)-2,3-dihydro-1H-pyrido[3,4-b][1,4]oxazin-7-yloxy]-pyrrolidin-1-yl}-(1-methyl-1H-imidazol-4-yl)-methanone<br>Buchwald amination condition: CA2<br>Amide bond condition: CB2<br>Side chain introduction condition: CC1<br>Precursors used: CAS 928118-43-8/127423-61-4/IA10/41716-18-1 | 0.73 (M1) | 455 |
| F4 | 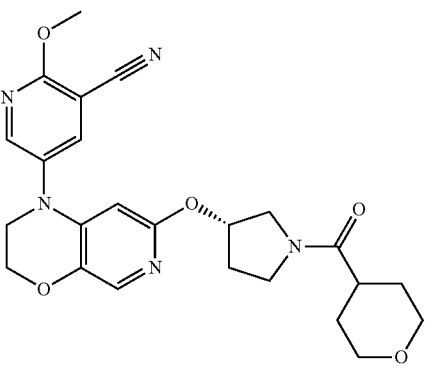 [SMILES: COc1ncc(N2CCOc3cnc(O[C@H]4CCN(C(=O)C5CCOCC5)C4)cc32)cc1C#N]<br>2-Methoxy-5-{7-[(S)-1-(tetrahydro-pyran-4-carbonyl)-pyrrolidin-3-yloxy]-2,3-dihydro-pyrido[3,4-b][1,4]oxazin-1-yl}-nicotinonitrile<br>Buchwald amination condition: CA2<br>Amide bond condition: CB6<br>Side chain introduction condition: CC1<br>Precursors used: CAS 928118-43-8, 127423-61-4, IA12, acyl chloride 40191-32-0 | 0.83 (M1) | 466 |
| F5 | 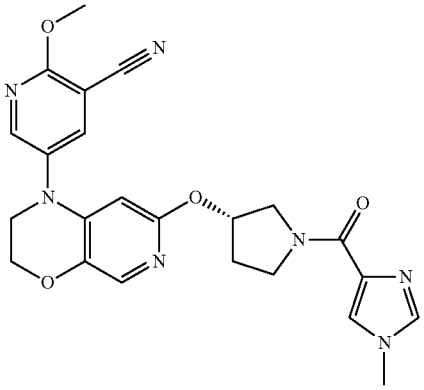 [SMILES: COc1ncc(N2CCOc3cnc(O[C@H]4CCN(C(=O)c5cn(C)cn5)C4)cc32)cc1C#N]<br>2-Methoxy-5-{7-[(S)-1-(1-methyl-1H-imidazole-4-carbonyl)-pyrrolidin-3-yloxy]-2,3-dihydro- | 0.73 (M1) | 462 |

TABLE 6-continued

| Example | Compound/ Reaction Conditions | HPLC Rt [min] (method) | MS [m/z; (M + 1)+] |
|---|---|---|---|
| | pyrido[3,4-b][1,4]oxazin-1-yl}-nicotinonitrile<br>Buchwald amination condition: CA2<br>Amide bond condition: CB1<br>Side chain introduction condition: CC1<br>Precursors used: CAS 928118-43-8, 127423-61-4, IA12, 41716-18-1 | | |
| F6 | {(S)-3-[1-(6-Methanesulfonyl-5-methyl-pyridin-3-yl)-2,3-dihydro-1H-pyrido[3,4-b][1,4]oxazin-7-yloxy]-pyrrolidin-1-yl}-(tetrahydro-pyran-4-yl)-methanone<br>Buchwald amination condition: CA4<br>Amide bond condition: CB6<br>Side chain introduction condition: CC1<br>Precursors used: CAS 928118-43-8, 127423-61-4, IA1, acyl chloride 40191-32-0 | 0.76 (M1) | 503 |
| F7 | {(S)-3-[1-(5-Difluoromethyl-6-methoxy-pyridin-3-yl)-2,3-dihydro-1H-pyrido[3,4-b][1,4]oxazin-7-yloxy]-pyrrolidin-1-yl}-(1,1-dioxo-hexahydro-1lambda*6*-thiopyran-4-yl)-methanone<br>Buchwald amination condition: CA2<br>Amide bond condition: CB2<br>Side chain introduction condition: CC1<br>Precursors used: CAS 928118-43-8/127423-61-4/IA6/64096-87-3 | 0.82 (M1) | 539 |

TABLE 6-continued

| Example | Compound/Reaction Conditions | HPLC Rt [min] (method) | MS [m/z; (M + 1)+] |
|---|---|---|---|
| F8 | 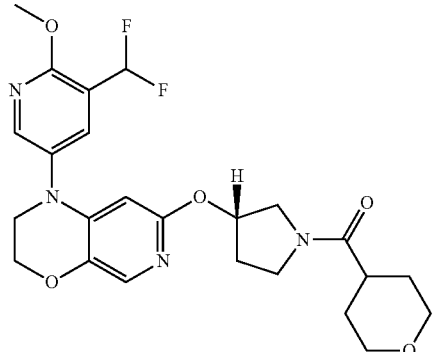 {(S)-3-[1-(5-Difluoromethyl-6-methoxy-pyridin-3-yl)-2,3-dihydro-1H-pyrido[3,4-b][1,4]oxazin-7-yloxy]-pyrrolidin-1-yl}-(tetrahydro-pyran-4-yl)-methanone<br>Buchwald amination condition: CA2<br>Amide bond condition: CB6<br>Side chain introduction condition: CC1<br>Precursors used: CAS 928118-43-8/127423-61-4/IA6/Acyl chloride 40191-32-0 | 0.88 (M1) | 491 |
| F9 | 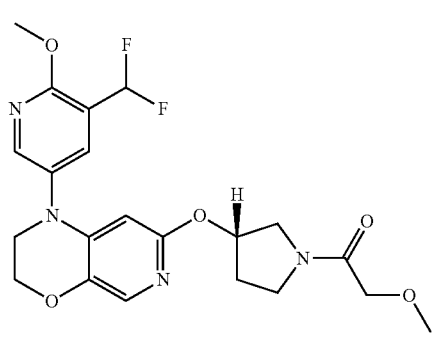 [SMILES: COCC(=O)N1CC[C@H](Oc2cc3c(cn2)OCCN3c2cnc(OC)c(C(F)F)c2)C1] 1-{(S)-3-[1-(5-Difluoromethyl-6-methoxy-pyridin-3-yl)-2,3-dihydro-1H-pyrido[3,4-b][1,4]oxazin-7-yloxy]-pyrrolidin-1-yl}-2-methoxy-ethanone<br>Buchwald amination condition: CA2<br>Amide bond condition: CB6<br>Side chain introduction condition: CC1<br>Precursors used: CAS 928118-43-8/127423-61-4/IA6/Acyl chloride: 38870-89-2 | 0.83 (M1) | 451 |
| F10 | 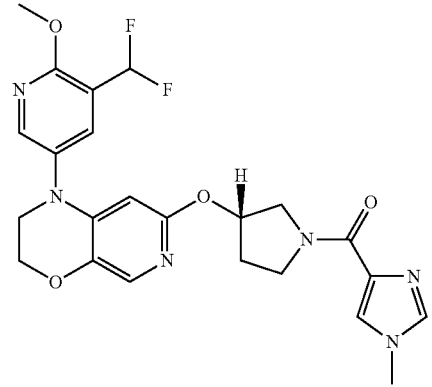 [SMILES: COc1ncc(N2CCOc3cnc(O[C@H]4CCN(C(=O)c5cn(C)cn5)C4)cc32)cc1C(F)F] {(S)-3-[1-(5-Difluoromethyl-6-methoxy-pyridin-3-yl)-2,3-dihydro-1H-pyrido[3,4-b][1,4]oxazin-7-yloxy]-pyrrolidin-1-yl}-(1-methyl-1H-imidazol-4-yl)-methanone | 0.77 (M1) | 487 |

TABLE 6-continued

| Example | Compound/Reaction Conditions | HPLC Rt [min] (method) | MS [m/z; (M + 1)+] |
|---|---|---|---|
| | Buchwald amination condition: CA2<br>Amide bond condition: CB3<br>Side chain introduction condition: CC1<br>Precursors used: CAS 928118-43-8/127423-61-4/IA6/41716-18-1 | | |
| F11 | 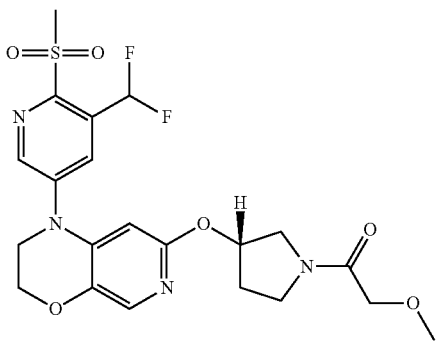 [SMILES: COCC(=O)N1CC[C@H](Oc2cc3c(cn2)OCCN3c2cnc(S(C)(=O)=O)c(C(F)F)c2)C1]<br>1-{(S)-3-[1-(5-Difluoromethyl-6-methanesulfonyl-pyridin-3-yl)-2,3-dihydro-1H-pyrido[3,4-b][1,4]oxazin-7-yloxy]-pyrrolidin-1-yl}-2-methoxy-ethanone<br>Buchwald amination condition: CA1<br>Amide bond condition: CB6<br>Side chain introduction condition: CC1<br>Precursors used: CAS 928118-43-8/127423-61-4/IA4/Acyl chloride: 38870-89-2 | 0.76 (M1) | 499 |
| F12 | 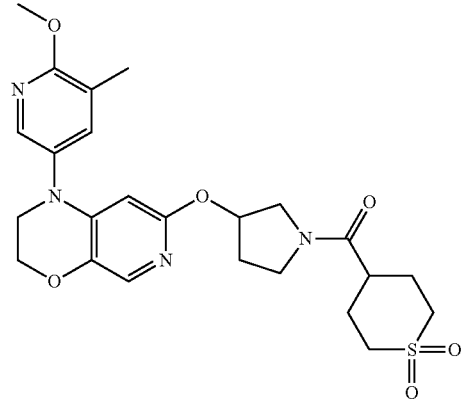<br>(1,1-Dioxo-hexahydro-1lambda*6*-thiopyran-4-yl)-{3-[1-(6-methoxy-5-methyl-pyridin-3-yl)-2,3-dihydro-1H-pyrido[3,4-b][1,4]oxazin-7-yloxy]-pyrrolidin-1-yl}-methanone<br>Buchwald amination condition: CA4<br>Amide bond condition: CB1<br>Side chain introduction condition: CC1<br>Precursors used: CAS 928118-43-8/141699-57-2/IA9/64096-87-3 | 0.81 (M1) | 503 |

TABLE 6-continued

| Example | Compound/Reaction Conditions | HPLC Rt [min] (method) | MS [m/z; (M + 1)+] |
|---|---|---|---|
| F13 | 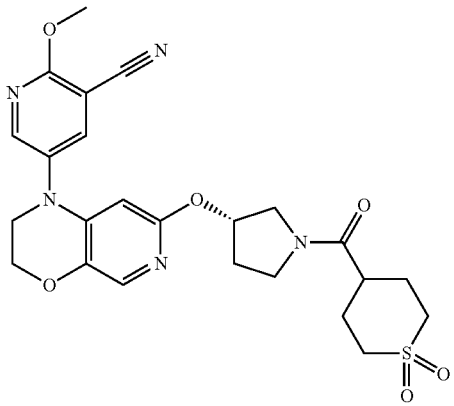 [SMILES: COc1ncc(N2CCOc3cnc(O[C@H]4CCN(C(=O)C5CCS(=O)(=O)CC5)C4)cc32)cc1C#N]<br>5-{7-[(S)-1-(1,1-Dioxo-hexahydro-1lambda*6*-thiopyran-4-carbonyl)-pyrrolidin-3-yloxy]-2,3-dihydro-pyrido[3,4-b][1,4]oxazin-1-yl}-2-methoxy-nicotinonitrile<br>Buchwald amination condition: CA2<br>Amide bond condition: CB1<br>Side chain introduction condition: CC1<br>Precursors used: CAS 928118-43-8, 127423-61-4, IA12, 64096-87-3 | 1.12 (M1) | 454 |
| F14 | 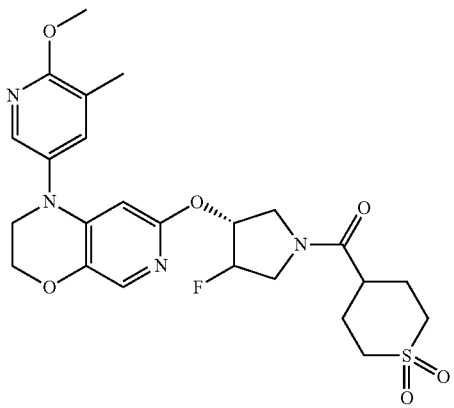 [SMILES: COc1ncc(N2CCOc3cnc(O[C@@H]4CN(C(=O)C5CCS(=O)(=O)CC5)CC4F)cc32)cc1C]<br>(1,1-Dioxo-hexahydro-1lambda*6*-thiopyran-4-yl)-{(R)-3-fluoro-4-[1-(6-methoxy-5-methyl-pyridin-3-yl)-2,3-dihydro-1H-pyrido[3,4-b][1,4]oxazin-7-yloxy]-pyrrolidin-1-yl}-methanone<br>Buchwald amination condition: CA2<br>Amide bond condition: CB4<br>Side chain introduction condition: CC1<br>Precursors used: CAS 869481-93-6/1174020-51-9<br>Chiral separation method: CD12 | 0.89 (M1)<br>35.9 (CD12) | 521 |

TABLE 6-continued

| Example | Compound/Reaction Conditions | HPLC Rt [min] (method) | MS [m/z; (M + 1)⁺] |
|---|---|---|---|
| F15 | 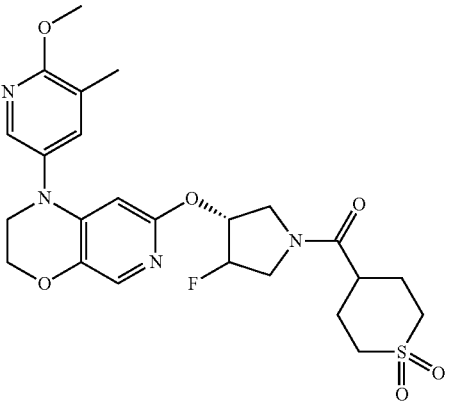 [SMILES: COc1ncc(N2CCOc3cnc(O[C@@H]4CN(C(=O)C5CCS(=O)(=O)CC5)CC4F)cc32)cc1C]<br>(1,1-Dioxo-hexahydro-1lambda*6*-thiopyran-4-yl)-{(R)-3-fluoro-4-[1-(6-methoxy-5-methyl-pyridin-3-yl)-2,3-dihydro-1H-pyrido[3,4-b][1,4]oxazin-7-yloxy]-pyrrolidin-1-yl}-methanone<br>Buchwald amination condition: CA2<br>Amide bond condition: CB4<br>Side chain introduction condition: CC1<br>Precursors used: CAS 869481-93-6/1174020-51-9<br>Chiral separation method: CD12 | 0.89 (M1)<br>45.8 (CD12) | 521 |

Example G1

Imidazo[2,1-b]thiazol-6-yl-{(S)-3-[1-(6-methoxy-5-trifluoromethyl-pyridin-3-yl)-2,3-dihydro-1H-pyrido[3,4-b][1,4]oxazin-7-yloxy]-pyrrolidin-1-yl}-methanone

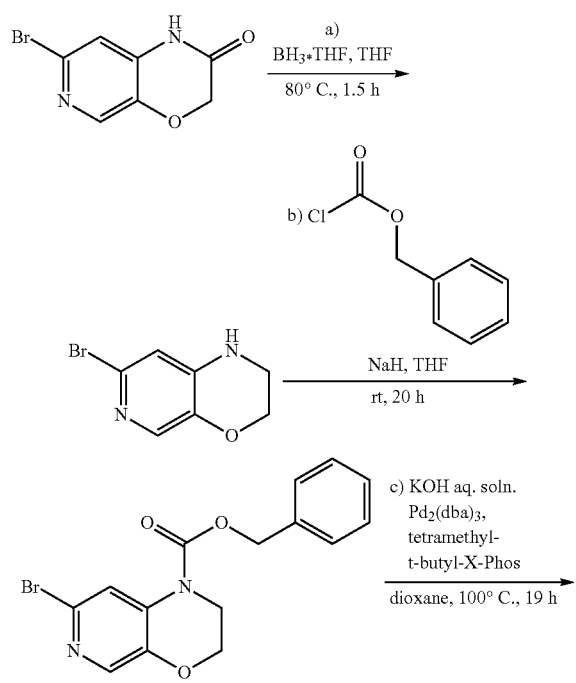

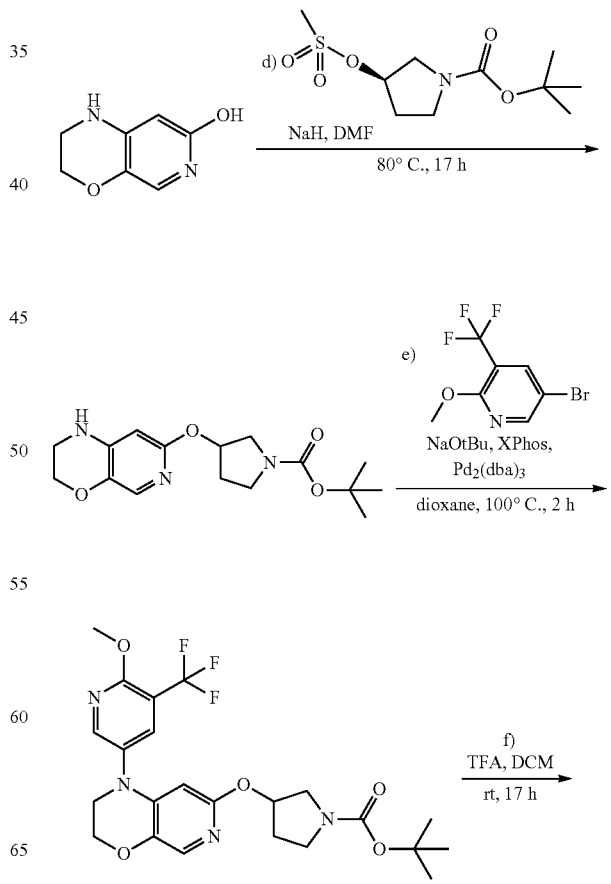

-continued

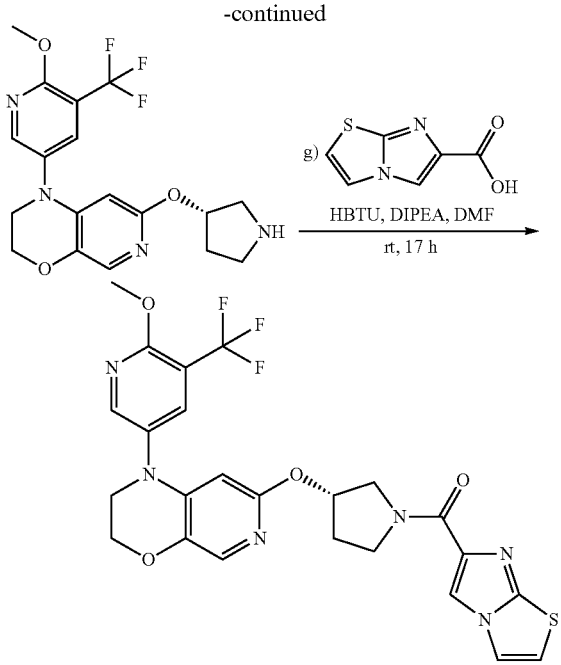

a)
7-Bromo-2,3-dihydro-1H-pyrido[3,4-b][1,4]oxazine

A solution of 7-bromo-1H-pyrido[3,4-b][1,4]oxazin-2-one (CAS registry 943995-72-0) (2.93 g, 12.79 mmol) in THF (40 ml) was treated with BH$_3$*THF (1M in THF, 30 ml, 30 mmol). The reaction mixture was stirred at 80° C. for 1.5 h, then cooled down to rt and quenched with methanol. The reaction mixture was concentrated under reduced pressure and the residue was taken up with EtOAc and washed with aq. 1M NaOH soln. The organic layer was dried over Na$_2$SO$_4$, filtered and concentrated under reduced pressure to afford the title product as a white solid. (2.48 g, 90% yield).

UPLC Rt$_{M1}$=0.49 min; ESIMS: 217 [(M+H)$^+$].

$^1$H NMR (400 MHz, CDCl$_3$): δ 7.72 (s, 1H), 6.60 (s, 1H), 4.42 (br s, 1H), 4.20-4.24 (m, 2H), 3.49 (m, 2H).

b) 7-Bromo-2,3-dihydro-pyrido[3,4-b][1,4]oxazine-1-carboxylic acid benzyl ester

A dry solution of 7-bromo-2,3-dihydro-1H-pyrido[3,4-b][1,4]oxazine (1.85 g, 8.60 mmol) in THF (50 ml) was portionwise treated at 0° C. with 60% NaH in mineral oil (0.52 g, 12.90 mmol) and the reaction mixture was stirred at 0° C. for 1 h. Benzyl chloroformate (CAS registry 501-53-1) (1.40 ml, 9.85 mmol) was dropwise added and the reaction mixture was allowed to warm to rt and to stir for 20 h, finally quenched with methanol and then diluted with sat. aq. NaHCO$_3$ soln. and extracted with EtOAc. The organic layer was dried over Na$_2$SO$_4$, filtered, concentrated and the title compound was obtained after flash chromatography on silica gel (heptane/EtOAc, 100:0 to 60:40) as a white solid (2.06 g, 68% yield).

UPLC Rt$_{M1}$=1.14 min; ESIMS: 349 [(M+H)$^+$].

$^1$H NMR (400 MHz, CDCl$_3$): δ 8.28 (br s, 1H), 7.98 (s, 1H), 7.35-7.46 (m, 5H), 5.30 (s, 2H), 4.20-4.27 (m, 2H), 3.92-4.01 (m, 2H).

c) 2,3-Dihydro-1H-pyrido[3,4-b][1,4]oxazin-7-ol

A mixture of 7-bromo-2,3-dihydro-pyrido[3,4-b][1,4]oxazine-1-carboxylic acid benzyl ester (1.27 g, 3.63 mmol), aq. KOH soln. (0.90 g, 16 mmol KOH in 3.2 ml water), 2-di-t-butylphosphino-3,4,5,6-tetramethyl-2',4',6-tri-i-propylbiphenyl 98% (0.26 g, 0.54 mmol) in dioxane (16 ml) was degassed with argon for 5 min, then Pd$_2$(dba)$_3$ (0.25 g, 0.27 mmol) was added. The tube was filled with argon, then sealed and the reaction mixture was stirred at 100° C. for 19 h. After cooling to rt, the reaction mixture was filtered through hyflo, rinsed with EtOAc and methanol. The filtrates were dried over Na$_2$SO$_4$, filtered, concentrated and the title compound was obtained after flash chromatography on silica gel (DCM/MeOH, 95:5 to 60:40) as an orange residue (262 mg, 47% yield).

UPLC Rt$_{M1}$=0.32 min; ESIMS: 153 [(M+H)$^+$]

$^1$H NMR (400 MHz, DMSO-d$_6$): δ 10.33 (br.s, 1H), 7.03 (br.s, 1H), 6.71 (s, 1H), 5.15 (s, 1H), 3.95 (t, 2H), 3.25 (td, 2H).

d) (S)-3-(2,3-Dihydro-1H-pyrido[3,4-b][1,4]oxazin-7-yloxy)-pyrrolidine-1-carboxylic acid tert-butyl ester A dry solution of 2,3-dihydro-1H-pyrido[3,4-b][1,4]oxazin-7-ol (200 mg, 0.66 mmol) and (R)-3-methanesulfonyloxy-pyrrolidine-1-carboxylic acid tert-butyl ester (CAS registry 127423-61-4) (262 mg, 0.99 mmol) in DMF (6 ml) was treated with sodium hydride 60% in mineral oil (53 mg, 1.33 mmol) and the reaction mixture was stirred at 80° C. for 17 h. After cooling to rt, the reaction mixture was diluted with TBME and washed with sat. aq. NaHCO$_3$ soln. The organic layer was dried over Na$_2$SO$_4$, filtered, concentrated and the title compound was obtained after flash chromatography on silica gel (heptane/EtOAc, 88:12 to 0:100) as an oil (140 mg, 66% yield).

UPLC Rt$_{M1}$=0.66 min; ESIMS: 322 [(M+H)$^+$].

$^1$H NMR (400 MHz, CDCl$_3$): δ 7.54 (s, 1H), 5.86 (s, 1H), 5.42 (br.s, 1H), 4.25-4.41 (m, 1H), 4.19 (t, 2H), 3.38-3.66 (m, 6H), 2.00-2.18 (m, 2H), 1.46 (d, 9H).

e) (S)-3-[1-(6-Methoxy-5-trifluoromethyl-pyridin-3-yl)-2,3-dihydro-1H-pyrido[3,4-b][1,4]oxazin-7-yloxy]-pyrrolidine-1-carboxylic acid tert-butyl ester A mixture of (S)-3-(2,3-dihydro-1H-pyrido[3,4-b][1,4]oxazin-7-yloxy)-pyrrolidine-1-carboxylic acid tert-butyl ester (115 mg, 0.36 mmol), 5-bromo-2-methoxy-3-trifluoromethylpyridine (CAS registry 1214377-42-0) (119 mg, 0.47 mmol), XPhos (14 mg, 0.03 mmol), and NaOtBu (76 mg, 0.79 mmol) in dioxane (2.5 ml) was degassed with argon for 5 min, then Pd$_2$(dba)$_3$ (13 mg, 0.01 mmol) was added. The tube was filled with argon, then sealed and the reaction mixture was stirred at 100° C. for 2 h. After cooling to rt, the reaction mixture was filtered through hyflo, rinsed with EtOAc and the filtrates were washed with sat. aq. NaHCO$_3$ soln. The organic layer was dried over Na$_2$SO$_4$, filtered, concentrated and the title compound was obtained after flash chromatography on silica gel (heptane/EtOAc, 93:7 to 40:60) as a clear gum. (91 mg, 51% yield).

UPLC Rt$_{M1}$=1.27 min; ESIMS: 497 [(M+H)$^+$].

$^1$H NMR (400 MHz, CDCl$_3$): δ 8.29 (d, 1H), 7.79 (d, 1H), 7.64 (d, 1H), 5.70 (s, 1H), 5.36-5.46 (m, 1H), 4.34 (br s, 2H), 4.09 (s, 3H), 3.70 (t, 2H), 3.34-3.62 (m, 4H), 2.02-2.11 (m, 2H), 1.44 (s, 9H).

f) 1-(6-Methoxy-5-trifluoromethyl-pyridin-3-yl)-7-((S)-pyrrolidin-3-yloxy)-2,3-dihydro-1H-pyrido[3,4-b][1,4]oxazine A solution of (S)-3-[1-(6-methoxy-5-trifluoromethyl-pyridin-3-yl)-2,3-dihydro-1H-pyrido[3,4-b][1,4]oxazin-7-yloxy]-pyrrolidine-1-carboxylic acid tert-butyl ester (88 mg, 0.18 mmol) in DCM (1.3 ml) was treated with TFA (0.14 ml, 1.77 mmol) and the reaction mixture was stirred at rt for 17 h, then quenched with sat. aq. $Na_2CO_3$ soln. and extracted with DCM. The organic layer was dried over $Na_2SO_4$, filtered and concentrated under reduced pressure to afford the title compound (66 mg, 94% yield).

UPLC $Rt_{M1}$=0.72 min; ESIMS: 397 [(M+H)$^+$].
$^1$H NMR (400 MHz, CDCl$_3$): δ 8.28 (d, 1H), 7.79 (d, 1H), 7.65 (s, 1H), 5.68 (s, 1H), 5.31-5.39 (m, 1H), 4.31-4.37 (m, 2H), 4.08 (s, 3H), 3.67-3.72 (m, 2H), 3.01-3.18 (m, 3H), 2.85-2.97 (m, 1H), 2.01-2.13 (m, 1H), 1.82-1.95 (m, 1H).

g) Imidazo[2,1-b]thiazol-6-yl-{(S)-3-[1-(6-methoxy-5-trifluoromethyl-pyridin-3-yl)-2,3-dihydro-1H-pyrido[3,4-b][1,4]oxazin-7-yloxy]-pyrrolidin-1-yl}-methanone A solution of imidazo[2,1-b]thiazole-6-carboxylic acid, hydrobromide (1:1) (CAS registry 725234-39-9) (25 mg, 0.10 mmol) in DMF (0.45 ml) was treated with HBTU (41 mg, 0.11 mmol) and DIPEA (0.04 ml, 0.21 mmol). The resulting orange solution was stirred at rt for 5 min, then a solution of 1-(6-methoxy-5-trifluoromethyl-pyridin-3-yl)-7-((S)-pyrrolidin-3-yloxy)-2,3-dihydro-1H-pyrido[3,4-b][1,4]oxazine (32 mg, 0.08 mmol) in DMF (0.45 ml) was added. The reaction mixture was stirred at rt for 17 h, then concentrated under reduced pressure and the residue was taken up with EtOAc and washed with brine. The organic layer was dried over $Na_2SO_4$, filtered, concentrated and the title compound was obtained after RP prep.

HPLC (Sunfire PrepC18 30×100 mm, 5 µm; solvent A: $H_2O$+0.1 Vol.-% TFA; solvent B: $CH_3CN$+0.1 Vol.-% TFA, gradient 15-45% B in 16 min). After filtration over an Agilent PL-HCO$_3$ MP SPE cartridge, the title compound was obtained as a solid (23 mg, 52% yield).

UPLC $Rt_{M1}$=1.00 min; ESIMS: 547 [(M+H)$^+$].
$^1$H NMR (400 MHz, DMSO-d$_6$): δ 8.49 (dd, 1H), 8.16-8.20 (m, 2H), 7.92 (dd, 1H), 7.57 (d, 1H), 7.37 (dd, 1H), 5.63 (d, 1H), 5.33-5.45 (m, 1H), 4.25-4.31 (m, 2H), 3.52-4.14 (m, 9H), 1.88-2.12 (m, 2H).

Examples G2 to G3

The compounds listed in Table 7 were prepared by a procedure analogous to that used in Example G1.

TABLE 7

| Example | Compound/Reaction Conditions | HPLC Rt [min] (method) | MS [m/z; (M + 1)$^+$] |
|---|---|---|---|
| G2 | (1,1-Dioxo-hexahydro-1lambda*6*-thiopyran-4-yl)-{(R)-3-[1-(6-methoxy-5-methyl-pyridin-3-yl)-2,3-dihydro-1H-pyrido[3,4-b][1,4]oxazin-7-yloxy]-pyrrolidin-1-yl}-methanone<br>Buchwald amination condition: CA2<br>Amide bond condition: CB1<br>Side chain introduction condition: CC1<br>Precursors used: CAS 943995-72-0/132945-75-6/IA9/64096-87-3 | 0.80 (M1) | 503 |

TABLE 7-continued

| Example | Compound/Reaction Conditions | HPLC Rt [min] (method) | MS [m/z; (M + 1)⁺] |
|---|---|---|---|
| G3 | (5-Amino-1-methyl-1H-imidazol-4-yl)-{(S)-3-[1-(6-methoxy-5-trifluoromethyl-pyridin-3-yl)-2,3-dihydro-1H-pyrido[3,4-b][1,4]oxazin-7-yloxy]-pyrrolidin-1-yl}-methanone<br>Buchwald amination condition: CA2<br>Amide bond condition: CB1<br>Side chain introduction condition: CC1<br>Precursors used: CAS 943995-72-0/127423-61-4/IA21)/IB3)/Product obtained after Deboc reaction using TFA in CH₂Cl₂ done in conventional way | 0.86 (M1M1) | 520 |

Examples H1 to H16

The compounds listed in Table 8 were prepared by chromatographic diastereomer separation.

TABLE 8

| Example | Compound/Reaction Conditions | HPLC Rt [min] (method) | MS [m/z; (M + 1)⁺] |
|---|---|---|---|
| H1 | (1,1-Dioxo-tetrahydro-1lambda*6*-thiophen-3-yl)-{(S)-3-[1-(6-methanesulfonyl-5-methyl-pyridin-3-yl)-2,3-dihydro-1H-pyrido[3,4-b][1,4]oxazin-7-yloxy]-pyrrolidin-1-yl}-methanone<br>Buchwald amination condition: CA6<br>Amide bond condition: CB4<br>Side chain introduction condition: CC2<br>Precursors used: IA1, CAS 127423-61-4/64096-87-3<br>Chiral separation method: CD5 | 0.87 (M2) | 531 |

TABLE 8-continued

| Example | Compound/Reaction Conditions | HPLC Rt [min] (method) | MS [m/z; (M + 1)+] |
|---|---|---|---|
| H2 | 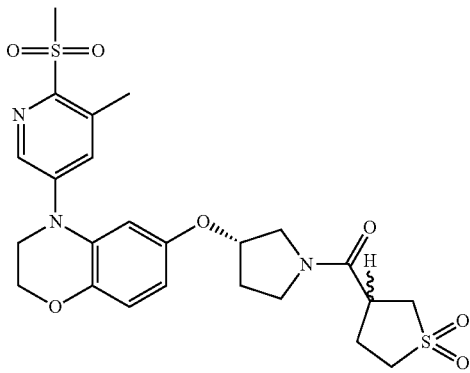 [SMILES: Cc1cc(N2CCOc3ccc(O[C@H]4CCN(C(=O)C5CCS(=O)(=O)C5)C4)cc32)cnc1S(C)(=O)=O]<br>(1,1-Dioxo-tetrahydro-1lamdba*6*-thiophen-3-yl)-{(S)-3-[1-(6-methanesulfonyl-5-methyl-pyridin-3-yl)-2,3-dihydro-1H-pyrido[3,4-b][1,4]oxazin-7-yloxy]-pyrrolidin-1-yl}-methanone<br>Buchwald amination condition: CA6<br>Amide bond condition: CB4<br>Side chain introduction conditions: CC2<br>Precursors used: IA1, CAS 127423-61-4/64096-87-3<br>Chiral separation method: CD5 | 0.87 (M2) | 536 |
| H3 | 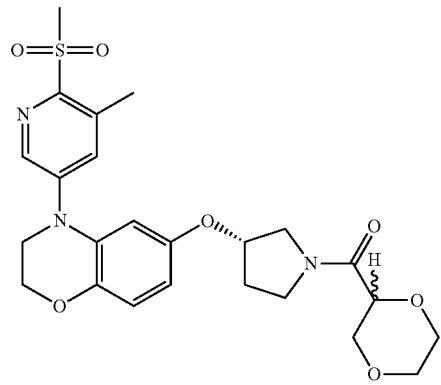 [SMILES: Cc1cc(N2CCOc3ccc(O[C@H]4CCN(C(=O)C5COCCO5)C4)cc32)cnc1S(C)(=O)=O]<br>[1,4]Dioxan-2-yl-{(S)-3-[4-(6-methanesulfonyl-5-methyl-pyridin-3-yl)-3,4-dihydro-2H-benzo[1,4]oxazin-6-yloxy]-pyrrolidin-1-yl}-methanone<br>Buchwald amination condition: CA6<br>Amide bond condition: CB4<br>Side chain introduction condition: CC2<br>Precursors used: IA1, CAS 127423-61-4/89364-41-0<br>Chiral separation method: CD6 | 0.88 (M2) | 504 |

TABLE 8-continued

| Example | Compound/ Reaction Conditions | HPLC Rt [min] (method) | MS [m/z; (M + 1)+] |
|---|---|---|---|
| H4 | 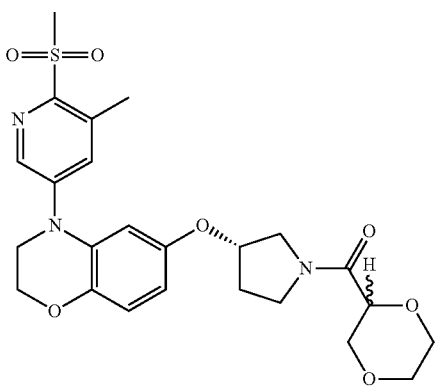 [SMILES: Cc1cc(N2CCOc3ccc(O[C@H]4CCN(C(=O)C5COCCO5)C4)cc32)cnc1S(C)(=O)=O]<br>[1,4]Dioxan-2-yl-{(S)-3-[4-(6-methanesulfonyl-5-methyl-pyridin-3-yl)-3,4-dihydro-2H-benzo[1,4]oxazin-6-yloxy]-pyrrolidin-1-yl}-methanone<br>Buchwald amination condition: CA6<br>Amide bond condition: CB4<br>Side chain introduction condition: CC2<br>Precursors used: IA1), CAS 127423-61-4/89364-41-0<br>Chiral separation method: CD6 | 0.88 (M2) | 504 |
| H5 | 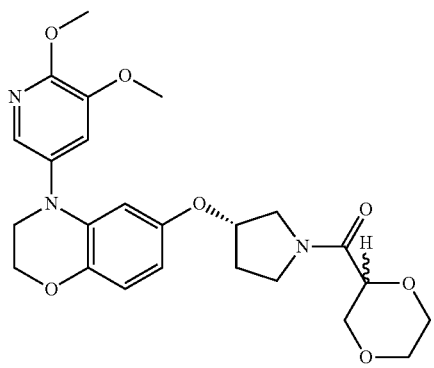 [SMILES: COc1cc(N2CCOc3ccc(O[C@H]4CCN(C(=O)C5COCCO5)C4)cc32)cnc1OC]<br>{(S)-3-[4-(5,6-Dimethoxy-pyridin-3-yl)-3,4-dihydro-2H-benzo[1,4]oxazin-6-yloxy]-pyrrolidin-1-yl}-[1,4]dioxan-2-yl-methanone<br>Buchwald amination condition: CA6<br>Amide bond condition: CB4<br>Side chain introduction condition: CC2<br>Precursors used: IA31, CAS 52605-98-8, 127423-61-4/89364-41-0<br>Chiral separation method: CD1 | 0.91 (M2) | 472 |

TABLE 8-continued

| Example | Compound/ Reaction Conditions | HPLC Rt [min] (method) | MS [m/z; (M + 1)+] |
|---|---|---|---|
| H6 | 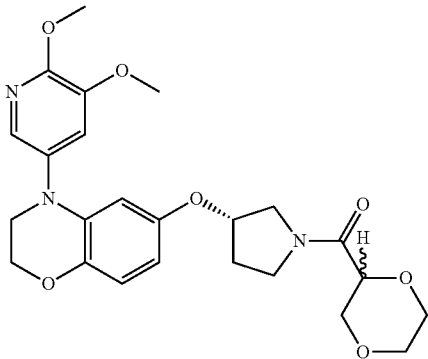 [SMILES: COc1cc(N2CCOc3ccc(O[C@H]4CCN(C(=O)C5COCCO5)C4)cc32)cnc1OC] {(S)-3-[4-(5,6-Dimethoxy-pyridin-3-yl)-3,4-dihydro-2H-benzo[1,4]oxazin-6-yloxy]-pyrrolidin-1-yl}-[1,4]dioxan-2-yl-methanone<br>Buchwald amination condition: CA6<br>Amide bond condition: CB4<br>Side chain introduction condition: CC2<br>Precursors used: IA31, CAS 52605-98-8, 127423-61-4/89364-41-0<br>Chiral separation method: CD1 | 0.91 (M2) | 472 |
| H7 | 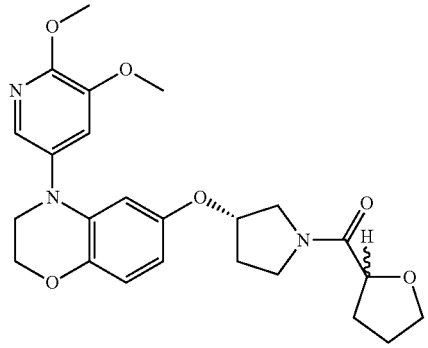 [SMILES: COc1cc(N2CCOc3ccc(O[C@H]4CCN(C(=O)C5CCCO5)C4)cc32)cnc1OC] {(S)-3-[4-(5,6-Dimethoxy-pyridin-3-yl)-3,4-dihydro-2H-benzo[1,4]oxazin-6-yloxy]-pyrrolidin-1-yl}-(tetrahydro-furan-2-yl)-methanone<br>Buchwald amination condition: CA9<br>Amide bond condition: CB4<br>Side chain introduction condition: CC2<br>Precursors used: IA29, CAS 52605-98-8, 127423-61-4/1264293-76-6<br>Chiral separation method: CD1 | 0.91 (M2) | 472 |

TABLE 8-continued

| Example | Compound/Reaction Conditions | HPLC Rt [min] (method) | MS [m/z; (M + 1)+] |
|---|---|---|---|
| H8 | {(S)-3-[4-(5,6-Dimethoxy-pyridin-3-yl)-3,4-dihydro-2H-benzo[1,4]oxazin-6-yloxy]-pyrrolidin-1-yl}-(tetrahydro-furan-2-yl)-methanone<br>Buchwald amination condition: CA6<br>Amide bond condition: CB4<br>Side chain introduction condition: CC2<br>Precursors used: IA29, CAS 52605-98-8, 127423-61-4/1264293-76-6<br>Chiral separation method: CD1 | 0.91 (M2) | 472 |
| H9 | {(S)-3-[4-(5,6-Dimethoxy-pyridin-3-yl)-3,4-dihydro-2H-benzo[1,4]oxazin-6-yloxy]-pyrrolidin-1-yl}-(1,1-dioxo-tetrahydro-1lambda*6*-thiophen-3-yl)-methanone<br>Buchwald amination condition: CA6<br>Amide bond condition: CB4<br>Side chain introduction condition: CC2<br>Precursors used: IA29, CAS 52605-98-8, 127423-61-4/64096-87-3<br>Chiral separation method: CD1 | 0.91 (M2) | 504 |

TABLE 8-continued

| Example | Compound/Reaction Conditions | HPLC Rt [min] (method) | MS [m/z; (M + 1)+] |
|---|---|---|---|
| H10 | 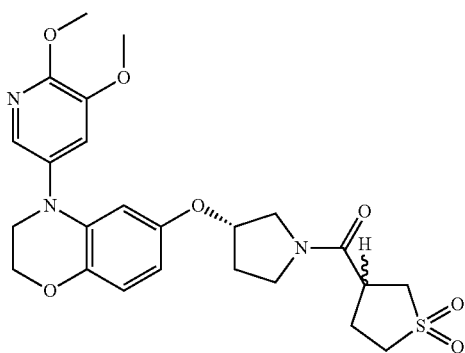 [SMILES: COc1cc(N2CCOc3ccc(O[C@H]4CCN(C(=O)C5CCS(=O)(=O)C5)C4)cc32)cnc1OC]<br>{(S)-3-[4-(5,6-Dimethoxy-pyridin-3-yl)-3,4-dihydro-2H-benzo[1,4]oxazin-6-yloxy]-pyrrolidin-1-yl}-(1,1-dioxo-tetrahydro-1lambda*6*-thiophen-3-yl)-methanone<br>Buchwald amination condition: CA6<br>Amide bond condition: CB4<br>Side chain introduction condition: CC2<br>Precursors used: IA29, CAS 52605-98-8, 127423-61-4/64096-87-3<br>Chiral separation method: CD1 | 0.91 (M2) | 504 |
| H11 | 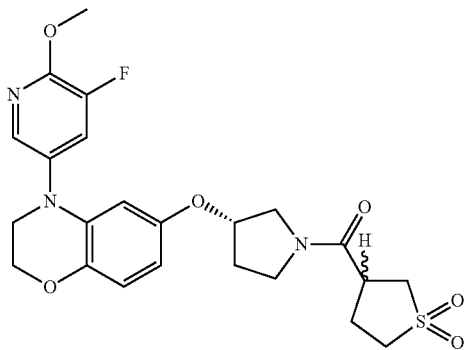<br>(1,1-Dioxo-tetrahydro-1lambda*6*-thiophen-3-yl)-{(S)-3-[4-(5-fluoro-6-methoxy-pyridin-3-yl)-3,4-dihydro-2H-benzo[1,4]oxazin-6-yloxy]-pyrrolidin-1-yl}-methanone<br>Buchwald amination condition: CA6<br>Amide bond condition: CB5<br>Side chain introduction condition: CC2<br>Precursors used: IA10, CAS 124432-70-8, 127423-61-4/64096-87-3<br>Chiral separation method: CD1 | 3.26 (M2) | 492 |

TABLE 8-continued

| Example | Compound/Reaction Conditions | HPLC Rt [min] (method) | MS [m/z; (M + 1)+] |
|---|---|---|---|
| H12 | 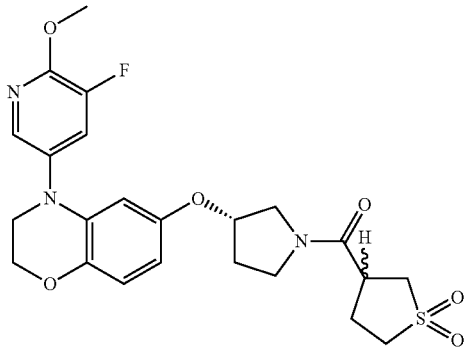<br>(1,1-Dioxo-tetrahydro-1lambda*6*-thiophen-3-yl)-{(S)-3-[4-(5-fluoro-6-methoxy-pyridin-3-yl)-3,4-dihydro-2H-benzo[1,4]oxazin-6-yloxy]-pyrrolidin-1-yl}-methanone<br>Buchwald amination condition: CA6<br>Amide bond condition: CB5<br>Side chain introduction condition: CC2<br>Precursors used: IA10, CAS 124432-70-8, 127423-61-4/64096-87-3<br>Chiral separation method: CD1 | 3.25 (M2) | 492 |
| H13 | 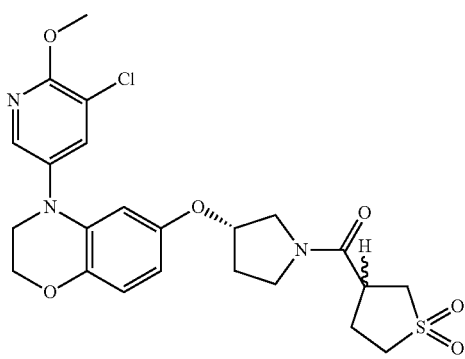 [SMILES: COc1ncc(N2CCOc3ccc(O[C@H]4CCN(C(=O)C5CCS(=O)(=O)C5)C4)cc32)cc1F]<br>{(S)-3-[4-(5-Chloro-6-methoxy-pyridin-3-yl)-3,4-dihydro-2H-benzo[1,4]oxazin-6-yloxy]-pyrrolidin-1-yl}-(1,1-dioxo-tetrahydro-1lambda*6*-thiophen-3-yl)-methanone<br>Buchwald amination condition: CA6<br>Amide bond condition: CB5<br>Side chain introduction condition: CC2<br>Precursors used: IA11, CAS 848366-28-9, 127423-61-4/64096-87-3<br>Chiral separation method: CD2 | 3.52 (M2) | 508 |

TABLE 8-continued

| Example | Compound/ Reaction Conditions | HPLC Rt [min] (method) | MS [m/z; (M + 1)⁺] |
|---|---|---|---|
| H14 | 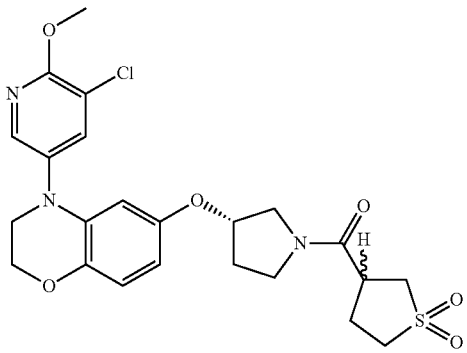<br>{(S)-3-[4-(5-Chloro-6-methoxy-pyridin-3-yl)-3,4-dihydro-2H-benzo[1,4]oxazin-6-yloxy]-pyrrolidin-1-yl}-(1,1-dioxo-tetrahydro-1lambda*6*-thiophen-3-yl)-methanone<br>Buchwald amination condition: CA6<br>Amide bond condition: CB5<br>Side chain introduction condition: CC2<br>Precursors used: IA11, CAS 848366-28-9, 127423-61-4/64096-87-3<br>Chiral separation method: CD2 | 3.52 (M2) | 508 |
| H15 | 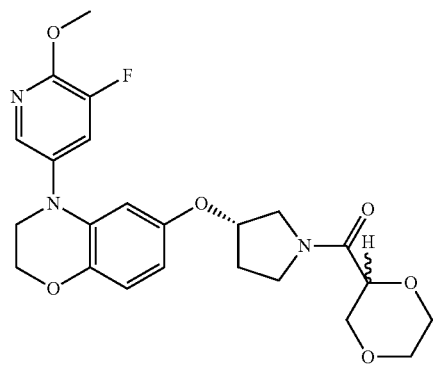 [SMILES: COc1ncc(N2CCOc3ccc(O[C@H]4CCN(C(=O)C5COCCO5)C4)cc32)cc1F]<br>[1,4]Dioxan-2-yl-{(S)-3-[4-(5-fluoro-6-methoxy-pyridin-3-yl)-3,4-dihydro-2H-benzo[1,4]oxazin-6-yloxy]-pyrrolidin-1-yl}-methanone<br>Buchwald amination condition: CA6<br>Amide bond condition: CB5<br>Side chain introduction condition: CC2<br>Precursors used: IA10, CAS 124432-70-8, 127423-61-4/89364-41-0<br>Chiral separation method: CD1 | 3.28 (M2) | 460 |

US 9,763,952 B2

TABLE 8-continued

| Example | Compound/<br>Reaction Conditions | HPLC Rt<br>[min]<br>(method) | MS<br>[m/z;<br>(M + 1)+] |
|---|---|---|---|
| H16 | 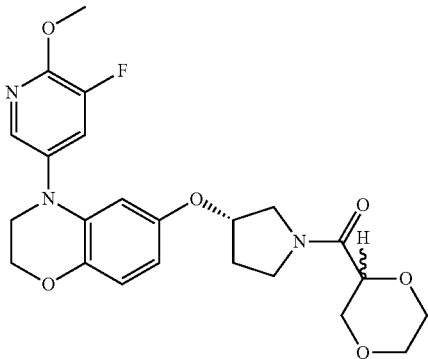 [SMILES: COc1ncc(N2CCOc3ccc(O[C@H]4CCN(C(=O)C5COCCO5)C4)cc32)cc1F]<br>[1,4]Dioxan-2-yl-{(S)-3-[4-(5-fluoro-6-methoxy-pyridin-3-yl)-3,4-dihydro-2H-benzo[1,4]oxazin-6-yloxy]-pyrrolidin-1-yl}-methanone<br>Buchwald amination condition: CA6<br>Amide bond condition: CB5<br>Side chain introduction condition: CC2<br>Precursors used: IA10, CAS 124432-70-8,<br>127423-61-4/89364-41-0<br>Chiral separation method: CD1 | 3.32 (M2) | 460 |

Example I1

(1,1-Dioxo-hexahydro-1lambda*6*-thiopyran-4-yl)-{(S)-3-[5-fluoro-4-(6-methoxy-5-methyl-pyridin-3-yl)-3,4-dihydro-2H-benzo[1,4]oxazin-6-yloxy]-pyrrolidin-1-yl}-methanone

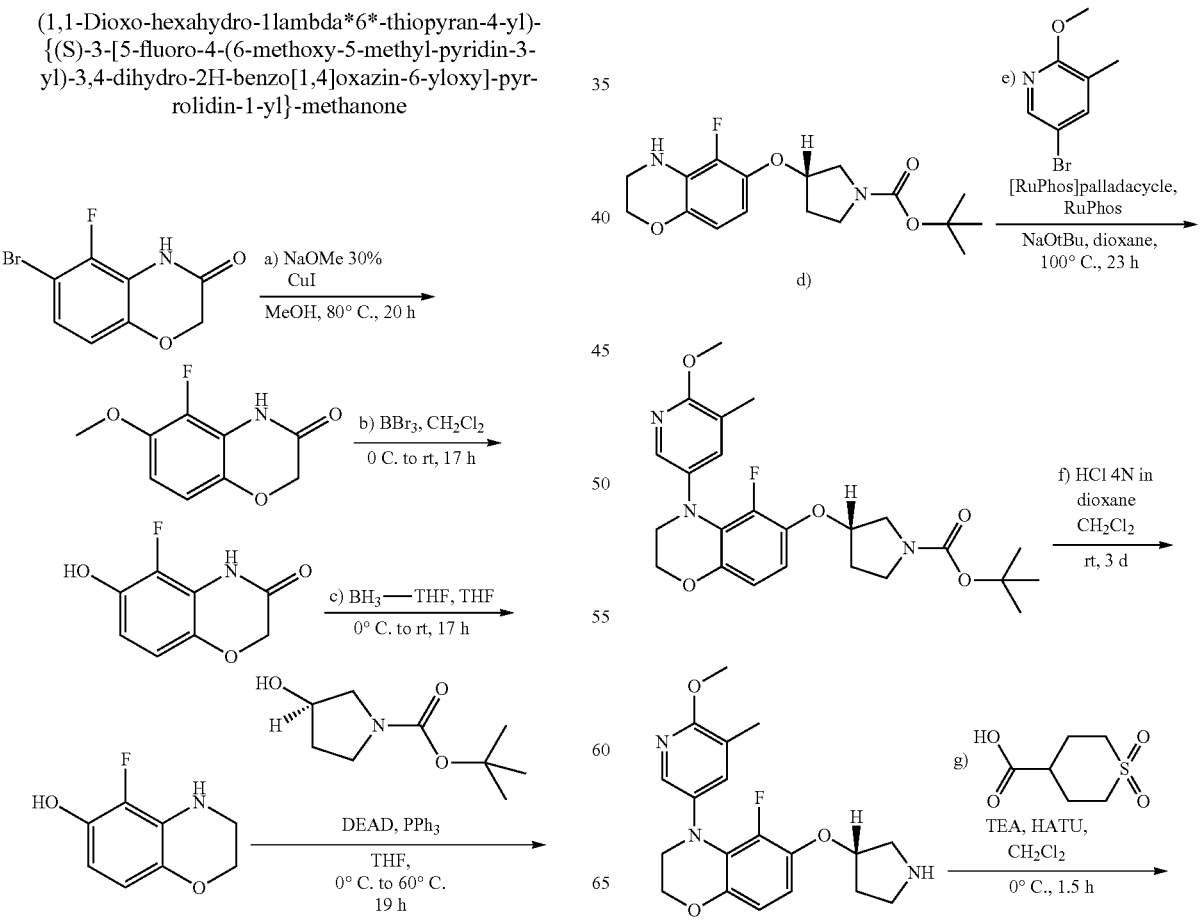

-continued

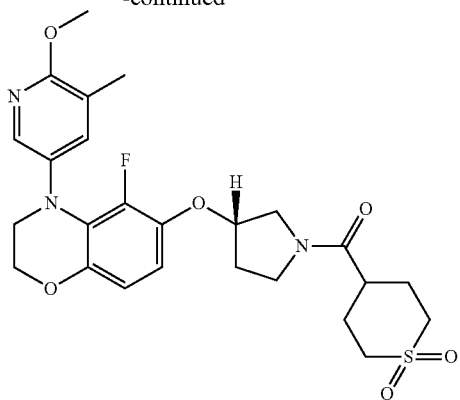

a) 5-Fluoro-6-methoxy-4H-benzo[1,4]oxazin-3-one

A solution of 6-bromo-5-fluoro-4H-benzo[1,4]oxazin-3-one (CAS registry 1029421-36-0) (5.0 g, 20 mmol) in MeOH (10 ml) was treated with sodium methoxide solution (30% in MeOH, 11.3 ml, 61 mmol) and CuI (0.4 g, 2 mmol). After stirring for 20 h at 80° C., the reaction was quenched with sat. aq. NaHCO$_3$ soln and extracted with EtOAc. The organic layer was dried over Na$_2$SO$_4$, filtered and concentrated under reduced pressure to obtain a pale yellow solid. (2.2 g, 92% yield).

UPLC Rt$_{M1}$=0.64 min.

$^1$H NMR (400 MHz, DMSO-d$_6$): δ 6.74 (m, 2H), 4.53 (s, 2H), 3.79 (s, 3H).

b) 5-Fluoro-6-hydroxy-4H-benzo[1,4]oxazin-3-one

A solution of 5-fluoro-6-methoxy-4H-benzo[1,4]oxazin-3-one (2.0 g, 10 mmol) in DCM (50 ml) was treated at 0° C. with boron tribromide (9.6 ml, 101 mmol). The reaction mixture was stirred at rt for 17 h, then cooled down to 0° C. and quenched with methanol. The mixture was concentrated under reduced pressure and the residue was taken up with EtOAc and washed with sat. aq. NaHCO$_3$ soln. The organic layer was washed with 10% aq. Na$_2$S$_2$O$_4$ soln, dried over Na$_2$SO$_4$, filtered and concentrated under reduced pressure. The title compound was obtained after flash chromatography on silica gel (hexane/EtOAc, 100:0 to 60:40) as a brown solid (780 mg, 42% yield).

UPLC Rt$_{M1}$=0.49 min; ESIMS: 228 [(M+HCOO)$^-$].

$^1$H NMR (400 MHz, DMSO-d$_6$): δ 11.00 (s, 1H), 6.65 (d, 1H), 6.45 (t, 1H), 4.50 (s, 2H).

c) 5-Fluoro-3,4-dihydro-2H-benzo[1,4]oxazin-6-ol

A solution of 5-fluoro-6-hydroxy-4H-benzo[1,4]oxazin-3-one (780 mg, 4.2 mmol) in THF (10 ml) was treated with BH$_3$*THF (1M in THF, 12.8 ml, 12.8 mmol). The reaction mixture was stirred at rt for 17 h, then cooled down to 0° C. and quenched with methanol (30 ml). The reaction mixture was concentrated under reduced pressure to obtain a brown oil (720 mg, quantitative yield).

UPLC Rt$_{M1}$=0.54 min; ESIMS: 170 [(M+H)$^+$].

$^1$H NMR (400 MHz, DMSO-d$_6$): δ 8.95 (s, 1H), 6.45 (d, 1H), 6.00 (t, 1H), 4.09 (m, 2H), 3.45 (m, 2H).

d) (S)-3-(5-Fluoro-3,4-dihydro-2H-benzo[1,4]oxazin-6-yloxy)-pyrrolidine-1-carboxylic acid tert-butyl ester A solution of triphenylphosphine (1.5 g, 5.7 mmol) in THF (20 ml) was treated at 0° C. with DEAD (0.900 ml, 5.69). The orange solution was stirred over 10 min at rt, then 5-fluoro-3,4-dihydro-2H-benzo[1,4]oxazin-6-ol (740 mg, 4.37 mmol) and (R)-tert-butyl 3-hydroxypyrrolidine-1-carboxylate (1065 mg, 5.69 mmol) were added. The reaction mixture was stirred for 19 h at 60° C. and then concentrated under reduced pressure. The title compound was obtained after flash chromatography on silica gel (Hexane/EtOAc, 100:0 to 70:30) as a colourless oil (1.1 g, 74% yield).

UPLC Rt$_{M1}$=1.07 min; ESIMS: 339 [(M+H)$^+$]

$^1$H NMR (400 MHz, DMSO-d$_6$): δ 6.45 (d, 1H), 6.00 (t, 1H), 5.42 (br.s, 1H), 4.25-4.41 (m, 1H), 4.19 (t, 2H), 3.38-3.66 (m, 6H), 2.00-2.18 (m, 2H), 1.46 (d, 9H)

e) (S)-3-[5-fluoro-4-(6-methoxy-5-methyl-pyridin-3-yl)-3,4-dihydro-2H-benzo[1,4]oxazin-6-yloxy]-pyrrolidine-1-carboxylic acid tert-butyl ester A mixture of (S)-3-(5-fluoro-3,4-dihydro-2H-benzo[1,4]oxazin-6-yloxy)-pyrrolidine-1-carboxylic acid tert-butyl ester (100 mg, 0.296 mmol), 5-bromo-2-methoxy-3-methylpyridine (CAS registry 760207-87-2, 179 mg, 0.887 mmol), RuPhos (6.90 mg, 0.015 mmol), NaOtBu (85 mg, 0.887 mmol) and (2-dicyclohylphosphino-2'6'-diisopropyl-11'-biphenyl)(2-(2-aminoethyl)phenyl)palladium(II) (12.07 mg, 0.015 mmol) in dioxane (2 ml) were degassed with argon then sealed and the reaction mixture was stirred at 100° C. for 23 h. After cooling to r.t., the reaction mixture was filtered through hyflo, rinsed with EtOAc and the filtrates were washed with sat. aq. NaHCO$_3$ soln. The organic layer was dried over Na$_2$SO$_4$, filtered, concentrated and the title compound was obtained after flash chromatography on silica gel (Hexane/EtOAc, 100:0 to 70:30) as a yellow oil (123 mg, 63% yield).

UPLC Rt$_{M1}$=1.29 min; ESIMS: 460 [(M+H)$^+$].

$^1$H NMR (400 MHz, DMSO-d$_6$): δ 7.75 (d, 1H), 7.45 (d, 1H), 6.55 (t, 1H), 6.35 (d, 1H), 4.75 (m, 1H), 4.15 (t, 2H), 3.84 (s, 3H), 3.60 (t, 2H), 3.38-3.66 (m, 4H), 2.12 (s, 3H), 2.00-2.18 (m, 2H), 1.46 (d, 9H).

f) 5-Fluoro-4-(6-methoxy-5-methyl-pyridin-3-yl)-6-((S)-pyrrolidin-3-yloxy)-3,4-dihydro-2H-benzo[1,4]oxazine A solution of (S)-3-[5-fluoro-4-(6-methoxy-5-methyl-pyridin-3-yl)-3,4-dihydro-2H-benzo[1,4]oxazin-6-yloxy]-pyrrolidine-1-carboxylic acid tert-butyl ester (123 mg, 0.185 mmol) in DCM (2 ml) was treated with 4N HCl/dioxane (0.046 ml, 0.185 mmol). The reaction mixture was stirred at rt for 3 d, then concentrated under reduced pressure to obtain a black oil (100 mg, 79% yield).

UPLC Rt$_{M1}$=0.73 min; ESIMS: 360 [(M+H)$^+$].

$^1$H NMR (400 MHz, DMSO-d$_6$): δ 7.75 (d, 1H), 7.45 (d, 1H), 6.80 (m, 1H), 6.75 (m, 1H), 5.20 (m, 1H), 4.15 (t, 2H), 3.84 (s, 3H), 3.60 (t, 2H), 3.38-3.66 (m, 4H), 2.12 (s, 3H), 2.00-2.18 (m, 2H).

g) (1,1-Dioxo-hexahydro-lambda*6*-thiopyran-4-yl)-{(S)-3-[5-fluoro-4-(6-methoxy-5-methyl-pyridin-3-yl)-3,4-dihydro-2H-benzo[1,4]oxazin-6-yloxy]-pyrrolidin-1-yl}-methanone A solution of 1,1-dioxo-hexahydro-1lambda*6*-thiopyran-4-carboxylic acid (CAS registry 64096-87-3) (33.9 mg, 0.15 mmol) in DCM (2 ml) was treated at rt with Et₃N (0.061 ml, 0.440 mmol) and HATU (55.7 mg, 0.147 mmol). The resulting orange solution was stirred at rt for 20 min, then a solution of 5-fluoro-4-(6-methoxy-5-methyl-pyridin-3-yl)-6-((S)-pyrrolidin-3-yloxy)-3,4-dihydro-2H-benzo[1,4]oxazine (100 mg, 0.147 mmol) in DCM (2 ml) was added. The reaction mixture was stirred at rt for 1.5 h, then diluted with EtOAc and washed with sat. aq. NaHCO₃ soln. The organic layer was dried over Na₂SO₄, filtered, concentrated and the title compound was obtained after prep. RP-HPLC (SunFire C18 column OBD 5 mm 30×100 mm, gradient 25% to 45% ACN in 16 min). The fractions were lyophilized and filtered over a PL-HCO₃ MP SPE cartridge to give a brown solid (54 mg, 71% yield).

UPLC Rt$_{M1}$=0.94 min; ESIMS: 520 [(M+H)⁺].

¹H NMR (400 MHz, DMSO-d₆): δ 7.75 (d, 1H), 7.45 (d, 1H), 6.55 (t, 1H), 6.35 (d, 1H), 4.75 (m, 1H), 4.15 (t, 2H), 3.84 (s, 3H), 3.59-3.79 (m, 3H), 3.41-3.56 (m, 2H), 3.21-3.39 (m, 1H), 2.98-3.21 (m, 4H), 2.67-2.83 (m, 1H), 1.84-2.20 (m, 9H).

Examples I2 to I3

The compounds listed in Table 9 were prepared by a procedure analogous to that used in Example I1.

TABLE 9

| Example | Compound/Reaction Conditions | HPLC Rt [min] (method) | MS [m/z; (M + 1)⁺] |
|---|---|---|---|
| I2 | {(S)-3-[4-(5-Difluoromethyl-6-methoxy-pyridin-3-yl)-5-fluoro-3,4-dihydro-2H-benzo[1,4]oxazin-6-yloxy]-pyrrolidin-1-yl}-(1,1-dioxo-hexahydro-1lamda*6*-thiopyran-4-yl)-methanone<br>Buchwald amination condition: CA11<br>Amide bond condition: CB3<br>Side chain introduction condition: CC4<br>Precursor used: IA6, CAS 1254123-51-7/127423-61-4/64096-87-3 | 0.97 (M2) | 556 |
| I3 | {(S)-3-[5-Fluoro-4-(6-methanesulfonyl-5-methyl-pyridin-3-yl)-3,4-dihydro-2H-benzo[1,4]oxazin-6-yloxy]-pyrrolidin-1-yl}-(tetrahydro-pyran-4-yl)-methanone<br>Buchwald amination condition: CA11<br>Amide bond condition: CB3<br>Side chain introduction condition:<br>Precursors used: IA1, CAS 127423-61-4/Acyl chloride 40191-32-0 | 0.85 (M2) | 520 |

Example J

5-{6-[(S)-1-((S)-1-Acetyl-pyrrolidine-3-carbonyl)-pyrrolidin-3-yloxy]-2,3-dihydro-benzo[1,4]-oxazin-4-yl}-2-methoxy-nicotinonitrile

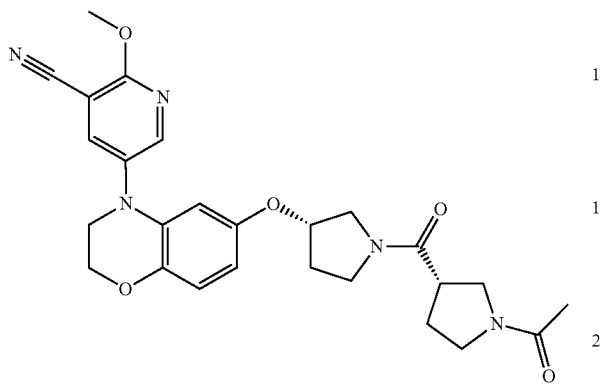

A solution of 2-methoxy-5-{6-[(S)-1-((S)-pyrrolidine-3-carbonyl)-pyrrolidin-3-yloxy]-2,3-dihydro-benzo[1,4]oxazin-4-yl}-nicotinonitrile (Example D39; 23 mg, 0.051 mmol) in DCM (1 ml) was treated with Et$_3$N (0.014 ml, 10.4 mg, 0.102 mmol). The solution was stirred at rt for 10 min, then acetyl chloride (0.0044 ml, 4.87 mg, 0.061 mmol) was added. The reaction mixture was stirred at rt for 1.5 h. Another 2 eq. of Et$_3$N (0.014 ml, 10.4 mg, 0.102 mmol). and 1 eq. of acetyl chloride ((0.0037 ml, 4.06 mg, 0.051 mmol) were added, stirring was continued at rt for 1.5 h. The reaction mixture was diluted with DCM and sat. aq. NaHCO$_3$ soln., then passed through a phase separator, the aq. layer was twice extracted with DCM, the combined org. layers were concentrated to give the title compound as a yellow oil which was purified by prep. RP-HPLC (column SunFire C18, 10-85% ACN in 20 min). The fractions were extracted with DCM/NaHCO$_3$, dried over MgSO$_4$, concentrated and lyophilized to give the title compound as a yellow foam (14 mg, 53% yield).

HPLC Rt$_{M10}$=2.55 min; ESIMS: 492 [(M+H)$^+$].

Example K

5-{6-[(S)-1-((R)-1-Acetyl-pyrrolidine-3-carbonyl)-pyrrolidin-3-yloxy]-2,3-dihydro-benzo[1,4]oxazin-4-yl}-2-methoxy-nicotinonitrile

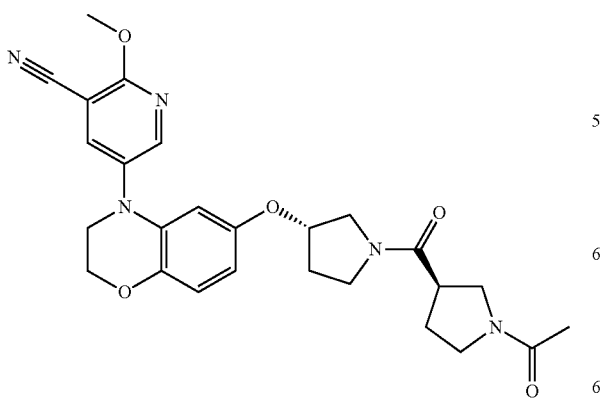

This example was prepared in analogy to Example J, starting from 2-methoxy-5-{6-[(S)-1-((R)-pyrrolidine-3-carbonyl)-pyrrolidin-3-yloxy]-2,3-dihydro-benzo[1,4]oxazin-4-yl}-nicotinonitrile (Example D40).

HPLC Rt$_{M10}$=2.55 min; ESIMS: 492 [(M+H)$^+$].

Example L

2-Methoxy-5-{6-[(S)-1-((R)-1-methyl-pyrrolidine-3-carbonyl)-pyrrolidin-3-yloxy]-2,3-dihydro-benzo[1,4]oxazin-4-yl}-nicotinonitrile

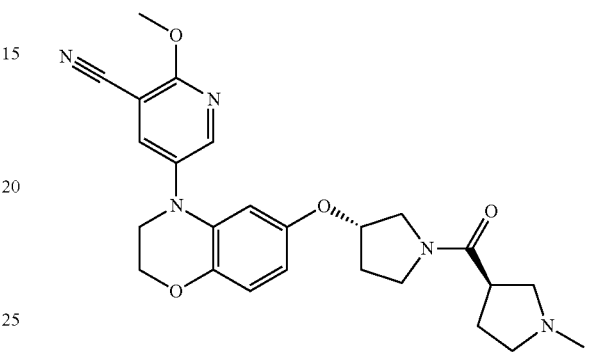

A solution of 2-methoxy-5-{6-[(S)-1-((R)-pyrrolidine-3-carbonyl)-pyrrolidin-3-yloxy]-2,3-dihydro-benzo[1,4]oxazin-4-yl}-nicotinonitrile (Example D40, 26 mg, 0.058 mmol) in MeOH (1 ml) was treated with a 37% aq. formaldehyde soln. (0.043 ml, 46.9 mg, 0.578 mmol) and acetic acid (0.004 ml, 4.17 mg, 0.0069 mmol). The solution was stirred under argon at rt for 45 min, then NaBH$_3$CN (5.65 mg of a 90% solid, 0.081 mmol) was added. The resulting mixture was stirred at rt for 45 min, diluted with DCM and sat. aq. NaHCO$_3$ soln. The aq. layer was twice reextracted with DCM, the combined org. layers were dried over MgSO$_4$ and concentrated to give the crude title compound that was purified by prep. RP-HPLC (column SunFire C18, gradient 5-75% ACN in 20 min). The fractions were extracted with DCM/sat. aq. NaHCO$_3$ soln, dried over MgSO$_4$, concentrated and lyophilized to give the title compound as a yellow foam (20 mg, 72% yield).

HPLC Rt$_{M11}$=2.24 min; ESIMS: 464 [(M+H)$^+$].

Example M 4-(6-Methanesulfonyl-5-methyl-pyridin-3-yl)-6-((S)-1-pyridin-2-yl-pyrrolidin-3-yloxy)-3,4-dihydro-2H-benzo[1,4]oxazine

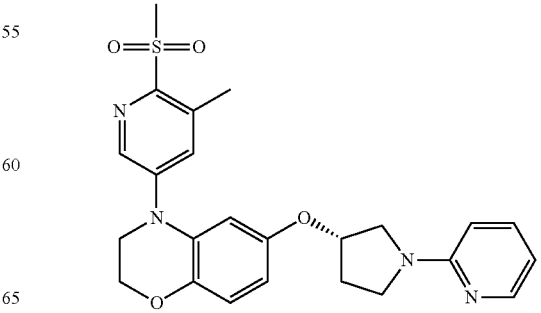

A solution of 4-(6-methanesulfonyl-5-methyl-pyridin-3-yl)-6-((S)-1-pyridin-2-yl-pyrrolidin-3-yloxy)-3,4-dihydro-2H-benzo[1,4]oxazine (prepared as described in example B1; 60 mg, 0.154 mmol), 2-chloropyridine (CAS 109-09-1, 0.017 ml, 21.0 mg, 0.185 mmol), Xphos (8.81 mg, 0.018 mmol) and $Cs_2CO_3$ (125 mg, 0.385 mmol) in dioxane (1 ml) was degassed with argon, then $Pd_2(dba)_3$ (7.05 mg, 0.0077 mmol) was added. The reaction mixture was heated at 80° C. for 6 h, XPhos (8.81 mg, 0.018 mmol) was added, the mixture was again degassed with argon and $Pd_2(dba)_3$ (7.05 mg, 0.0077 mmol) was added. Stirring was continued over night at 80° C. The mixture was filtered through celite and concentrated to give the title compound that was purified by NP-HPLC (column Grace Grom Saphir 65 Si, gradient heptane:EtOAc:MeOH 68:30:2 to 0:65:35 in 12 min), yield 32 mg (45%).

HPLC $Rt_{M1}$=0.72 min; ESIMS: 467 [(M+H)$^+$]

$^1$H NMR (400 MHz, CDCl$_3$): δ 8.32 (d, 1H), 8.14-8.12 (m, 1H), 7.49-7.39 (m, 2H), 6.86 (d, 1H), 6.61 (d, 1H), 6.57-6.46 (m, 2H), 6.37 (d, 1H), 4.92-4.85 (m, 1H), 4.26-4.24 (m, 2H), 3.76-3.74 (m, 2H), 3.71 (d, 2H), 3.63-3.55 (m, 2H), 3.32 (s, 3H), 2.67 (s, 3H), 2.35-2.27 (m, 1H), 2.26-2.15 (m, 1H).

Example N 4-(6-Methanesulfonyl-5-methyl-pyridin-3-yl)-6-((S)-1-pyrimidin-2-yl-pyrrolidin-3-yloxy)-3,4-dihydro-2H-benzo[1,4]oxazine

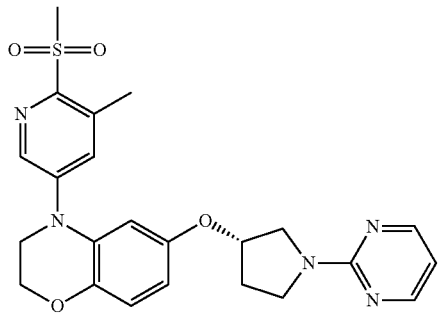 [SMILES: Cc1cc(N2CCOc3ccc(O[C@H]4CCN(c5ncccn5)C4)cc32)cnc1S(C)(=O)=O]

A solution of 4-(6-methanesulfonyl-5-methyl-pyridin-3-yl)-6-((S)-1-pyridin-2-yl-pyrrolidin-3-yloxy)-3,4-dihydro-2H-benzo[1,4]oxazine (prepared as described in example B1; 60 mg, 0.154 mmol), 2-chloropyrimidine (CAS 1722-12-9, 24.7 mg, 0.216 mmol) and DIPEA (0.054 ml, 39.8 mg, 0.308 mmol) in ACN (1 ml) was heated at 140° C. for 30 min in a microwave reactor. The product was extracted with sat. aq. NaHCO$_3$ soln. and EtOAc, filtered and concentrated to yield the title compound that was purified by prep. NP-HPLC (column Grace Grom Saphir 65 Si, gradient heptane: EtOAc:MeOH 68:30:2 to 0:65:35 in 12 min), yield 45 mg (63%)

HPLC $Rt_{M1}$=0.97 min; ESIMS: 468 [(M+H)$^+$]

$^1$H NMR (400 MHz, CDCl$_3$): δ 8.37-8.26 (m, 3H), 7.44 (d, 1H), 6.87 (d, 1H), 6.62 (d, 1H), 6.56-6.46 (m, 2H), 4.92-4.84 (m, 1H), 4.27-4.25 (m, 2H), 3.90-3.63 (m, 6H), 3.33 (s, 3H), 2.69 (s, 3H), 2.37-2.13 (m, 2H).

Example O1

2-Methoxy-5-{2-methyl-6-[(S)-1-(tetrahydro-pyran-4-carbonyl)-pyrrolidin-3-yloxy]-2,3-dihydro-benzo[1,4]oxazin-4-yl}-nicotinonitrile

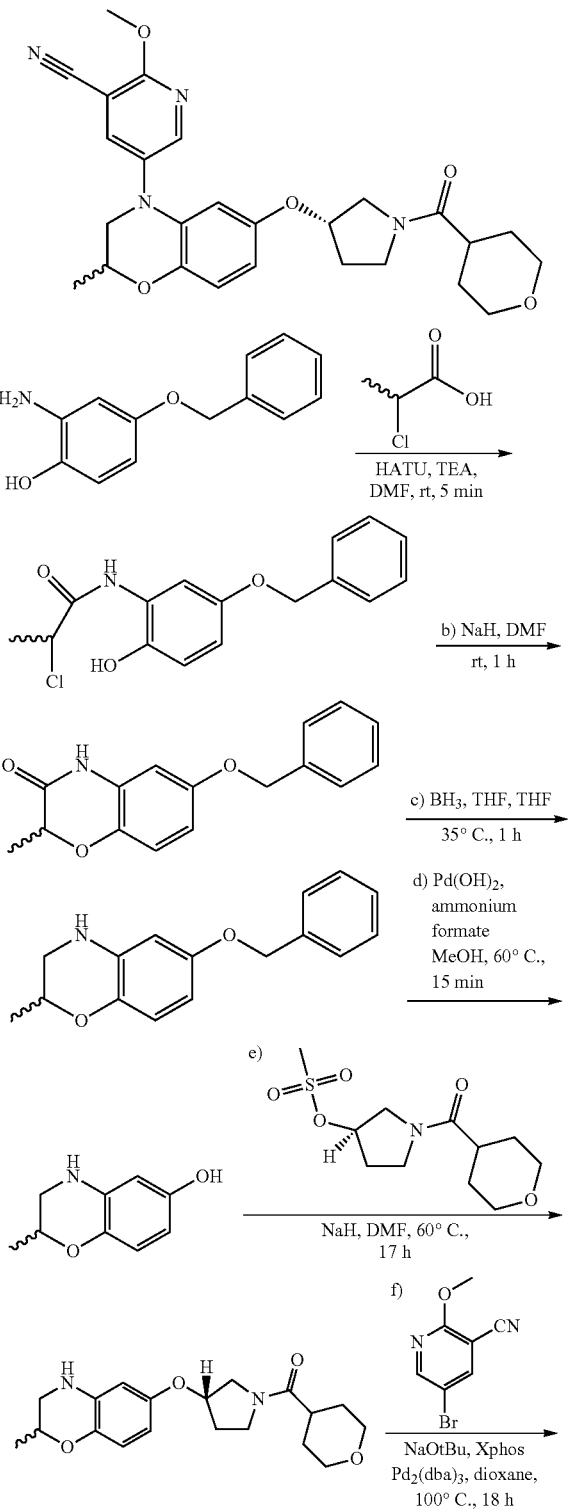

-continued

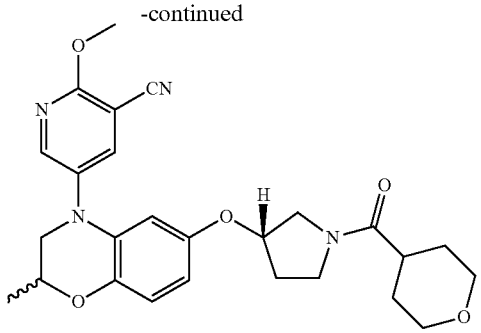

a) N-(5-Benzyloxy-2-hydroxy-phenyl)-2-chloro-propionamide

A solution of 2-chloro-propionic acid (CAS registry 598-78-7) (0.914 ml, 7.53 mmol) in DMF (20 ml) was treated with Et$_3$N (1.259 ml, 9.03 mmol) and HATU (3.05 g, 8.03 mmol). The resulting solution was stirred at rt for 30 min, then 2-amino-4-benzyloxy-phenol (CAS registry 102580-07-4) (1.08 g, 5.02 mmol) was added. The reaction mixture was stirred at rt for 5 min, diluted with EtOAc and concentrated. The title compound was obtained after flash chromatography on silica gel (cyclohexane/EtOAc, 100:0 to 50:50) as orange solid (617 mg, 40% yield).

UPLC Rt$_{M14}$=1.32 min; ESIMS: 306 [(M+H)$^+$].

$^1$H NMR (400 MHz, DMSO-d$_6$): δ 9.50 (d, 1H), 7.70 (br, s 1H), 7.45 (m, 5H), 6.80 (d, 1H), 6.65 (dd, 1H), 5.00 (s, 2H), 2.65 (s, 3H).

b) 6-Benzyloxy-2-methyl-4H-benzo[1,4]oxazin-3-one

A dry solution of N-(5-benzyloxy-2-hydroxy-phenyl)-2-chloro-propionamide (617 mg, 2.0 mmol) in DMF (15 ml) was treated at 0° C. with sodium hydride 95% (58.1 mg, 2.4 mmol). After stirring at rt for 1 h, the reaction mixture was diluted with DCM and washed with water. The organic layer was dried over Na$_2$SO$_4$, filtered, concentrated and the title compound was obtained after flash chromatography on silica gel (cyclohexane/EtOAc, 100:0 to 80:20) as a white solid (146 mg, 27% yield).

UPLC Rt$_{M14}$=1.30 min; ESIMS: 270 [(M+H)$^+$].

$^1$H NMR (400 MHz, DMSO-d$_6$): δ 10.80 (s, 1H), 7.45 (m, 5H), 6.85 (d, 1H), 6.65 (m, 2H), 5.00 (s, 2H), 4.55 (q, 1H), 1.45 (d, 3H).

c) 6-Benzyloxy-2-methyl-3,4-dihydro-2H-benzo[1,4]oxazine

A solution of 6-benzyloxy-2-methyl-4H-benzo[1,4]oxazin-3-one (146 mg, 0.54 mmol) in THF (4 ml) was treated at 0° C. with BH$_3$*THF (1M in THF, 0.813 ml, 0.813 mmol). After stirring at 35° C. for 1 h, the reaction mixture was cooled down to 0° C., quenched with water (0.5 ml) and an aqueous NaOH 4N soln. (0.5 ml) and then diluted with EtOAc. The organic layer was dried over Na$_2$SO$_4$, filtered, concentrated and the title compound was obtained as a white solid (125 mg, 90% yield).

UPLC Rt$_{M14}$=1.40 min; ESIMS: 256 [(M+H)$^+$].

$^1$H NMR (400 MHz, DMSO-d$_6$): δ 7.45 (m, 5H), 6.50 (d, 1H), 6.20 (d, 1H), 6.10 (dd, 1H), 5.35 (s, 1H), 4.90 (s, 2H), 4.00 (m, 1H), 3.25 (m, 1H), 2.90 (m, 1H), 1.35 (d, 3H).

d) 2-Methyl-3,4-dihydro-2H-benzo[1,4]oxazin-6-ol

A solution of 6-benzyloxy-2-methyl-3,4-dihydro-2H-benzo[1,4]oxazine (124 mg, 0.486 mmol) in MeOH (10 ml) was treated at rt with ammonium formate (276 mg, 4.37 mmol) and Pd(OH)$_2$ (68.2 mg, 0.486 mmol). The reaction mixture was stirred at 60° C. for 15 min. After cooling to rt, the reaction mixture was filtered through hyflo, rinsed with DCM and MeOH and then the filtrates were concentrated. The title compound was obtained after flash chromatography on silica gel (DCM/MeOH, 100:0 to 90:10) as a brown solid. (69.4 mg, 87% yield).

UPLC Rt$_{M14}$=0.56 min; ESIMS: 166 [(M+H)$^+$].

$^1$H NMR (400 MHz, DMSO-d$_6$): δ 8.50 (s, 1H), 6.45 (d, 1H), 6.00 (d, 1H), 5.85 (dd, 1H), 5.25 (s, 1H), 4.00 (m, 1H), 3.25 (m, 1H), 2.90 (m, 1H), 1.35 (d, 3H).

e) [(S)-3-(2-Methyl-3,4-dihydro-2H-benzo[1,4]oxazin-6-yloxy)-pyrrolidin-1-yl]-(tetrahydro-pyran-4-yl)-methanone A dry solution of 2-methyl-3,4-dihydro-2H-benzo[1,4]oxazin-6-ol (69 mg, 0.42 mmol) and (R)-1-(tetrahydro-2H-pyran-4-carbonyl)pyrrolidin-3-yl methanesulfonate (intermediate C1, 209 mg, 0.75 mmol) in DMF (1.4 ml) was treated with sodium hydride 60% in mineral oil (15.8 mg, 0.63 mmol) and the reaction mixture was stirred at 50° C. for 18 h. The reaction mixture was diluted with EtOAc and washed with sat. aq. NaHCO$_3$ soln. The organic layer was dried over Na$_2$SO$_4$, filtered, concentrated and the title compound was obtained after flash chromatography on silica gel (DCM/MeOH, 100:0 to 95:5) as a red orange sticky solid (128 mg, 88% yield).

UPLC Rt$_{M14}$=1.01 min; ESIMS: 347 [(M+H)$^+$]

$^1$H NMR (400 MHz, DMSO-d$_6$): δ 6.50 (d, 1H), 6.25 (d, 1H), 6.00 (d, 1H), 6.05 (m, 1H), 5.65 (m, 2H), 5.35 (d, 2H), 4.45 (d, 2H), 3.00-4.00 (m, 6H), 2.00-2.40 (m, 4H), 1.5 (m, 4H)

f) 2-Methoxy-5-{2-methyl-6-[(S)-1-(tetrahydro-pyran-4-carbonyl)-pyrrolidin-3-yloxy]-2,3-dihydro-benzo[1,4]oxazin-4-yl}-nicotinonitrile A mixture of (S)-(3-(2-methyl-3,4-dihydro-2H-benzo[b][1,4]oxazin-6-yloxy)pyrrolidin-1-yl)(tetrahydro-2H-pyran-4-yl)methanone (128 mg, 0.369 mmol), 5-bromo-2-methoxynicotinonitrile (CAS registry 941294-54-8, IA12), (94 mg, 0.443 mmol), XPhos (8.81 mg, 0.018 mmol), NaOtBu (53.3 mg, 0.554 mmol) and Pd$_2$(dba)$_3$ (16.92 mg, 0.018 mmol) in toluene (2.5 ml) was degassed with argon. The reaction mixture was stirred at 80° C. for 20 min. After cooling to rt, the reaction mixture was filtered through hyflo, rinsed with EtOAc and the filtrates were washed with sat. aq. NaHCO$_3$ soln. The organic layer was dried over Na$_2$SO$_4$, filtered and concentrated. The title compound was obtained after prep. RP-HPLC (SunFire C18 column OBD 5 mm 30×100 mm, gradient 32% to 67% ACN in 15 min). The fractions were lyophilized and filtered over a PL-HCO$_3$ MP SPE cartridge to give a brown solid (39.1 mg, 22% yield).

UPLC Rt$_{M14}$=1.10 min; ESIMS: 479 [(M+H)$^+$].

$^1$H NMR (400 MHz, DMSO-d$_6$, 394 K): δ 8.40-8.30 (m, 1H), 8.10-8.00 (m, 1H), 6.75 (d, 1H), 6.35 (m, 1H), 6.15 (m, 1H), 4.75 (m, 1H), 4.00 (s, 3H), 3.85 (m, 1H), 3.75-3.00 (m, 5H), 2.65 (m, 1H), 2.00 (m, 1H), 1.65 (m, 2H), 1.44 (d, 3H).

Examples O2 to O3

The compounds listed in Table 10 were prepared by chromatographic diastereomer separation.

TABLE 10

| Example | Compound/Reaction Conditions | HPLC Rt [min] (method) | MS [m/z; (M + 1)⁺] |
|---------|------------------------------|------------------------|---------------------|
| O2 | 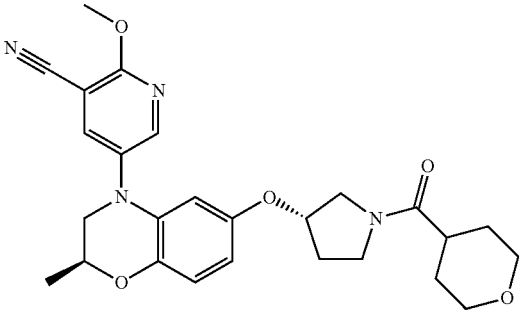 [SMILES: COc1ncc(N2C[C@H](C)Oc3ccc(O[C@H]4CCN(C(=O)C5CCOCC5)C4)cc32)cc1C#N]<br>Peak 1 diastereomer separation<br>2-Methoxy-5-{(S)-2-methyl-6-[(S)-1-(tetrahydro-pyran-4-carbonyl)-pyrrolidin-3-yloxy]-2,3-dihydro-benzo[1,4]oxazin-4-yl}-nicotinonitrile<br>Buchwald amination condition: CA6<br>Amide bond condition: CB6<br>Side chain introduction condition: CC2<br>Precursors used: IO, IA12, CAS 104706-47-0/<br>acyl chloride 40191-32-0<br>Chromatographic diasteroemer separation: CD11 | 19.89 (M15) | |
| O3 | 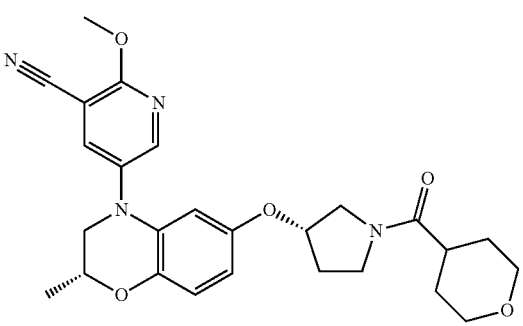 [SMILES: COc1ncc(N2C[C@@H](C)Oc3ccc(O[C@H]4CCN(C(=O)C5CCOCC5)C4)cc32)cc1C#N]<br>Peak 2 diastereomer separation<br>2-Methoxy-5-{(R)-2-methyl-6-[(S)-1-(tetrahydro-pyran-4-carbonyl)-pyrrolidin-3-yloxy]-2,3-dihydro-benzo[1,4]oxazin-4-yl}-nicotinonitrile<br>Buchwald amination condition: CA6<br>Amide bond condition: CB6<br>Side chain introduction condition: CC2<br>Precursors used: IO, IA12, CAS 104706-47-0/<br>Acyl chloride 40191-32-0<br>Chromatographic diasteroemer separation: CD11 | 27.33 (M15) | |

Example P

2-Methoxy-5-{6-[(S)-1-(1-methyl-piperidin-4-ylmethyl)-pyrrolidin-3-yloxy]-2,3-dihydro-benzo[1,4]oxazin-4-yl}-nicotinonitrile

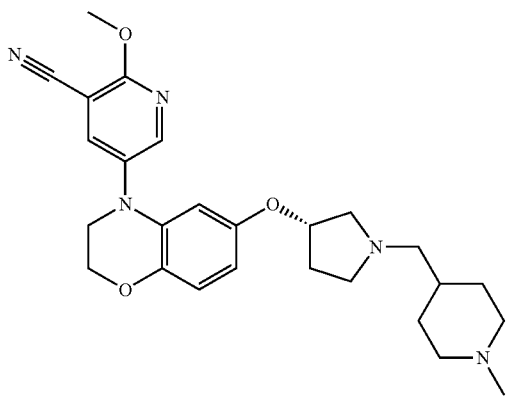 [SMILES: COc1ncc(N2CCOc3ccc(O[C@H]4CCN(CC5CCN(C)CC5)C4)cc32)cc1C#N]

a) (S)-tert-butyl 4-((3-(4-(5-cyano-6-methoxypyridin-3-yl)-3,4-dihydro-2H-benzo[b][1,4]oxazin-6-yloxy)pyrrolidin-1-yl)methyl)piperidine-1-carboxylate A solution of 2-methoxy-5-[6-((S)-pyrrolidin-3-yloxy)-2,3-dihydro-benzo[1,4]oxazin-4-yl]-nicotinonitrile (see analogue B1, c), 95 mg, 0.270 mmol) in DCE (4.5 ml) was treated with tert-butyl 4-formylpiperidine-1-carboxylate (60 mg, 0.281 mmol). After stirring for 2 d at rt, the reaction mixture was diluted with DCM and sat. aq. NaHCO₃ soln. The organic layer was dried over Na₂SO₄, filtered, concentrated and the title compound was obtained after flash chromatography on silica gel (cyclohexane/EtOAc, 100:0 to 0:100), yield 66 mg, (40%).

UPLC Rt$_{M1}$=1.66 min; ESIMS: 550 [(M+H)⁺].
¹H NMR (400 MHz, DMSO-d₆): δ 8.35 (d, 1H), 7.75 (d, 1H), 7.35 (s, 1H), 7.85 (d, 1H), 6.35 (dd, 1H), 6.10 (d, 1H), 4.65 (m, 1H), 4.45 (m, 2H), 3.60 (m, 2H), 2.75-2.15 (m, 4H), 1.50 (s, 9H).

b) (S)-2-methoxy-5-(6-(1-(piperidin-4-ylmethyl)pyrrolidin-3-yloxy)-2H-benzo[b][1,4]oxazin-4(3H)-yl)nicotinonitrile A solution of (S)-tert-butyl 4-((3-(4-(5-cyano-6-methoxypyridin-3-yl)-3,4-dihydro-2H-benzo[b][1,4]oxazin-6-yloxy)pyrrolidin-1-yl)methyl)piperidine-1-carboxylate) (66 mg, 0.120 mmol) in DCM (2 ml) was treated with TFA (0.093 ml, 1.20 mmol). The reaction mixture was stirred at rt for 17 h, then quenched with sat. aq. Na₂CO₃ soln. and extracted with DCM. The organic layer was dried over Na₂SO₄, filtered and concentrated under reduced pressure to afford the title product (36 mg, 67% yield).

UPLC Rt$_{M1}$=1.03 min; ESIMS: 450 [(M+H)⁺].
¹H NMR (400 MHz, DMSO-d₆): δ 8.35 (d, 1H), 7.80 (d, 1H), 7.25 (s, 1H), 6.80 (d, 1H), 6.25 (m, 1H), 6.15 (d, 1H), 4.65 (m, 1H), 4.45 (m, 2H), 3.60 (m, 2H), 2.75-2.15 (m, 4H).

c) (S)-2-methoxy-5-(6-(1-((1-methylpiperidin-4-yl)methyl)pyrrolidin-3-yloxy)-2H-benzo[b][1,4]oxazin-4(3H)-yl)nicotinonitrile A solution of (S)-2-methoxy-5-(6-(1-(piperidin-4-ylmethyl)pyrrolidin-3-yloxy)-2H-benzo[1,4]oxazin-4(3H)-yl)nicotinonitrile (36 mg, 0.080 mmol) in DCE (2 ml) was treated with a 37% aq. formaldehyde soln. (8.94 μl, 0.120 mmol). The solution was stirred under argon at rt for 15 min, then NaBH₃CN (50.9 mg, 0.240 mmol) was added. The resulting mixture was stirred at rt for 30 min, diluted with DCM and sat. aq. NaHCO₃ soln. The organic layer was dried over Na₂SO₄ and concentrated. The title compound was obtained after purification by prep. RP-HPLC (column SunFire C18, gradient 15-50% ACN in 15 min). The fractions were extracted with DCM/sat. aq. NaHCO₃ soln, dried over Na₂SO₄, concentrated and lyophilized to give the title compound (18 mg, 48% yield).

UPLC Rt$_{M1}$=1.04 min; ESIMS: 464 [(M+H)⁺].
¹H NMR (400 MHz, CDCl₃): δ 8.35 (d, 1H), 7.85 (d, 1H), 7.45 (s, 1H), 6.75 (d, 1H), 6.35 (dd, 1H), 6.15 (d, 1H), 4.65 (m, 1H), 4.45 (m, 2H), 3.25 (m, 2H), 2.75-2.15 (m, 4H), 2.65 (s, 3H), 1.95 (m, 2H), 1.65 (m, 2H).

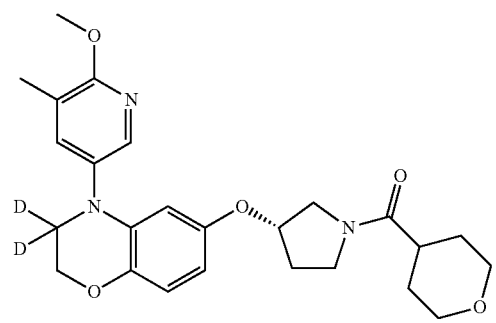 [SMILES: [2H]C1([2H])COc2ccc(O[C@H]3CCN(C(=O)C4CCOCC4)C3)cc2N1c1cnc(OC)c(C)c1]

Example Q

{(S)-3-[4-(6-Methoxy-5-methyl-pyridin-3-yl)-3,4-dihydro-2H-benzo[1,4]oxazin-6-yloxy]-pyrrolidin-1-yl}-(tetrahydro-pyran-4-yl)-methanone

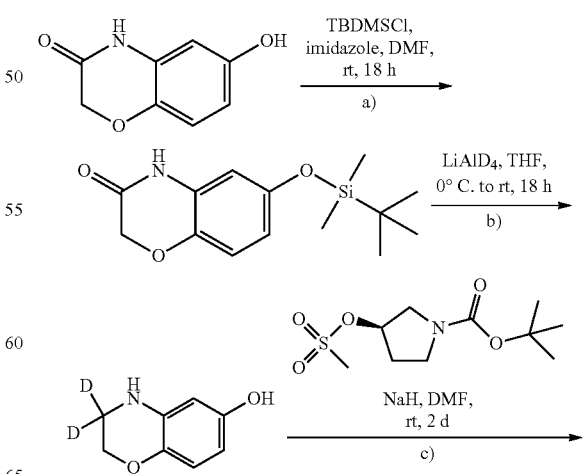

-continued

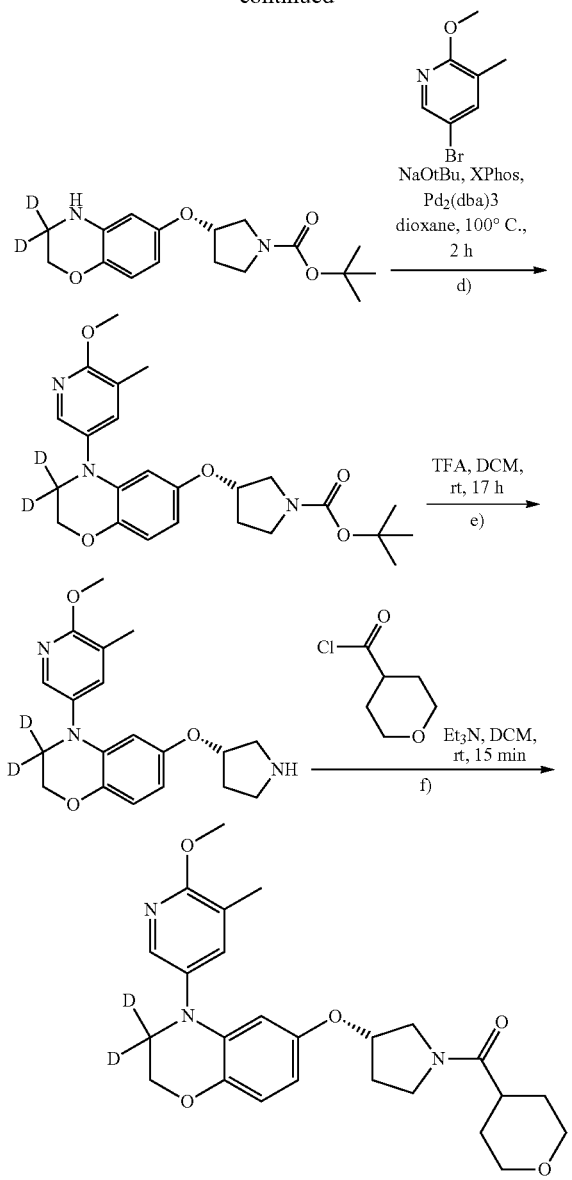

a) 6-(tert-Butyl-dimethyl-silanyloxy)-4H-benzo[1,4]oxazin-3-one

A solution of 6-hydroxy-2H-benzo[b][1,4]oxazin-3(4H)-one (CAS registry 53412-38-7) (1076 mg, 6.52 mmol) in DMF (8 ml) was treated at rt with TBDMSCl (1080 mg, 7.17 mmol) and imidazole (532 mg, 7.82 mmol). After stirring for 18 h at rt, the reaction mixture was diluted with DCM and washed with water. The organic layer was dried over $Na_2SO_4$, filtered, concentrated and the title compound was obtained after flash chromatography on silica gel (cyclohexane/EtOAc, 100:0 to 50:50) as a white solid (1.18 g, 65% yield).

UPLC $Rt_{M2}$=1.91 min; ESIMS: 280 [(M+H)$^+$].

$^1$H NMR (400 MHz, CDCl$_3$): δ 7.85 (br, s 1H), 7.35 (s, 1H), 6.85 (d, 1H), 6.45 (m, 1H), 6.30 (d, 1H), 4.50 (s, 2H), 1.00 (s, 9H), 0.25 (s, 6H).

b) 3,3-Dideutero-3,4-dihydro-2H-benzo[1,4]oxazin-6-ol

A solution of 6-(tert-butyl-dimethyl-silanyloxy)-4H-benzo[1,4]oxazin-3-one (8.34 g, 29.8 mmol) in THF (100 ml) was treated at 00° C. with lithium aluminium deuteride (2.26 g, 59.7 mmol). After stirring for 18 h at rt the reaction mixture was added to a cold aqueous 1 M Rochelle's salt soln. and was extracted with EtOAc. The organic layer was dried over $Na_2SO_4$, filtered, concentrated and the title compound was obtained after flash chromatography on silica gel (cyclohexane/EtOAc, 100:0 to 0:100) as a white solid (1.40 g, 31% yield).

UPLC $Rt_{M9}$=0.69 min; ESIMS: 154 [(M+H)$^+$].

$^1$H NMR (400 MHz, DMSO-d$_6$): δ 8.50 (s 1H), 6.45 (d, 1H), 6.00 (d, 1H), 5.85 (m, 1H), 5.15 (s, 1H), 4.00 (s, 2H).

c) (S)-3-(3,3-Dideutero-3,4-dihydro-2H-benzo[1,4]oxazin-6-yloxy)-pyrrolidine-1-carboxylic acid tert-butyl ester A dry solution of 3,3-dideutero-3,4-dihydro-2H-benzo[1,4]oxazin-6-ol (1.44 g, 9.40 mmol) and (R)-3-methanesulfonyloxy-pyrrolidine-1-carboxylic acid tert-butyl ester (CAS registry 127423-61-4) (5.49 g, 20.68 mmol) in DMF (10 ml) was treated with sodium hydride 60% in mineral oil (0.752 g, 18.80 mmol) and the reaction mixture was stirred at rt for 2 d. The reaction mixture was diluted with EtOAc and washed with sat. aq. NaHCO$_3$ soln. The organic layer was dried over $Na_2SO_4$, filtered, concentrated and purified by flash chromatography on silica gel (cyclohexane/EtOAc, 100:0 to 0:100), to yield 4.12 g, (quantitative yield) of the title compound.

UPLC $Rt_{M1}$=1.07 min; ESIMS: 323 [(M+H)$^+$].

$^1$H NMR (400 MHz, CDCl$_3$): δ 6.65 (m, 1H), 6.15 (m, 2H), 5.35 (m, 1H), 4.85 (m, 2H), 3.50 (m, 4H), 2.15 (m, 2H), 1.50 (s, 9H).

d) (S)-3-[4-(6-Methoxy-5-methyl-pyridin-3-yl)-3,3-dideutero-3,4-dihydro-2H-benzo[1,4]oxazin-6-yloxy]-pyrrolidine-1-carboxylic acid tert-butyl ester This example was prepared in analogy to Example G1, e).
UPLC $Rt_{M1}$=2.00 min; ESIMS: 444 [(M+H)$^+$].
$^1$H NMR (400 MHz, CDCl$_3$): δ 7.95 (br.s, 1H), 7.45 (br.s, 1H), 6.80 (m, 1H), 6.25 (m, 1H), 4.75 (m, 1H), 4.35 (s, 2H), 4.00 (s, 3H), 3.50 (m, 4H), 2.25 (m, 2H), 1.50 (s, 9H).

e) 4-(6-Methoxy-5-methyl-pyridin-3-yl)-3,3-dideutero-6-((S)-pyrrolidin-3-yloxy)-3,4-dihydro-2H-benzo-[1,4]oxazine This example was prepared in analogy to Example G1, f).
UPLC $Rt_{M1}$=1.26 min; ESIMS: 342 [(M+H)$^+$].
$^1$H NMR (400 MHz, CDCl$_3$): δ 7.95 (br.s, 1H), 7.45 (br.s, 1H), 6.80 (m, 1H), 6.25 (m, 1H), 4.75 (m, 1H), 4.35 (s, 2H), 4.00 (s, 3H), 3.15 (m, 2H), 2.75 (m, 2H), 2.25 (m, 2H).

f) {(S)-3-[4-(6-Methoxy-5-methyl-pyridin-3-yl)-3,4-dihydro-2H-benzo[1,4]oxazin-6-yloxy]-pyrrolidin-1-yl}-(tetrahydro-pyran-4-yl)-methanone This example was prepared in analogy to Example B1, d).
UPLC $Rt_{M1}$=1.65 min; ESIMS: 456 [(M+H)$^+$].
$^1$H NMR (400 MHz, CDCl$_3$, 298 K): δ 8.45 (m, 1H), 8.29 (s, 1H), 7.21 (t, 1H), 6.20 (t, 1H), 6.10 (s, 1H), 5.00 (d, 1H), 4.37 (t, 2H), 4.00 (m, 3H), 3.39-3.74 (m, 4H), 2.50 (m, 2H), 2.35 (s, 3H), 1.09-2.10 (m, 5H).

Example R

5-{6-[(S)-1-(4-Hydroxy-cyclohexanecarbonyl)-pyrrolidin-3-yloxy]-2,3-dihydro-benzo[1,4]oxazin-4-yl}-2-methoxy-nicotinonitrile

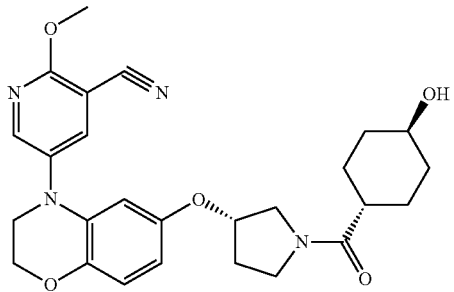 [SMILES: COc1ncc(N2CCOc3ccc(O[C@H]4CCN(C(=O)[C@H]5CC[C@H](O)CC5)C4)cc32)cc1C#N]

This example was prepared in analogy to Example J, starting from 2-methoxy-5-{6-[(S)-1-((S)-pyrrolidine-3-carbonyl)-pyrrolidin-3-yloxy]-2,3-dihydro-benzo[1,4]oxazin-4-yl}-nicotinonitrile.

UPLC Rt$_{M14}$=0.91 min; ESIMS: 478 [(M+H)$^+$].

$^1$H NMR (400 MHz, DMSO-d6): δ 8.43 (d, 1H), 8.28 (d, 1H), 6.73 (m, 1H), 6.34 (m, 1H), 6.08 (dd, 1H), 4.76 (d, 1H), 4.51 (m, 1H), 4.22 (s, 2H), 4.00 (s, 3H), 3.20-3.71 (m, 9H), 1.09-2.10 (m, 10H).

Example S

2-Methoxy-5-{6-[(S)-1-(2-pyridin-4-yl-acetyl)-pyrrolidin-3-yloxy]-2,3-dihydro-benzo[1,4]oxazin-4-yl}-nicotinonitrile

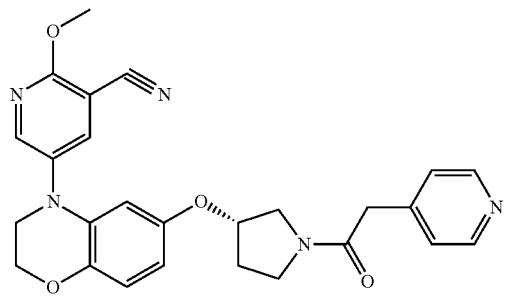 [SMILES: COc1ncc(N2CCOc3ccc(O[C@H]4CCN(C(=O)Cc5ccncc5)C4)cc32)cc1C#N]

This example was prepared in analogy to Example J, starting from 2-methoxy-5-{6-[(S)-1-((S)-pyrrolidine-3-carbonyl)-pyrrolidin-3-yloxy]-2,3-dihydro-benzo[1,4]oxazin-4-yl}-nicotinonitrile.

UPLC Rt$_{M14}$=0.82 min; ESIMS: 471 [(M+H)$^+$]

$^1$H NMR (400 MHz, DMSO-d6): δ 8.45 (m, 3H), 8.29 (s, 1H), 7.21 (m, 2H), 6.74 (m, 1H), 6.33 (m, 1H), 6.10 (m, 1H), 4.87 (d, 1H), 4.22 (s, 2H), 4.00 (s, 3H), 3.39-3.74 (m, 8H), 1.09-2.10 (m, 2H).

Example T

{(S)-3-[4-(5-Amino-6-methoxy-pyridin-3-yl)-3,4-dihydro-2H-benzo[1,4]oxazin-6-yloxy]-pyrrolidin-1-yl}-(1-methyl-1H-imidazol-4-yl)-methanone a) 5-[6-((S)-1-tert-Butoxycarbonyl-pyrrolidin-3-yloxy)-2,3-dihydro-benzo[1,4]oxazin-4-yl]-2-methoxy-nicotinic acid methyl ester

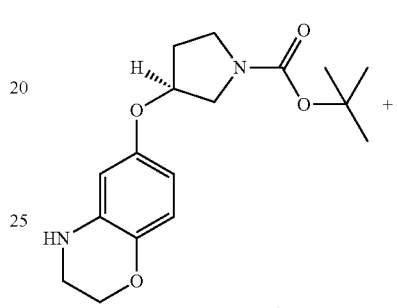

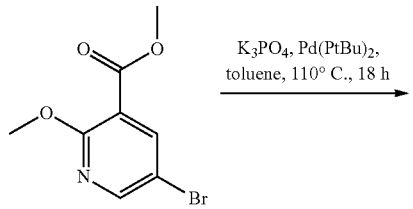

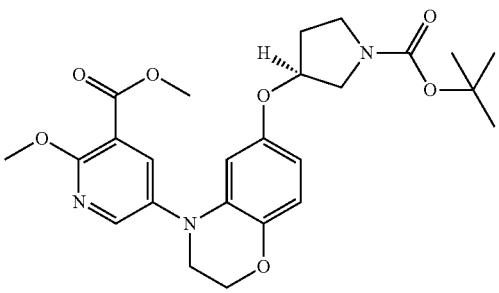

Under argon, K$_3$PO$_4$ (815 mg, 2.00 mmol) and bis-(t-butylphosphine)palladium (29.4 mg. 0.06 mmol) were added to a solution of (S)-3-(3,4-dihydro-2H-benzo[1,4]oxazin-6-yloxy)-pyrrolidine-1-carboxylic acid tert-butyl ester (prepared as described in step a) example B) (615 mg, 1.92 mmol) and 5-bromo-2-methoxy-nicotinic acid methyl ester (IA 22, CAS registry 122433-41-4) (614 mg, 1.30 mmol) in toluene (6 ml). The reaction mixture was degassed with argon for 15 min, then stirred at 110° C. for 18 h, diluted with EtOAc and washed with a sat. aq. NaHCO$_3$ soln. The organic layer was dried over MgSO$_4$ and concentrated to afford the crude title compound that was purified by flash chromatography on silica gel (heptane/EtOAc 90:10 to 0:100) to give a yellow gum (474 mg, 51% yield).

UPLC Rt$_{M2}$=1.36 min; ESIMS: 486 [(M+H)$^+$].

b) 5-[6-((S)-1-tert-Butoxycarbonyl-pyrrolidin-3-yloxy)-2,3-dihydro-benzo[1,4]oxazin-4-yl]-2-methoxy-nicotinic acid

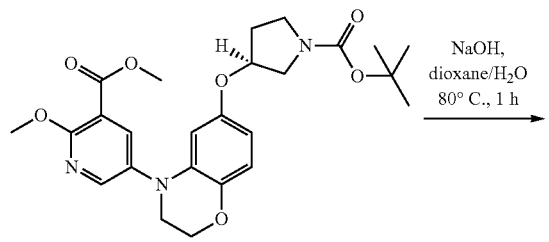

A solution of 5-[6-((S)-1-tert-butoxycarbonyl-pyrrolidin-3-yloxy)-2,3-dihydro-benzo[1,4]oxazin-4-yl]-2-methoxy-nicotinic acid methyl ester (483 mg, 0.99 mmol) in dioxane (5 ml) was treated with a solution of sodium hydroxide pellets (119 mg, 2.98 mmol) in water (2 ml). The solution was stirred at 80° C. for 1 h. The reaction mixture was acidified to pH3 with aq. 1N HCl soln. and extracted with EtOAc. The combined organic phases were dried over MgSO$_4$ and concentrated to afford the title compound after flash chromatography on silica gel (heptane/EtOAc 100:0 to 0:100 then EtOAc/MeOH 90:10 to 80:20) as a solid (370 mg, 79% yield).

UPLC Rt$_{M6}$=1.79 min; ESIMS: 372 [(M+H-100)$^+$]

$^1$H NMR (400 MHz, CDCl$_3$): δ 8.22-8.48 (m, 2H), 6.82 (d, 1H), 6.33 (m, 1H), 6.21 (d, 1H), 4.60-4.76 (m, 1H), 4.27-4.41 (m, 2H), 4.15-4.27 (m, 3H), 3.62-3.77 (m, 2H), 3.31-3.58 (m, 5H), 1.85-2.19 (m, 2H), 1.34-1.56 (m, 9H)

c) (S)-3-[4-(5-tert-Butoxycarbonylamino-6-methoxy-pyridin-3-yl)-3,4-dihydro-2H-benzo[1,4]oxazin-6-yloxy]-pyrrolidine-1-carboxylic acid tert-butyl ester

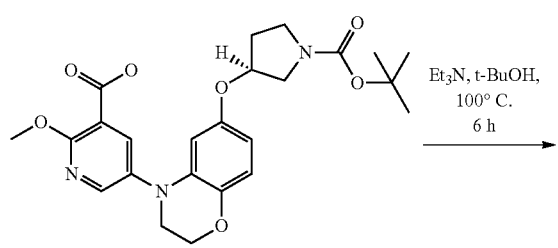

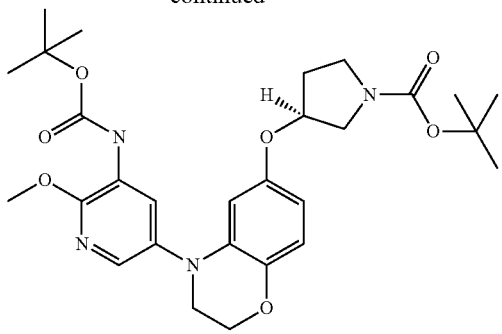

A solution of 5-[6-((S)-1-tert-butoxycarbonyl-pyrrolidin-3-yloxy)-2,3-dihydro-benzo[1,4]oxazin-4-yl]-2-methoxy-nicotinic acid (370 mg, 0.78 mmol) and Et$_3$N (0.28 ml, 1.96 mmol) in tBuOH (5 ml) was treated with DPPA (CAS registry 26386-88-9) (0.17 ml, 0.78 mmol) and stirred at 100° C. for 6 h. DCM and sat. aq. NaHCO$_3$ soln. were added, the organic layer was separated by elution through a separating phase cartridge and concentrated to afford the title compound after flash chromatography on silica gel (heptane/EtOAc 100:0 to 50:50) as a pink gum (114 mg, 24%).

UPLC Rt$_{M2}$=1.36 min; ESIMS: 486 [(M+H)$^+$].

$^1$H NMR (400 MHz, CDCl$_3$): δ 8.42 (br s, 1H), 7.75 (d, 1H), 7.02 (s, 1H), 6.78 (d, 1H), 6.15-6.41 (m, 1H), 4.71 (br s, 1H), 4.23-4.39 (m, 2H), 4.09-4.22 (m, 3H), 3.62-3.75 (m, 2H), 3.31-3.58 (m, 4H), 1.86-2.26 (m, 2H), 1.40-1.60 (m, 18H).

d) 2-Methoxy-5-[6-((S)-pyrrolidin-3-yloxy)-2,3-dihydro-benzo[1,4]oxazin-4-yl]-pyridin-3-ylamine

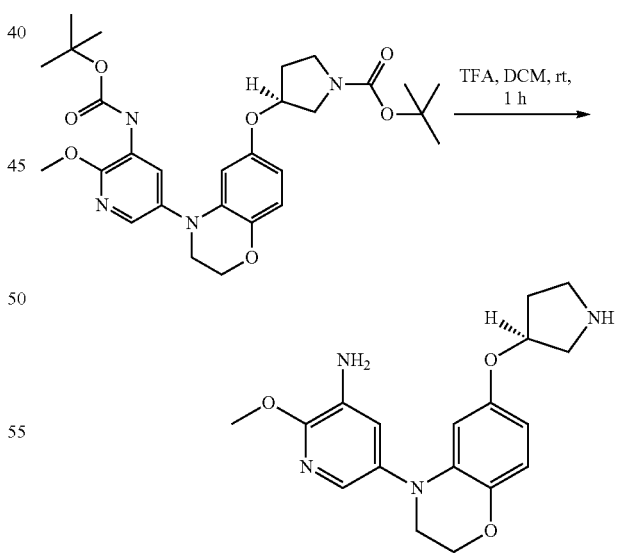

A solution of (S)-3-[4-(5-tert-butoxycarbonylamino-6-methoxy-pyridin-3-yl)-3,4-dihydro-2H-benzo[1,4]oxazin-6-yloxy]-pyrrolidine-1-carboxylic acid tert-butyl ester (130 mg, 0.24 mmol) in DCM (2 ml) was treated with TFA (CAS registry 76-05-1) and stirred at rt for 1 h. The reaction mixture was concentrated to afford the title compound after

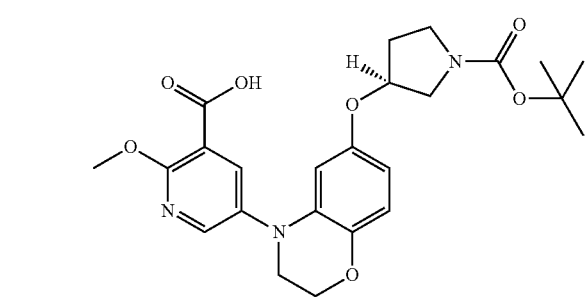

elution from a 2 g Isolute SCX-2 cartridge (eluent MeOH, then 2M NH$_3$/MeOH) as a yellow gum (88 mg, quant. crude).

UPLC Rt$_{M2}$=1.25 min; ESIMS: 343 [(M+H)$^+$].

e) {(S)-3-[4-(5-Amino-6-methoxy-pyridin-3-yl)-3,4-dihydro-2H-benzo[1,4]oxazin-6-yloxy]-pyrrolidin-1-yl}-(1-methyl-1H-imidazol-4-yl)-methanone

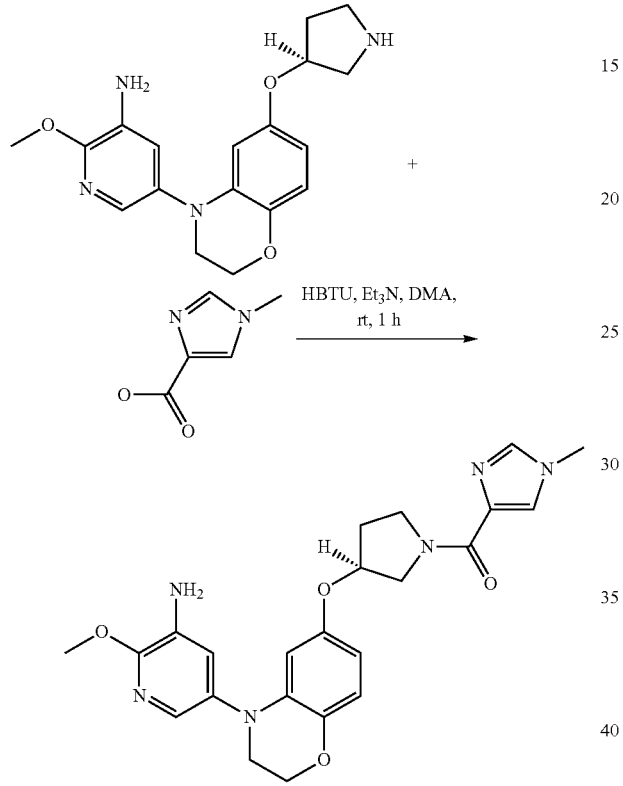

A solution of 1-methyl-1H-imidazole-4-carboxylic acid (CAS registry 41716-18-1) (36.0 mg, 0.26 mmol) and Et$_3$N (0.11 ml, 0.78 mmol) in DMF (1 ml) was treated with HBTU (CAS registry 94790-37) (107 mg, 0.28 mmol). After stirring at rt for 20 min, the reaction mixture was cooled down to 5° C. and a solution of 2-methoxy-5-[6-((S)-pyrrolidin-3-yloxy)-2,3-dihydro-benzo[1,4]oxazin-4-yl]-pyridin-3-ylamine (88 mg, 0.26 mmol) in DMF (3 ml) was added. The reaction mixture was stirred at rt for 1 h, concentrated and the residue was taken up in DCM (10 ml), washed with a sat. aq. NaHCO$_3$ soln. (5 ml), the organic layer was separated by elution through a separating phase cartridge and concentrated. The residue was purified by flash chromatography on silica gel (heptane/EtOAc 100:0 to 0:100), the combined fractions were concentrated, dissolved in tBuOH/H$_2$O and lyophilized to afford the title compound as a colourless solid (21 mg, 37% yield).

UPLC Rt$_{M2}$=0.85 min; ESIMS: 451 [(M+H)$^+$].

$^1$H NMR (400 MHz, CD$_3$OD): δ 7.64 (s, 1H), 7.62 (s, 1H), 7.65 m, 1H), 6.93 (m, 1H), 6.70 (m, 1H), 6.20-6.34 (m, 1H), 6.15 (m, 1H), 4.81 (m, 1H), 4.19-4.31 (m, 2H), 3.90-4.05 (m, 4H), 3.55-3.83 (m, 8H), 2.04-2.28 (m, 2H).

Example U

N-(2-Methoxy-5-{6-[(S)-1-(1-methyl-1H-imidazole-4-carbonyl)-pyrrolidin-3-yloxy]-2,3-dihydro-benzo[1,4]oxazin-4-yl}-pyridin-3-yl)-methanesulfonamide

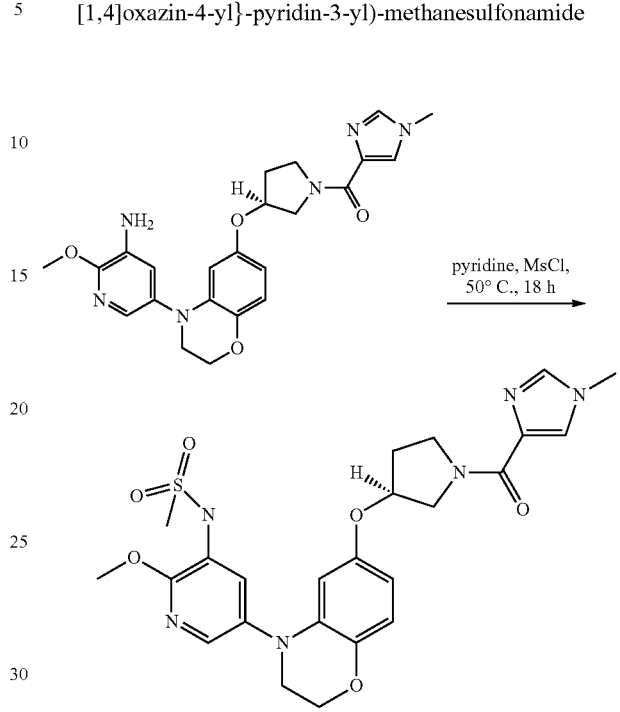

A solution of {(S)-3-[4-(5-Amino-6-methoxy-pyridin-3-yl)-3,4-dihydro-2H-benzo[1,4]-oxazinyloxy]-pyrrolidin-1-yl}-(1-methyl-1H-imidazol-4-yl)-methanone (22.9 mg, 0.05 mmol) in pyridine (1 ml) was treated with methanesulfonyl chloride (CAS registry 124-63-0) (0.08 ml, 0.97 mmol) and stirred at 50° C. for 18 h. The reaction mixture was diluted with DCM and H$_2$O, the organic layer was separated by elution through a separating phase cartridge and concentrated. The residue was purified by flash chromatography on silica gel (heptane/EtOAc 100:0 to 0:100 then EtOAc/MeOH 90:10 to 80:20), the combined fractions were concentrated, dissolved in tBuOH/H$_2$O and lyophilized to afford the title compound as a colourless solid (14 mg, 49%).

UPLC Rt$_{M2}$=1.39 min; ESIMS: 529 [(M+H)$^+$].

$^1$H NMR (400 MHz, CD$_3$OD): δ 7.87 (d, 1H), 7.41-7.76 (m, 3H), 6.73 (m, 1H), 6.02-6.44 (m, 2H), 4.14-4.39 (m, 2H), 3.87-4.12 (m, 5H), 3.55-3.84 (m, 8H), 2.85-3.08 (m, 3H), 1.75-2.40 (m, 2H).

Example V (1,1-Dioxo-hexahydro-1lambda*6*-thiopyran-4-yl)-{(S)-3-[4-(6-methoxy-5-methyl-pyridin-3-yl)-5-methyl-3,4-dihydro-2H-benzo[1,4]oxazin-6-yloxy]-pyrrolidin-1-yl}-methanone

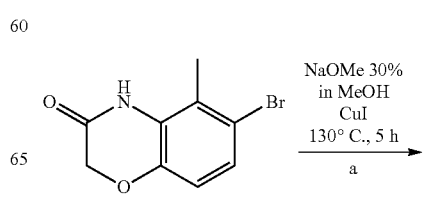

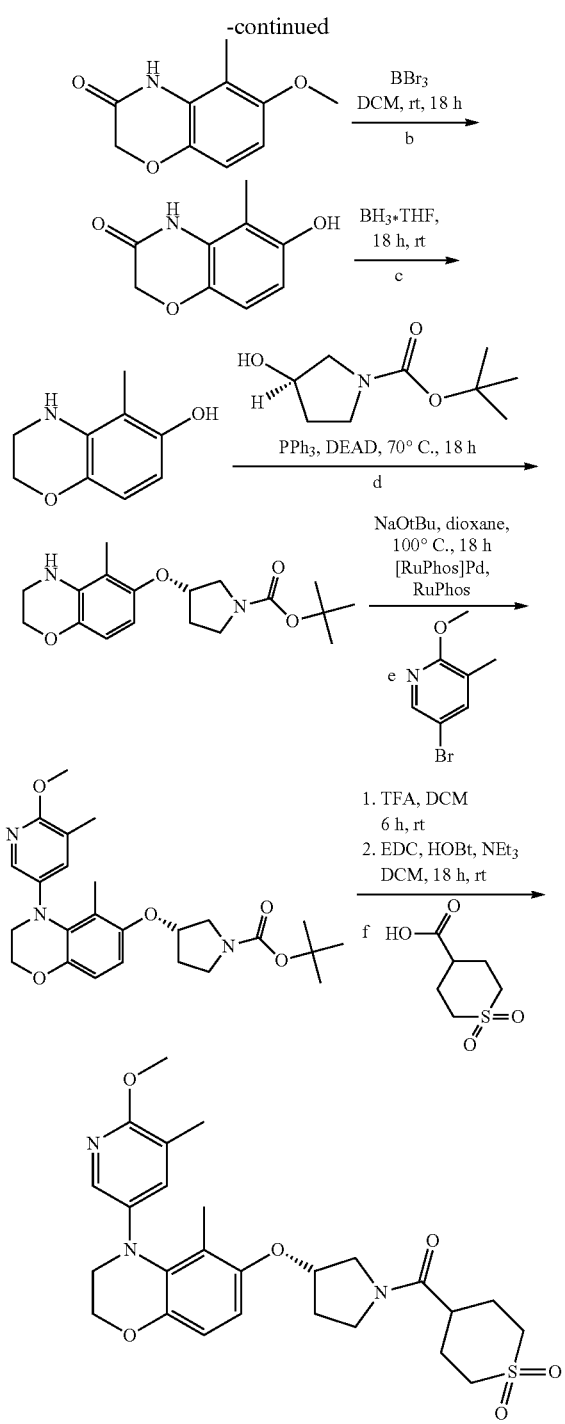

a) 6-Methoxy-5-methyl-4H-benzo[1,4]oxazin-3-one

A solution of 6-bromo-5-methyl-4H-benzo[1,4]oxazin-3-one (CAS registry 1154740-47-2) (1000 mg, 4.13 mmol) and CuI (79 mg, 0.41 mmol) in NaOMe 30% in MeOH (8.1 ml) was stirred at 130° C. for 5 h. The orange/brown mixture was cooled to rt, diluted with EtOAc and washed with a sat. aq. NaHCO$_3$ soln. The combined organic layers were dried over MgSO$_4$, and concentrated to afford an orange solid. Trituration with cyclohexane afforded the title compound as a pink solid (647 mg, 70% yield).

HPLC Rt$_{M1}$=0.73 min.

$^1$H NMR (400 MHz, DMSO-d$_6$): δ 10.21 (s, 1H), 6.76 (d, 1H), 6.53 (d, 1H), 4.42 (s, 2H), 3.71 (s, 3H), 2.05 (s, 3H).

b) 6-Hydroxy-5-methyl-4H-benzo[1,4]oxazin-3-one

A suspension of 6-methoxy-5-methyl-4H-benzo[1,4]oxazin-3-one (647 mg, 3.35 mmol) in DCM (30 ml) was treated under argon at rt with BBr$_3$ (3.16 ml, 33.5 mmol) and stirred for 18 h at rt. The reaction mixture was quenched by dropwise addition of MeOH at 0° C. until obtention of a clear solution. After removal of the solvents, the residue was poured onto ice/sat. aq. NaHCO$_3$ soln. and extracted with EtOAc. The organic layer was dried over MgSO$_4$ and concentrated to afford the title compound as a brown solid (647 mg, crude), which was used in the next step without further purification.

HPLC Rt$_{M1}$=0.49 min.

$^1$H NMR (400 MHz, DMSO-d$_6$): δ 10.11 (s, 1H), 6.43 (d, 1H), 5.98 (d, 1H), 4.57 (s, 2H), 1.89 (s, 3H).

c) 5-Methyl-3,4-dihydro-2H-benzo[1,4]oxazin-6-ol

A solution of 6-hydroxy-5-methyl-4H-benzo[1,4]oxazin-3-one (647 mg, 3.61 mmol) in THF (20 ml) was treated under argon at 0° C. with BH$_3$*THF (1M in THF, 10.83 ml, 10.83 mmol) and stirred for 18 h at rt. MeOH was added and the solution was stirred at rt for 1 h, concentrated to afford a residue which was dissolved in THF (20 ml), treated with BH$_3$*THF (1M in THF, 10.83 ml, 10.83 mmol) and stirred at rt for 18 h. MeOH was added, the solution was stirred at rt for 4 h, concentrated to dryness to afford the title compound as a brown solid (600 mg, crude), which was used in the next step without further purification.

HPLC Rt$_{M1}$=0.49 min; ESIMS: 166 [(M+H)$^+$].

d) (S)-3-(5-Methyl-3,4-dihydro-2H-benzo[1,4]oxazin-6-yloxy)-pyrrolidine-1-carboxylic acid tert-butyl ester A solution of triphenylphosphine (1.33 g, 5.09 mmol) in THF (10 ml) was treated with DEAD (0.8 ml, 5.09 mmol) followed by (R)-3-hydroxy-pyrrolidine-1-carboxylic acid tert-butyl ester (CAS registry 127423-61-4) (1 g, 5.45 mmol) and 5-methyl-3,4-dihydro-2H-benzo[1,4]oxazin-6-ol (600 mg, 3.63 mmol). The resulting red/brown solution was stirred at 70° C. for 18 h. The brown mixture was cooled down, diluted with EtOAc and washed with sat. aq. NaHCO$_3$ soln. The combined organic layers were dried over MgSO$_4$, filtered and concentrated to afford a brown oil. The crude product was three times purified by flash chromatography on silica gel (cyclohexane/EtOAc 90:10 to 40:60) to afford the title compound as a colourless oil (130 mg, 11% yield)

HPLC Rt$_{M1}$=1.09 min; ESIMS: 335 [(M+H)$^+$].

$^1$H NMR (400 MHz, DMSO-d$_6$): δ 6.44 (d, 1H), 6.22-6.04 (m, 1H), 5.24 (br s, 1H), 4.75 (br s, 1H), 4.07-3.93 (m, 2H), 3.45-3.33 (m, 3H), 3.28 (d, 7H), 2.00 (d, 2H), 1.83 (d, 3H), 1.46-1.32 (m, 9H).

e) (S)-3-[4-(6-Methoxy-5-methyl-pyridin-3-yl)-5-methyl-3,4-dihydro-2H-benzo[1,4]oxazin-6-yloxy]-pyrrolidine-1-carboxylic acid tert-butyl ester A solution of (S)-3-(5-methyl-3,4-dihydro-2H-benzo[1,4]oxazin-6-yloxy)-pyrrolidine-1-carboxylic acid tert-butyl ester (120 mg, 0.36 mmol), 5-bromo-2-methoxy-3-methylpyridine (CAS registry 760207-87-2) (145 mg, 0.72 mmol), NaOtBu (103 mg, 1.08 mmol), RuPhos (CAS registry 787618-22-8) (8 mg, 0.02 mmol) and [RuPhos]palladacycle (CAS registry 787618-22-8) (15 mg, 0.02 mmol) in dioxane (2 ml) was stirred at 100° C. for 18 h. The orange/brown mixture was cooled, diluted with EtOAc and washed with water. The combined organic layers were dried over MgSO$_4$, filtered and concentrated to afford a brown oil. The crude product was three times purified by flash chromatography on silica gel (cyclohexane/EtOAc 95:05 to 60:40) to afford the title compound as a yellow oil (97 mg, 60% yield)

HPLC Rt$_{M1}$=1.37 min; ESIMS: 456 [(M+H)$^+$].

$^1$H NMR (400 MHz, DMSO-d$_6$): δ 7.40 (d, 1H), 7.28-7.07 (m, 1H), 6.74 (s, 2H), 4.84 (br s, 1H), 3.96 (br s, 2H), 3.80 (s, 2H), 3.57 (br s, 2H), 3.44-3.19 (m, 10H), 2.08 (s, 3H), 2.05-1.92 (m, 2H), 1.60 (d, 3H), 1.34 (d, 9H).

f) (1,1-Dioxo-hexahydro-1 lambda*6*-thiopyran-4-yl)-{(S)-3-[4-(6-methoxy-5-methyl-pyridin-3-yl)-5-methyl-3,4-dihydro-2H-benzo[1,4]oxazin-6-yloxy]-pyrrolidin-1-yl}-methanone A solution of (S)-3-[4-(6-methoxy-5-methyl-pyridin-3-yl)-5-methyl-3,4-dihydro-2H-benzo[1,4]oxazin-6-yloxy]-pyrrolidine-1-carboxylic acid tert-butyl ester (97 mg, 0.21 mmol) in DCM (3 ml) was treated under argon at rt with TFA (0.16 ml, 2.13 mmol) and stirred for 6 h. The reaction mixture was quenched with sat. aq. NaHCO$_3$ soln. and the organic solution was separated through a phase separating cartridge affording a yellow solution. 1,1-Dioxo-hexahydro-1lambda*6*-thiopyran-4-carboxylic acid (CAS registry 64096-87-3) (49 mg, 0.28 mmol), Et$_3$N (0.09 ml, 0.64 mmol), EDC (62 mg, 0.32 mmol), HOBT (49 mg, 0.32 mmol) were added to the yellow solution and stirred at rt for 18 h. The reaction mixture was quenched with sat. aq. NaHCO$_3$ soln. and the organic layer was separated by passing through a phase separating cartridge, then concentrated and purified by prep. RP-HPLC (column SunFire C18 OBD 5 mm 30×100 mm, Solvent A: H$_2$O (0.1% TFA) Solvent B: CH$_3$CN (0.1% TFA) afforded the title compound as white solid (76 mg, 70% yield)

HPLC Rt$_{M1}$=0.98 min; ESIMS: 516 [(M+H)$^+$].

$^1$H NMR (400 MHz, DMSO-d$_6$, 375K): δ 7.44 (br s, 1H), 7.18 (br s, 1H), 6.75 (s, 2H), 4.88 (br s, 1H), 4.02 (t, 2H), 3.86 (s, 3H), 3.81-3.33 (m, 6H), 3.24-3.06 (m, 4H), 2.83 (br s, 1H), 1.66 (s, 3H). Rotamers.

Example W

{(S)-3-[4-(6-Methanesulfonyl-5-methyl-pyridin-3-yl)-5-methyl-3,4-dihydro-2H-benzo[1,4]oxazin-6-yloxy]-pyrrolidin-1-yl}-(tetrahydro-pyran-4-yl)-methanone Le

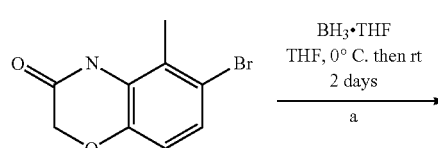

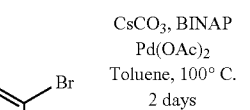

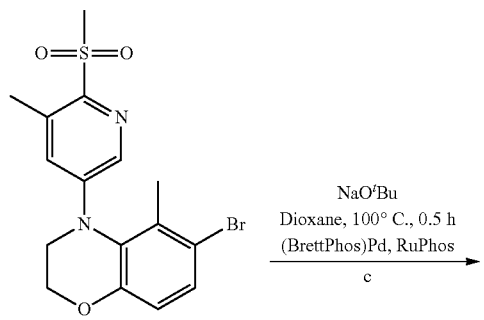

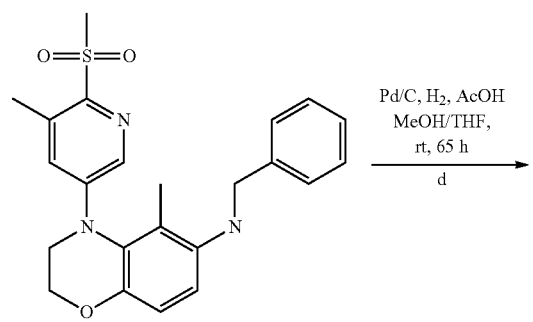

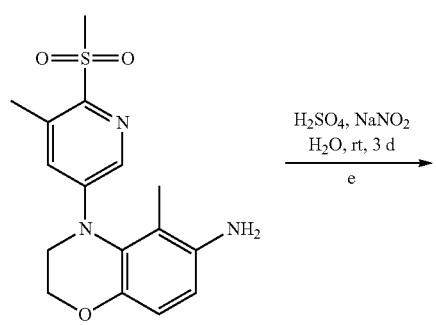

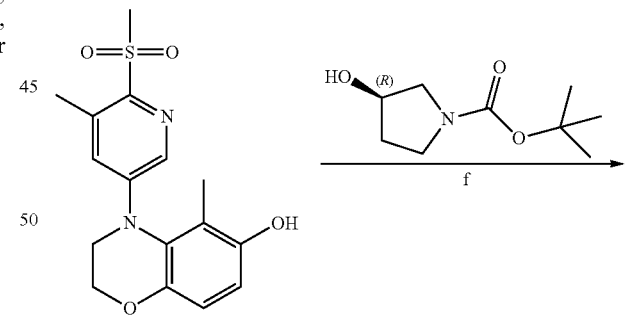

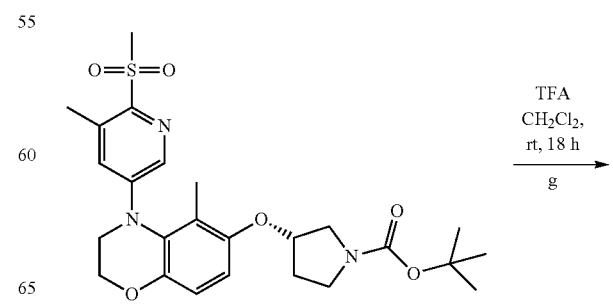

-continued

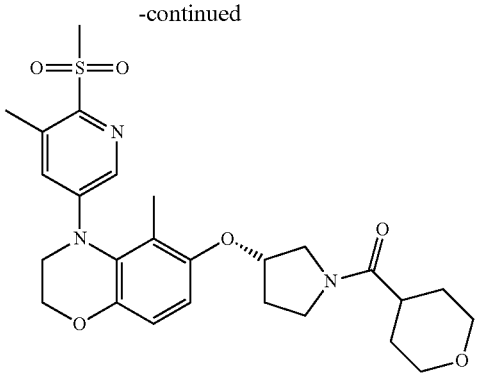

a) 6-Bromo-5-methyl-3,4-dihydro-2H-benzo[1,4]oxazine

A solution of 6-bromo-5-methyl-4H-benzo[1,4]oxazin-3-one (CAS registry 1154740-47-2) (425 mg, 1.56 mmol) in THF (9 ml) was treated under argon at 0° C. with $BH_3$*THF (1M in THF, 4.7 ml, 4.69 mmol) and stirred for 18 h at rt. $BH_3$.THF 1M (2 ml) was added and stirring was continued for another 24 h. The reaction mixture was concentrated and purified by flash chromatography on silica gel (cyclohexane/EtOAc 100:0 to 80:20) to afford the title compound as an orange solid (324 mg, 86% yield)

HPLC $Rt_{M1}$=1.04 min; ESIMS: 228, 230 [(M+H)$^+$].

$^1$H NMR (400 MHz, DMSO-d$_6$): δ 6.68 (d, 1H), 6.48 (d, 1H), 5.54 (br s, 1H), 4.04 (t, 2H), 3.36-3.26 (m, 2H), 2.11 (s, 3H).

b) 6-Bromo-4-(6-methanesulfonyl-5-methyl-pyridin-3-yl)-5-methyl-3,4-dihydro-2H-benzo[1,4]oxazine A solution of 6-bromo-5-methyl-3,4-dihydro-2H-benzo[1,4]oxazine (324 mg, 1.42 mmol), Intermediate IA1 (391 mg, 1.56 mmol), Cs$_2$CO$_3$ (1018 mg, 3.13 mmol), BINAP (CAS registry 98327-87-8) (44 mg, 0.07 mmol), Pd(OAc)$_2$ (CAS registry 3375-31-3) (32 mg, 0.14 mmol) in toluene (13 ml) was stirred at 100° C. for 18 h. Catalyst and ligand were reloaded and stirring was continued for another 24 h at 100° c. The reaction mixture was cooled to rt, diluted with EtOAc and washed with water. Concentration of the organic layer and purification by flash chromatography on silica gel (cyclohexane/EtOAc 97:03 to 40:60) afforded the title compound as an orange solid (345 mg, 58% yield).

HPLC $Rt_{M1}$=1.13 min; ESIMS: 397,399 [(M+H)$^+$].

$^1$H NMR (400 MHz, DMSO-d$_6$): δ 7.99 (br. s, 1H), 7.37 (d, 1H), 7.24 (br. s, 1H), 6.83 (d, 1H), 4.13 (t, 2H), 3.97-3.86 (m, 2H), 3.30 (s, 3H), 2.52 (s, 3H), 1.93 (s, 3H).

c) Benzyl-[4-(6-methanesulfonyl-5-methyl-pyridin-3-yl)-5-methyl-3,4-dihyd ro-2H-benzo[1,4]oxazin-6-yl]-amine A solution of 6-bromo-4-(6-methanesulfonyl-5-methyl-pyridin-3-yl)-5-methyl-3,4-dihydro-2H-benzo[1,4]oxazine (324 mg, 0.82 mmol), benzylamine (350 mg, 3.26 mmol), NaOtBu (157 mg, 1.63 mmol), RuPhos (CAS registry 787618-22-8) (30 mg, 0.06 mmol) and [BrettPhos]palladacycle (CAS registry 1148148-01-9) (52 mg, 0.06 mmol) in dioxane (16 ml) was stirred at 80° C. for 0.5 h. Filtration, concentration of the filtrate and purification by flash chromatography on silica gel (cyclohexane/EtOAc 88:12 to 35:65) afforded the title compound as a yellow oil (228 mg, 66% yield).

HPLC $Rt_{M1}$=1.13 min; ESIMS: 424 [(M+H)$^+$].

$^1$H NMR (400 MHz, DMSO-d$_6$): δ 7.94 (br s, 1H), 7.40-7.33 (m, 2H), 7.30 (t, 2H), 7.19 (t, 2H), 6.58 (d, 1H), 6.30 (d, 1H), 5.25 (t, 1H), 4.30 (d, 2H), 4.04-3.97 (m, 2H), 3.90 (d, 2H), 3.29 (s, 3H), 2.51 (br s, 3H), 1.76 (s, 3H).

d) 4-(6-Methanesulfonyl-5-methyl-pyridin-3-yl)-5-methyl-3,4-dihydro-2H-benzo[1,4]oxazin-6-ylamine A solution of benzyl-[4-(6-methanesulfonyl-5-methyl-pyridin-3-yl)-5-methyl-3,4-dihydro-2H-benzo[1,4]oxazin-6-yl]-amine (228 mg, 0.53 mmol), acetic acid (0.21 ml, 3.70 mmol), Pd/C in MeOH/THF (2.5/2.5 ml) was hydrogenated with H$_2$ at rt for 65 h. Filtration and concentration of the filtrate afforded the title compound as a green oil (200 mg, crude, including remaining AcOH).

HPLC $Rt_{M1}$=0.64 min; ESIMS: 334 [(M+H)$^+$].

$^1$H NMR (400 MHz, DMSO-d$_6$): δ 7.96 (br s, 1H), 7.17 (br s, 1H), 6.62-6.54 (d, 1H), 6.54-6.45 (d, 1H), 4.48 (br s, 2H), 4.01 (t, 2H), 3.88 (br s, 2H), 3.28 (s, 3H), 1.88 (d, 3H), 1.63 (s, 3H).

e) 4-(6-Methanesulfonyl-5-methyl-pyridin-3-yl)-5-methyl-3,4-dihydro-2H-benzo[1,4]oxazin-6-ol A solution of 4-(6-methanesulfonyl-5-methyl-pyridin-3-yl)-5-methyl-3,4-dihydro-2H-benzo[1,4]oxazin-6-ylamine (200 mg, 0.60 mmol) in water (3.5 ml) and H$_2$SO$_4$ (0.32 ml) was added dropwise to a solution of sodium nitrite (49.7 mg, 0.72 mmol) in water (10 ml) at 0° C. The mixture was stirred at rt for 3 d. The reaction mixture was filtered and the filtrate was quenched with sat. aq. NaHCO$_3$ soln. and extracted with EtOAc. The organic layer was dried over MgSO$_4$, filtered and concentrated to afford a brown oil. Purification by flash chromatography on silica gel (DCM/MeOH 88:12 to 80:20) afforded the title compound as a brown oil (50 mg, 25% yield).

HPLC $Rt_{M1}$=0.78 min; ESIMS: 335 [(M+H)$^+$].

f) (1,1-Dioxo-hexahydro-1lambda*6*-thiopyran-4-yl)-{(S)-3-[4-(6-methoxy-5-methyl-pyridin-3-yl)-5-methyl-3,4-dihydro-2H-benzo[1,4]oxazin-6-yloxy]-pyrrolidin-1-yl}-methanone A solution of triphenylphosphine (55 mg, 0.21 mmol) in THF (2.5 ml) was treated with DEAD (0.03 ml, 0.21 mmol), followed by (R)-3-hydroxy-pyrrolidine-1-carboxylic acid tert-butyl ester (CAS registry 127423-61-4) (33 mg, 0.18 mmol) and 4-(6-methanesulfonyl-5-methyl-pyridin-3-yl)-5-methyl-3,4-dihydro-2H-benzo[1,4]oxazin-6-ol (50 mg, 0.15 mmol). The resulting red/brown solution was stirred at 70° C. for 18 h. The reaction mixture was cooled down to rt, diluted with EtOAc and washed with sat. aq. NaHCO$_3$ soln. The organic layer was dried over MgSO$_4$. concentrated and purified by flash chromatography on silica gel (cyclohexane/EtOAc 90:10 to 40:60) to afford the title compound as an orange solid (44 mg, 58% yield) HPLC $Rt_{M1}$=1.16 min; ESIMS: 504 [(M+H)$^+$].

g) {(S)-3-[4-(6-Methanesulfonyl-5-methyl-pyridin-3-yl)-5-methyl-3,4-dihydro-2H-benzo[1,4]oxazin-6-yloxy]-pyrrolidin-1-yl}-(tetrahydro-pyran-4-yl)-methanone A solution of (1,1-dioxo-hexahydro-1lambda*6*-thiopyran-4-yl)-{(S)-3-[4-(6-methoxy-5-methyl-pyridin-3-yl)-5- methyl-3,4-dihydro-2H-benzo[1,4]oxazin-6-yloxy]-pyrrolidin-1-yl}-methanone (44 mg, 0.09 mmol) in DCM (4 ml) was treated under argon at rt with TFA (0.07 ml, 0.17 mmol) and stirred for 18 h. The reaction mixture was quenched with sat. aq. NaHCO$_3$ soln. and the organic solution was separated through a phase separating cartridge, concentrated and purified by flash chromatography on silica gel (DCM/MeOH 100:0 to 90:10). The obtained product was dissolved in DCM (4 ml) and Et$_3$N was added. Tetrahydro-pyran-4-carbonyl chloride (CAS registry 40191-32-0) (15 mg, 0.10 mmol) was added to the reaction mixture at 0° C. and the resulting orange solution was stirred at rt for 4 h. The reaction mixture was quenched with sat. aq. NaHCO$_3$ soln. and the organic layer was separated by elution through a phase separating cartridge, concentrated and purified by SFC (column NH$_2$ (250×30 mm (l×w), 60 A, 5 μm, Princeton, gradient of methanol in supercritical CO$_2$) to afford the title compound as a yellow oil (15 mg, 32% yield)

HPLC Rt$_{M1}$=0.88 min; ESIMS: 516 [(M+H)$^+$].

$^1$H NMR (400 MHz, DMSO-d$_6$, 375K): δ 7.98 (br s, 1H), 7.19 (br s, 1H), 6.92-6.85 (m, 1H), 6.85-6.77 (m, 1H), 4.95 (br s, 1H), 4.12 (t, 2H), 3.92 (t, 2H), 3.88 (br s, 2H), 3.61 (br s, 3H), 3.38 (td, 2H), 3.27 (s, 3H), 2.68 (d, 1H), 2.56 (s, 3H), 2.17 (br s, 2H), 1.73 (s, 3H), 1.58 (br s, 4H). Rotamers.

Example X

{(S)-3-[4-(5-Difluoromethyl-6-methoxy-pyridin-3-yl)-5-methyl-3,4-dihydro-2H-benzo[1,4]oxazin-6-yloxy]-pyrrolidin-1-yl}-(1,1-dioxo-hexahydro-1 lambda*6*-thiopyran-4-yl)-methanone

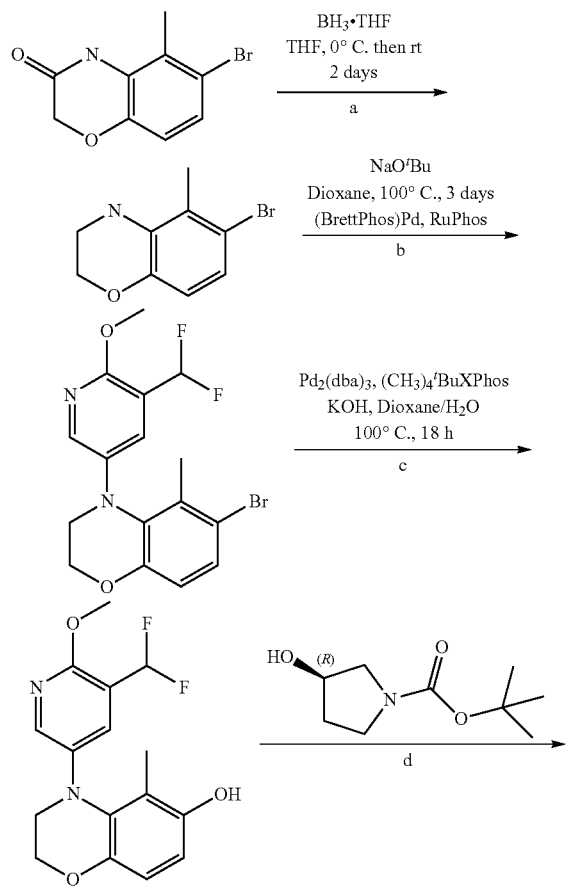

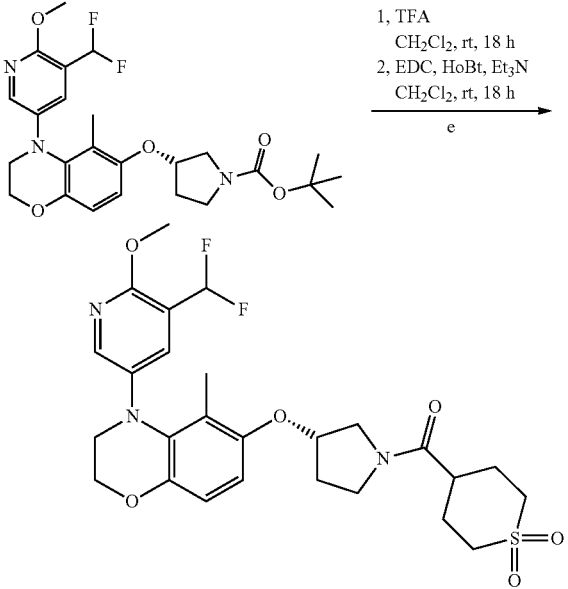

a) 6-Bromo-5-methyl-3,4-dihydro-2H-benzo[1,4]oxazine

A solution of 6-bromo-5-methyl-4H-benzo[1,4]oxazin-3-one (CAS registry 1154740-47-2) (2.8 g, 11.56 mmol) in THF (50 ml) was treated under argon with BH$_3$*THF (1M in THF, 34.7 ml, 34.70 mmol) and heated under reflux for 2 h. MeOH was added and the solution was stirred at rt for 1 h, concentrated and purified by flash chromatography on silica gel (cyclohexane/EtOAc 100:0 to 80:20) to afford the title compound as an orange solid (1.8 g, 68% yield).

HPLC Rt$_{M1}$=1.04 min; ESIMS: 228, 230 [(M+H)$^+$].

$^1$H NMR (400 MHz, DMSO-d$_6$): δ 6.68 (d, 1H), 6.48 (d, 1H), 5.54 (br s, 1H), 4.04 (t, 2H), 3.36-3.26 (m, 2H), 2.11 (s, 3H).

b) 6-Bromo-4-(5-difluoromethyl-6-methoxy-pyridin-3-yl)-5-methyl-3,4-dihydro-2H-benzo[1,4]oxazine A solution of 6-bromo-5-methyl-3,4-dihydro-2H-benzo[1,4]oxazine (500 mg, 2.19 mmol), Intermediate IA6 (574 mg, 2.41 mmol), NaOtBu (421 mg, 4.38 mmol), BrettPhos (CAS registry 1070663-78-3) (59 mg, 0.11 mmol) and [BrettPhos]palladacycle (CAS registry 1148148-01-9) (88 mg, 0.11 mmol) in dioxane (11 ml) was stirred at 100° C. for 18 h. Catalyst and ligand were reloaded and stirring was continued at 100° C. for 48 h. The reaction mixture was cooled down to rt, diluted with EtOAc and washed with sat. aq. NaHCO$_3$ soln. The organic layer was dried over MgSO$_4$, concentrated to afford a brown oil. Purification by flash chromatography on silica gel (cyclohexane/EtOAc 100:0 to 80:20) afforded the title compound as a brown oil (150 mg, 18% yield).

HPLC Rt$_{M1}$=1.34 min; ESIMS: 385, 387 [(M+H)$^+$].

c) 4-(5-Difluoromethyl-6-methoxy-pyridin-3-yl)-5-methyl-3,4-dihydro-2H-benzo[1,4]oxazin-6-ol A mixture of 6-bromo-4-(5-difluoromethyl-6-methoxy-pyridin-3-yl)-5-methyl-3,4-dihydro-2H-benzo[1,4]oxazine (150 mg, 0.39 mmol), KOH (65 mg, 1.17 mmol) in water (0.33 ml), tetramethyl-t-butyl-XPhos (CAS registry 857356-94-6) (18.72 mg, 0.04 mmol) and Pd$_2$(dba)$_3$ (17.83 mg, 0.02 mmol) in dioxane (2 ml) was degassed with nitrogen and heated at 100° C. for 18 h. Filtration, concentration and purification by flash chromatography on silica gel (cyclohexane/EtOAc 100:0 to 70:30) afforded the title compound as an orange oil (65 mg, 52% yield).

HPLC Rt$_{M1}$=1.01 min; ESIMS: 323 [(M+H)$^+$].

$^1$H NMR (400 MHz, DMSO-d$_6$): δ 8.83 (s, 1H), 7.89 (d, 1H), 7.36 (d, 1H), 7.00 (t, 1H), 6.61 (d, 1H), 6.55 (d, 1H), 3.93 (t, 2H), 3.88 (s, 3H), 3.65 (t, 2H), 1.60 (s, 3H).

d) (S)-3-[4-(5-Difluoromethyl-6-methoxy-pyridin-3-yl)-5-methyl-3,4-dihydro-2H-benzo[1,4]oxazin-6-yloxy]-pyrrolidine-1-carboxylic acid tert-butyl ester A solution of triphenylphosphine (74 mg, 0.28 mmol) in THF (2 ml) was treated with DEAD (0.04 ml, 0.28 mmol) followed by (R)-3-hydroxy-pyrrolidine-1-carboxylic acid tert-butyl ester (CAS registry 127423-61-4) (45 mg, 0.24 mmol) and 4-(5-difluoromethyl-6-methoxy-pyridin-3-yl)-5-methyl-3,4-dihydro-2H-benzo[1,4]oxazin-6-ol (65 mg, 0.20 mmol). The resulting red/brown solution was stirred at 70° C. for 18 h, cooled down to rt, diluted with EtOAc and washed with sat. aq. NaHCO$_3$ soln. The organic layer was dried over MgSO$_4$, concentrated and purified by flash chromatography on silica gel (cyclohexane/EtOAc 100:0 to 70:30) to afford the title compound as a yellow solid (51 mg, 42% yield).

HPLC Rt$_{M1}$=1.36 min; ESIMS: 492 [(M+H)$^+$].

$^1$H NMR (400 MHz, DMSO-d$_6$): δ 7.92-7.75 (m, 1H), 7.46-7.33 (m, 1H), 7.19-6.84 (t, 1H), 6.77 (s, 2H), 4.86 (br s, 1H), 3.98 (br s, 2H), 3.88 (s, 3H), 3.73-3.55 (m, 2H), 3.46-3.33 (m, 2H), 2.12-1.95 (m, 2H), 1.65-1.55 (m, 3H), 1.34 (br s, 9H). Rotamers.

e) {(S)-3-[4-(5-Difluoromethyl-6-methoxy-pyridin-3-yl)-5-methyl-3,4-dihydro-2H-benzo[1,4]oxazin-6-yloxy]-pyrrolidin-1-yl}-(1,1-dioxo-hexahydro-1lambda*6*-thiopyran-4-yl)-methanone A solution of (S)-3-[4-(5-difluoromethyl-6-methoxy-pyridin-3-yl)-5-methyl-3,4-dihydro-2H-benzo[1,4]oxazin-6-yloxy]-pyrrolidine-1-carboxylic acid tert-butyl ester (51 mg, 0.10 mmol) in DCM (3 ml) was treated under argon at rt with TFA (0.08 ml, 1.10 mmol) and stirred for 18 h. The reaction mixture was quenched with sat. aq. NaHCO$_3$ soln. and the organic solution was separated through a phase separating affording a yellow solution. 1,1-Dioxo-hexahydro-1lambda*6*-thiopyran-4-carboxylic acid (CAS registry 64096-87-3) (25 mg, 0.14 mmol), Et$_3$N (0.05 ml, 0.33 mmol), EDC (31 mg, 0.16 mmol) and HOBT (25 mg, 0.16 mmol) were added and the reaction mixture was stirred at rt for 3 h. The reaction mixture was quenched with sat. aq. NaHCO$_3$ soln. The organic layer was separated by elution through a phase separating cartridge, the crude product was purified over SFC (column Reprosil NH$_2$ (250×30 mm (lxw), 60 A, 5 μm, Princeton, gradient of methanol in supercritical CO$_2$) to afford the title compound as a yellow oil (19 mg, 30% yield)

HPLC Rt$_{M1}$=1.00 min; ESIMS: 552 [(M+H)$^+$].

$^1$H NMR (400 MHz, DMSO-d$_6$, 375K): δ 7.85 (br s, 1H), 7.43 (br s, 1H), 6.96 (t, 1H), 6.80 (s, 1H), 5.11-4.71 (m, 1H), 4.04 (t, 2H), 3.94 (s, 3H), 3.70 (d, 2H), 3.63 (br s, 2H), 3.52 (br s, 2H), 3.23-3.04 (m, 4H), 2.92-2.73 (m, 1H), 2.16 (br s, 2H), 2.06 (br s, 4H), 1.67 (s, 3H), Rotamers.

Example Y

2-Methoxy-5-{6-[(S)-1-(tetrahydro-pyran-4-carbonyl)-pyrrolidin-3-ylamino]-2,3-dihydro-benzo[1,4]oxazin-4-yl}-nicotinonitrile

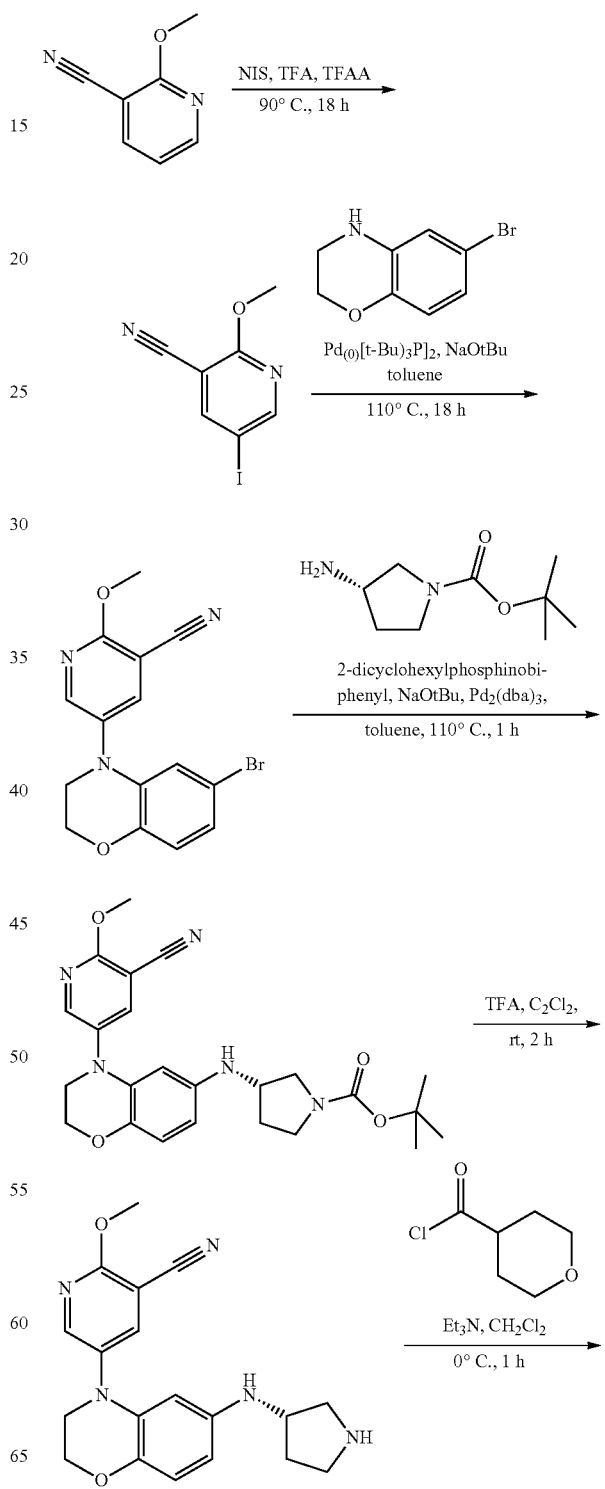

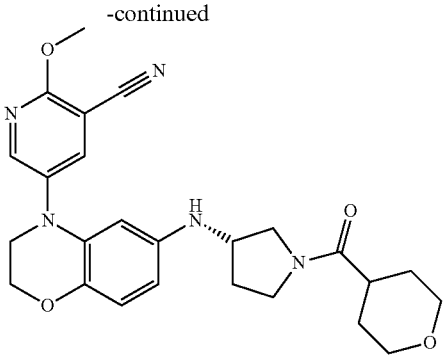

a) 5-Iodo-2-methoxy-nicotinonitrile

A mixture of 2-methoxy-nicotinonitrile (CAS registry 7254-34-4) (10 g, 74.6 mmol) and N-iodosuccinimide (CAS registry 516-12-1) (25.2 g, 112 mmol) was treated with trifluoroacetic acid (CAS registry 76-05-1) (68.9 ml, 895 mmol) and trifluoroacetic anhydride (CAS registry 407-25-0) (31.6 ml, 224 mmol) and the reaction mixture was heated at 90° C. for 18 h then cooled to rt and poured onto ice. The mixture was slowly basified using 30% aq. NaOH soln., diluted with water and extracted with EtOAc. The organic layer was successively washed with 20% aq. sodium thiosulfate soln., and sat. aq. NaHCO$_3$ soln., dried over Na$_2$SO$_4$, filtered and concentrated. The title compound was obtained after flash chromatography on silica gel (cyclohexane/EtOAc, 100:0 to 20:80) as a solid (12.2 g, 63% yield)

UPLC Rt$_{M14}$=1.30 min; ESIMS: 261 [(M+H)$^+$].

$^1$H NMR (400 MHz, CDCl$_3$): δ 8.54 (d, 1H), 8.11 (d, 1H), 4.06 (s, 3H).

b) 5-(6-Bromo-2,3-dihydro-benzo[1,4]oxazin-4-yl)-2-methoxy-nicotinonitrile

A mixture of 6-bromo-3,4-dihydro-2H-benzo[1,4]oxazine (CAS registry 105655-01-4) (5.0 g, 23.36 mmol), 5-iodo-2-methoxy-nicotinonitrile (12.2 g, 46.7 mmol) and NaOtBu (2.69 g, 28.0 mmol) in toluene (50 ml) was degassed with argon for 10 min, then bis(tri-tert-butylphosphine)-palladium(0) (0.36 g, 0.70 mmol) was added. The reaction mixture stirred at 110° C. for 18 h under argon. After cooling to rt, the reaction mixture was filtered through celite, rinsed with EtOAc and the filtrates were washed with sat. aq. NaHCO$_3$ soln. The organic layer was dried over Na$_2$SO$_4$, filtered, concentrated and purified by flash chromatography on silica gel (cyclohexane/EtOAc, 100:0 to 50:50) to yield the title compound (4.2 g, 52% yield).

UPLC Rt$_{M14}$=1.55 min; ESIMS: 348 [(M+H)$^+$].

$^1$H NMR (400 MHz, CDCl$_3$): δ 8.31 (d, 1H), 7.80 (d, 1H), 6.89 (dd, 1H), 6.78 (d, 1H), 6.67 (d, 1H), 4.30-4.35 (m, 2H), 4.10 (s, 3H), 3.61-3.66 (m, 2H).

c) (S)-3-[4-(5-Cyano-6-methoxy-pyridin-3-yl)-3,4-dihydro-2H-benzo[1,4]oxazin-6-ylamino]-pyrrolidine-1-carboxylic acid tert-butyl ester A mixture of 5-(6-bromo-2,3-dihydro-benzo[1,4]oxazin-4-yl)-2-methoxy-nicotinonitrile (300 mg, 0.87 mmol), (S)-3-amino-pyrrolidine-1-carboxylic acid tert-butyl ester (CAS registry 147081-44-5) (0.26 ml, 1.47 mmol), 2-(dicyclohexylphosphino)biphenyl (CAS registry 247940-06-3) (18.2 mg, 0.05 mmol) and NaOtBu (100 mg, 1.04 mmol) in toluene (10 ml) was degassed with argon for 10 min, then Pd$_2$(dba)$_3$ (23.8 mg, 0.03 mmol) was added. The reaction mixture was stirred at 110° C. for 1 h under argon. After cooling to rt, the reaction mixture was filtered through celite, rinsed with EtOAc and the filtrates were concentrated. The title compound was obtained after flash chromatography on silica gel (cyclohexane/EtOAc, 100:0 to 70:30) as a yellow foam (150 mg, 37% yield).

UPLC Rt$_{M11}$=2.73 min; ESIMS: 452 [(M+H)$^+$].

$^1$H NMR (400 MHz, CD$_3$OD): δ 8.36 (d, 1H), 8.04 (d, 1H), 6.68 (s, 1H), 6.19 (dd, 1H), 6.03 (s, 1H), 4.19-4.24 (m, 2H), 4.06 (s, 3H), 3.81-3.89 (m, 1H), 3.62-3.68 (m, 2H), 3.48-3.56 (m, 1H), 3.35-3.48 (m, 2H), 3.08-3.18 (m, 1H), 2.05-2.18 (m, 1H), 1.75-1.87 (m, 1H), 1.46 (s, 9H).

d) 2-Methoxy-5-[6-((S)-pyrrolidin-3-ylamino)-2,3-dihydro-benzo[1,4]oxazin-4-yl]-nicotinonitrile A solution of (S)-3-[4-(5-cyano-6-methoxy-pyridin-3-yl)-3,4-dihydro-2H-benzo[1,4]oxazin-6-ylamino]-pyrrolidine-1-carboxylic acid tert-butyl ester (144 mg, 0.32 mmol) in CH$_2$Cl$_2$ (4 ml) was treated with TFA (0.49 ml, 6.38 mmol). The reaction mixture was stirred at rt for 2 h, quenched with sat. aq. NaHCO$_3$ soln. and extracted with DCM. The organic layer was dried over Na$_2$SO$_4$, filtered and concentrated under reduced pressure to afford the title product as a yellow foam (120 mg, 100% yield).

UPLC Rt$_{M11}$=2.06 min; ESIMS: 352 [(M+H)$^+$].

$^1$H NMR (400 MHz, CD$_3$OD): δ 8.36 (d, 1H), 8.04 (d, 1H), 6.69 (d, 1H), 6.17 (dd, 1H), 6.00 (d, 1H), 4.19-4.26 (m, 2H), 4.06 (s, 3H), 3.80-3.90 (m, 1H), 3.62-3.69 (m, 2H), 3.10-3.20 (m, 2H), 2.98-3.09 (m, 1H), 2.82-2.90 (m, 1H), 2.06-2.18 (m, 1H), 1.70-1.81 (m, 1H).

e) 2-Methoxy-5-{6-[(S)-1-(tetrahydro-pyran-4-carbonyl)-pyrrolidin-3-ylamino]-2,3-dihydro-benzo[1,4]oxazin-4-yl}-nicotinonitrile At 0° C., a solution of 2-methoxy-5-[6-((S)-pyrrolidin-3-ylamino)-2,3-dihydro-benzo[1,4]oxazin-4-yl]-nicotinonitrile (27 mg, 0.08 mmol) in CH$_2$Cl$_2$ (1 ml) was treated with Et$_3$N (0.02 ml, 0.12 mmol) and tetrahydro-pyran-4-carbonyl chloride (CAS registry 40191-32-0) (11 μl, 0.09 mmol). The reaction mixture was stirred at 0° C. for 1 h, then quenched with sat. aq. NaHCO$_3$ soln. and extracted with DCM. The organic layer was dried over Na$_2$SO$_4$, filtered and concentrated and the title compound was obtained after prep. RP-HPLC (column Sunfire PrepC18 OBD 30×100 mm, 5 μm; solvent A: H$_2$O+0.1 Vol.-% TFA; solvent B: CH$_3$CN+0.1 Vol.-% TFA, gradient 5-60% B in 20 min) and filtration over Agilent PL-HCO$_3$ MP SPE cartridge as a yellow solid (9 mg, 25% yield).

UPLC Rt$_{M2}$=1.19 min; ESIMS: 464 [(M+H)$^+$].

$^1$H NMR (400 MHz, CD$_3$OD): δ 8.36 (d, 1H), 8.05 (m, 1H), 6.69 (dd, 1H), 6.15-6.23 (m, 1H), 5.97-6.07 (m, 1H), 4.15-4.29 (m, 2H), 4.06 (s, 3H), 3.82-4.03 (m, 3H), 3.35-3.80 (m, 8H), 2.65-2.84 (m, 1H), 2.03-2.28 (m, 1H), 1.49-2.03 (m, 5H).

Coupling Conditions

A) Buchwald Aminations or Hydroxylations

| Condition # | Pd source | Ligand | Base | Solvents used | Typical temperature | Typical reaction time |
|---|---|---|---|---|---|---|
| CA1 | $Pd_2(dba)_3$ | Rac-BINAP | $Cs_2CO_3$ | toluene | 60-100° C. | 16 h |
| CA2 | $Pd_2(dba)_3$ | XPhos | $NaO^tBu$ | dioxane | 100° C. | 1-18 h |
| CA3 | $Pd_2(dba)_3$ | XPhos | $Cs_2CO_3$ | toluene | 100° C. | |
| CA4 | $Pd_2(dba)_3$ | XPhos | $Cs_2CO_3$ | dioxane | 100° C. | 1-18 h |
| CA5 | $Pd_2(dba)_3$ | tetramethyl-t-butyl-XPhos | KOH | dioxane/$H_2O$ | 100° C. | 18-72 h |
| CA6 | $Pd_2(dba)_3$ | XPhos | $NaO^tBu$ | toluene | 80-110° C. | 20 min-18 h |
| CA7 | $Pd(P(tBu_3))_2$ | | $NaO^tBu$ | toluene | 140° C. (mw) | 30 min |
| CA8 | $Pd(P(tBu_3))_2$ | | $NaO^tBu$ | toluene | 120° C. | 18 h |
| CA9 | $Pd_2(dba)_3$ | XPhos | $NaO^tBu$ | toluene | 125° C. (mw) | 25 min |
| CA10 | $Pd(OAc)_2$ | Rac-BINAP | $Cs_2CO_3$ | toluene | 60-100° C. | 21 h |
| CA11 | Pd[Ruphos] | RuPhos | $NaO^tBu$ | dioxane | 100° C. | 18 h |
| CA12 | $Pd(P(tBu_3))_2$ | | $K_3PO_4$ | toluene | 120° C. | 18 h |
| CA13 | $Pd_2(dba)_3$ | XPhos | $K_3PO_4$ | toluene | 100° C. | 12 h |
| CA14 | $Pd_2(dba)_3$ | XPhos | $K_3PO_4$ | toluene | 110-120° C. | 12 h |
| CA15 | $Pd(P(tBu_3))_2$ | | $NaO^tBu$ | THF | 110° C. | 18 h |
| CA16 | $Pd_2(dba)_3$ | XPhos | $NaO^tBu$ | THF | 110° C. | 1 h-18 h |

B) Amide Bond Formation Conditions

| Condition# | Coupling reagents | Solvents used | Typical temperature | Typical reaction time |
|---|---|---|---|---|
| CB1 | HBTU | DMF or DMA | rt | 1 h-18 h |
| CB2 | HOBT, EDC | DMF | rt | 1 h-18 h |
| CB3 | HATU | $CH_2Cl_2$ | 0° C. to rt | 30 min |
| CB4 | HOBT, EDC | $CH_2Cl_2$ | rt | 18 h |
| CB5 | COMU, DIPEA | DMF | rt | 12 h |
| CB6 | none | $CH_2Cl_2$ | rt | 1 h-18 h |
| CB7 | HBTU | $CH_2Cl_2$ | rt | 30 min |

C) Side Chain Introduction Conditions

CC1) Using Mesylate

At rt, a dry solution of pyridin-2-ol intermediate (1 eq.) and mesylate intermediate (1.1-2 eq.) in DMF (0.17 M) was treated with NaH in mineral oil (2-3 eq.) and the reaction mixture was stirred at 20-80° C. for 4 to 72 h.

CC2) Using Mesylate

At rt, a dry solution aryl-6-ol intermediate (1 eq.) and mesylate intermediate (1.1-2 eq.) in DMF (0.17M) was treated with NaH in mineral oil (2-3 eq.) and the reaction mixture was stirred at 50-80° C. for 4 to 72 h.

CC3) Using Mesylate

At rt, a dry solution of aryl-6-ol intermediate (1 eq.) and mesylate intermediate (2.5 eq.) in DMF (0.06M) was treated with $K_2CO_3$ (4 eq.) and the reaction mixture was stirred at 85° C. to 100° C. for 4 to 50 h.

CC4) Using Mitsunobu

At rt, DEAD (1.4 eq.), (R)-3-Hydroxy-pyrrolidine-1-carboxylic acid tert-butyl ester (1.5 eq.) and aryl-6-ol intermediate (1 eq.) were added to a solution of triphenylphosphine (1.4 eq.) in THF (0.30M). The red/brown solution was stirred at 70° C. for 18 h.

D) Conditions for Chiral Separation Chromatography

| Method# | Column | Eluent | UV Detection |
|---|---|---|---|
| CD1 | Chiralpak IC 250 × 30 mm, 5 μm | n-Heptane/DMME/IPA/DEA 20:50:30:0.05 | 230 nm |
| CD2 | Chiralpak IC 250 × 30 mm, 5 μm | ACN 100% | 230 nm |
| CD3 | Chiralcel ODH 250 × 30 mm, 5 μm | EtOH/MeOH 60:40 | 220 nm |
| CD4 | Chiralpak IC 250 × 30 mm, 5 μm | DMME/IPA/MeOH/DEA 70:25:5:0.05, | 230 nm |
| CD5 | Chiralpak IC 250 × 30 mm, 5 μm | ACN 100% | 220 nm |
| CD6 | Chiralpak IC 250 × 30 mm, 5 μm | MeOH 100% | 220 nm |
| CD7 | Chiralpak IC 250 × 46 mm, 5 μm | n-Heptane/DMME/EtOH/DEA 40:50:10:0.05 | 240 nm |
| CD8 | Chiralcel OD-H, 4.6 × 250 mm | $CO_2$/IPA 70:30 (isocratic | 215 nm |
| CD9 | Chiralpak AD-H, 5 μm | Heptane/EtOH 60:40 | |
| CD10 | Chiralpak IC 250 × 46 mm, 5 μm | DMME/IPA/MeOH/DEA 70:25:5:0.05, | 230 nm |
| CD11 | Chiralcel ODH 250 × 20 mm, 5 μm | EtOH/MeOH 60:40 | 220 nm |
| CD12 | Chiralpak IC 765 × 37.5 cm, 20 μm | EtOH/MeOH 50:50 | 210 nm |

Preparation of Intermediates
IA) Aromatic Bromides

| Intermediate # | IA) Aromatic Bromides Structure | Autonom name | Comment on synthesis |
|---|---|---|---|
| IA1 | 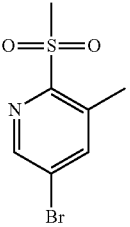 | 5-Bromo-2-methanesulfonyl-3-methyl-pyridine | 1 step from CAS 1289270-74-1 |
| IA2 | 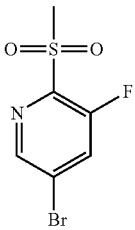 | 5-Bromo-3-fluoro-2-methanesulfonyl-pyridine | 1 step from CAS 1289007-85-7 |
| IA3 | 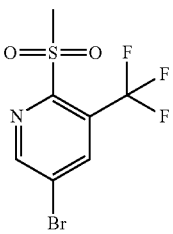 | 5-Bromo-2-methanesulfonyl-3-trifluoromethyl-pyridine | 1 step from CAS 211122-42-8 |
| IA4 | 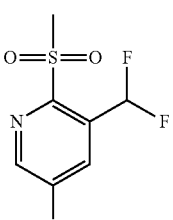 | 5-Bromo-3-difluoromethyl-2-methanesulfonyl-pyridine | 2 steps from CAS 852181-11-4 |
| IA5 | 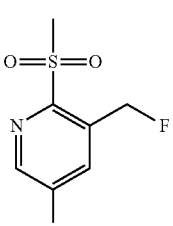 | 5-Bromo-3-fluoromethyl-2-methanesulfonyl-pyridine | 2 steps from CAS 742100-75-0 |
| IA6 | 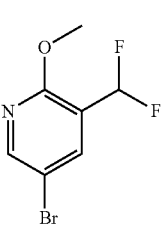 | 5-Bromo-3-difluoromethyl-2-methoxy-pyridine | CAS 1254123-51-7 |

| Intermediate # | IA) Aromatic Bromides Structure | Autonom name | Comment on synthesis |
|---|---|---|---|
| IA7 | 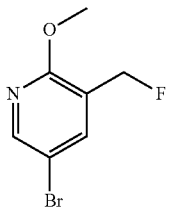 | 5-Bromo-3-fluoromethyl-2-methoxy-pyridine | 1 step from CAS 351410-47-4 |
| IA8 | 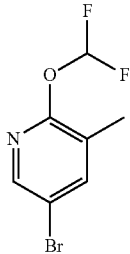 | 5-Bromo-2-difluoromethoxy-3-methyl-pyridine | CAS 1214337-94-6 |
| IA9 | 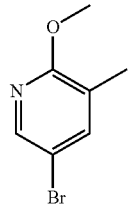 | 5-Bromo-2-methoxy-3-methyl-pyridine | CAS 760207-87-2 |
| IA10 | 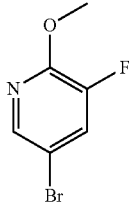 | 5-Bromo-3-fluoro-2-methoxy-pyridine | CAS 124432-70-8 |
| IA11 | 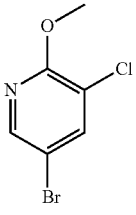 | 5-Bromo-3-chloro-2-methoxy-pyridine | CAS 848366-28-9 |
| IA12 | 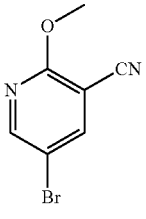 | 5-Bromo-2-methoxy-nicotinonitrile | CAS 941294-54-8 |

| Intermediate # | IA) Aromatic Bromides Structure | Autonom name | Comment on synthesis |
|---|---|---|---|
| IA13 | 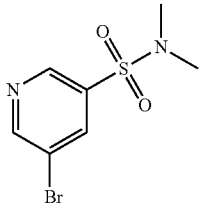 | 5-Bromo-pyridine-3-sulfonic acid dimethylamide | CAS 896160-99-9 |
| IA14 | 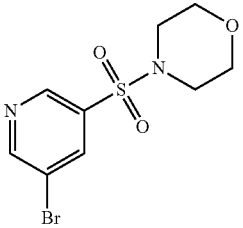 [SMILES: O=S(=O)(c1cncc(Br)c1)N1CCOCC1] | 4-(5-Bromo-pyridine-3-sulfonyl)-morpholine | CAS 889676-35-1 |
| IA15 | 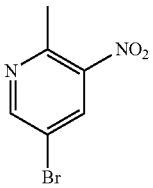 | 5-Bromo-2-methyl-3-nitro-pyridine | CAS 911434-05-4 |
| IA16 | 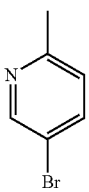 | 5-Bromo-2-methyl-pyridine | CAS 3430-13-5 |
| IA17 | 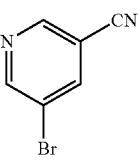 | 5-Bromo-nicotinonitrile | CAS 35590-37-5 |
| IA18 | 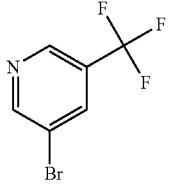 [SMILES: FC(F)(F)c1cncc(Br)c1] | 5-bromo-trifluoromethylpyridine | CAS 436799-33-6 |
| IA19 | 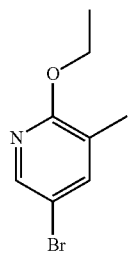 | 5-Bromo-2-ethoxy-3-methyl-pyridine | CAS 610279-03-3 |

-continued

| Intermediate # | IA) Aromatic Bromides Structure | Autonom name | Comment on synthesis |
|---|---|---|---|
| IA20 | | 5-bromo-2-methoxypyridine | CAS 13472-85-0 |
| IA21 | | 5-bromo-2-methoxy-3-trifluoromethylpyridine | CAS 1214377-42-0 |
| IA22 | | 5-Bromo-2-methoxy-nicotinic acid methyl ester | CAS 122433-41-4 |
| IA23 | | 2-amino-5-bromo-3-trifluoromethylpyridine | CAS 79456-34-1 |
| IA24 | | 1-(5-Bromo-2-methoxy-pyridine-3-sulfonyl)-4-methyl-piperazine | |
| IA25 | | 5-Bromo-2-methoxymethyl-pyridine | CAS 1000787-43-8 |

| Intermediate # | IA) Aromatic Bromides Structure | Autonom name | Comment on synthesis |
|---|---|---|---|
| IA26 | 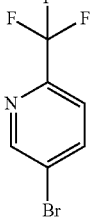 | 5-bromo-2-trifluromethylpyridine | CAS 436799-32-5 |
| IA27 | 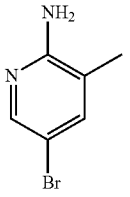 | 5-Bromo-3-methyl-pyridin-2-ylamine | CAS 3430-21-5 |
| IA28 | 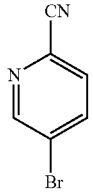 | 5-Bromo-pyridine-2-carbonitrile | CAS 97483-77-7 |
| IA29 | 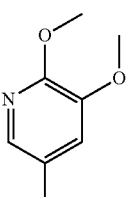 | 5-Bromo-2,3-dimethoxy-pyridine | CAS 52605-98-8 |
| IA30 | 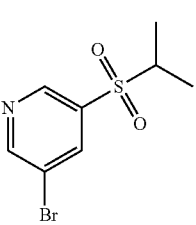 | 3-Bromo-5-(propane-2-sulfonyl)-pyridine | |
| IA31 | 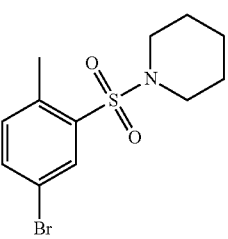 [SMILES: Cc1ccc(Br)cc1S(=O)(=O)N1CCCCC1] | 1-(5-Bromo-2-methyl-benzenesulfonyl)-piperidine | CAS 364736-61-8 |
| IA32 | 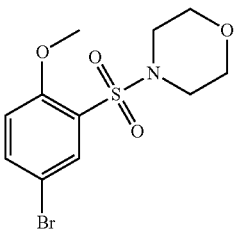 [SMILES: COc1ccc(Br)cc1S(=O)(=O)N1CCOCC1] | 4-(5-Bromo-2-methoxy-benzenesulfonyl)-morpholine | CAS 325809-68-5 |

-continued

| Intermediate # | IA) Aromatic Bromides Structure | Autonom name | Comment on synthesis |
|---|---|---|---|
| IA33 | 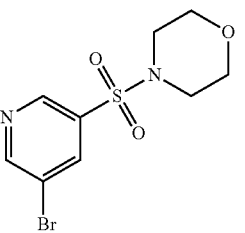 [SMILES: O=S(=O)(c1cncc(Br)c1)N1CCOCC1] | 4-(5-Bromo-pyridine-3-sulfonyl)-morpholine | CAS 889676-35-1 |
| IA34 | 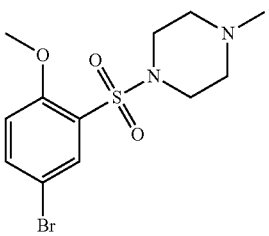 [SMILES: COc1ccc(Br)cc1S(=O)(=O)N1CCN(C)CC1] | 1-(5-Bromo-2-methoxy-benzenesulfonyl)-4-methyl-piperazine | CAS 325809-71-0 |
| IA35 | 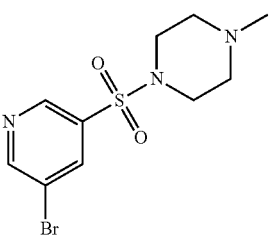 [SMILES: CN1CCN(S(=O)(=O)c2cncc(Br)c2)CC1] | 1-(5-Bromo-pyridine-3-sulfonyl)-4-methyl-piperazine | CAS 1007212-08-9 |
| IA36 | 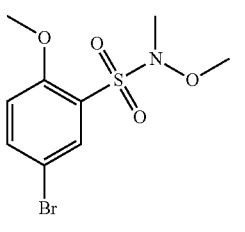 [SMILES: COc1ccc(Br)cc1S(=O)(=O)N(C)OC] | 5-Bromo-2,N-dimethoxy-N-methyl-benzenesulfonamide | CAS 1247891-51-5 |
| IA37 | 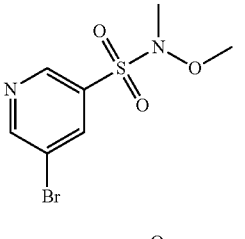 | 5-Bromo-pyridine-3-sulfonic acid methoxy-methyl-amide | CAS 1248282-54-3 |
| IA38 | 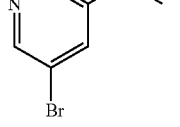 | 3-Bromo-5-methoxy-pyridine | CAS 50720-12-2 |
| IA39 |  | 3-Bromo-5-chloro-pyridine | CAS 73583-39-8 |

-continued

| Intermediate # | IA) Aromatic Bromides Structure | Autonom name | Comment on synthesis |
|---|---|---|---|
| IA40 | 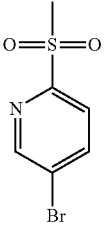 | 5-Bromo-2-methanesulfonyl-pyridine | CAS 98626-95-0 |
| IA41 | 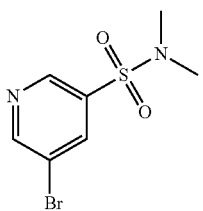 | 5-Bromo-pyridine-3-sulfonic acid dimethylamide | CAS 896160-99-9 |
| IA42 | 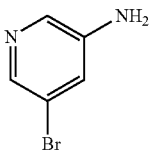 | 5-Bromo-pyridin-3-ylamine | CAS 13535-01-8 |
| IA43 | 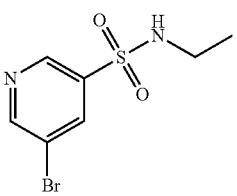 | 5-Bromo-pyridine-3-sulfonic acid ethylamide | CAS 1065074-78-3 |
| IA44 | 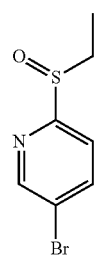 | 5-Bromo-2-ethanesulfinyl-pyridine | |
| IA45 | 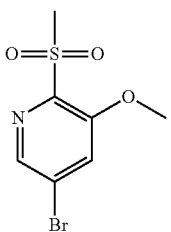 | 5-Bromo-2-methanesulfonyl-3-methoxy-pyridine | |
| IA46 | 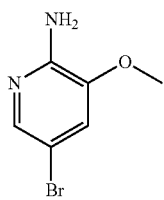 | 5-Bromo-3-methoxy-pyridin-2-ylamine | CAS 42409-58-5 |

| Intermediate # | IA) Aromatic Bromides Structure | Autonom name | Comment on synthesis |
|---|---|---|---|
| IA47 |  | N-(5-Bromo-2-methoxy-pyridin-3-yl)-methanesulfonamide | CAS 1083327-58-5 |
| IA48 | 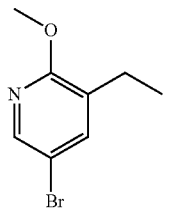 | 5-Bromo-3-ethyl-2-methoxy-pyridine | CAS 1256788-92-7 |
| IA49 | 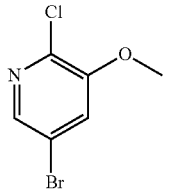 | 5-Bromo-2-chloro-3-methoxy-pyridine | CAS 286947-03-3 |
| IA50 | 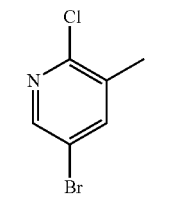 | 5-Bromo-2-chloro-3-methyl-pyridine | CAS 29241-60-9 |
| IA51 | 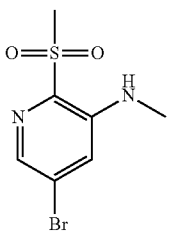 | (5-Bromo-2-methanesulfonyl-pyridin-3-yl)-methyl-amine | |
| IA52 | 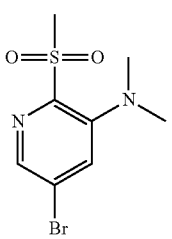 | (5-Bromo-2-methanesulfonyl-pyridin-3-yl)-dimethyl-amine | |

-continued

| Intermediate # | IA) Aromatic Bromides Structure | Autonom name | Comment on synthesis |
|---|---|---|---|
| IA53 | 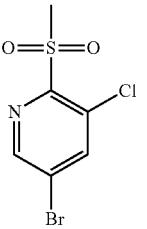 | 5-Bromo-3-chloro-2-methanesulfonyl-pyridine | 1335052-54-4 |
| IA54 | 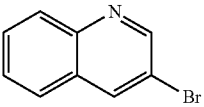 [SMILES: Brc1cnc2ccccc2c1] | 3-Bromo-quinoline | CAS 5332-24-1 |
| IA55 | 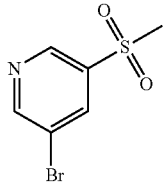 | 3-Bromo-5-methanesulfonyl-pyridine | CAS 445491-71-4 |
| IA56 | 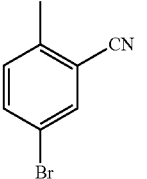 | 5-Bromo-2-methyl-benzonitrile | CAS 156001-51-3 |
| IA57 | 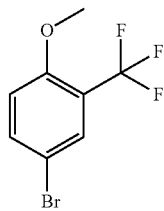 | 4-Bromo-1-methoxy-2-trifluoromethyl-benzene | CAS 1514-11-0 |
| IA58 | 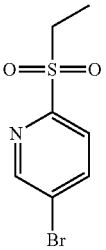 | 5-Bromo-2-ethanesulfonyl-pyridine | CAS 223556-06-7 |
| IA59 | 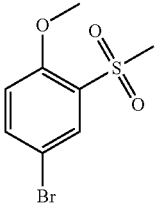 | 4-Bromo-2-methanesulfonyl-1-methoxy-benzene | CAS 90531-99-0 |

-continued

| Intermediate # | IA) Aromatic Bromides Structure | Autonom name | Comment on synthesis |
|---|---|---|---|
| IA60 | 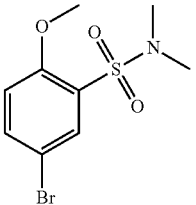 | 5-Bromo-2-methoxy-N,N-dimethyl-benzenesulfonamide | CAS 871269-16-8 |
| IA61 | 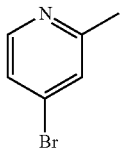 | 4-Bromo-2-methyl-pyridine | CAS 22282-99-1 |
| IA62 | 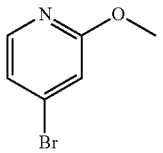 | 4-Bromo-2-methoxy-pyridine | CAS 100367-39-3 |
| IA63 | 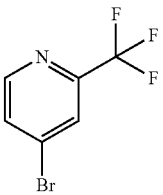 [SMILES: FC(F)(F)c1cc(Br)ccn1] | 4-Bromo-2-trifluoromethyl-pyridine | CAS 887583-90-6 |
| IA64 | 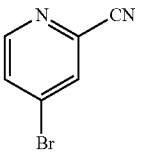 | 4-Bromo-pyridine-2-carbonitrile | CAS 62150-45-2 |
| IA65 | 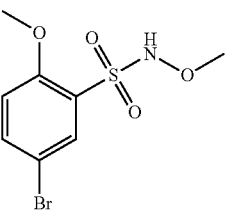 | 5-Bromo-2,N-dimethoxy-benzenesulfonamide | |
| IA66 | 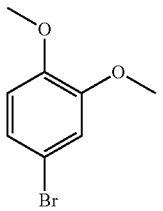 | 4-Bromo-1,2-dimethoxy-benzene | CAS 2859-78-1 |
| IA67 | 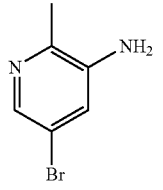 | 5-Bromo-2-methyl-pyridin-3-ylamine | CAS 914358-73-9 |

-continued

| Intermediate # | IA) Aromatic Bromides Structure | Autonom name | Comment on synthesis |
|---|---|---|---|
| IA68 | | (5-Bromo-2-methyl-pyridin-3-yl)-dimethyl-amine | CAS 1280592-37-1 |
| IA69 | | 2-(Benzyloxy)-5-bromo-3-methylpyridine | CAS 1289270-73-0 |
| IA70 | | 5-Bromo-3-(dimethoxymethyl)-2-methoxypyridine | CAS 351410-59-8 |

Intermediate IA1

5-bromo-2-methanesulfonyl-3-methyl-pyridine

A solution of 5-bromo-2-methylsulfanyl-3-methyl-pyridine (9.04 g, 41.4 mmol) in DCM (83 ml) was treated at 0° C. with mCPBA (21.46 g, 124 mmol). After stirring for 18 h at rt, the reaction mixture was added to 2N aq. NaOH soln. and was extracted with DCM. The organic layer was dried over $Na_2SO_4$, concentrated and the title compound was obtained after trituration with cyclohexane to afford a white solid (9.25 g, 89% yield).

UPLC $Rt_{M1}$=0.81 min; MS (ESI, m/z): 250.1 [(M+H$^+$]

$^1$H NMR (400 MHz, DMSO-$d_6$): δ 8.68 (d, 1H), 8.30 (d, 1H), 3.37 (s, 3H), 2.58 (s, 3H).

Intermediate IA2

5-bromo-3-fluoro2-methanesulfonyl-pyridine

A solution of 5-bromo-3-fluoro-2-methylsulfanyl-pyridine (222 mg, 1.0 mmol) in DCM (5 ml) was treated at 0° C. with mCPBA (518 mg, 3.0 mmol). After stirring for 1.5 h at rt the reaction mixture was added to 2N aq. NaOH soln. and was extracted with DCM. The organic layer was dried over $Na_2SO_4$, concentrated and the title compound was obtained as a white solid (241 mg, 95% yield) which was used without further purification.

UPLC $Rt_{M1}$=0.63 min;

$^1$H NMR (400 MHz, DMSO-$d_6$): δ 8.75 (d, 1H), 8.60 (d, 1H), 3.40 (s, 3H).

Intermediate IA3

5-Bromo-2-methanesulfonyl-3-trifluoromethyl-pyridine

A solution of 5-bromo-2-methylsulfanyl-3-trifluoromethyl-pyridine (1.40 g, 1.16 mmol) in DCM (30 ml) was treated at 0° C. with mCPBA (2.67 g, 15.48 mmol). After stirring for 18 h at rt the reaction mixture was added to a 4N aq. NaOH soln. and was extracted with DCM. The organic layer was dried over $Na_2SO_4$, filtered, concentrated and the title compound was obtained after flash chromatography on silica gel (hexane/EtOAc, 100:0 to 70:30) as a white solid (940 mg, 60% yield).

UPLC $Rt_{M1}$=0.87 min; MS (ESI, m/z): 323.0 [(M+NH$_4$)$^+$].

$^1$H NMR (400 MHz, CDCl$_3$): δ 9.45 (d, 1H), 8.76 (d, 1H), 3.57 (s, 3H).

Intermediate IA4

5-Bromo-3-difluoromethyl-2-methanesulfonyl-pyridine a) 2,5-Dibromo-3-difluoromethyl-pyridine A solution of Et$_3$N trifluoride (1.80 ml, 11.3 mmol) in DCM (40 ml) was treated at 0° C. with Xtalfluor-E (2.67 g, 15.5 mmol) and 2,5-dibromo-pyridine-3-carbaldehyde (1.0 g, 3.77 mmol). After stirring for 19 h at rt the reaction mixture was diluted with TBME and washed with sat. aq. NaHCO$_3$ soln. The organic layer was dried over Na$_2$SO$_4$, concentrated to leave a yellow oil (950 mg, 88% yield) which was used without further purification.

UPLC Rt$_{M1}$=1.05 min;

$^1$H NMR (400 MHz, DMSO-d$_6$): δ 8.57 (d, 1H), 8.48 (d, 1H), 7.14 (t, 1H), 3.35 (s, 3H).

b) 5-Bromo-3-difluoromethyl-2-methanesulfonyl-pyridine

A solution of 2,5-dibromo-3-difluoromethyl-pyridine (1400 mg, 1.16 mmol) in DMF (10 ml) was treated at 0° C. with sodium methanethiolate (348 mg, 4.97 mmol). After stirring for 1.5 h at rt, the reaction was cooled at 0° C. and mCPBA (2857 mg, 16.56 mmol) was added to the reaction mixture. After stirring for 1 h at rt the reaction mixture was added to a 4N aq. NaOH soln. and was extracted with TBME. The organic layer was dried over Na$_2$SO$_4$, filtered, concentrated and the title compound was obtained after flash chromatography on silica gel (hexane/EtOAc, 100/0 to 80/20) as a white solid (498 mg, 53% yield).

UPLC Rt$_{M1}$=0.86 min;

$^1$H NMR (400 MHz, CDCl$_3$): δ 8.67 (d, 1H), 8.45 (d, 1H), 7.37 (t, 1H), 3.37 (s, 3H).

Intermediate IA5

5-Bromo-3-fluoromethyl-2-methanesulfonyl-pyridine a) 5-Bromo-2-chloro-3-fluoromethyl-pyridine A solution of Et$_3$N trifluoride (1.76 ml, 10.79 mmol) in DCM (20 ml) was treated at 0° C. with Xtalfluor-E (1.65 g, 7.19 mmol) and (5-bromo-2-chloro-pyridin-3-yl)-methanol (0.80 g, 3.60 mmol). After stirring for 18 h at rt the reaction mixture was diluted with TBME and washed with sat. aq. NaHCO$_3$ soln. The organic layer was dried over Na$_2$SO$_4$, concentrated and the title compound was obtained after flash chromatography on silica gel (hexane/EtOAc, 100/0 to 90/10) as a colourless oil (286 mg, 35% yield).

UPLC Rt$_{M1}$=0.98 min;

$^1$H NMR (400 MHz, CDCl$_3$): δ 8.53 (d, 1H), 8.45 (d, 1H), 5.52 (d, 1H)

b) 5-Bromo-3-fluoromethyl-2-methanesulfonyl-pyridine

A solution of 2,5-dibromo-3-difluoromethyl-pyridine (1.4 g, 1.16 mmol) in DMF (10 ml) was treated at 0° C. with sodium methanethiolate (348 mg, 4.97 mmol). After stirring at rt for 1.5 h, the reaction was cooled down to 0° C. and mCPBA (2857 mg, 16.56 mmol) was introduced to the reaction mixture. After stirring for 1 h at rt the reaction mixture was added to an 4N aq. NaOH soln. and was extracted with TBME. The organic layer was dried over Na$_2$SO$_4$, filtered, concentrated and the title compound was obtained after flash chromatography on silica gel (hexane/EtOAc, 100/0 to 80/20) as a white solid (498 mg, 53% yield) UPLC Rt$_{M1}$=0.86 min;

$^1$H NMR (400 MHz, CDCl$_3$): δ 8.67 (d, 1H), 8.45 (d, 1H), 7.37 (t, 1H), 3.37 (s, 3H).

Intermediate IA7

5-Bromo-3-fluoromethyl-2-methoxy-pyridine

A solution of (5-bromo-2-methoxy-pyridin-3-yl)-methanol (343 mg, 1.57 mmol) in DCM (7 ml) was treated at 0° C. with deoxofluor (1.5 ml, 3.46 mmol) and EtOH (27.6 μl, 0.47 mmol). The reaction mixture was stirred at rt, quenched with sat. aq. NaHCO$_3$ soln. and was extracted with DCM. The organic layer was dried over Na$_2$SO$_4$, concentrated to afford the title compound after flash chromatography on silica gel (hexane/EtOAc 80:20) as a yellow oil (80 mg, 23% yield).

UPLC Rt$_{M1}$=1.07 min;

$^1$H NMR (400 MHz, DMSO-d$_6$): δ 8.32 (t, 1H), 8.00 (t, 1H), 5.37 (d, 2H), 3.89 (s, 3H).

Intermediate IA24

1-(5-Bromo-2-methoxy-pyridine-3-sulfonyl)-4-methyl-piperazine a)(5-Bromo-2-methanesulfonyl-pyridin-3-yl)-methyl-amine

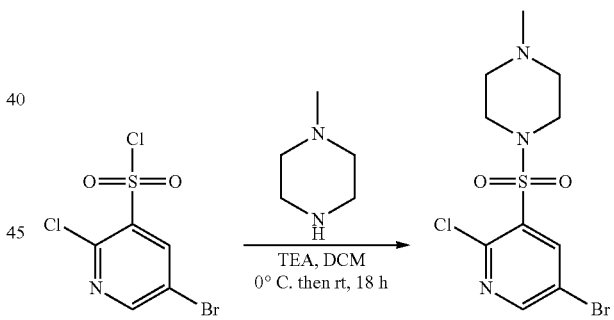

A solution of 5-bromo-2-chloro-pyridine-3-sulfonyl chloride (CAS registry 1146290-19-8) (580 mg, 1.99 mmol) and Et$_3$N (0.55 ml, 3.99 mmol) in DCM (20 ml) at 0° C. was treated with 1-methyl-piperazine (0.33 ml, 2.99 mmol), the resulting mixture was stirred at 0° C. for 20 min and at rt for 18 h. The mixture was diluted with DCM (30 ml) and washed with sat.aq. NaHCO$_3$ soln. The organic layer was dried over MgSO$_4$, concentrated and purified by flash chromatography on silica gel (DCM/MeOH 100:0 to 90:10) to afford the title compound as an orange solid (420 mg, 59% yield).

HPLC Rt$_{M2}$=1.49 min; ESIMS: 356 [(M+H)$^+$].

$^1$H NMR (400 MHz, CDCl$_3$): δ 8.62 (d, 1H), 8.50 (d, 1H), 3.57-3.29 (t, 4H), 2.50 (t, 4H), 2.33 (s, 3H).

b) 1-(5-Bromo-2-methoxy-pyridine-3-sulfonyl)-4-methyl-piperazine

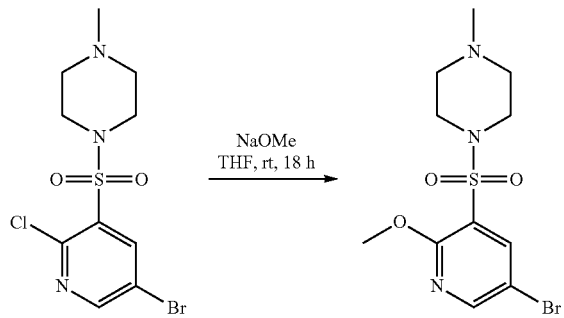 [SMILES: CN1CCN(S(=O)(=O)c2cc(Br)cnc2Cl)CC1 ; COc1ncc(Br)cc1S(=O)(=O)N1CCN(C)CC1]

A solution of 1-(5-bromo-2-chloro-pyridine-3-sulfonyl)-4-methyl-piperazine (420 mg, 1.18 mmol) in THF (10 ml) was treated portionwise with sodium methoxide (192 mg, 3.55 mmol). The resulting mixture was stirred at rt for 18 h. The mixture was quenched by addition of water and extracted with EtOAc. The combined organic layers were washed with sat. aq. NaHCO$_3$ soln. and dried over MgSO$_4$, concentrated and purified by flash chromatography on silica gel (DCM/MeOH 100:0 to 90:10) to afford the title compound (358 mg, 85% yield).

HPLC Rt$_{M2}$=1.47 min; ESIMS: 350, 352 [(M+H)$^+$].
$^1$H NMR (400 MHz, CDCl$_3$): δ 8.36 (d, 1H), 8.28 (d, 1H), 4.05 (s, 3H), 3.35 (br s, 4H), 2.49 (br s, 4H), 2.33 (s, 3H).

Intermediate IA30

3-Bromo-5-(propane-2-sulfonyl)-pyridine

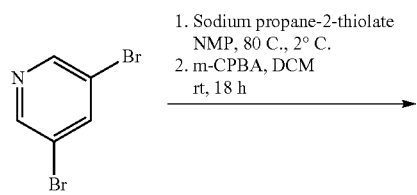

A solution of 3,5-dibromo-pyridine (CAS registry 625-92-3) (495 mg, 2.09 mmol) in NMP (5 ml) was treated with sodium propane-2-thiolate (CAS registry 20607-43-6) (205 mg, 2.09 mmol), the resulting mixture was stirred at 80° C. for 2 h. The mixture was cooled down and diluted with EtOAc, washed with water (2×), then brine. The organic layer was dried over MgSO$_4$ and concentrated. The obtained residue was dissolved in DCM (10 ml), treated with mCPBA (1083 mg, 6.27 mmol) and stirred at rt for 18 h. 10% aq. sodium sulfite soln. was added and the mixture was stirred at rt for 1 h. The phases were separated and the organic layer was washed with sat. aq. NaHCO$_3$ soln., dried over MgSO$_4$, concentrated and purified by flash chromatography on silica gel (cyclohexane/EtOAc 100:0 to 00:100) to afford the title compound (364 mg, 59% yield).

HPLC Rt$_{M2}$=0.77 min; ESIMS: 264, 266 [(M+H)$^+$].
$^1$H NMR (400 MHz, CDCl$_3$): δ 8.98 (dd, 2H), 8.33 (t, 1H), 3.34-3.17 (m, 1H), 1.37 (d, 6H).

Intermediate IA44

5-Bromo-2-ethanesulfinyl-pyridine a) 5-Bromo-2-ethylsulfanyl-pyridine

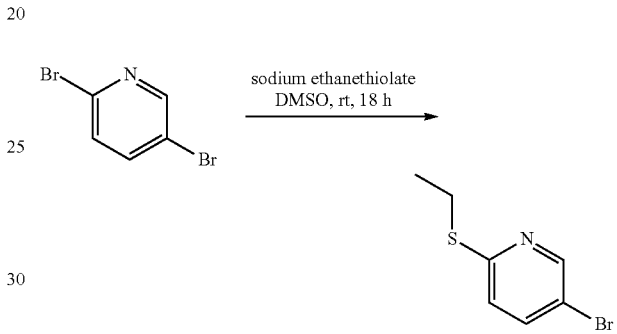

A mixture of 2,5-dibromo-pyridine (CAS registry 588729-99-1) (1.15 g, 4.85 mmol) and sodium ethanthiolate (CAS registry 811-51-8) (2.04 g, 24.27 mmol) in DMSO (15 ml) was stirred at rt for 18 h. Water was added and the mixture was extracted with DCM. The organic layer was dried by passing it through a phase separating cartridge, was concentrated and purified by flash chromatography on silica gel (cyclohexane/EtOAc 100:0 to 70:30) to afford the title compound as an orange oil (1.09 g, 92% yield).

HPLC Rt$_{M2}$=1.25 min; ESIMS: 218, 220 [(M+H)$^+$].

b) 5-Bromo-2-ethanesulfinyl-pyridine

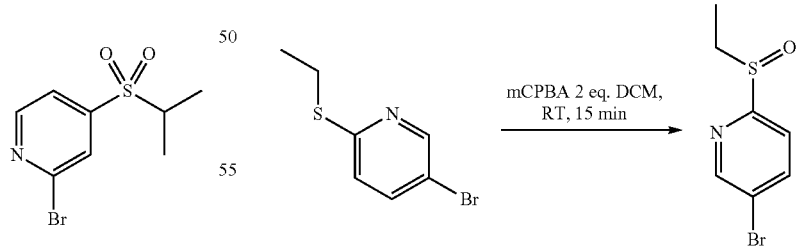

A solution of 5-Bromo-2-ethylsulfanyl-pyridine (1.09 g, 4.49 mmol) in DCM (15 ml) was treated with mCPBA (1.55 g, 8.98 mmol). The resulting solution was stirred at rt for 15 min. The mixture was quenched by addition of aq. 2M NaOH soln., and extracted with DCM. The combined organic layers were dried over MgSO$_4$ and concentrated. The compound was purified by prep. RP-HPLC (column SunFire C18 OBD, gradient 5-60% ACN in 15 min) to afford the title compound as a colourless oil (490 mg, 45% yield).

HPLC $Rt_{M2}$=0.65 min; ESIMS: 234, 236 [(M+H)$^+$].

$^1$H NMR (400 MHz, DMSO-d$_6$): δ 8.85 (d, 1H), 8.37 (dd, 1H), 7.80 (d, 1H), 3.33 (s, 2H), 3.27-3.10 (m, 1H), 2.94-2.72 (m, 1H), 1.01 (t, 3H).

Intermediate IA45

5-Bromo-2-methanesulfonyl-3-methoxypyridine a) 5-Bromo-3-methoxy-2-methylsulfanyl-pyridine

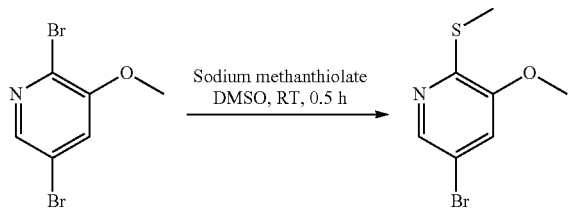

A mixture of 2,5-dibromo-3-methoxy-pyridine (CAS registry 1142191-57-8) (550 mg, 2.06 mmol) and sodium methanethiolate (CAS registry 5188-07-8)(722 mg, 10.30 mmol) in DMSO (1.5 ml) was stirred at rt for 0.5 h. Water was added and the mixture was extracted with DCM. The organic layer was dried by passing it through a phase separating cartridge and was concentrated to afford the title compound as a colourless oil (1.50 g, 93% yield, crude).

$^1$H NMR (400 MHz, DMSO-d$_6$): δ 8.19 (d, 1H), 7.53 (d, 1H), 3.89 (s, 3H), 3.32 (s, 3H).

b) 5-Bromo-2-methanesulfonyl-3-methoxypyridine

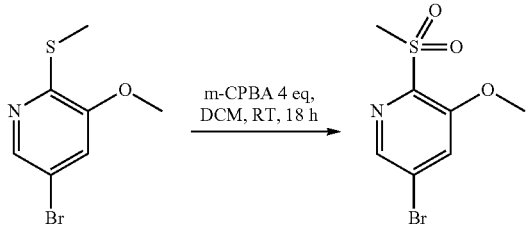

A solution of 5-bromo-3-methoxy-2-methylsulfanyl-pyridine (1.50 g, 2.24 mmol) in DCM (10 ml) was treated with mCPBA (1.55 g, 8.97 mmol). The resulting mixture was stirred at rt for 18 h. The mixture was quenched by addition of aq. 2M NaOH soln., and extracted with DCM. The organic layer was dried by passing through a phase separating cartridge and concentrated to afford the title compound (400 mg, 33% yield as crude).

HPLC $Rt_{M2}$=0.75 min; ESIMS: 268 [(M+H)$^+$].

$^1$H NMR (400 MHz, DMSO-d$_6$): δ 8.41 (d, 1H), 8.17 (s, 1H), 4.01 (s, 3H), 3.30 (s, 3H).

Intermediate IA51

(5-Bromo-2-methanesulfonyl-pyridin-3-yl)-methyl-amine a) (5-Bromo-2-chloro-pyridin-3-yl)-methyl-amine

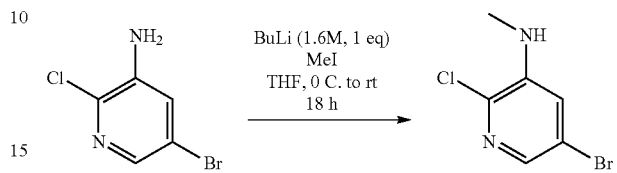

A solution of 5-bromo-2-chloro-pyridin-3-ylamine (CAS registry 588729-99-1) (565 mg, 2.72 mmol) in THF (4 ml) at 0° C. was treated with BuLi 1.6M in hexane (0.17 ml, 0.17 mmol), the resulting mixture was stirred at 0° C. for 0.5 h, then methyl iodide (0.17 ml, 2.72 mmol) was slowly added. The reaction mixture was allowed to warm to rt and was stirred for 18 h. The orange/brown mixture was poured into sat. aq. NaHCO$_3$ soln., and extracted with EtOAc. The organic layer was dried over MgSO$_4$, concentrated and purified by flash chromatography on silica gel (cyclohexane/EtOAc 95:5 to 60:40) to afford the title compound as an orange solid (354 mg, 59% yield).

HPLC $Rt_{M1}$=0.94 min; ESIMS: 221, 223, 225 [(M+H)$^+$].

$^1$H NMR (400 MHz, DMSO-d$_6$): δ 7.65 (d, 1H), 7.14 (d, 1H), 6.11 (d, 1H), 2.74 (d, 3H).

b) (5-Bromo-2-methanesulfonyl-pyridin-3-yl)-methyl-amine

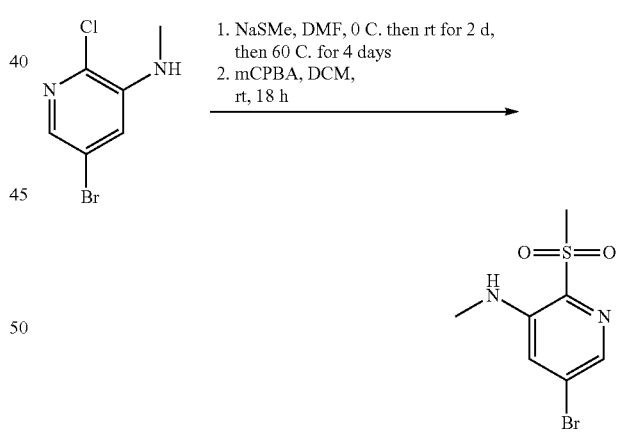

A solution of (5-bromo-2-chloro-pyridin-3-yl)-methyl-amine (354 mg, 1.60 mmol) in DMF (2.6 ml) was treated with sodium methanethiolate (168 mg, 2.40 mmol) at 0° C. The resulting solution was stirred at rt for 2 d and heated at 60° C. for 4 d. The mixture was quenched at 0° C. by addition of aq. 2M NaOH soln., and extracted with DCM. The combined organic layers were dried over MgSO$_4$ and concentrated to afford an orange oil which was dissolved in DCM (5 ml) and treated at 0° C. with mCPBA (CAS registry 937-14-4) (827 mg, 4.79 mmol) and stirred for 18 h at rt. The mixture was quenched at 0° C. by addition of aq. NaOH 2M soln. and extracted with DCM. Combined organics were dried over MgSO₄, concentrated and purified by flash chromatography on silica gel (cyclohexane/EtOAc 92:8 to 32:68) to afford the title compound as an orange solid (174 mg, 41% yield).

HPLC Rt$_{M1}$=0.78 min; ESIMS: 265, 267 [(M+H)⁺].

¹H NMR (400 MHz, DMSO-d₆): δ 7.95 (d, 1H), 7.50 (d, 1H), 6.70-6.59 (m, 1H), 3.26 (s, 3H), 2.82 (d, 3H).

Intermediate IA52

(5-Bromo-2-methanesulfonyl-pyridin-3-yl)-dimethyl-amine a) (5-Bromo-2-chloro-pyridin-3-yl)-methyl-amine

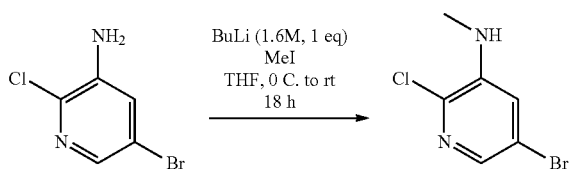

A solution of 5-bromo-2-chloro-pyridin-3-ylamine (CAS registry 588729-99-1) (1 g, 4.82 mmol) in THF (7 ml) at 0° C. was treated with BuLi 1.6M in hexane (6 ml, 9.64 mmol), the resulting mixture was stirred at 0° C. for 0.5 h, then methyl iodide (0.60 ml, 9.64 mmol) was slowly added. The reaction mixture was allowed to warm at rt and was stirred for 18 h. The orange/brown mixture was poured onto sat. aq. NaHCO₃ soln., and extracted with EtOAc, the organic layer was dried over MgSO₄, concentrated and purified by flash chromatography on silica gel (cyclohexane/EtOAc 95:05 to 70:30) to afford the title compound as an orange solid (182 mg, 17% yield).

HPLC Rt$_{M1}$=0.94 min; ESIMS: 221, 223 [(M+H)⁺].

¹H NMR (400 MHz, DMSO-d₆): δ 7.65 (d, 1H), 7.14 (d, 1H), 6.11 (d, 1H), 2.74 (d, 3H).

b) (5-Bromo-2-chloro-pyridin-3-yl)-dimethyl-amine

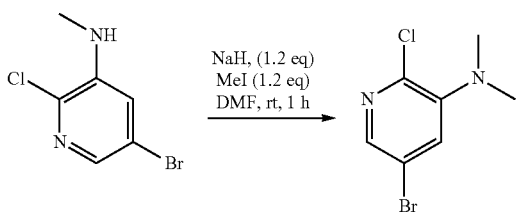

A solution of (5-bromo-2-chloro-pyridin-3-yl)-methyl-amine (182 mg, 0.82 mmol) in DMF (4 ml) was treated with NaH (23 mg, 0.99 mmol) at rt, and the mixture was stirred at rt for 0.5 h, methyl iodide (0.06 ml, 0.99 mmol) was added and the resulting mixture was stirred at rt for 1 h. The mixture was diluted with TBME and washed with a sat. aq. NaHCO₃ soln., the organic layer was dried over MgSO₄ and concentrated to afford the title compound as an orange oil (174 mg, 90% yield). It was used without further purification.

HPLC Rt$_{M1}$=1.03 min; ESIMS: 235, 237 [(M+H)⁺].

¹H NMR (400 MHz, DMSO-d₆): δ 8.10 (d, 1H), 7.70 (d, 1H), 2.78 (s, 6H).

c) (5-Bromo-2-methanesulfonyl-pyridin-3-yl)-methyl-amine

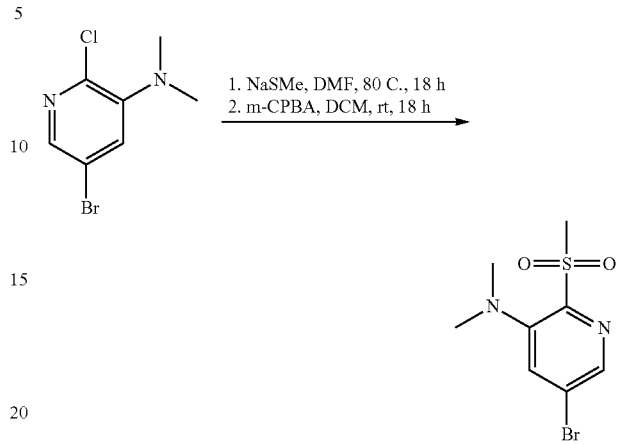

A solution of (5-bromo-2-chloro-pyridin-3-yl)-dimethyl-amine (174 mg, 0.74 mmol) in DMF (5 ml) was treated with sodium methanethiolate (104 mg, 1.48 mmol) at rt, the resulting solution was stirred at 80° C. for 18 h. At 0° C., the mixture was quenched by addition of aq. 2M NaOH soln. then extracted with TBME. The combined organic layers were dried over MgSO₄ and concentrated to afford an orange oil which was dissolved in DCM (5 ml), treated at 0° C. with mCPBA (CAS registry 937-14-4) (382 mg, 2.21 mmol) and stirred for 18 h at rt. At 0° C., the mixture was quenched by addition of aq. 2M NaOH soln., then extracted with DCM. The combined organic layers were dried over MgSO₄, concentrated and purified by flash chromatography on silica gel (cyclohexane/EtOAc 88:12 to 00:100) to afford the title compound as an orange solid (50 mg, 24% yield).

HPLC Rt$_{M1}$=0.83 min; ESIMS: 279, 281 [(M+H)⁺].

¹H NMR (400 MHz, DMSO-d₆): δ 8.25 (d, 1H), 7.90 (d, 1H), 3.29 (s, 3H), 2.91 (s, 6H).

Intermediate IA65

5-Bromo-2,N-dimethoxy-benzenesulfonamide

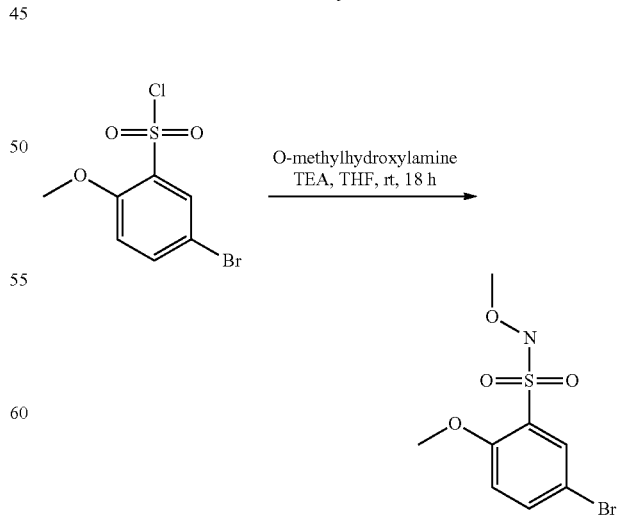

A solution of 5-bromo-2-methoxy-benzenesulfonyl chloride (CAS registry 23095-05-8) (218 mg, 0.76 mmol) and Et₃N (0.55 ml, 3.99 mmol) in DCM (20 ml) at 0° C. was stirred for 15 min and treated with O-methylhydroxylamine (36 mg, 0.76 mmol), the resulting mixture was stirred at rt for 18 h. The mixture was partitioned between EtOAc and water. The organic layer was washed with sat.aq. NaHCO₃ soln., dried over MgSO₄ concentrated and purified by flash chromatography on silica gel (cyclohexane/EtOAc 100:0 to 0:100) to afford the title compound (189 mg, 84% yield).

¹H NMR (400 MHz, CDCl₃): δ 8.10 (d, 1H), 7.78 (s, 1H), 7.72 (dd, 1H), 6.97 (d, 1H), 4.01 (s, 3H), 3.81 (s, 3H).

IB) Carboxylic Acids or Acid Chlorides

| Intermediate # | IB) Carboxylic acids or acid chlorides Structure | Autonom name |
|---|---|---|
| IB1 | enantiomer 1 | Tetrahydro-furan-3-carboxylic acid (pure enantiomer) |
| IB2 | enantiomer 2 | Tetrahydro-furan-3-carboxylic acid (pure enantiomer) |
| IB3 | | 5-tert-butoxycarbonylamino-1-methyl-1H-imidazole-4-carboxylic acid |

Example IB1/IB2

(S)-Tetrahydro-furan-3-carboxylic acid/(R)-Tetrahydro-furan-3-carboxylic acid a) Tetrahydro-furan-3-carboxylic acid benzyl ester

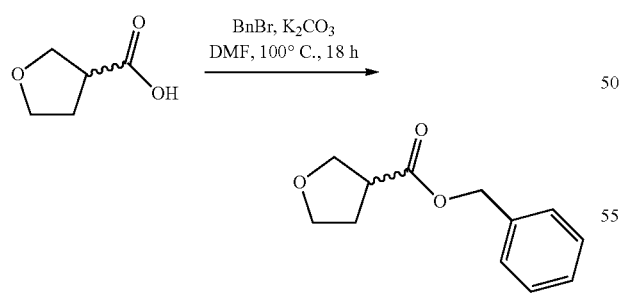

A solution of tetrahydro-furan-3-carboxylic acid (CAS registry 89364-31-8) (4.00 g, 34.40 mmol) in DMF (20 ml) was treated with K₂CO₃ (9.52 g, 68.9 mmol) and benzyl bromide (CAS registry 100-39-0) (8.18 ml, 68.9 mmol) at 100° C. for 18 h. The mixture was cooled down to rt, diluted with EtOAc, washed with water and brine. Combined organic layers were dried over MgSO₄, concentrated and purified by flash chromatography on silica gel (cyclohexane/EtOAc 92:8 to 34:66) to afford the title compound as colourless oil (6.93 g, 98% yield)

HPLC Rt$_{M2}$=0.94 min; ESIMS: 207 [(M+H)⁺].

¹H NMR (400 MHz, CDCl₃): δ 7.50-7.26 (m, 5H), 5.17 (m, 2H), 4.05-3.75 (m, 4H), 3.29-3.05 (m, 1H), 2.36-2.09 (m, 2H).

b) Enantiomer separation of tetrahydro-furan-3-carboxylic acid benzyl ester

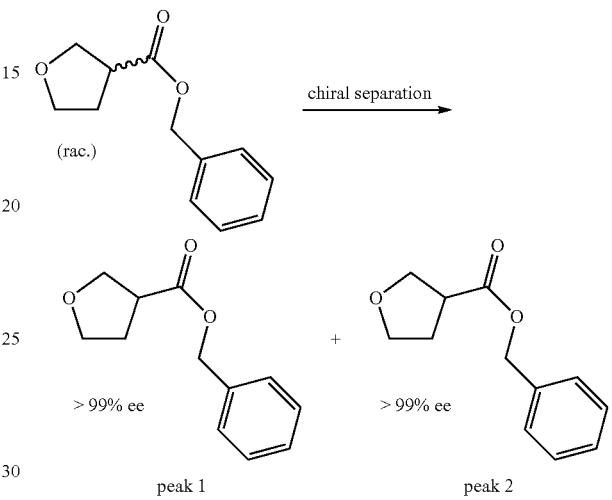

Method Information:
Column: Chiralpak AD-PREP
Solvent: HEPTANE/ETOH/MEOH 95/2.5/2.5
Flow: 1.0 ml/min
Long onde: 210 nm
Engine: Agilent 1200 DAD Magellan
Solution EtOH After separation of 6.347 g of racemic, 2 peaks were obtained: peak 1 at 9.086 min (2.43 g, ee>99%) and peak 2 at 10.584 min (2.19 g, ee>99%).

HPLC (peak 1 or 2) Rt$_{M2}$=0.92 min; ESIMS: 207 [(M+H)⁺].

¹H NMR (peak 1) (400 MHz, CDCl₃): δ 7.48-7.29 (m, 5H), 5.23-5.07 (m, 2H), 4.05-3.77 (m, 4H), 3.23-3.10 (m, 1H), 2.35-2.06 (m, 2H).

¹H NMR (peak 2) (400 MHz, CDCl₃): δ 7.51-7.31 (m, 5H), 5.23-5.09 (m, 2H), 4.07-3.77 (m, 4H), 3.24-3.07 (m, 1H), 2.35-2.06 (m, 2H).

c) (S)-Tetrahydro-furan-3-carboxylic acid/(R)-Tetrahydro-furan-3-carboxylic acid

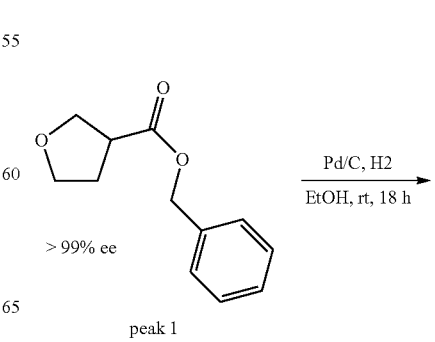

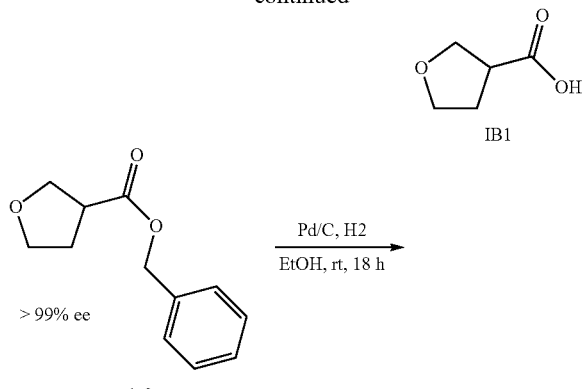

peak 2

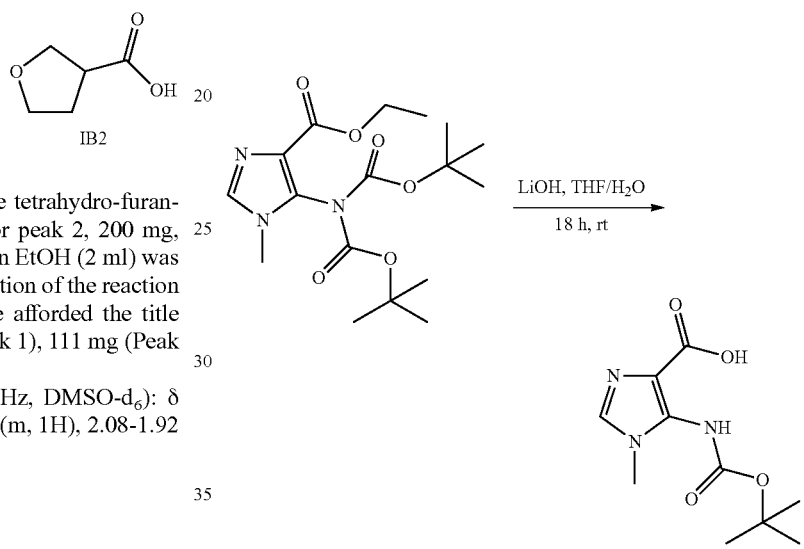

A solution of an enantiomerically pure tetrahydro-furan-3-carboxylic acid benzyl ester (peak 1 or peak 2, 200 mg, 0.97 mmol), Pd/C (103 mg, 0.97 mmol) in EtOH (2 ml) was hydrogenated with H₂ at rt for 18 h. Filtration of the reaction mixture and concentration of the filtrate afforded the title compound as colourless oil (125 mg (Peak 1), 111 mg (Peak 2), crude).

¹H NMR (both enantiomers) (400 MHz, DMSO-d₆): δ 12.40 (br s, 1H), 3.84-3.59 (m, 4H), 3.00 (m, 1H), 2.08-1.92 (m, 1H).

Example IB3

5-tert-Butoxycarbonylamino-1-methyl-1H-imidazole-4-carboxylic acid a) 5-di(tert-Butoxycarbonyl)amino-1-methyl-1H-imidazole-4-carboxylic acid ethyl ester

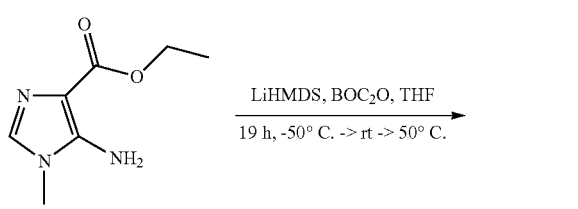

A solution of 5-amino-1-methyl-1H-imidazole-4-carboxylic acid ethyl ester (CAS registry 54147-04-5) (82 mg, 0.49 mmol) in THF (4 ml) was treated at −50° C. with 1M LiHMDS in THF soln. (0.97 ml, 0.97 mmol) and the reaction mixture was stirred at −50° C. for 10 min, then a solution of Boc₂O (237 mg, 1.07 mmol) in THF (1.5 ml) was added. The reaction mixture was allowed to warm slowly to rt, then to 50° C. and to stir for 15 h at 50° C. The reaction mixture was cooled to rt, diluted with EtOAc and quenched with H₂O. The organic layer was dried over Na₂SO₄, filtered, concentrated and the title compound was obtained after flash chromatography on silica gel (heptane/EtOAc, 85:15 to 0:100) as a white solid (140 mg, 78% yield).

UPLC Rt$_{M1}$=0.96 min; ESIMS: 370 [(M+H)⁺]

¹H NMR (400 MHz, CDCl₃, 298 K): δ 4.33 (q, 2H), 3.50 (s, 3H), 1.41 (s, 18H), 1.35 (t, 3H).

b) 5-tert-Butoxycarbonylamino-1-methyl-1H-imidazole-4-carboxylic acid

A solution of 5-di(tert-butoxycarbonyl)amino-1-methyl-1H-imidazole-4-carboxylic acid ethyl ester (167 mg, 0.452 mmol) in THF (2.2 ml) and H₂O (2.2 ml) was treated with LiOH (54.1 mg, 2.26 mmol) and the reaction mixture was stirred at rt for 18 h, then quenched with 1M aq. HCl soln. to reach pH 2 and extracted with EtOAc. The organic layer was dried over Na₂SO₄, filtered, concentrated to afford the title compound. (70 mg, 65% yield).

UPLC Rt$_{M1}$=0.47 min; ESIMS: 242 [(M+H)⁺]

¹H NMR (400 MHz, DMSO-d₆): δ 12.42 (br.s., 1H), 8.98 (br.s., 1H), 7.82 (s, 1H), 3.45 (s, 3H), 1.41 (s, 9H).

IC) Pyrrolidinol Derivatives or Analogues

| Inter-mediate # | Autonom name | Used for example # | Comment on synthesis |
|---|---|---|---|
| IC1 | Methanesulfonic acid (R)-(tetrahydro-pyran-4-carbonyl)-pyrrolidin-3-yl ester | C1 | 2 steps from CAS 104706-47-0 |
| IC2 | Methanesulfonic acid (S)-(tetrahydro-pyran-4-carbonyl)-pyrrolidin-3-yl ester | C2 | 2 steps from CAS 100243-39-8 |
| IC3 | Methanesulfonic acid (S)-1-propionyl-pyrrolidin-3-yl ester | C3 | 2 steps from CAS 100243-39-8 |
| IC4 | Methanesulfonic acid (R)-1-propionyl-pyrrolidin-3-yl ester | C4 | 2 steps from CAS 2799-21-5 |

Intermediate IC1

Methanesulfonic acid (R)-1-(tetrahydro-pyran-4-carbonyl)-pyrrolidin-3-yl ester a) ((R)-3-Hydroxy-pyrrolidin-1-yl)-(tetrahydro-pyran-4-yl)-methanone

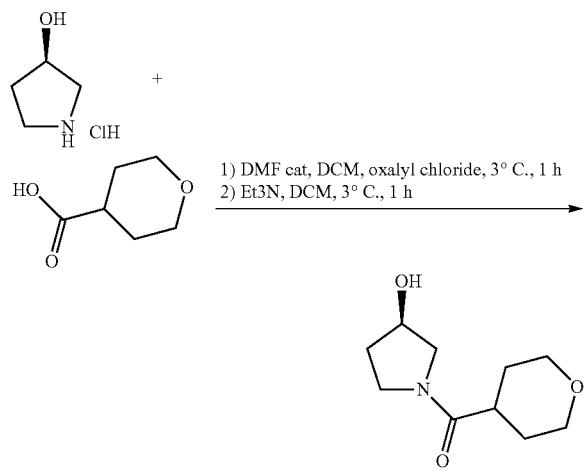

1) DMF cat, DCM, oxalyl chloride, 3° C., 1 h
2) Et3N, DCM, 3° C., 1 h

Oxalyl chloride (0.20 ml, 3.84 mmol) was added to a solution of tetrahydro-pyran-4-carboxylic acid (CAS registry 5337-03-1) and DMF (0.012 ml, 0.15 mmol). The reaction mixture was stirred at 3° C. for 1 h. Concentration of the reaction mixture under reduced pressure (170 mbar) at 40° C. (water bath) afforded the acyl intermediate as a colourless oil. The intermediate was dissolved in DCM (2 ml) and added to a solution of (R)-pyrrolidin-3-ol hydrochloride (CAS registry 104706-47-0) (190 mg, 1.54 mmol) in DCM (3 ml), cooled down to 3° C., the formed white suspension was stirred at 3° C. for 1 h. The reaction mixture was concentrated; EtOAc was added to the residue which was filtered off and washed with EtOAc. Concentration and purification of the filtrate by flash chromatography on silica gel (DCM/DCM: MeOH (9:1), 100:0 to 60:40 over 11 min) afforded the title compound as white solid (250 mg, 82% yield).

ESIMS: 200 [(M+H)$^+$].

$^1$H NMR (400 MHz, CDCl$_3$): δ 4.43-4.65 (m, 1H), 3.95-4.16 (m, 2H), 3.30-3.82 (m, 6H), 2.45-2.75 (m, 1H), 1.83-2.30 (m, 4H), 1.54-1.78 (m, 3H).

b) Methanesulfonic acid (R)-1-(tetrahydro-pyran-4-carbonyl)-pyrrolidin-3-yl ester

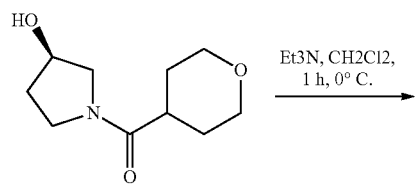

Et3N, CH2Cl2, 1 h, 0° C.

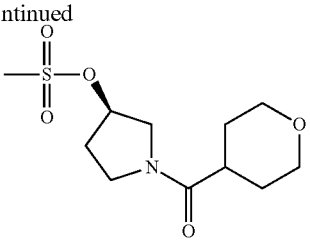

Under argon, methanesulfonyl chloride (CAS registry 124-63-0) (3.52 ml, 45.2 mmol) was added to a solution of ((R)-3-hydroxy-pyrrolidin-1-yl)-(tetrahydro-pyran-4-yl)-methanone (6 g, 22.6 mmol) and Et$_3$N (6.30 ml, 45.2 mmol) in DCM (100 ml) at −10° C. The solution was stirred at 0° C. for 1 h, diluted with H$_2$O and DCM, the organic layer was washed twice with H$_2$O and brine and dried over MgSO$_4$. Concentration and trituration of the resulting oil with diethyl ether afforded the title compound as an off-white solid (5.3 g, 84%).

ESIMS: 278 [(M+H)$^+$].

$^1$H NMR (400 MHz, CDCl$_3$): δ 5.22-5.44 (m, 1H), 3.96-4.13 (m, 2H), 3.85-3.96 (m, 1H), 3.56-3.83 (m, 3H), 3.36-3.53 (m, 2H), 3.08 (d, 3H), 2.07-2.75 (m, 3H), 1.93 (m, 2H), 1.51-1.75 (m, 3H).

Intermediate IC2

Methanesulfonic acid (S)-(tetrahydro-pyran-4-carbonyl)-pyrrolidin-3-yl ester a) ((S)-3-Hydroxy-pyrrolidin-1-yl)-(tetrahydro-pyran-4-yl)-methanone

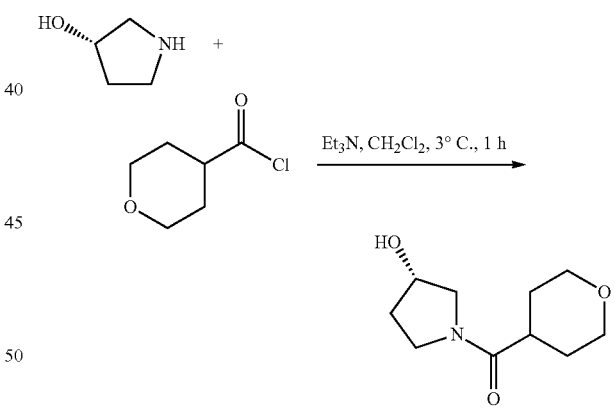

Et3N, CH2Cl2, 3° C., 1 h

A solution of tetrahydro-pyran-4-carbonyl chloride (CAS registry 40191-32-0) (316 mg, 2.02 mmol) in DCM (2 ml) was dropwise added (0° C.<T<10° C.) to a solution of (S)-pyrrolidin-3-ol (CAS registry 100243-39-8) (250 mg, 2.02 mmol) and Et$_3$N (0.62 ml, 4.45 mmol) in DCM (5 ml). The reaction mixture was stirred at 3° C. for 1 h. The volatiles were concentrated and EtOAc was added to the residue, remaining solid was filtered off and washed with EtOAc, concentration of the filtrate afforded the title compound as a white solid (390 mg, 97% yield).

ESIMS: 200 [(M+H)$^+$].

$^1$H NMR (400 MHz, CDCl$_3$): δ 4.55 (d, 1H), 3.96-4.11 (m, 2H), 3.36-3.80 (m, 6H), 2.48-2.74 (m, 1H), 1.52-2.20 (m, 7H).

b) Methanesulfonic acid (S)-1-(tetrahydro-pyran-4-carbonyl)-pyrrolidin-3-yl ester

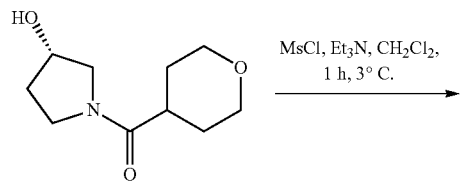

Under argon, methanesulfonyl chloride (CAS registry 124-63-0) (0.23 ml, 2.94 mmol) was added to a solution of ((S)-3-hydroxy-pyrrolidin-1-yl)-(tetrahydro-pyran-4-yl)-methanone (0.39 g, 1.96 mmol) and Et₃N (0.55 ml, 3.91 mmol) in DCM (10 ml) at −10° C. The solution was stirred at 3° C. for 1 h, diluted with H₂O and DCM, the organic layer was washed twice with H₂O and brine, then dried over MgSO₄. Concentration and trituration of the resulting oil with diethyl ether afforded the title compound as white solid (0.45 g, 83% yield).

ESIMS: 278 [(M+H)⁺].

¹H NMR (400 MHz, CDCl₃): δ 5.25-5.44 (m, 1H), 3.99-4.16 (m, 2H), 3.85-3.95 (m, 1H), 3.56-3.83 (m, 3H), 3.37-3.54 (m, 2H), 3.08 (d, 3H), 2.09-2.78 (m, 3H), 1.93 (m, 2H), 1.51-1.76 (m, 2H)

Intermediate IC3

Methanesulfonic acid (S)-1-propionyl-pyrrolidin-3-yl ester a) 1-((S)-3-Hydroxy-pyrrolidin-1-yl)-propan-1-one

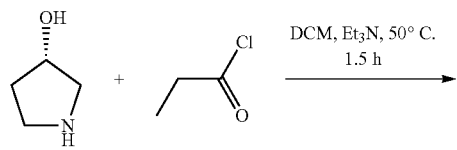

Propionyl chloride (CAS registry 79-03-8) (4.78 ml, 54.8 mmol) was dropwise added over a period of 15 min to a solution of (S)-pyrrolidin-3-ol (CAS registry 100243-39-8) (4.8 g, 55.9 mmol) and Et₃N (8.74 ml, 63.1 mmol) at 5° C., the solution was allowed to warm to rt and was stirred for 1 h. H₂O (10 ml) and sat. aq. NaHCO₃ soln (10 ml) were added to the solution, the organic phase was washed with brine (10 ml) and a 0.25M aq. HCl soln (20 ml). The combined aqueous layers were concentrated and extracted with EtOAc (2×100 ml), the combined organic phases were dried over MgSO₄ and concentrated to afford the title compound as a pale yellow oil (4.80 g, 54% yield).

¹H NMR (400 MHz, CDCl₃): δ 4.54 (d, 1H), 3.31-3.73 (m, 3H), 3.12 (m, 1H), 1.82-2.46 (m, 5H), 1.17 (t, 3H)

b) Methanesulfonic acid (S)-1-propionyl-pyrrolidin-3-yl ester

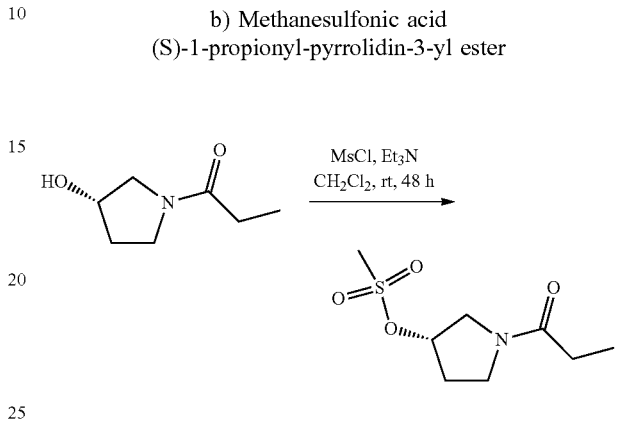

Under argon, methanesulfonyl chloride (CAS registry 124-63-0) (1.36 ml, 17.46 mmol) was added over a period of 10 min to a solution of 1-((S)-3-hydroxy-pyrrolidin-1-yl)-propan-1-one (2.5 g, 17.4 mmol) and Et₃N (2.43 ml, 17.4 mmol) in DCM (50 ml) at 5° C. The solution was allowed to warm to rt and was stirred for 18 h, methanesulfonyl chloride (CAS registry 124-63-0) (1.36 ml, 17.46 mmol) and Et₃N (2.43 ml, 17.4 mmol) were then added to the reaction mixture which was stirred for 48 h at rt. DCM and H₂O were added to the solution and the organic phase was separated through a phase separation cartridge, concentrated and the title compound was obtained after flash chromatography on silica gel (EtOAc/MeOH 100:0 to 95:5 over 40 min) as a colourless oil (2.7 g, 66% yield).

¹H NMR (400 MHz, CDCl₃): δ 5.19-5.42 (m, 1H), 3.48-3.99 (m, 4H), 3.06 (d, 3H). 2.04-2.54 (m, 4H), 1.16 (t, 3H).

Intermediate IC4

Methanesulfonic acid (R)-1-propionyl-pyrrolidin-3-yl ester a) 1-((R)-3-Hydroxy-pyrrolidin-1-yl)-propan-1-one

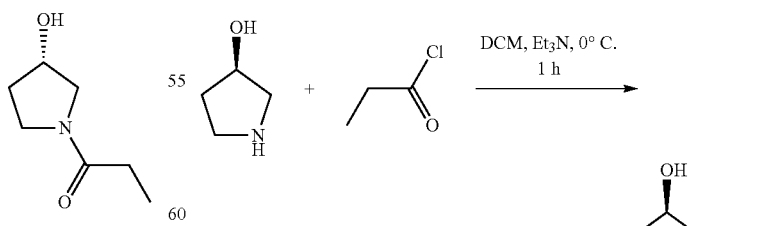

Propionyl chloride (CAS registry 79-03-8) (7.06 ml, 81 mmol) was added (0° C.<T<10° C.) over a period of 15 min to a suspension of (R)-pyrrolidin-3-ol (CAS registry 2799-21-5) (10 g, 81 mmol) and Et$_3$N (23.6 ml, 170 mmol) in DCM (150 ml) that was precooled at −10° C. The off-white suspension was stirred at 0° C. for 2 h, MeOH (9.82 ml, 243 mmol) was added and the mixture was allowed to stir at rt for 1 h. Concentration and dilution of the residue with Et$_2$O (200 ml) afforded, after filtration and concentration of the filtrate, the title compound as a yellow oil (11.2 g, 95%).

ESIMS: 144 [(M+H)$^+$].

$^1$H NMR (400 MHz, DMSO-d$_6$): δ 4.81-5.04 (m, 1H), 4.15-4.38 (m, 1H), 3.35-3.59 (m, 2H), 3.16-3.29 (m, 2H), 2.11-2.33 (m, 2H), 1.65-2.00 (m, 2H), 0.98 (td, 3H).

b) Methanesulfonic acid (R)-1-propionyl-pyrrolidin-3-yl ester

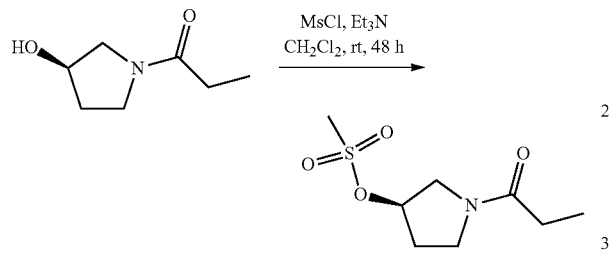

Under argon, methanesulfonyl chloride (CAS registry 124-63-0) (0.16 ml, 2.09 mmol) was dropwise added over a period of 5 min to a solution of 1-((R)-3-hydroxy-pyrrolidin-1-yl)-propan-1-one (300 mg, 2.09 mmol) and Et$_3$N (0.29 ml, 2.09 mmol) in DCM (10 ml) at 5° C., the reaction mixture was allowed to stir at rt for 18 h. Methanesulfonyl chloride (CAS registry 124-63-0) (0.16 ml, 2.09 mmol) and Et$_3$N (0.29 ml, 2.09 mmol) were then added to the reaction mixture which was stirred at rt for 48 h. DCM and H$_2$O were added to the solution and the organic phase was separated through a phase separation cartridge and concentrated. The title compound was obtained after flash chromatography on silica gel (EtOAc/MeOH 100:0 to 95:5 over 25 min) as a colourless oil (420 mg, 86%).

$^1$H NMR (400 MHz, CDCl$_3$): δ 5.21-5.44 (m, 1H). 3.49-4.03 (m, 4H), 2.98-3.12 (m, 3H), 1.97-2.54 (m, 4H), 1.18 (t, 3H).

ID) DBO Derivatives or Analogues

| Inter-mediate # | ID) DBO derivative or analogue Structure | Autonom name | Comment on synthesis |
|---|---|---|---|
| ID1 | | 3,3-Dideutero-3,4-dihydro-2H-benzo[1,4]oxazin-6-ol | 2 steps from CAS 53412-38-7, see Example Q steps a), b) |

Biological Evaluation

The activity of a compound according to the present invention can be assessed by the following in vitro & in vivo methods.

Biological Assays

1 Determination of enzymatic PI3K alpha and PI3K Delta Isoform Inhibition 1.1 Test of Lipid Kinase Activity The efficacy of the compounds of examples 1-117 as PI3 kinase inhibitors can be demonstrated as follows:

The kinase reaction is performed in a final volume of 50 µl per well of a half area COSTAR, 96 well plate. The final concentrations of ATP and phosphatidyl inositol in the assay are 5 µM and 6 µg/mL, respectively. The reaction is started by the addition of PI3 kinase, e.g. PI3 kinase δ.

p110δ. The components of the assay are added per well as follows:

10 µl test compound in 5% DMSO per well in columns 2-1.

Total activity is determined by addition 10 µl of 5% vol/vol DMSO in the first 4 wells of column 1 and the last 4 wells of column 12.

The background is determined by addition of 10 µM control compound to the last 4 wells of column 1 and the first 4 wells of column 12.

2 mL 'Assay mix' are prepared per plate:
  1.912 mL of HEPES assay buffer
  8.33 µl of 3 mM stock of ATP giving a final concentration of 5 µM per well
  1 µl of [$^{33}$P]ATP on the activity date giving 0.05 µCi per well
  30 µl of 1 mg/mL PI stock giving a final concentration of 6 g/mL per well
  5 µl of 1 M stock MgCl$_2$ giving a final concentration of 1 mM per well 20 µl of the assay mix are added per well.

2 mL 'Enzyme mix' are prepared per plate (x* µl PI3 kinase p110β in 2 mL of kinase buffer). The 'Enzyme mix' is kept on ice during addition to the assay plates.

20 µl 'Enzyme mix' are added/well to start the reaction. The plate is then incubated at room temperature for 90 minutes.

The reaction is terminated by the addition of 50 µl WGA-SPA bead (wheat germ agglutinin-coated Scintillation Proximity Assay beads) suspension per well.

The assay plate is sealed using TopSeal-S (heat seal for polystyrene microplates, PerkinElmer LAS [Deutschland] GmbH, Rodgau, Germany) and incubated at room temperature for at least 60 minutes.

The assay plate is then centrifuged at 1500 rpm for 2 minutes using the Jouan bench top centrifuge (Jouan Inc., Nantes, France).

The assay plate is counted using a Packard TopCount, each well being counted for 20 seconds.

The volume of enzyme is dependent on the enzymatic activity of the batch in use.

In a more preferred assay, the kinase reaction is performed in a final volume of 10 µl per well of a low volume non-binding CORNING, 384 well black plate (Cat. No. #3676). The final concentrations of ATP and phosphatidyl inositol (PI) in the assay are 1 µM and 10 µg/mL, respectively. The reaction is started by the addition of ATP.

The components of the assay are added per well as follows:

50 nl test compounds in 90% DMSO per well, in columns 1-20, 8 concentrations (1/3 and 1/3.33 serial dilution step) in single.

Low control: 50 nl of 90% DMSO in half the wells of columns 23-24 (0.45% in final).

High control: 50 nl of reference compound (e.g. compound of Example 7 in WO 2006/122806) in the other half of columns 23-24 (2.5 µM in final).

Standard: 50 nl of reference compound as just mentioned diluted as the test compounds in columns 21-22.

20 mL 'buffer' are prepared per assay:
  200 µl of 1M TRIS HCl pH7.5 (10 mM in final)
  60 µl of 1M MgCl$_2$ (3 mM in final)
  500 µl of 2M NaCl (50 mM in final)
  100 µl of 10% CHAPS (0.05% in final)
  200 µl of 100 mM DTT (1 mM in final)
  18.94 mL of nanopure water 10 mL 'PI' are prepared per assay:
  200 µl of 1 mg/mL 1-alpha-Phosphatidylinositol (Liver Bovine, Avanti Polar Lipids Cat. No. 840042C MW=909.12) prepared in 3% OctylGlucoside (10 µg/mL in final)
  9.8 mL of 'buffer'

10 mL 'ATP' are prepared per assay:
  6.7 µl of 3 mM stock of ATP giving a final concentration of 1 µM per well
  10 mL of 'buffer'

2.5 mL of each PI3K construct are prepared per assay in 'PI' with the following final concentration:
  10 nM PI3K alfa EMV B1075
  25 nM beta EMV BV949
  10 nM delta EMV BV1060
  150 nM gamma EMV BV950

5 µl of 'PI/PI3K' are added per well.
5 µl 'ATP' are added per well to start the reaction.
The plates are then incubated at room temperature for 60 minutes (alfa, beta, delta) or 120 minutes (gamma).
The reaction is terminated by the addition of 10 µl Kinase-Glo (Promega Cat. No. #6714).
The assay plates are read after 10 minutes in Synergy 2 reader (BioTek, Vermont USA) with an integration time of 100 milliseconds and sensitivity set to 191.

Output: The High control is around 60'000 counts and the Low control is 30'000 or lower
This luminescence assay gives a useful Z' ratio between 0.4 and 0.7
The Z'value is a universal measurement of the robustness of an assay. A Z' between 0.5 and 1.0 is considered an excellent assay.

For this assay, the PI3K constructs mentioned are prepared as follows:

1.2 Generation of Gene Constructs

Two different constructs, BV 1052 and BV 1075, are used to generate the PI3 Kinase a proteins for compound screening.

PI3Kα BV-1052 p85(iSH2)-Gly Linker-p110a(D20aa)-C-Term His Tag

PCR products for the inter SH2 domain (iSH2) of the p85 subunit and for the p110-a subunit (with a deletion of the first 20 amino acids) are generated and fused by overlapping PCR.

The iSH2 PCR product is generated from first strand cDNA using initially primers

```
                                            (SEQ ID NO: 1)
gwG130-p01  (5'-CGAGAATATGATAGATTATATGAAGAAT-3')
and
                                            (SEQ ID NO: 2)
gwG130-p02  (5'-TGGTTT-AATGCTGTTCATACGTTTGTCAAT-3').
```

Subsequently in a secondary PCR reaction, Gateway (Invitrogen AG, Basel, Switzerland) recombination AttB1 sites and linker sequences are added at the 5'end and 3'end of the p85 iSH2 fragment respectively, using primers

```
gwG130-p03
                                            (SEQ ID NO: 3)
(5'-GGGACAAGTTTGTACAAAAAAGCAGGCTACGAAGGAGATATAC
ATAT-GCGAGAATATGATAGATTATATGAAGAAT-3')
and gwG152-p04
                                            (SEQ ID NO: 4)
(5'-TACCATAATTCCACCACCACCACCGGAAATTCCCCCTGGTTT-
AATGCTGTTCATACGTTTGTCAAT-3').
```

The p110-a fragment is also generated from first strand cDNA, initially using primers

```
gwG152-p01
                                            (SEQ ID NO: 5)
(5'-CTAGTGGAATGTTTACTACCAAATGG-3')
and gwG152-p02
                                            (SEQ ID NO: 6)
(5'-GTTCAATG-CATGCTGTTTAATTGTGT-3').
```

In a subsequent PCR reaction, linker sequence and a Histidine tag are added at the 5'end and 3'end of the p110-a fragment respectively, using primers

```
gw152-p03
                                            (SEQ ID NO: 7)
(5'-GGGGGAATTTCCGGTGGTGGTGGTGGAATTATGGTAC-TAGTG
GAATGTTTACTACC-AAATGGA-3')
and gwG152-p06
                                            (SEQ ID NO: 8)
(5'-AGCTCCGTGATGGTGATGGTGATGTGCTCCGTTCAATG-CATG
CTGTTTAATTGTGT-3').
```

The p85-iSH2/p110-a fusion protein is assembled in a third PCR reaction by the overlapping linkers at the 3'end of the iSH2 fragment and the 5'end of the p110-a fragment, using the above mentioned gwG130-p03 primer and a primer containing an overlapping Histidine tag and the AttB2 recombination sequences

```
(SEQ ID NO: 9)
(5'-GGGACCACTTTGTACAAGAAAGCTGGGTTTAAGCTCCGTGATG
GTGATGGTGAT-GTGCTCC-3').
```

This final product is recombined in a (Invitrogen) OR reaction into the donor vector pDONR201 to generate the ORF318 entry clone. This clone is verified by sequencing and used in a Gateway LR reaction to transfer the insert into the Gateway adapted pBlueBac4.5 (Invitrogen) vector for generation of the baculovirus expression vector LR410.

PI3Kα BV-1075 p85(iSH2)-12 XGly Linker-p110a (D20aa)-C-Term His Tag

The construct for Baculovirus BV-1075 is generated by a three-part ligation comprised of a p85 fragment and a p110-a fragment cloned into vector pBlueBac4.5. The p85 fragment is derived from plasmid p1661-2 digested with Nhe/Spe. The p110-a fragment derived from LR410 (see above) as a SpeI/HindIII fragment. The cloning vector pBlueBac4.5 (Invitrogen) is digested with Nhe/HindIII. This results in the construct PED 153.8

The p85 component (iSH2) is generated by PCR using ORF 318 (described above) as a template and one forward primer

```
KAC1028
                                         (SEQ ID NO: 10)
(5'-GCTAGCATGCGAGAATATGATAGATTATATGAAGAATATACC)
and two reverse primers,
KAC1029
                                         (SEQ ID NO: 11)
(5'-GCCTCCACCACCTCCGCCTGGTTTAATGCTGTTCATACGTTTGTC)
and KAC1039
                                         (SEQ ID NO: 12)
(5'-TACTAGTCCGCCTCCACCACCTCCGCCTCCACCACCTCCGCC).
```

The two reverse primers overlap and incorporate the 12× Gly linker and the N-terminal sequence of the p110a gene to the SpeI site. The 12× Gly linker replaces the linker in the BV1052 construct. The PCR fragment is cloned into pCR2.1 TOPO (Invitrogen). Of the resulting clones, p1661-2 is determined to be correct. This plasmid is digested with Nhe and SpeI and the resulting fragment is gel-isolated and purified for sub-cloning. The p110-a cloning fragment is generated by enzymatic digest of clone LR410 (see above) with Spe I and HindIII. The SpeI site is in the coding region of the p110a gene. The resulting fragment is gel-isolated and purified for sub-cloning.

The cloning vector, pBlueBac4.5 (Invitrogen) is prepared by enzymatic digestion with Nhe and HindIII. The cut vector is purified with Qiagen (Quiagen N.V, Venlo, Netherlands) column and then dephosphorylated with Calf Intestine alkaline phosphatase (CIP) (New England BioLabs, Ipswich, Mass.). After completion of the CIP reaction the cut vector is again column purified to generate the final vector. A 3 part ligation is performed using Roche Rapid ligase and the vendor specifications.

PI3Kβ BV-949 p85(iSH2)-Gly Linker-p110b(Full-Length)-C-Term His Tag

PCR products for the inter SH2 domain (iSH2) of the p85 subunit and for the full-length p110-b subunit are generated and fused by overlapping PCR.

The iSH2 PCR product is generated from first strand cDNA initially using primers

```
gwG130-p01
                                         (SEQ ID NO: 1)
(5'-CGAGAATATGATAGATTATATGAAGAAT-3')
and gwG130-p02
                                         (SEQ ID NO: 2)
(5'-TGGTTT-AATGCTGTTCATACGTTTGTCAAT-3').
```

Subsequently, in a secondary PCR reaction Gateway (Invitrogen) recombination AttB1 sites and linker sequences are added at the 5'end and 3'end of the p85 iSH2 fragment respectively, using primers

```
gwG130-p03
                                         (SEQ ID NO: 3)
(5'-GGGACAAGTTTGTACAAAAAAGCAGGCTACGAAGGAGATA-TA
CATATGCGAGAATATGATAGATTATATGAAGAAT-3')
and
```

```
gwG130-p05
                                         (SEQ ID NO: 13)
(5'-ACTGAAGCATCCTCCTCCTCCTCCTCCTGGTTTAAT-GCTGTT
CATACGTTTGTC-3').
```

The p110-b fragment is also generated from first strand cDNA initially using primers

```
gwG130-p04
                                         (SEQ ID NO: 4)
(5'-ATTAAACCAGGAGGAGGAGGAGGAGGATGCTTCAGTTTCATAA
TGCC-TCCTGCT-3')
``` which contains linker sequences and the 5'end of p110-b and

```
gwG130-p06
                                         (SEQ ID NO: 14)
(5'-AGCTCCGTGATGGTGATGGTGATGTGCTCCAGATCTGTAGTCT
TT-CCGAACTGTGTG-3')
``` which contains sequences of the 3'end of p110-b fused to a Histidine tag.

The p85-iSH2/p110-b fusion protein is assembled by an overlapping PCR a reaction of the linkers at the 3'end of the iSH2 fragment and the 5'end of the p110-b fragment, using the above mentioned gwG130-p03 primer and a primer containing an overlapping Histidine tag and the AttB2 recombination sequences

```
                                         (SEQ ID NO: 15)
(5'-GGGACCACTTTGTACAAGAAAGCTGGGTTT-AAGCTCCGTGAT
GGTGATGGTGATGTGCTCC-3').
```

This final product is recombined in a Gateway (Invitrogen) OR reaction into the donor vector pDONR201 to generate the ORF253 entry clone. This clone is verified by sequencing and used in a Gateway LR reaction to transfer the insert into the Gateway adapted pBlueBac4.5 (Invitrogen) vector for generation of the baculovirus expression vector LR280.

PI3Kδ BV-1060 p85(iSH2)-Gly Linker-p110d(Full-Length)-C-Term His Tag

PCR products for the inter SH2 domain (iSH2) of the p85 subunit and for the full-length p110-d subunit are generated and fused by overlapping PCR.

The iSH2 PCR product is generated from first strand cDNA using initially primers

```
gwG130-p01
                                         (SEQ ID NO: 1)
(5'-CGAGAATATGATAGATTATATGAAGAAT-3')
and gwG130-p02
                                         (SEQ ID NO: 2)
(5'-TGGTTT-AATGCTGTTCATACGTTTGTCAAT-3').
```

Subsequently, in a secondary PCR reaction Gateway (Invitrogen) recombination AttB1 sites and linker sequences are added at the 5'end and 3'end of the p85 iSH2 fragment respectively, using primers

```
gwG130-p03
                                         (SEQ ID NO: 3)
(5'-GGGACAAGTTTGTACAAAAAAGCAGGCTACGAAGGAGATATAC
AT-ATGCGAGAATATGATAGATTATATGAAGAAT-3')
and
```

-continued gwG154-p04
(SEQ ID NO: 16)
(5'-TCCTCCTCCTCCTCCTCCTGGTTTAATGCTGTTCATACGTTTG
TC-3').

The p110-a fragment is also generated from first strand cDNA using initially primers gwG154-p01
(SEQ ID NO: 17)
(5'-ATGCCCCCTGGGGTGGACTGCCCCAT-3')
and gwG154-p02
(SEQ ID NO: 18)
(5'-CTACTG-CCTGTTGTCTTTGGACACGT-3').

In a subsequent PCR reaction linker sequences and a Histidine tag is added at the 5'end and 3'end of the p110-d fragment respectively, using primers gw154-p03
(SEQ ID NO: 19)
(5'-ATTAAACCAGGAGGAGGAGGAGGAGGACCCCCTGGGGTGGAC-
TGCCCCATGGA-3')
and gwG154-p06
(SEQ ID NO: 20)
(5'-AGCTCCGTGATGGTGAT-GGTGATGTGCT-CCCTGCCTGTTGT
CTTTGGACACGTTGT-3').

The p85-iSH2/p110-d fusion protein is assembled in a third PCR reaction by the overlapping linkers at the 3'end of the iSH2 fragment and the 5'end of the p110-d fragment, using the above mentioned gwG130-p03 primer and a primer containing an overlapping Histidine tag and the Gateway (Invitrogen) AttB2 recombination sequences (SEQ ID NO: 21)
(5'-GGGACCACTTTGTA-CAAGAAAGCTGGGTTT-AAGCTCCGTGA
TGGTGATGGTGATGTGCTCC-3').

This final product is recombined in a Gateway (Invitrogen) OR reaction into the donor vector pDONR201 to generate the ORF319 entry clone. This clone is verified by sequencing and used in a Gateway LR reaction to transfer the insert into the Gateway adapted pBlueBac4.5 (Invitrogen) vector for generation of the baculovirus expression vector LR415.

PI3Kv BV-950 p110g(D144aa)-C-Term His Tag

This construct is obtained from Roger Williams lab, MRC Laboratory of Molecular Biology, Cambridge, UK (November, 2003). Description of the construct in: Pacold M. E. et al. (2000) Cell 103, 931-943.

1.3 Protein Expression and Purification

Methods to generate recombinant baculovirus and protein for PI3K isoforms: The pBlue-Bac4.5 (for a, b, and d isoforms) or pVL1393 (for g) plasmids containing the different PI3 kinase genes are co-transfected with Baculo-Gold WT genomic DNA (BD Biosciences, Franklin Lakes, N.J., USA) using methods recommended by the vendor. Subsequently, the recombinant baculovirus obtained from the transfection is plaque-purified on Sf9 insect cells to yield several isolates expressing recombinant protein. Positive clones are selected by anti-HIS or anti-isoform antibody western. For PI3K alpha and delta isoforms, a secondary plaque-purification is performed on the first clonal virus stocks of PI3K. Amplification of all baculovirus isolates is performed at low multiplicity of infection (moi) to generate high-titer, low passage stock for protein. production. The baculoviruses are designated BV1052 (α) and BV1075 (α), BV949 (β), BV1060 (δ) and BV950 (γ).

Protein production involves infection (passage 3 or lower) of suspended Tn5 (*Trichoplusia ni*) or TiniPro (Expression Systems, LLC, Woodland, Calif., USA) cells in protein-free media at moi of 2-10 for 39-48 hours in 2 l glass Erlenmyer flasks (110 rpm) or wave-bioreactors (22-25 rpm). Initially, 10 l working volume wave-bioreactors are seeded at a density of 3e5 cells/mL at half capacity (5 L). The reactor is rocked at 15 rpm during the cell growth phase for 72 hours, supplemented with 5% oxygen mixed with air (0.2 l per minute). Immediately prior to infection, the wave-reactor cultures are analyzed for density, viability and diluted to approximately 1.5e6 cell/mL. 100-500 mL of high titer, low passage virus is added following 2-4 hours of additional culture. Oxygen is increased to 35% for the 39-48 hour infection period and rocking platform rpm increased to 25. During infection, cells are monitored by Vicell viability analyzer (Beckman Coulter, Inc, Fullerton, Calif., USA) bioprocess for viability, diameter and density. Nova Bioanalyzer (NOVA Biomedical Corp., Waltham, Mass., USA) readings of various parameters and metabolites (pH, $O_2$ saturation, glucose, etc.) are taken every 12-18 hours until harvest. The wave-bioreactor cells are collected within 40 hours post infection. Cells are collected by centrifugation (4 degrees C. at 1500 rpm), and subsequently maintained on ice during pooling of pellets for lysis and purification. Pellet pools are made with small amounts of cold, un-supplemented Grace's media (w/o protease inhibitors).

PI3K alpha Purification Protocol for HTS (BV1052)

PI3K alpha is purified in three chromatographic steps: immobilized metal affinity chromatography on a Ni Sepharose resin (GE Healthcare, belonging to General Electric Company, Fairfield, Conn., USA), gel filtration utilizing a Superdex 200 26/60 column (GE Healthcare), and finally a cation exchange step on a SP-XL column (GE Healthcare). All buffers are chilled to 4° C. and lysis is performed chilled on ice. Column fractionation is performed rapidly at room temperature.

Typically frozen insect cells are lysed in a hypertonic lysis buffer and applied to a prepared IMAC column. The resin is washed with 3-5 column volumes of lysis buffer, followed by 3-5 column volumes wash buffer containing 45 mM imidazole, and the target protein is then eluted with a buffer containing 250 mM imidazole. Fractions are analyzed by Coomassie stained SDS-PAGE gels, and fractions containing target protein are pooled and applied to a prepared GFC column. Fractions from the GFC column are analyzed by Coomassie stained SDS-PAGE gels, and fractions containing target protein are pooled. The pool from the GFC column is diluted into a low salt buffer and applied to a prepared SP-XL column. The column is washed with low salt buffer until a stable A280 baseline absorbance is achieved, and eluted using a 20 column volume gradient from 0 mM NaCl to 500 mM NaCl. Again, fractions from the SP-XL column are analyzed by Coomassie stained SDS-PAGE gels, and fractions containing the target protein are pooled. The final pool is dialyzed into a storage buffer containing 50% glycerol and stored at –20° C. The final pool is assayed for activity in a phosphoinositiol kinase assay.

PI3K beta Purification Protocol for HTS (BV949)

PI3K beta is purified in two chromatographic steps: immobilized metal affinity chromatography (IMAC) on a Ni Sepharose resin (GE Healthcare) and gel filtration (GFC)

utilizing a Superdex 200 26/60 column (GE Healthcare). All buffers are chilled to 4° C. and lysis is performed chilled on ice. Column fractionation is performed rapidly at room temperature.

Typically frozen insect cells are lysed in a hypertonic lysis buffer and applied to a prepared IMAC column. The resin is washed with 3-5 column volumes of lysis buffer, followed by 3-5 column volumes wash buffer containing 45 mM imidazole, and the target protein is then eluted with a buffer containing 250 mM imidazole. Fractions are analyzed by Coomassie stained SDS-PAGE gels, and fractions containing target protein are pooled and applied to a prepared GFC column. Fractions from the GFC column are analyzed by Coomassie stained SDS-PAGE gels, and fractions containing target protein are pooled. The final pool is dialyzed into a storage buffer containing 50% glycerol and stored at −20° C. The final pool is assayed for activity in the phosphoinositol kinase assay.

PI3K gamma Purification Protocol for HTS (BV950)

PI3K gamma is purified in two chromatographic steps: immobilized metal affinity chromatography (IMAC) on a Ni Sepharose resin (GE Healthcare) and gel filtration (GFC) utilizing a Superdex 200 26/60 column (GE Healthcare). All buffers are chilled to 4° C. and lysis is performed chilled on ice. Column fractionation is performed rapidly at room temperature. Typically frozen insect cells are lysed in a hypertonic lysis buffer and applied to a prepared IMAC column. The resin is washed with 3-5 column volumes of lysis buffer, followed by 3-5 column volumes wash buffer containing 45 mM imidazole, and the target protein is then eluted with a buffer containing 250 mM imidazole. Fractions are analyzed by Coomassie stained SDS-PAGE gels, and fractions containing target protein are pooled and applied to a prepared GFC column. Fractions from the GFC column are analyzed by Coomassie stained SDS-PAGE gels, and fractions containing target protein are pooled. The final pool is dialyzed into a storage buffer containing 50% glycerol and stored at −20° C. The final pool is assayed for activity in the phosphoinositol kinase assay.

PI3K delta Purification Protocol for HTS (BV1060)

PI3K delta is purified in three chromatographic steps: immobilized metal affinity chromatography on a Ni Sepharose resin (GE Healthcare), gel filtration utilizing a Superdex 200 26/60 column (GE Healthcare), and finally a anion exchange step on a Q-HP column (GE Healthcare). All buffers are chilled to 4° C. and lysis is performed chilled on ice. Column fractionation is performed rapidly at room temperature. Typically frozen insect cells are lysed in a hypertonic lysis buffer and applied to a prepared IMAC column. The resin is washed with 3-5 column volumes of lysis buffer, followed by 3-5 column volumes wash buffer containing 45 mM imidazole, and the target protein is then eluted with a buffer containing 250 mM imidazole. Fractions are analyzed by Coomassie stained SDS-PAGE gels, and fractions containing the target protein are pooled and applied to a prepared GFC column. Fractions from the GFC column are analyzed by Coomassie stained SDS-PAGE gels, and fractions containing the target protein are pooled. The pool from the GFC column is diluted into a low salt buffer and applied to a prepared Q-HP column. The column is washed with low salt buffer until a stable A280 baseline absorbance is achieved, and eluted using a 20 column volume gradient from 0 mM NaCl to 500 mM NaCl. Again, fractions from the Q-HP column are analyzed by Coomassie stained SDS-PAGE gels, and fractions containing the target protein are pooled. The final pool is dialyzed into a storage buffer containing 50% glycerol and stored at −20° C. The final pool is assayed for activity in the phosphoinositol kinase assay.

$IC_{50}$ is determined by a four parameter curve fitting routine that comes along with "excel fit". A four parameter logistic equation is used to calculate $IC_{50}$ values (IDBS XLfit) of the percentage inhibition of each compound at 8 concentrations (usually 10, 3.0, 1.0, 0.3, 0.1, 0.030, 0.010 and 0.003 μM). Alternatively, $IC_{50}$ values are calculated using idbsXLfit model 204, which is a 4 parameter logistic model.

Yet alternatively, for an ATP depletion assay, compounds of the formula I to be tested are dissolved in DMSO and directly distributed into a white 384-well plate at 0.5 μl per well. To start the reaction, 10 μl of 10 nM PI3 kinase and 5 μg/mL 1-alpha-phosphatidylinositol (PI) are added into each well followed by 10 μl of 2 μM ATP. The reaction is performed until approx 50% of the ATP is depleted, and then stopped by the addition of 20 μl of Kinase-Glo solution (Promega Corp., Madison, Wis., USA). The stopped reaction is incubated for 5 minutes and the remaining ATP is then detected via luminescence. $IC_{50}$ values are then determined.

In one embodiment of the present invention, the PI3K inhibitor, wherein said inhibitor has an inhibitory action on the PI3K isoform delta, wherein the range of activity, expressed as $IC_{50}$, in the enzymatic PI3K delta assay is from is between 1 nM and 500 nM.

In another embodiment of the present invention, the PI3K inhibitor, wherein said inhibitor has an inhibitory action on the PI3K isoform delta, wherein the range of activity, expressed as $IC_{50}$, in the enzymatic PI3K delta assay is from is between 1 nM and 100 nM.

In another embodiment of the present invention, the PI3K inhibitor, wherein said inhibitor has an inhibitory action on the PI3K isoform delta, wherein the range of activity, expressed as $IC_{50}$, in the enzymatic PI3K delta assay is from is between 0.5 nM and 10 nM.

In one embodiment of the present invention, the PI3K inhibitor, wherein said inhibitor has an inhibitory action on the PI3K isoform delta, wherein the range of activity, expressed as $IC_{50}$, in the cellular PI3K delta assay is from is between 1 nM and 1000 nM.

In another embodiment of the present invention, the PI3K inhibitor, wherein said inhibitor has an inhibitory action on the PI3K isoform delta, wherein the range of activity, expressed as $IC_{50}$, in the cellular PI3K delta assay is from is between 1 nM and 500 nM.

In another embodiment of the present invention, the PI3K inhibitor, wherein said inhibitor has an inhibitory action on the PI3K isoform delta where the inhibitor shows a selectivity for the PI3K isoform delta over one or more of the other isoforms wherein this selectivity is at least 10 fold.

In another embodiment of the present invention, the PI3K inhibitor, wherein said inhibitor has an inhibitory action on the PI3K isoform delta where the inhibitor shows a selectivity for the PI3K isoform delta over one or more of the other isoforms wherein this selectivity is at least 20 fold.

In another embodiment of the present invention, the PI3K inhibitor, wherein said inhibitor has an inhibitory action on the PI3K isoform delta where the inhibitor shows a selectivity for the PI3K isoform delta over the different paralogs PI3K α and ☐β, wherein this selectivity is at least 10 fold.

In another embodiment of the present invention, the PI3K inhibitor, wherein said inhibitor has an inhibitory action on the PI3K isoform delta where the inhibitor shows a selectivity for the PI3K isoform delta over the different paralogs PI3K α and ☐β, wherein this selectivity is at least 20 fold.

In another embodiment of the present invention, the PI3K inhibitor, wherein said inhibitor has an inhibitory action on the PI3K isoform delta, wherein the range of activity, expressed as $IC_{50}$, in the cellular PI3K delta assay is from is between 1 nM and 500 nM and wherein said inhibitor has an inhibitory action on the PI3K isoform delta where the inhibitor shows a selectivity for the PI3K isoform delta over the different paralogs PI3K α and □β, wherein this selectivity is at least 10 fold.

In another embodiment of the present invention, the PI3K inhibitor, wherein said inhibitor has an inhibitory action on the PI3K isoform delta, wherein the range of activity, expressed as $IC_{50}$, in the cellular PI3K delta assay is from is between 1 nM and 500 nM and wherein said inhibitor has an inhibitory action on the PI3K isoform delta where the inhibitor shows a selectivity for the PI3K isoform delta over the different paralogs PI3K α and □β, wherein this selectivity is at least 20 fold.

2. Cellular Assays 2.1 Phosphoinositide-3 Kinase (PI3K)-Mediated Akt 1/2 (S473) Phosphorylation in Rat-1 Cells Rat-1 cells stably overexpressing a myristoylated form of the catalytic subunit of human phosphoinositide-3 kinase (PI3K) alpha, beta or delta were plated in 384-well plates at a density of 7500 (PI3K alpha), 6200 (PI3K beta), or 4000 (PI3K delta) cells in 30 ul complete growth medium (Dulbecco's modified Eagle's medium (DMEM high glucose) supplemented with 10% (v/v) fetal bovine serum, 1% (v/v) MEM non essential amino acids, 10 mM HEPES, 2 mM L-glutamine, 10 μg/mL puromycin and 1% (v/v) Penicillin/Streptomycin) and were incubated at 37% C/5% $CO_2$/95% humidity for 24 h. Compounds were diluted in 384-well compound plates to obtain 8-point serial dilutions for 40 test compounds in 90% DMSO, as well as 4 reference compounds plus 16 high controls and 16 low (inhibited) controls. Predilution plates were prepared by dispensing pipetting 250 nl of compound solutions into 384-well polypropylen plates using a Hummingwell nanoliter dispensor. Compounds were prediluted by the addition of 49.75 ul complete growth medium. 10 ul of prediluted compound solution were transferred to the cell plate using a 384-well pipettor, resulting in a final DMSO concentration of 0.11%. Cells were incubated for 1 h at 37% C/5% $CO_2$/95% humidity. The supernatant was removed, the cells were lysed in 20 ul of lysis buffer for AlphaScreen® SureFire® detection.

For detection of p-AKT(Ser473), the SureFire® p-Akt 1/2 (Ser473) Assay Kit (PerkinElmer, U.S.A.) was used. 5 ul of cell lysate was transferred to 384-well low volume Proxiplates for detection using a 384-well pipettor. Addition of AlphaScreen® SureFire® reagents was done according to the manufacturer's protocol. First, 5 ul of reaction buffer plus activation buffer mix containing AlphaScreen® acceptor beads was added, the plate was sealed, and incubated on a plate shaker for 2 hours at room temperature. Second, 2 ul of dilution buffer containing AlphaScreen® donor beads was added, and the plate was incubated on plate shaker as above for a further 2 hours. The plate was read on an AlphaScreen® compatible plate reader, using standard AlphaScreen® settings.

2.2 Determination of Murine B Cell Activation

PI3Kδ has been recognized to modulate B cell function when cells are stimulated through the B cell receptor (BCR) (Okkenhaug et al. Science 297:1031 (2002). For assessing the inhibitory property of compounds on B cell activation, the upregulation of activation markers CD86 and CD69 on murine B cells derived from mouse spleen antibody is measured after stimulation with anti-IgM. CD69 is a well known activation marker for B and T cells (Sancho et al. Trends Immunol. 26:136 (2005). CD86 (also known as B7-2) is primarily expressed on antigen-presenting cells, including B cells. Resting B cells express CD86 at low levels, but upregulate it following stimulation of e.g. the BCR or IL-4 receptor. CD86 on a B cell interacts with CD28 on T cells. This interaction is required for optimal T cell activation and for the generation of an optimal IgG1 response (Carreno et al. Annu Rev Immunol. 20:29 (2002)).

Spleens from Balb/c mice are collected, splenocytes are isolated and washed twice with RPMI containing 10% foetal bovine serum (FBS), 10 mM HEPES, 100 Units/mL penicilline/streptomycine. RPMI supplemented in this way is subsequently referred to as medium. The cells are adjusted to $2.5×10^6$ cells/mL in medium and 200 μl cell suspension ($5×10^6$ cells) are added to the appropriate wells of 96 well plates.

Then the cells are stimulated by adding 50 μl anti-IgM mAb in medium (final concentration: 30 μg/mL). After incubation for 24 hours at 37° C., the cells are stained with the following antibody cocktails: anti-mouse CD86-FITC, anti-mouse CD69-PerCP-Cy5.5, anti-mouse CD19-PerCP for the assessment of B cells, and anti-mouse CD3-FITC, anti-mouse CD69-PE for the assessment of T cells (2 μl of each antibody/well). After one hour at room temperature (rt) in the dark the cells are transferred to 96 Deepwell plates. The cells are washed once with 1 mL PBS containing 2% FBS and after re-suspension in 200 μl the samples are analyzed on a FACS Calibur flow cytometer. Lymphocytes are gated in the FSC/SSC dot plot according to size and granularity and further analyzed for expression of CD19, CD3 and activation markers (CD86, CD69). Data are calculated from dot blots as percentage of cells positively stained for activation markers within the CD19+ or CD3+ population using BD CellQest Software.

For assessing the inhibitory property of compounds, compounds are first dissolved and diluted in DMSO followed by a 1:50 dilution in medium. Splenocytes from Balb/c mice are isolated, re-suspended and transferred to 96 well plates as described above (200 μl/well). The diluted compounds or solvent are added to the plates (25 μl) and incubated at 37° C. for 1 hour. Then the cultures are stimulated with 25 μl anti-IgM mAb/well (final concentration 30 μg/mL) for 24 hours at 37° C. and stained with anti-mouse CD86-FITC and anti-mouse CD19-PerCP (2 μl of each antibody/well). CD86 expression on CD19 positive B cells is quantified by flow cytometry as described above.

2.3 Determination of Rat B Cell Activation

PI3Kδ has been recognized to modulate B cell function when cells are stimulated through the B cell receptor (BCR) (Okkenhaug et al. Science 297:1031 (2002). For assessing the inhibitory property of compounds on B cell activation, the upregulation of activation markers CD86 on rat B cells derived from whole blood is measured after stimulation with anti-IgM and recombinant IL-4. The CD86 molecule (also known as B7-2) is primarily expressed on antigen-presenting cells, including B cells. Resting B cells express CD86 at low levels, but upregulate it following stimulation of e.g. the BCR or IL-4 receptor. CD86 on a B cell interacts with CD28 on T cells. This interaction is required for optimal T cell activation and for the generation of an optimal IgG1 response (Carreno et al. Annu Rev Immunol. 20:29 (2002)).

Collection of Rat Blood

Whole blood was collected from the abdominal aorta adult male Lewis rats (LEW/HanHsd) oby using a 10 ml syringe with hypodermic needle pre-coated with sodium heparin. Blood was transferred into 50 ml Falcon tubes and the anticoagulant concentration was adjusted to 100 U/ml.

Stimulation of Rat B Cells and Treatment with Specific Inhibitor

For assessment of the in vitro effects of immunosuppressive drugs, heparinized blood was prediluted to 50% with medium. As medium served DMEM high glucose (Animed cat#1-26F01-I) supplemented with 100 U/ml penicillin, 100 mg/ml streptomycin, 2 mM L-glutamin, 50 mg/ml dextran 40 and 5% fetal calf serum (FCS, Fetaclone I, Gibco #10270-106). Then, 190 µl prediluted blood was spiked with 10 µl of pre-diluted test compound in 96 well U-bottomed microtiter plates (Nunc) resulting in a 3-fold serial dilution with a concentration range from 20 to 0.0003 µM. Control wells were pretreated with DMSO to obtain a final concentration of 0.5% DMSO. Cultures were set up in duplicates, mixed well by agitation on a plate shaker (Heidolph Titramax 101; 30 sec, speed 900), pipetting up and down and agitated on the plate shaker again. Cultures were incubated at 37° C., 5% $CO_2$ for 1 hr. Then, 20 µl of polyclonal goat anti-rat IgM Ab (Serotec, cat#302001) and 10 µl of diluted recombinant rIL-4 (Immunotools #340085) were added to obtain final concentrations of 30 µg/ml and 5 ng/ml, respectively. Plates were mixed by agitation on a plate shaker as above and incubated for 24 hrs at 37° C., 5% $CO_2$.

Determination of B Cell Activation by Flow Cytometry

After incubation, 15 µl of a 25 mM EDTA solution was added per well and shaken for 15 min to detach adherent cells. For analysis of surface activation markers, samples were then stained with PE-Cy5-labeled anti-ratCD45RA (BD cat#557015) to allow gating on B cells in FACS analysis. In addition, samples were stained with PE-labeled anti-rat CD86 (BD cat#551396). All staining procedures were performed at rt for 30 min in the dark. After incubation, samples were transferred to 96-deep well V-bottomed microtiter plates (Corning #396096) containing 2 ml/well of BD Lysing Solution (BD #349202). After lysis of erythrocytes samples were washed with 2 ml of CellWASH (BD #349524). Data was acquired on an LSRII or FACScalibur flow cytometer (BD Biosciences) using Cellquest Plus or DIVA (version 6.1.1) software, respectively. Lymphocytes were gated in the FSC/SSC dot blot according to size and granularity and further analyzed for expression of CD45RA and activation markers. Data were calculated from dot blots or histograms as percentage of cells positively stained for activation markers within the CD45RA+ population.

Statistical Evaluation

The percentage inhibition of B cell activation after exposure to drug was calculated by the following formula:

$$\% \text{ Inhibition} = 100 \times \frac{\text{stimulation without drug} - \text{stimulation with drug}}{\text{stimulation without drug} - \text{unstimulated}}$$

ORIGIN 7 software (OriginLab Corporation, Northampton, Mass.) was used for non-linear regression curve fitting. The drug concentration resulting in 50% inhibition ($IC_{50}$) was obtained by fitting the Hill equation to inhibition data.

2.4 Determination of TLR9-Induced IL-6 in Mouse Splenocytes

Preparation of Single Cell Suspension from Mouse Spleen

Spleens were dissected from C57BL/6 mice immediately following euthanasia. Excess fat was trimmed from the spleens prior to mashing the spleen through a 0.4 µM cell strainer using a plunger from a 5 ml syringe. A single cell suspension was prepared and the volume was adjusted to 15 ml in a 50 ml Falcon tube using cold PBS. Cells were centrifuged at 1500 rpm for 5 minutes at 4° C. degrees prior to removal of supernatant and re-suspension in 5 ml of red blood cell lysis buffer per spleen and incubation for 5 minutes at room temperature. Ice cold PBS (30 ml) was added to the cells prior to centrifugation at 1500 rpm for 5 minutes at 4° C. The supernatant was removed and the cells were washed twice with 40 ml of murine splenocyte culture media (MSCM). MSCM consisted of RPMI supplemented with 100 units/ml Penicillin and 100 µg/ml Streptomycin, 1×nonessential amino acids, 1 mM Sodium Pyruvate, 0.05 mM β-mercaptoethanol, and 10% heatinactivated Fetal Bovine Serum (FBS). Cells were re-suspended in 10-20 ml of MSCM and counted using a Countess cell counter. Approximately $60 \times 10^6$ splenocytes were obtained from a single C57BL/6 mouse spleen.

Stimulation of Murine Splenocytes and Treatment with Specific Inhibitor

Splenocytes were plated at a final density of $2 \times 10^5$ cells/well in a volume of 100 µl in 96 well flat bottomed plates and incubated in a humidified 37° C. incubator for 2-4 hours. Afterwards, compounds to be tested were dispensed using an automated liquid handling machine using previously prepared compound stock plates. Stock plates consisted of compounds (in 90%/10% DMSO/dd$H_2$O) arrayed in 8-10 point using 2- or 3-fold dilutions. The liquid handling machine dispensed 1 µl of each dilution from the previously prepared compound source plate into the appropriate destination well in the 96-well plate. The final starting concentration of the compounds in the cell culture was 10 µM. The final concentration of DMSO in the cell cultures was 0.5%. Cells were incubated with compounds for 1 hour prior to addition of TLR ligand. Then, a 10× $EC_{80}$ concentration of CpG1826 was added in a volume of 20 µl (for a final culture volume of 200 µl) whereupon cultures were incubated overnight in a humidified 37° C. incubator.

Determination of Interleukin-6 by ELISA

After overnight culture, plates were centrifuged at 2000 rpm for 5 minutes at room temperature. Subsequently 150 µl of each culture was transferred to 96-well V-bottomed plates and IL-6 levels were measured using commercially available mouse IL-6 sandwich ELISA kit. Briefly, plates were coated overnight with the capture antibody prior to blocking for 1 hour with PBS/0.1% BSA. Samples and standards were added in a volume of 50 µl and the plate was incubated for 2 hours at room temperature. After removal of the standards/samples, the plate was washed using PBS/0.05% Tween prior to addition of 50 µl of the biotinylated detection antibody whereupon the plate was incubated for 2 hours at room temperature with agitation. Plates were washed again prior to addition of 50 µl streptavidin-horseradish peroxidase per well for 20 minutes. Following additional plate washes 50 µl TMB substrate was added to each well and plates were incubated for 20 minutes prior addition of 25 µl/well stop solution. IL-6 levels were measured using a SpectraMax 190 Plate Reader (450 nm) and analyzed using SoftMax Pro and GraphPad Prism software.

2.5 Determination of TLR9-Induced IFNalpha in Human Peripheral Blood Mononuclear Cells (PBMC)

Preparation of PBMC from Fresh Human Blood

Human blood (ca. 75 ml) was collected in 10 S-Monovette tubes containing Heparin (S-Monovette 7.5 mL NH Heparin 16 IU/mL blood; Starstedt). Leucosep™ tubes (30 mL #227290; Greiner Bio-one) were prepared by addition of 15 ml lymphocyte separation medium LSM1077™ per tube (#J15-004; PAA Laboratories) and centrifugation for 30 sec at 1000 g. Some 25 ml blood was transferred to Leucosep™ tubes following dilution with equal parts of PBS (without Ca2+/Mg2+; #14190-094). Samples were centrifuged at 800 g for 20 min at 22° C. using an Eppendorf 5810R centrifuge without brake. The PBMC layer was carefully removed from plasma:separation medium interface and transferred into clean 50 ml tube. Cells were washed once by addition of PBS (up to 45 ml) and centrifuged (1400 rpm, 10 min at 22° C.) with brake (set at speed 9) using an Eppendorf 5810R. Pelleted cells were carefully resuspended in Media (RPMI 1640+GlutaMAX-I, 0.05 mM 2-mercaptoethanol, 10 mM HEPES and 5% v/v FCS) and samples pooled. The medium components 2-mercaptoethanol (#31350-010; 50 mM), Hepes (#15630-056, 1M) and RPMI 1640 (1×)+GlutaMAX-I (#61870-010) were obtained from Gibco. FCS (#2-01F36-1) was obtained from Amimed. The PBMC were counted using a Countess® Automated cell counter (sample was pre-diluted 1:10 in Media, prior to the addition of equal volume (10 µl) of Trypan Blue). Cells were diluted to $4 \times 10^6$ cells/ml and seeded in 384-well plates (#353962; Becton Dickinson AG) to give a final volume of 25 µl (i.e. $1 \times 10^5$ cells/well).

Stimulation of PBMC and Treatment with Specific Inhibitor

Compounds were pre-diluted in 100% v/v DMSO (#41640-100 mL; Sigma-Aldrich), followed by transfer in Media (to achieve a final DMSO concentration of 0.25%). Cells were treated with appropriate compound dilution (5 µl) or vehicle control (5 µl) and incubated for 30 min at 37° C. in a humidified incubator in air with 5% (v/v) $CO_2$. Cells were stimulated with CpG2216 (0.3 µM; #tlrl-hodna; Invivogen) or vehicle control (10 µl/well) and incubated for 20 h. Plates were briefly centrifuged (200×g for 2 min at 22° C.) and supernatant samples (30 µl) removed for quantification of IFNα levels.

Quantification of IFNα Using AlphaLisa Technology

For quantification of IFNalpha the human interferon AlphaLISA Kit (#AL264F) from PerkinElmer was used. An antibody mix containing anti-IFNα acceptor beads (5 µg/ml final) and biotinylated antibody anti-IFNα (0.5 nM final) is prepared fresh and dispensed (5 µl) into 384-well Optiplates™ (#6007299; PerkinElmer). Dilution of known IFNα standards (human IFNα B (2b)) were prepared and together with cell supernatants (5 µl) were added to plates above. Plates were briefly centrifuged (pulse at 200 g), covered with adhesive sealing film, vortexed and incubated 1 h at room temperature in the dark. Streptavidin-coated donor beads (20 µg/ml final) was prepared and added to each well (5 µl) in a dark lit area (light sensitive mix). Plates were incubated 30 min at room temperature (Pates must not be centrifuged or covered). After incubation, the plates were read with an EnVision™ multiplate reader equipped with the ALPHA option using the instrument's own "AlphaScreen standard settings" (e.g. total measurement time: 550 ms, Laser 680 nm excitation time: 180 ms, mirror: D640 as, emission filter: M570w, center wavelength 570 nm, bandwidth 100 nm, transmittance 75%). Data were collected for analysis and quantification of IFNα levels.

Data Evaluation and Analysis

Data were analysed using Excel XL fit 4.0 (Microsoft) with XLfit add-in (IDBS; version 4.3.2). Specific IFNα concentrations were determined following extrapolation to standard curves using human IFNα B (2b). Individual $IC_{50}$ values of compounds were determined by nonlinear regression after fitting of curves to the experimental data.

3 Determination of Antibody Production to Sheep Red Blood Cells (SRBC).

In brief, OFA rats were injected i.v. with sheep erythrocytes on d0 and treated orally on four consecutive days (d0 to d3) with the compounds under investigation. Spleen cell suspensions were prepared on d4 and lymphocytes were plated onto soft agar in presence of indicator cells (SRBC) and complement. Lysis of the indicator cells due to secretion of SRBC-specific antibody (predominantly of the IgM subclass) and presence of complement yielded plaques. The number of plaques per plate were counted and expressed as number of plaques per spleen.

Immunization:

Groups of five female OFA rats were immunized on day 0 with $2 \times 10^8$/ml SRBC (obtained from Laboratory Animal Services LAS, Novartis Pharma AG) in a volume of 0.5 ml per rat by i.v. injection.

Compound Treatment:

Animals were treated with compound suspended in 0.5% CMC, 0.5% Tween80 in for 4 consecutive days (days 0, 1, 2 and 3) starting on the day of immunization. Compound was administered orally twice daily with 12 hours intervalls between doses in an application volume of 5 ml/kg body weight.

Preparation of Spleen Cell Suspensions:

On day 4, animals were euthanized with $CO_2$. Spleens were removed, weighed, and deposited in plastic tubes containing 10 ml of cold (4° C.) Hank's balanced salt solution (HBSS; Gibco, pH 7.3, containing 1 mg Phenol red/100 ml) for each rat spleen. Spleens were homogenized with a glass potter, left on ice for 5 minutes and 1 ml supernatant was transferred into a new tube. Cells were washed once in 4 ml HBSS then supernatants were discarded and pellets re-suspended in 1 ml of HBSS. Lymphocyte numbers per spleen were determined by automated cell counter and spleen cell suspensions were adjusted to a cell concentration of $30 \times 10^6$/ml.

Plaque Forming Assay:

Soft agar petri dishes were prepared with 0.7% agarose (SERVA) in HBSS.

In addition, one ml of 0.7% agarose was prepared in plastic tubes and kept at 48° C. in a water bath. Some 50 µl of a $30 \times 10^6$/ml spleen cell suspension and 50 µl of SRBC at $40 \times 10^8$/ml were added, mixed rapidly (Vortex) and poured onto the prepared agarose dishes. Petri dishes were slightly tilted to achieve even distribution of cell mixture on agarose layer. The dishes were left at room temperature for 15 minutes and were then incubated at 37° C. for 60 minutes. Then, 1.4 ml guinea pig complement (Harlan; 10%) was added and the incubation continued for another 60 minutes at 37° C. SRBC-specific antibodies released by the plated-out B cells bound to the antigen (SRBC) in their vicinity. These antigen-antibody complexes activated complement and led to the lysis of the SRBC leaving a bright spot (plaque) within the red erythrocyte layer. Plaques were counted with a microscope.

The following formula for determination of inhibition of plaque formation was used:

$$\% \text{ Inhibition} = C*100/V - 100$$

with: V=mean number of plaques/spleen for vehicle group; C=mean number of plaques/spleen for compound treated group

REFERENCES

N. K. Jerne & A. A. Nordin (1963) Plaque formation in agar by single antibody-producing cells. Science 140:405.

N. K. Jerne, A. A. Nordin & C. Henry (1963) The agar plaque technique for recognizing antibody-producing cells. In: "Cell Bound Antibodies", B. Amos & H. Koprowski, Eds., Wistar Inst. Press, Philadelphia pp. 109-125.

Biological Data
Enzymatic Assay

| Example | PI3K alpha (uM) | PI3K delta (uM) |
|---|---|---|
| A1 | 0.322 | 0.006 |
| A2 | 0.047 | 0.006 |
| A3 | 0.313 | 0.003 |
| A4 | >9.1 | |
| A5 | 4.663 | 0.037 |
| A6 | 0.377 | 0.009 |
| A7 | 1.915 | 0.031 |
| A8 | 5.928 | 0.04 |
| A9 | 0.410 | 0.014 |
| A10 | 0.220 | 0.018 |
| A11 | 2.279 | 0.069 |
| A12 | 0.182 | 0.003 |
| A13 | 0.292 | 0.005 |
| A14 | >9.1 | 5.399 |
| A15 | 4.892 | 0.184 |
| A16 | >9.1 | 0.323 |
| A17 | 0.104 | 0.014 |
| A18 | 0.895 | 0.011 |
| A19 | 7.547 | 0.38 |
| A20 | >9.1 | |
| A21 | 8.429 | |
| A22 | 0.757 | 0.021 |
| A23 | 1.573 | 0.17 |
| A24 | 6.878 | 0.317 |
| A25 | 5.755 | |
| A26 | 0.152 | 0.022 |
| A27 | >9.1 | |
| A28 | 0.531 | 0.016 |
| A29 | 2.730 | 0.042 |
| A30 | 0.260 | 0.031 |
| A31 | 6.022 | 0.088 |
| A32 | 3.195 | 0.074 |
| A33 | 1.702 | 0.085 |
| A34 | 0.773 | 0.009 |
| A35 | 5.589 | 1.419 |
| A36 | 1.269 | 0.078 |
| A37 | 0.370 | 0.078 |
| A38 | 0.343 | 0.064 |
| A39 | 0.071 | 0.009 |
| A40 | 5.361 | 0.462 |
| A41 | 2.794 | 0.296 |
| A42 | 1.141 | 0.03 |
| A43 | 4.689 | 0.054 |
| B1 | 0.390 | 0.014 |
| B2 | 1.641 | 0.026 |
| B3 | >9.1 | |
| B4 | 1.234 | 0.083 |
| B5 | 0.236 | 0.025 |
| B6 | 2.242 | 0.11 |
| B7 | 3.544 | 0.114 |
| B8 | 0.188 | 0.025 |
| B9 | 1.770 | 0.078 |
| B10 | 0.870 | 0.035 |
| B11 | 0.823 | 0.014 |
| B12 | 0.365 | 0.011 |
| B13 | 0.862 | 0.062 |
| B14 | 0.244 | 0.006 |
| B15 | 2.647 | 0.031 |
| B16 | 4.117 | 0.037 |
| B17 | 2.087 | 0.023 |
| B18 | 0.723 | 0.012 |
| B19 | 1.158 | 0.033 |
| B20 | 0.339 | 0.047 |
| B21 | 0.666 | 0.013 |
| B22 | 0.589 | 0.005 |
| B23 | 1.004 | 0.028 |
| B24 | 0.212 | 0.008 |
| B25 | 0.665 | 0.04 |
| B26 | 0.281 | <0.009 |
| B27 | 2.507 | 0.055 |
| B28 | 0.788 | 0.012 |
| B29 | 0.558 | 0.041 |
| B30 | 0.216 | 0.0155 |
| B31 | 0.977 | 0.003 |
| B32 | 0.369 | 0.036 |
| B33 | 0.610 | <0.009 |
| B34 | 0.795 | 0.046 |
| B35 | 1.387 | 0.027 |
| B36 | 0.801 | <0.003 |
| B37 | 1.104 | 0.103 |
| B38 | 0.166 | 0.003 |
| B39 | 0.176 | 0.011 |
| B40 | 0.249 | 0.012 |
| B41 | 0.421 | 0.025 |
| B42 | 0.502 | 0.033 |
| B43 | 0.514 | 0.057 |
| B44 | 0.071 | 0.022 |
| B45 | 0.574 | 0.0745 |
| B46 | 2.076 | 0.2265 |
| B47 | 0.241 | 0.0106667 |
| B48 | 0.109 | 0.007 |
| B49 | 0.450 | 0.007 |
| B50 | 0.933 | 0.013 |
| B51 | 1.026 | 0.01 |
| B52 | 0.556 | <0.003 |
| B53 | 0.343 | 0.0045 |
| B54 | 0.756 | 0.011 |
| B55 | 3.850 | 0.065 |
| B56 | 1.415 | 0.023 |
| B57 | 2.270 | 0.095 |
| B58 | 0.366 | 0.004 |
| B59 | 0.461 | 0.017 |
| B60 | 0.463 | 0.011 |
| B61 | 0.732 | 0.037 |
| B62 | 0.496 | 0.041 |
| B63 | 1.518 | 0.068 |
| B64 | 0.193 | 0.032 |
| B65 | 0.795 | 0.035 |
| B66 | 0.446 | 0.011 |
| B67 | 0.804 | 0.025 |
| B68 | 0.840 | 0.039 |
| B69 | 0.189 | 0.005 |
| B70 | 0.134 | 0.003 |
| B71 | 0.360 | 0.0055 |
| B72 | 2.057 | 0.032 |
| B73 | 1.771 | 0.03 |
| B74 | 0.054 | 0.009 |
| B75 | 0.211 | 0.011 |
| B76 | 0.399 | 0.061 |
| B77 | 0.897 | 0.032 |
| B78 | 0.243 | 0.023 |
| B79 | 0.661 | 0.003 |
| B80 | 0.295 | 0.004 |
| B81 | 0.482 | 0.081 |
| B82 | 0.353 | 0.066 |
| B83 | 0.214 | 0.029 |
| B84 | 0.346 | 0.08 |
| B85 | | |
| B86 | 6.626 | 0.061 |
| B87 | 7.092 | 0.029 |
| B88 | 0.234 | 0.008 |
| B89 | 0.133 | 0.009 |
| B90 | 1.456 | 0.011 |
| B91 | 0.353 | 0.012 |
| B92 | 0.346 | 0.008 |
| B93 | 0.525 | 0.004 |
| B94 | 0.416 | 0.005 |
| B95 | 0.438 | 0.009 |
| B96 | >9.1 | 0.118 |
| B97 | 0.476 | 0.0215 |
| B98 | 0.910 | 0.013 |

| Example | PI3K alpha (uM) | PI3K delta (uM) |
| --- | --- | --- |
| B99 | 0.302 | 0.057 |
| B100 | 0.567 | 0.014 |
| B101 | 0.471 | 0.015 |
| B102 | 0.209 | 0.01025 |
| B103 | 0.241 | 0.046 |
| B104 | 1.374 | 0.162 |
| B105 | 0.762 | 0.02 |
| B106 | 0.247 | 0.017 |
| B107 | 0.239 | 0.004 |
| B108 | 0.094 | <0.003 |
| B109 | 0.118 | <0.003 |
| B110 | 0.148 | 0.003 |
| B111 | 0.685 | 0.06 |
| B112 | 0.38 | 0.026 |
| B113 | 2.73 | 0.109 |
| B114 | 1.440 | 0.071 |
| B115 | 0.468 | 0.023 |
| B116 | 0.304 | 0.022 |
| B117 | 1.212 | 0.008 |
| B118 | 0.498 | 0.01 |
| B119 | 0.124 | 0.006 |
| B120 | 0.088 | 0.006 |
| B121 | 3.357 | 0.075 |
| B122 | 0.425 | 0.024 |
| C1 | 0.300 | 0.0190 |
| C2 | 1.218 | 0.243 |
| C3 | 3.377 | 1.207 |
| C4 | 3.001 | 0.028 |
| C5 | 5.510 | 0.095 |
| C6 | 4.259 | 0.181 |
| C7 | >9.1 | |
| C8 | 0.374 | 0.013 |
| C9 | 0.185 | 0.006 |
| C10 | 0.147 | 0.015 |
| C11 | 0.353 | 0.023 |
| C12 | 0.303 | 0.116 |
| C13 | 0.667 | 0.077 |
| C14 | 0.250 | 0.005 |
| C15 | 0.383 | 0.017 |
| C16 | 0.478 | 0.015 |
| C17 | 0.358 | 0.008 |
| C18 | 0.425 | 0.012 |
| C19 | 0.488 | 0.021 |
| C20 | 0.193 | 0.006 |
| C21 | 0.698 | 0.028 |
| C22 | 0.202 | 0.02 |
| C23 | 0.658 | 0.032 |
| C24 | 0.560 | 0.003 |
| C25 | 0.474 | 0.0125 |
| C26 | 6.946 | 3.219 |
| D1 | 0.424 | 0.005 |
| D2 | 2.743 | 0.149 |
| D3 | 4.418 | 0.219 |
| D4 | 0.236 | |
| D5 | 0.802 | 0.042 |
| D6 | 0.650 | 0.009 |
| D7 | 0.234 | |
| D8 | 0.463 | 0.011 |
| D9 | 0.494 | 0.015 |
| D10 | 0.385 | 0.062 |
| D11 | 0.442 | 0.019 |
| D12 | 0.142 | <0.003 |
| D13 | 0.5225 | 0.005 |
| D14 | 0.415 | |
| D15 | 0.711 | 0.058 |
| D16 | 0.503 | 0.007 |
| D17 | 0.705 | 0.012 |
| D18 | 0.281 | 0.019 |
| D19 | 0.273 | 0.013 |
| D20 | 0.206 | 0.007 |
| D21 | 0.519 | 0.041 |
| D22 | 1.018 | 0.024 |
| D23 | 2.534 | 0.214 |
| D24 | >9.1 | 7.085 |
| D25 | >9.1 | 2.693 |
| D26 | 1.236 | 0.028 |
| D27 | 1.574 | 0.064 |
| D28 | 0.411 | 0.005 |
| D29 | 0.534 | 0.003 |
| D30 | 5.150 | 0.127 |
| D31 | 0.135 | 0.009 |
| D32 | 0.094 | 0.009 |
| D33 | 0.117 | 0.008 |
| D34 | 0.273 | 0.009 |
| D35 | 0.414 | <0.003 |
| D36 | 0.346 | |
| D37 | 0.298 | 0.127 |
| D38 | 0.516 | 0.018 |
| D39 | 0.987 | 0.036 |
| D40 | 0.7045 | 0.025 |
| E1 | 0.098 | 0.004 |
| E2 | | |
| E3 | 0.494 | <0.003 |
| E4 | 0.870 | 0.010 |
| E5 | | |
| E6 | 0.341 | 0.009 |
| E7 | 0.133 | 0.022 |
| E8 | | |
| E9 | 0.593 | 0.007 |
| E10 | 0.229 | 0.013 |
| E11 | 0.377 | <0.003 |
| F1 | 0.109 | 0.003 |
| F2 | 0.725 | 0.005 |
| F3 | 0.337 | 0.006 |
| F4 | 0.577 | 0.003 |
| F5 | 0.444 | 0.025 |
| F6 | 0.783 | 0.003 |
| F7 | 0.071 | <0.003 |
| F8 | 0.038 | 0.005 |
| F9 | 0.028 | <0.003 |
| F10 | 0.039 | <0.003 |
| F11 | 0.078 | 0.076 |
| F12 | 0.440 | <0.003 |
| F13 | 0.704 | 0.024 |
| G1 | 0.049 | 0.017 |
| G2 | 1.195 | 0.207 |
| G3 | 0.372 | 0.056 |
| H1 | 0.850 | 0.008 |
| H2 | 0.913 | 0.013 |
| H3 | 0.559 | 0.008 |
| H4 | 0.8475 | 0.011 |
| H5 | 0.477 | 0.011 |
| H6 | 0.846 | 0.053 |
| H7 | 0.703 | 0.005 |
| H8 | 0.521 | 0.007 |
| H9 | 0.616 | 0.011 |
| H10 | 0.727 | 0.018 |
| H11 | 0.299 | 0.008 |
| H12 | 0.530 | 0.007 |
| H13 | 0.387 | 0.009 |
| H14 | 0.103 | 0.005 |
| H15 | 0.724 | 0.008 |
| H16 | 0.871 | 0.016 |
| I1 | 0.842 | 0.018 |
| I2 | 0.308 | 0.005 |
| I3 | 0.836 | 0.006 |
| J | 0.998 | 0.065 |
| K | 0.393 | <0.003 |
| L | 0.538 | 0.013 |
| M | 0.304 | 0.006 |
| N | 0.838 | 0.012 |
| O1 | 4.574 | 0.053 |
| O2 | 5.692 | 0.049 |
| P | 0.954 | 0.072 |
| Q | 1.144 | 0.014 |
| R | 0.602 | 0.011 |
| S | 0.612 | 0.036 |
| T | 1.876 | 0.076 |
| U | 0.192 | 0.015 |
| V | 3.196 | 0.079 |
| W | 2.979 | 0.056 |
| X | 3.575 | 0.061 |
| Y | 1.925 | |

Cellular Assays

| Example | Cell PI3Kδ/ IC50 [umol l−1] | RWB/IC50 CD86 [nmol l−1] |
|---|---|---|
| A1 | 0.043 | 37 |
| B1 | 0.154 | 29 |
| C1 | 0.081 | 68 |
| D1 | 0.147 | 84 |
| E1 | 0.007 | 78 |
| E3 | 0.018 | 14 |
| F1 | 0.011 | 7 |
| F3 | 0.050 | |
| F7 | 0.018 | 40 |
| Q | 0.145 | 37 |

The invention claimed is:

1. A method of inhibiting the activity of PI3Kδ isoform in a subject, wherein the method comprises administering to the subject a therapeutically effective amount of a compound according Formula (I):

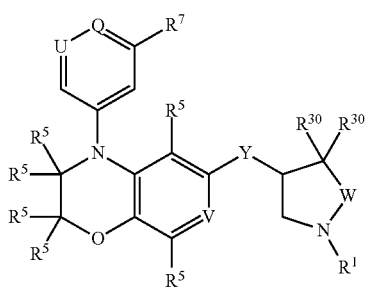

or a pharmaceutically acceptable salt thereof, wherein
Y is selected from O or NH;
V is selected from $CR^5$ or N;
W is selected from $CH_2$, or O;
U is selected from N or CH;
Q is selected from N or $CR^6$;
wherein U and Q are not both N;
$R^1$ is selected from phenyl, pyridyl, pyrimininyl, pyrazinyl, pyridazinyl, 1,2,3-triazinyl, 1,2,4-triazinyl, 1,3,5-triazinyl,
or
—X—$R^4$
wherein X is selected from C(O), S(O)$_2$ or $CH_2$ and
$R^4$ is selected from $C_1$-$C_8$-alkyl, halo-$C_1$-$C_8$-alkyl, hydroxy-$C_1$-$C_8$-alkyl, $C_1$-$C_8$-alkoxy-$C_1$-$C_8$-alkyl, cyano-$C_1$-$C_8$-alkyl, N,N-di-$C_1$-$C_4$-alkyl-amino-$C_1$-$C_8$-alkyl, $C_1$-$C_4$-alkyl-sulfonyl-$C_1$-$C_8$-alkyl, phenyl, heterocyclyl, heterocyclyl-oxy, heterocyclyl-$C_1$-$C_8$-alkyl, $C_3$-$C_{12}$-cycloalkyl, $C_3$-$C_{12}$-cycloalkyl-oxy, $C_3$-$C_{12}$-cycloalkyl-$C_1$-$C_8$-alkyl, heteroaryl, heteroaryl-oxy, heteroaryl-$C_1$-$C_8$-alkyl, hydroxy, $C_1$-$C_8$-alkoxy, amino, N—$C_1$-$C_8$-alkyl-amino or N,N-di-$C_1$-$C_8$-alkyl-amino,
wherein $C_1$-$C_8$-alkyl in N—$C_1$-$C_8$-alkyl-amino and in N,N-di-$C_1$-$C_8$-alkyl-amino may be unsubstituted or substituted by halogen, hydroxy or $C_1$-$C_4$-alkoxy,
wherein $C_3$-$C_{12}$-cycloalkyl in $C_3$-$C_{12}$-cycloalkyl and in $C_3$-$C_{12}$-cycloalkyl-$C_1$-$C_8$-alkyl may be unsubstituted or substituted by 1-5 substituents selected from halogen, hydroxy or $C_1$-$C_4$-alkoxy;
wherein 'heterocyclyl' is a 3 to 7 membered saturated or partially unsaturated monocyclic ring system containing 1 to 3 heteroatoms selected from N, O or S, each of which is unsubstituted or substituted by 1-5 substituents selected from oxo, halogen, $C_1$-$C_8$-alkyl, halo-$C_1$-$C_8$-alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, halo-$C_1$-$C_8$-alkyl-carbonyl, hydroxy-$C_1$-$C_8$-alkyl-carbonyl or $C_1$-$C_8$-alkoxy-$C_1$-$C_8$-alkyl-carbonyl; wherein 'heterocyclyl' can be attached at a heteroatom or a carbon atom and where the N and/or S heteroatoms can also optionally be oxidized to various oxidation states,
wherein 'heteroaryl' is a 3 to 7 membered fully unsaturated monocyclic ring system containing 1 to 3 heteroatoms selected from N, O or S, or pyrazolo[1,5-a]pyrimidine or imidazo[2,1-b]thiazole, each of which is unsubstituted or substituted by 1-5 substituents selected from halogen, $C_1$-$C_8$-alkyl, halo-$C_1$-$C_8$-alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, halo-$C_1$-$C_8$-alkyl-carbonyl, hydroxy-$C_1$-$C_8$-alkyl-carbonyl or $C_1$-$C_8$-alkoxy-$C_1$-$C_8$-alkyl-carbonyl; wherein 'heteroaryl' can be attached at a heteroatom or a carbon atom and where the N and/or S heteroatoms can also optionally be oxidized to various oxidation states;
$R^6$ is selected from hydrogen, halogen, $C_1$-$C_4$-alkyl, halo-$C_1$-$C_4$-alkyl, $C_1$-$C_4$-alkoxy, $C_1$-$C_4$-alkyl-sulfonyl, $C_1$-$C_4$-alkyl-sulfinyl, $C_1$-$C_4$-alkyl-sulfanyl, halo-$C_1$-$C_4$-alkoxy, $C_1$-$C_4$-alkoxy-$C_1$-$C_4$-alkyl, amino, N—$C_1$-$C_8$-alkyl-amino, N,N-di-$C_1$-$C_8$-alkyl-amino;
$R^7$ is selected from hydrogen, halogen, cyano, nitro, $C_1$-$C_4$-alkyl, halo-$C_1$-$C_4$-alkyl, $C_1$-$C_4$-alkoxy, N($R^8$)$_2$-sulfonyl, $C_1$-$C_4$-alkyl-sulfonyl, $C_1$-$C_4$-alkyl-sulfonyl-amino, $C_1$-$C_8$-alkoxy-$C_1$-$C_8$-alkyl, amino, N—$C_1$-$C_8$-alkyl-amino, or N,N-di-$C_1$-$C_8$-alkyl-amino;
or $R^6$ and $R^7$, together are CH=CH—CH=CH,
wherein $R^8$ is independently selected from hydrogen, $C_1$-$C_4$-alkyl, $C_1$-$C_4$-alkoxy or two $R^8$ together with the nitrogen they are attached to form a 4 to 7 membered heterocyclic ring containing 1-2 heteroatoms selected from N, O, S, which is unsubstituted or substituted by 1-3 substituents selected from $C_1$-$C_4$-alkyl;
$R^5$ is independently selected from H, D, F or $C_1$-$C_2$-alkyl;
$R^{30}$ is independently selected from H, D or F.

2. A method of ameliorating a disorder or a disease selected from rheumatoid arthritis (RA), systemic lupus erythematosus (SLE), multiple sclerosis (MS), myasthenia gravis (MG), Sjögren's syndrome (SS) transplant rejection, lymphoctic leukemia, non-Hodgkin lymphoma, and lymphomas comprising administering to a subject suffering from the disease or disorder a therapeutically effective amount of a compound according Formula (I):

(I)

or a pharmaceutically acceptable salt thereof, wherein
Y is selected from O or NH;
V is selected from $CR^5$ or N;
W is selected from $CH_2$, or O;
U is selected from N or CH;
Q is selected from N or $CR_6$;
wherein U and Q are not both N;
$R^1$ is selected from phenyl, pyridyl, pyrimininyl, pyrazinyl, pyridazinyl, 1,2,3-triazinyl, 1,2,4-triazinyl, 1,3,5-triazinyl,
or
—X—$R^4$
  wherein X is selected from C(O), S(O)$_2$ or $CH_2$
  and
  $R^4$ is selected from $C_1$-$C_8$-alkyl, halo-$C_1$-$C_8$-alkyl, hydroxy-$C_1$-$C_8$-alkyl, $C_1$-$C_8$-alkoxy-$C_1$-$C_8$-alkyl, cyano-$C_1$-$C_8$-alkyl, N,N-di-$C_1$-$C_4$-alkyl-amino-$C_1$-$C_8$-alkyl, $C_1$-$C_4$-alkyl-sulfonyl-$C_1$-$C_8$-alkyl, phenyl, heterocyclyl, heterocyclyl-oxy, heterocyclyl-$C_1$-$C_8$-alkyl, $C_3$-$C_{12}$-cycloalkyl, $C_3$-$C_{12}$-cycloalkyl-oxy, $C_3$-$C_{12}$-cycloalkyl-$C_1$-$C_8$-alkyl, heteroaryl, heteroaryl-oxy, heteroaryl-$C_1$-$C_8$-alkyl, hydroxy, $C_1$-$C_8$-alkoxy, amino, N—$C_1$-$C_8$-alkyl-amino or N,N-di-$C_1$-$C_8$-alkyl-amino,
  wherein $C_1$-$C_8$-alkyl in N—$C_1$-$C_8$-alkyl-amino and in N,N-di-$C_1$-$C_8$-alkyl-amino may be unsubstituted or substituted by halogen, hydroxy or $C_1$-$C_4$-alkoxy,
  wherein $C_3$-$C_{12}$-cycloalkyl in $C_3$-$C_{12}$-cycloalkyl and in $C_3$-$C_{12}$-cycloalkyl-$C_1$-$C_8$-alkyl may be unsubstituted or substituted by 1-5 substituents selected from halogen, hydroxy or $C_1$-$C_4$-alkoxy;
  wherein 'heterocyclyl' is a 3 to 7 membered saturated or partially unsaturated monocyclic ring system containing 1 to 3 heteroatoms selected from N, O or S, each of which is unsubstituted or substituted by 1-5 substituents selected from oxo, halogen, $C_1$-$C_8$-alkyl, halo-$C_1$-$C_8$-alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, halo-$C_1$-$C_8$-alkyl-carbonyl, hydroxy-$C_1$-$C_8$-alkyl-carbonyl or $C_1$-$C_8$-alkoxy-$C_1$-$C_8$-alkyl-carbonyl; wherein 'heterocyclyl' can be attached at a heteroatom or a carbon atom and where the N and/or S heteroatoms can also optionally be oxidized to various oxidation states,
  wherein 'heteroaryl' is a 3 to 7 membered fully unsaturated monocyclic ring system containing 1 to 3 heteroatoms selected from N, O or S, or pyrazolo[1,5-a]pyrimidine or imidazo[2,1-b]thiazole, each of which is unsubstituted or substituted by 1-5 substituents selected from halogen, $C_1$-$C_8$-alkyl, halo-$C_1$-$C_8$-alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, halo-$C_1$-$C_8$-alkyl-carbonyl, hydroxy-$C_1$-$C_8$-alkyl-carbonyl or $C_1$-$C_8$-alkoxy-$C_1$-$C_8$-alkyl-carbonyl; wherein 'heteroaryl' can be attached at a heteroatom or a carbon atom and where the N and/or S heteroatoms can also optionally be oxidized to various oxidation states;

$R^6$ is selected from hydrogen, halogen, $C_1$-$C_4$-alkyl, halo-$C_1$-$C_4$-alkyl, $C_1$-$C_4$-alkoxy, $C_1$-$C_4$-alkyl-sulfonyl, $C_1$-$C_4$-alkyl-sulfinyl, $C_1$-$C_4$-alkyl-sulfanyl, halo-$C_1$-$C_4$-alkoxy, $C_1$-$C_4$-alkoxy-$C_1$-$C_4$-alkyl, amino, N—$C_1$-$C_8$-alkyl-amino, N,N-di-$C_1$-$C_8$-alkyl-amino;

$R^7$ is selected from hydrogen, halogen, cyano, nitro, $C_1$-$C_4$-alkyl, halo-$C_1$-$C_4$-alkyl, $C_1$-$C_4$-alkoxy, N($R^8$)$_2$-sulfonyl, $C_1$-$C_4$-alkyl-sulfonyl, $C_1$-$C_4$-alkyl-sulfonyl-amino, $C_1$-$C_8$-alkoxy-$C_1$-$C_8$-alkyl, amino, N—$C_1$-$C_8$-alkyl-amino, or N,N-di-$C_1$-$C_8$-alkyl-amino;

or $R^6$ and $R^7$, together are CH=CH—CH=CH,
  wherein $R^8$ is independently selected from hydrogen, $C_1$-$C_4$-alkyl, $C_1$-$C_4$-alkoxy or two $R^8$ together with the nitrogen they are attached to form a 4 to 7 membered heterocyclic ring containing 1-2 heteroatoms selected from N, O, S, which is unsubstituted or substituted by 1-3 substituents selected from $C_1$-$C_4$-alkyl;

$R^5$ is independently selected from H, D, F or $C_1$-$C_2$-alkyl;

$R^{30}$ is independently selected from H, D or F.

3. The method of claim 2, wherein the compound of Formula I is a compound of formula (Ic'):

(Ic')

4. The method of claim 2, wherein the compound of Formula I is a compound of formula (Id')

(Id')

5. The method of claim 2, wherein the compound of Formula I is a compound of formula (Ie')

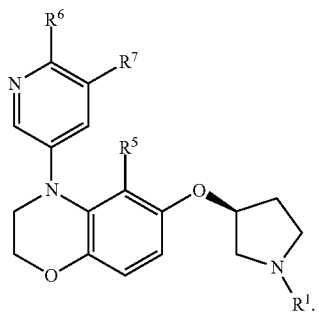

(Ie′)

6. The method of claim 2, wherein the compound of Formula I is a compound of formula (If′)

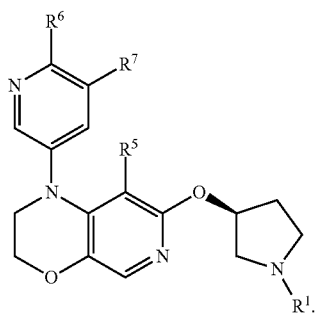

(If′)

7. The method of claim 4, wherein the compound of Formula I is a compound of formula (If′)

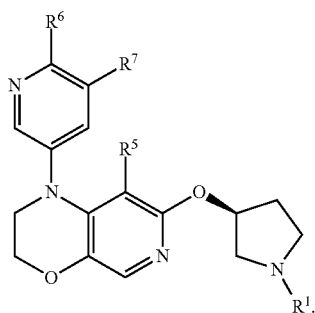

(If′)

8. The method of claim 2, wherein the compound of Formula I is a compound in which $R^1$ is selected from phenyl, pyridyl, pyrimininyl, pyrazinyl, pyridazinyl, 1,2,3-triazinyl, 1,2,4-triazinyl, 1,3,5-triazinyl, or —X—$R^4$, wherein $R^4$ is selected from $C_1$-$C_8$-alkyl, hydroxy-$C_1$-$C_8$-alkyl, $C_1$-$C_8$-alkoxy-$C_1$-$C_8$-alkyl, cyano-$C_1$-$C_8$-alkyl, N,N-di-$C_1$-$C_4$-alkyl-amino-$C_1$-$C_8$-alkyl, $C_1$-$C_4$-alkyl-sulfonyl-$C_1$-$C_8$-alkyl, phenyl, heterocyclyl, heterocyclyl-$C_1$-$C_8$-alkyl, $C_3$-$C_{12}$-cycloalkyl, heteroaryl, heteroaryl-$C_1$-$C_8$-alkyl, $C_1$-$C_8$-alkoxy, wherein $C_1$-$C_8$-alkyl in N—$C_1$-$C_8$-alkyl-amino and in N,N-di-$C_1$-$C_8$-alkyl-amino may be unsubstituted or substituted by halogen, hydroxy or $C_1$-$C_4$-alkoxy, wherein $C_3$-$C_{12}$-cycloalkyl in $C_3$-$C_{12}$-cycloalkyl and in $C_3$-$C_{12}$-cycloalkyl-$C_1$-$C_8$-alkyl may be unsubstituted or substituted by halogen, hydroxy or $C_1$-$C_4$-alkoxy;

wherein 'heterocyclyl' is a 3 to 7 membered saturated or partially unsaturated monocyclic ring system containing 1 to 3 heteroatoms selected from N, O or S, which is unsubstituted or substituted by 1-5 substituents selected from oxo, halogen, $C_1$-$C_8$-alkyl, halo-$C_1$-$C_8$-alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, halo-$C_1$-$C_8$-alkyl-carbonyl, hydroxy-$C_1$-$C_8$-alkyl-carbonyl or $C_1$-$C_8$-alkoxy-$C_1$-$C_8$-alkyl-carbonyl; wherein 'heterocyclyl' can be attached at a heteroatom or a carbon atom and where the N and/or S heteroatoms can also optionally be oxidized to various oxidation states, wherein 'heteroaryl' is a 3 to 7 membered fully unsaturated monocyclic ring system containing 1 to 3 heteroatoms selected from N, O or S, or pyrazolo[1,5-a]pyrimidine or imidazo[2,1-b]thiazole, each of which is unsubstituted or substituted by 1-5 substituents selected from halogen, $C_1$-$C_8$-alkyl, halo-$C_1$-$C_8$-alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, halo-$C_1$-$C_8$-alkyl-carbonyl, hydroxy-$C_1$-$C_8$-alkyl-carbonyl or $C_1$-$C_8$-alkoxy-$C_1$-$C_8$-alkyl-carbonyl; wherein 'heteroaryl' can be attached at a heteroatom or a carbon atom and where the N and/or S heteroatoms can also optionally be oxidized to various oxidation states.

9. The method of claim 2, wherein the compound of Formula I is a compound in which $R^1$ is selected from —X—$R^4$, wherein $R^4$ is selected from $C_1$-$C_8$-alkyl, hydroxy-$C_1$-$C_8$-alkyl, $C_1$-$C_8$-alkoxy-$C_1$-$C_8$-alkyl, cyano-$C_1$-$C_8$-alkyl, N,N-di-$C_1$-$C_4$-alkyl-amino-$C_1$-$C_8$-alkyl, $C_1$-$C_4$-alkyl-sulfonyl-$C_1$-$C_8$-alkyl, phenyl, heterocyclyl, heterocyclyl-$C_1$-$C_8$-alkyl, $C_3$-$C_{12}$-cycloalkyl, heteroaryl, heteroaryl-$C_1$-$C_8$-alkyl, $C_1$-$C_8$-alkoxy, wherein $C_1$-$C_8$-alkyl in N—$C_1$-$C_8$-alkyl-amino and in N,N-di-$C_1$-$C_8$-alkyl-amino may be unsubstituted or substituted by halogen, hydroxy or $C_1$-$C_4$-alkoxy, wherein $C_3$-$C_{12}$-cycloalkyl in $C_3$-$C_{12}$-cycloalkyl and in $C_3$-$C_{12}$-cycloalkyl-$C_1$-$C_8$-alkyl may be unsubstituted or substituted by halogen, hydroxy or $C_1$-$C_4$-alkoxy, wherein 'heterocyclyl' is a 3 to 7 membered saturated or partially unsaturated monocyclic ring system containing 1 to 3 heteroatoms selected from N, O or S, which is unsubstituted or substituted by 1-5 substituents selected from oxo, halogen, $C_1$-$C_8$-alkyl, halo-$C_1$-$C_8$-alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, halo-$C_1$-$C_8$-alkyl-carbonyl, hydroxy-$C_1$-$C_8$-alkyl-carbonyl or $C_1$-$C_8$-alkoxy-$C_1$-$C_8$-alkyl-carbonyl; wherein 'heterocyclyl' can be attached at a heteroatom or a carbon atom and where the N and/or S heteroatoms can also optionally be oxidized to various oxidation states, wherein 'heteroaryl' is a 3 to 7 membered fully unsaturated monocyclic ring system containing 1 to 3 heteroatoms selected from N, O or S, or pyrazolo[1, 5-a]pyrimidine or imidazo[2,1-b]thiazole, each of which is unsubstituted or substituted by 1-5 substituents selected from halogen, $C_1$-$C_8$-alkyl, halo-$C_1$-$C_8$-alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, halo-$C_1$-$C_8$-alkyl-carbonyl, hydroxy-$C_1$-$C_8$-alkyl-carbonyl or $C_1$-$C_8$-alkoxy-$C_1$-$C_8$-alkyl-carbonyl; wherein 'heteroaryl' can be attached at a heteroatom or a carbon atom and where the N and/or S heteroatoms can also optionally be oxidized to various oxidation states;

$R^6$ is selected from halogen, $C_1$-$C_4$-alkoxy, $C_1$-$C_4$-alkylsulfonyl or halo-$C_1$-$C_4$-alkoxy and $R^7$ is selected from hydrogen, halogen, cyano, $C_1$-$C_4$-alkyl, halo-$C_1$-$C_4$-alkyl or $C_1$-$C_4$-alkoxy.

10. The method of claim 2, wherein the compound of Formula I is a compound in crystalline form.

\* \* \* \* \*